(12) United States Patent
Wang et al.

(10) Patent No.: US 7,652,023 B2
(45) Date of Patent: Jan. 26, 2010

(54) HETEROCYCLIC CETP INHIBITORS

(75) Inventors: Yufeng Wang, North Brunswick, NJ (US); Wu Yang, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/560,388

(22) Filed: Nov. 16, 2006

(65) Prior Publication Data

US 2007/0135467 A1  Jun. 14, 2007

Related U.S. Application Data

(60) Provisional application No. 60/739,344, filed on Nov. 23, 2005.

(51) Int. Cl.
*A61K 31/506* (2006.01)
*A61K 31/4745* (2006.01)
*A61K 31/4439* (2006.01)
*C07D 403/02* (2006.01)

(52) U.S. Cl. .................. 514/275; 514/337; 514/338; 514/340; 514/370; 514/336; 544/331; 546/268.4; 546/272.7; 546/268.1; 546/269.7; 548/190; 548/202

(58) Field of Classification Search .......... 514/336, 514/340, 370; 546/268.1, 268.4, 269.7; 548/190, 548/202

See application file for complete search history.

(56) References Cited

U.S. PATENT DOCUMENTS

| 5,041,458 A | 8/1991 | Basarab |
| 2002/0177708 A1 | 11/2002 | Sikorski et al. |
| 2004/0127574 A1 | 7/2004 | Kori et al. |

FOREIGN PATENT DOCUMENTS

| WO | WO 2005/030185 | 4/2005 |
| WO | WO 2005/037796 | 4/2005 |
| WO | WO 2005/092845 | 10/2005 |
| WO | WO 2005/095395 | 10/2005 |
| WO | WO 2005/095409 | 10/2005 |
| WO | WO 2005/097805 | 10/2005 |
| WO | WO 2005/097806 | 10/2005 |
| WO | WO 2005/100298 | 10/2005 |
| WO | WO 2007/062342 | 5/2007 |

OTHER PUBLICATIONS

Wu and Farrelly, Toxicology 236:1-6, 2007.*
Cholesterol ester transfer protein, Wikipedia.*
Cited ref-STN-search-11560388.*
Alcaide, B. et al., "The reaction of alpha-diketones with primary heteroaromatic amines. Synthesis and reactions of imidazo[1,2-a]pyridine-3(2H0-ones and N-heteroaryl alpha-iminoketones", Tetrahedron, vol. 45, No. 21, pp. 6841-6856 (1989).
Lau, C. K. et al., "Structure based design of a series of potent and selective non peptidic PTP-1B inhibitors", Bioorganic & Medicinal Chemistry Letters, vol. 14, pp. 1043-1048 (2004).
Scapin, G. et al., "The structural basis for the selectivity of benzotriazole inhibitors of PTP1B", Biochemistry, vol. 42, pp. 11451-11459 (2003).

* cited by examiner

*Primary Examiner*—Yong Chu
(74) *Attorney, Agent, or Firm*—Terence J. Bogie

(57) ABSTRACT

Compounds of formula Ia and Ib

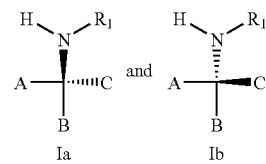

wherein A, B, C and $R_1$ are described herein.

15 Claims, No Drawings

HETEROCYCLIC CETP INHIBITORS

RELATED APPLICATION

This application claims the benefit of U.S. Provisional Application No. 60/739,344, filed on Nov. 23, 2005, incorporated herein by reference in its entirety.

FIELD OF THE INVENTION

This present invention provides for cholesteryl ester transfer protein (CETP) inhibitors, pharmaceutical compositions containing such inhibitors and the use of such inhibitors to elevate certain plasma lipid levels, including high density lipoprotein (HDL)-cholesterol and to lower certain other plasma lipid levels, such as low density lipoprotein (LDL)-cholesterol and triglycerides and accordingly to treat diseases which are affected by low levels of HDL cholesterol and/or high levels of LDL-cholesterol and triglycerides, such as atherosclerosis and cardiovascular diseases in certain mammals (i.e., those which have CETP in their plasma), including humans.

BACKGROUND OF THE INVENTION

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S., where cardiovascular disease accounts for 44% of all deaths, with 53% of these associated with atherosclerotic coronary heart disease.

Risk for development of atherosclerosis has been shown to be strongly correlated with certain plasma lipid levels. While elevated LDL-C may be the most recognized form of dyslipidemia, it is by no means the only significant lipid associated contributor to CHD. Low HDL-C is also a known risk factor for CHD (Gordon, D. J. et al., "High-density Lipoprotein Cholesterol and Cardiovascular Disease", Circulation, 79:8-15 (1989)).

High LDL-cholesterol and triglyceride levels are positively correlated, while high levels of HDL-cholesterol are negatively correlated with the risk for developing cardiovascular diseases. Thus, dyslipidemia is not a unitary risk profile for CHD but may be comprised of one or more lipid aberrations.

Among the many factors controlling plasma levels of these disease dependent principles, cholesteryl ester transfer protein (CETP) activity affects all three. The role of this 70,000 dalton plasma glycoprotein found in a number of animal species, including humans, is to transfer cholesteryl ester and triglyceride between lipoprotein particles, including high density lipoproteins (HDL), low density lipoproteins (LDL), very low density lipoproteins (VLDL), and chylomicrons. The net result of CETP activity is a lowering of HDL cholesterol and an increase in LDL cholesterol. This effect on lipoprotein profile is believed to be pro-atherogenic, especially in subjects whose lipid profile constitutes an increased risk for CHD.

No wholly satisfactory HDL-elevating therapies exist. Niacin can significantly increase HDL, but has serious toleration issues which reduce compliance. Fibrates and the HMG CoA reductase inhibitors raise HDL-C only modestly (about. 10-12%). As a result, there is a significant unmet medical need for a well-tolerated agent which can significantly elevate plasma HDL levels, thereby reversing or slowing the progression of atherosclerosis.

Thus, although there are a variety of anti-atherosclerosis therapies, there is a continuing need and a continuing search in this field of art for alternative therapies.

SUMMARY OF THE INVENTION

In accordance with the present invention, heterocyclic compounds and related compounds are provided that have the general structures:

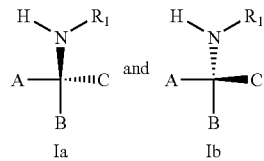

wherein A, B, C and $R_1$ are defined below.

By use of a respective effective amount of at least one compound described herein, provided are methods of treating, preventing or slowing the progression of a disease requiring cholesteryl ester transfer protein inhibition, or inhibiting the cholesteryl ester transfer protein.

Also provided are pharmaceutical compositions comprising a therapeutically effective amount of at least one compound described herein and a pharmaceutically acceptable vehicle or carrier thereof Such compositions can further comprise one or more additional therapeutic agents.

Definitions

The terms "alk" or "alkyl" refer to straight or branched chain hydrocarbon groups having 1 to 12 carbon atoms, or 1 to 8 carbon atoms, such as methyl, ethyl, n-propyl, i-propyl, n-butyl, i-butyl, t-butyl, pentyl, hexyl, heptyl, octyl, or any subset of the foregoing. The term "substituted alkyl" refers to alkyl groups substituted with one or more groups (such as by groups described above in the definition of $R^{20}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkenyl" refers to straight or branched chain hydrocarbon groups having 2 to 12 carbon atoms, or 2 to 4 carbon atoms, and at least one double carbon to carbon bond (either cis or trans), such as ethenyl. The term "substituted alkenyl" refers to alkenyl groups substituted with one or more groups (such as by groups described above in the definition of $R^{20}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkynyl" refers to straight or branched chain hydrocarbon groups having 2 to 12 carbon atoms, or 2 to 4 carbon atoms, and at least one triple carbon to carbon bond, such as ethynyl. The term "substituted alkynyl" refers to alkynyl groups substituted with one or more groups (such as by groups described above in the definition of $R^{20}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "aryl" refers to aromatic homocyclic (i.e., hydrocarbon) mono-, bi- or tricyclic ring-containing groups such as having 6 to 12 members such as phenyl, naphthyl and biphenyl. Phenyl is an example of an aryl group. The term "substituted aryl" refers to aryl groups substituted with one or more groups (such as by groups described above in the definition of $R^{20}$), such as selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane and sulfonyl, or any subset of the foregoing, where optionally one or more pair of substituents together with the atoms to which they are bonded form a 3 to 7 member ring.

The term "cycloalkyl" refers to mono-, bi- or tri homocyclic ring groups of 3 to 15 carbon atoms which are, respectively, fully saturated and partially unsaturated. The rings of multi-ring cycloalkyl groups may be either fused, bridged and/or joined through one or more spiro unions. The term "substituted cycloalkyl" refers to a cycloalkyl group substituted with one or more groups (such as by groups described above in the definition of $R^{20}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The terms "halogen" and "halo" refer to fluorine, chlorine, bromine and iodine.

The terms "heterocycle", "heterocyclic", "heterocyclic group" or "heterocyclyl" refer to fully saturated or partially or completely unsaturated, including aromatic ("heteroaryl") or nonaromatic cyclic groups (for example, 3 to 13 ring member monocyclic, 7 to 17 ring member bicyclic, or 10 to 20 ring member tricyclic ring systems, such as, in certain embodiments, a monocyclic or bicyclic ring containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions.

Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl,

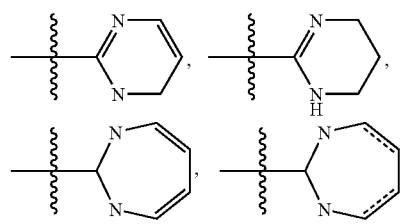

and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranyl, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4 dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl),

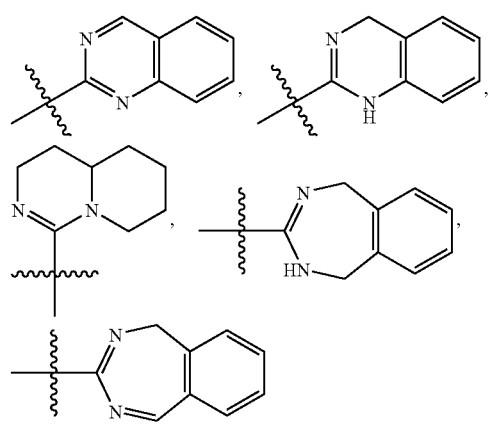

and the like.

Exemplary tricyclic heterocyclic groups include carbazolyl, benzidolyl, phenanthrolinyl, acridinyl, phenanthridinyl, xanthenyl and the like.

The terms "substituted heterocycle", "substituted heterocyclic", "substituted heterocyclic group" and "substituted heterocyclyl" refer to heterocycle, heterocyclic and heterocyclo groups substituted with one or more groups (such as by groups described above in the definition of $R^{20}$), such as selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, or any subset of the foregoing, where optionally one or more pair of substituents together with the atoms to which they are bonded form a 3 to 7 member ring.

Throughout the specification, groups and substituents thereof may be chosen to provide stable moieties and compounds.

The compounds of formulas Ia and Ib form salts or solvates which are also within the scope of this invention. Reference to a compound of the formula Ia or Ib herein is understood to include reference to salts thereof, unless otherwise indicated. The term "salt(s)", as employed herein, denotes acidic and/or basic salts formed with inorganic and/or organic acids and bases. In addition, when a compound of formula Ia or Ib contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula Ia and Ib may be formed, for example, by reacting a compound of formula Ia or Ib with an amount of acid or base, such as an equivalent amount, in a medium such as one in which the salt precipitates or in an aqueous medium followed by lyophilization.

The compounds of formula Ia and Ib which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula Ia and Ib which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g., decyl, lauryl, myristyl and stearyl chlorides, bromides and iodides), aralkyl halides (e.g. benzyl and phenethyl bromides), and others.

Any compound that can be converted in vivo to provide the bioactive agent (i.e., a compound of formula Ia or Ib) is a prodrug within the scope and spirit of the invention.

The term "prodrugs" as employed herein includes esters and carbonates formed by reacting one or more hydroxyls of compounds of formula Ia and Ib with alkyl, alkoxy, or aryl substituted acylating agents employing procedures known to those skilled in the art to generate acetates, pivalates, methylcarbonates, benzoates, and the like.

Various forms of prodrugs are well known in the art and are described in:
a) *The Practice of Medicinal Chemistry*, Camille G. Wermuth et al., Ch. 31 (Academic Press, 1996);
b) *Design of Prodrugs*, edited by H. Bundgaard (Elsevier, 1985);
c) *A Textbook of Drug Design and Development*, P. Krogsgaard-Larson and H. Bundgaard, eds. Ch. 5, pp. 113-191 (Harwood Academic Publishers, 1991); and
d) *Hydrolysis in Drug and Prodrug Metabolism*, Bernard Testa and Joachim M. Mayer (Wiley-VCH, 2003).

Said references are incorporated herein by reference.

In addition, compounds of the present invention are, subsequent to their preparation, preferably isolated and purified to obtain a composition containing an amount by weight equal to or greater than 99% formula Ia or Ib compound ("substantially pure" compound Ia or Ib), which may be used or formulated as described herein. Such "substantially pure" compounds of formula Ia and Ib are also contemplated herein as part of the present invention.

To the extent that compounds of the formula Ia and Ib, and salts thereof, may exist in their tautomeric form, all such tautomeric forms are contemplated herein as part of the present invention.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this invention. Individual stereoisomers of the compounds of the invention may, for example, be substantially free of other isomers, or may be admixed, for example, as racemates or with all other, or other selected, stereoisomers.

The terms "including", "such as", "for example" and the like are intended to refer to exemplary embodiments and not to limit the scope of the present invention.

DETAILED DESCRIPTION OF THE INVENTION

It will be understood that any given exemplary embodiment can be combined with one or more additional exemplary embodiments.

In accordance with the present invention, compounds of formula Ia and Ib are provided

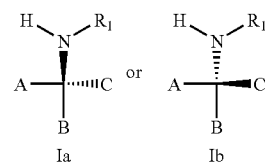

or stereoisomers or prodrugs or pharmaceutically acceptable salt forms thereof, wherein:

A is:
(a) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) —$SO_2NHR_6$, 19) —$COOR_6$, 20) —NHC(CN)$NHR_6$, 21) —$CONR_6R_6$, and 22) cycloalkyl, which may be optionally substituted with one or more $R_{20}$'s;

(b) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3)—$OR_6$, 4)($C_1$—$C_6$)-alkylthio, 5) cyano, 6) nitro, 7)—$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) —$SO_2NHR_6$, 19) —$COOR_6$, 20) —NHC(CN)$NHR_6$, 21) —$CONR_6R_6$, and 22) cycloalkyl, which may be optionally substituted with one or more $R_{20}$'s; or (c) phenyl, which may be substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) —$SO_2NHR_6$, 19) —$COOR_6$, 20) —NHC(CN)$NHR_6$, 21) —$CONR_6R_6$, 22) ($C_2$-$C_6$)-alkynyl, which may be optionally substituted with one or more $R_{20}$'s, 23) ($C_2$-$C_6$)-alkenyl, which may be optionally substituted with one or more $R_{20}$'s, 24) —$OCOR_6$, 25) —$OCOOR_6$, 26) —$OCONR_6R_6$, or 27) cycloalkyl, which may be optionally substituted with one or more $R_{20}$'s; or any two adjacent substituents may join together to form a 4- to 8-membered ring, which optionally may contain 1-4 heteroatoms selected from N, O, and S and be optionally substituted with one or more $R_{20}$'s;

B is:
(a) phenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) —$S(O)_pR_6$, 17) —$SO_2NHR_6$, 18) —$COOR_6$, 19) —NHC(CN)$NHR_6$, 20) —$CONR_6R_6$, and 21) cycloalkyl, which may be optionally substituted with one or more $R_{20}$'s; or (b) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) —$S(O)_pR_6$, 17) —$SO_2NHR_6$, 18) —$COOR_6$, 19) —NHC(CN)$NHR_6$, 20) —$CONR_6R_6$, and 21) cycloalkyl, which may be optionally substituted with one or more $R_{20}$'s;

C is:
(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) —$S(O)_pR_6$, 15) —$SO_2NHR_6$, 16) —$COOR_6$, 17) —NHC(CN)$NHR_6$, and 18) cycloalkyl, which may be optionally substituted with one or more $R_{20}$'s;

(b) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, and 15) cycloalkyl, which may be optionally substituted with one or more $R_{20}$'s;
- (c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) —$S(O)_pR_6$, 15) —$SO_2NHR_6$, 16) —$COOR_6$, 17) —NHC(CN)$NHR_6$, and 18) cycloalkyl, which may be optionally substituted with one or more $R_{20}$'s; or
- (d) heterocyclo, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) —$S(O)_pR_6$, 15) —$SO_2NHR_6$, 16) —$COOR_6$, 17) —NHC(CN)$NHR_6$, and 18) cycloalkyl, which may be optionally substituted with one or more $R_{20}$'s;

$R_1$ is:
- (a) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) —$SO_2NHR_6$, 19) —$COOR_6$, 20) —NHC(CN)$NHR_6$, 21) —$CONR_6R_6$, 22) —$CONR_9NR_9R_{10}$, and 23) cycloalkyl, which may be optionally substituted with one or more $R_{20}$'s;
- (b) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) —$SO_2NHR_6$, 19) —$COOR_6$, 20) —NHC(CN)$NHR_6$, 21) —$CONR_6R_6$, 22) —$CONR_9NR_9R_{10}$, and 23) cycloalkyl, which may be optionally substituted with one or more $R_{20}$'s; or
- (c) —C(NH)NHC(O)$OR_6$;

$R_6$, at each occurrence, is independently:
- (a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, 22) —NHC(CN)$NHR_{36}$, and 23) cycloalkyl, which may be optionally substituted with one or more $R_{20}$'s;
- (b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, 24) —NHC(CN)$NHR_{36}$, and 25) cycloalkyl, which may be optionally substituted with one or more $R_{20}$'s;
- (c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —NHC(CN)$NHR_{36}$, and 26) cycloalkyl, which may be optionally substituted with one or more $R_{20}$'s;
- (d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —NHC(CN)$NHR_{36}$, and 26) cycloalkyl, which may be optionally substituted with one or more $R_{20}$'s;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —NHC(CN)$NHR_{36}$, and 26) cycloalkyl, which may be optionally substituted with one or more $R_{20}$'s; or (f) hydrogen;

or two $R_6$'s are taken together to form a 3- to 9-membered ring, which optionally may contain 1-4 heteroatoms selected from N, O, and S and be optionally substituted with one or more $R_{20}$'s;

$R_9$ and $R_{10}$ are independently: (a) hydrogen; (b) —[(C=O)$O_r$]$_s$aryl, wherein the aryl may be optionally substituted with one or more $R_{20}$'s; (c) —[(C=O)$O_r$]$_s$($C_2$-$C_8$)-alkenyl, wherein the alkenyl may be optionally substituted with one or more $R_{20}$'s; (d) —[(C=O)$O_r$]$_s$($C_1$-$C_8$)-alkyl, wherein the alkyl may be optionally substituted with one or more $R_{20}$'s; (e) heterocyclyl optionally substituted with one or more $R_{20}$'s; (f) —$CONR_{26}R_{26}$; (g) —($C_2$-$C_6$)-alkynyl; (h) —$COR_{26}$; (i) —$S(O)_pR_{26}$; (j) —$SO_2NHR_{26}$; (k) —$COOR_{26}$; (l) —NHC(CN)$NHR_{26}$; or (m) —[(C=O)$O_r$]$_s$cycloalkyl, wherein the cycloalkyl may be optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) =O; (q) —($C_2$-$C_6$)-alkynyl; (r) —$COR_{26}$; (s) —$S(O)_pR_{26}$; (t) —$SO_2NHR_{26}$; (u) —$COOR_{26}$; (v) —NHC(CN)$NHR_{26}$; (w) cycloalkyl, which may be optionally substituted with one or more $R_{21}$'s; (x) cycloalkylalkyl, which may be optionally substituted with one or more $R_{21}$'s; or (y) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) =O; (r) ($C_2$-$C_6$)-alkynyl; (s) cycloalkyl; (t) cycloalkylalkyl; (u) —$COR_{26}$; (v) —$S(O)_pR_{26}$; (w) —$SO_2NHR_{26}$; (x) —$COOR_{26}$; or (y) —NHC(CN)$NHR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, 22) —NHC(CN)$NHR_{36}$, and 23) cycloalkyl, which may be optionally substituted with one or more $R_{40}$'s;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, 24) —NHC(CN)$NHR_{36}$, and 25) cycloalkyl, which may be optionally substituted with one or more $R_{40}$'s;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, 25) —NHC(CN)NHR$_{36}$, and 26) cycloalkyl, which may be optionally substituted with one or more $R_{40}$'s;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, 25) —NHC(CN)NHR$_{36}$, and 26) cycloalkyl, which may be optionally substituted with one or more $R_{40}$'s;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, 25) —NHC(CN)NHR$_{36}$, and 26) cycloalkyl, which may be optionally substituted with one or more $R_{40}$'s; or (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —[(C=O)O$_r$]$_s$aryl, —[(C=O)O$_r$]$_s$alkenyl, —[(C=O)O$_r$]$_s$alkyl, heterocyclyl, —CONR$_{36}$R$_{36}$, alkynyl, —COR$_{36}$, —S(O)$_p$R$_{36}$, —SO$_2$NHR$_{36}$, —COOR$_{36}$, —C(CN)NHR$_{36}$, or cycloalkyl, wherein the aryl, alkyl, alkenyl, cycloalkyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —NR$_{49}$R$_{50}$, aryl, arylalkyl, heteroaryl, heteroarylalkyl, heterocyclyl, heterocyclylalkyl, haloalkyl, haloalkyloxy, —CONR$_{49}$R$_{50}$, alkenyl, arylalkyloxy, =O, alkynyl, cycloalkyl, cycloalkylalkyl, —COR$_{49}$, —S(O)$_p$R$_{49}$, —SO$_2$NHR$_{49}$, —COOR$_{49}$, or -NHC(CN)NHR$_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

In one embodiment, compounds of the present invention are provided wherein the compound is a compound of formula Ib

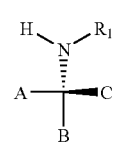

Ib

In one embodiment, compounds of the present invention are provided wherein:

A is:

(a) heteroaryl, which is substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —COR$_6$, 16) =O, 17) —S(O)$_p$R$_6$, 18) —SO$_2$NHR$_6$, 19) —COOR$_6$, 20) —NHC(CN)NHR$_6$, 21) —CONR$_6$R$_6$, and 22) cycloalkyl, which may be optionally substituted with one or more $R_{20}$'s;

(b) heterocyclyl, other than heteroaryl, which is substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) —$SO_2NHR_6$, 19) —$COOR_6$, 20) —$NHC(CN)NHR_6$, 21) —$CONR_6R_6$, and 22) cycloalkyl, which may be optionally substituted with one or more $R_{20}$'s; or (c) phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) —$SO_2NHR_6$, 19) —$COOR_6$, 20) —$NHC(CN)NHR_6$, 21) —$CONR_6R_6$, 22) ($C_2$-$C_6$)-alkynyl, which may be optionally substituted with one or more $R_{20}$'s, 23) ($C_2$-$C_6$)-alkenyl, which may be optionally substituted with one or more $R_{20}$'s, 24) —$OCOR_6$, 25) —$OCOOR_6$, 26) —$OCONR_6R_6$, and 27) cycloalkyl, which may be optionally substituted with one or more $R_{20}$'s; or any two adjacent substituents may join together to form a 4- to 8-membered ring, which optionally may contain 1-4 heteroatoms selected from N, O, and S and be optionally substituted with one or more $R_{20}$'s;

B is:
(a) phenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) —$S(O)_pR_6$, 17) —$SO_2NHR_6$, 18) —$COOR_6$, 19) —$NHC(CN)NHR_6$, and 20) cycloalkyl, which may be optionally substituted with one or more $R_{20}$'s; or (b) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) —$S(O)_pR_6$, 17) —$SO_2NHR_6$, 18) —$COOR_6$, 19) —$NHC(CN)$ $NHR_6$, and 20) cycloalkyl, which may be optionally substituted with one or more $R_{20}$'s;

C is:
(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) —$S(O)_pR_6$, 15) —$SO_2NHR_6$, 16) —$COOR_6$, 17) —$NHC(CN)NHR_6$, and 18) cycloalkyl, which may be optionally substituted with one or more $R_{20}$'s;

(b) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, and 15) cycloalkyl, which may be optionally substituted with one or more $R_{20}$'s; or (c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) —$S(O)_pR_6$, 15) —$SO_2NHR_6$, 16) —$COOR_6$, 17) —$NHC(CN)NHR_6$, and 18) cycloalkyl, which may be optionally substituted with one or more $R_{20}$'s;

$R_1$ is:
(a) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) —$SO_2NHR_6$, 19) —$COOR_6$, 20) —$NHC(CN)NHR_6$, 21) —$CONR_6R_6$, 22) —$CONR_9NR_9R_{10}$, and 23) cycloalkyl, which may be optionally substituted with one or more $R_{20}$'s;

(b) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) —$SO_2NHR_6$, 19) —$COOR_6$, 20) —NHC(CN)NHR$_6$, 21) —$CONR_6R_6$, 22) —$CONR_9NR_9R_{10}$, and 23) cycloalkyl, which may be optionally substituted with one or more $R_{20}$'s; or (c) —C(NH)NHC(O)$OR_6$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, 22) —NHC(CN)NHR$_{36}$, and 23) cycloalkyl, which may be optionally substituted with one or more $R_{20}$'s;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, 24) —NHC(CN)NHR$_{36}$, and 25) cycloalkyl, which may be optionally substituted with one or more $R_{20}$'s;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —NHC(CN)NHR$_{36}$, and 26) cycloalkyl, which may be optionally substituted with one or more $R_{20}$'s;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —NHC(CN)NHR$_{36}$, and 26) cycloalkyl, which may be optionally substituted with one or more $R_{20}$'s;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —NHC(CN)NHR$_{36}$, and 26) cycloalkyl, which may be optionally substituted with one or more $R_{20}$'s; or (f) hydrogen;

or two $R_6$'s are taken together to form a 3- to 9-membered ring, which optionally may contain 1-4 heteroatoms selected from N, O, and S and be optionally substituted with one or more $R_{20}$'s;

$R_9$ and $R_{10}$ are independently: (a) hydrogen; (b) —[(C=O)O$_r$]$_s$aryl, wherein the aryl may be optionally substituted with one or more $R_{20}$'s; (c) —[(C=O)O$_r$]$_s$($C_2$-$C_8$)-alkenyl, wherein the alkenyl may be optionally substituted with one or more $R_{20}$'s; (d) —[(C=O)O$_r$]$_s$($C_1$-$C_8$) alkyl, wherein the alkyl may be optionally substituted with one or more $R_{20}$'s; (e) heterocyclyl optionally substituted with one or more $R_{20}$'s; (f) —$CONR_{26}R_{26}$; (g) —($C_2$-$C_6$)-alkynyl; (h) —$COR_{26}$; (i) —$S(O)_pR_{26}$; (j) —$SO_2NHR_{26}$; (k) —$COOR_{26}$; (l) —NHC(CN)NHR$_{26}$;

or (m) —[(C=O)O$_r$]$_s$cycloalkyl, which may be optionally substituted with one or more R$_{20}$'s;

or R$_9$ and R$_{10}$ are taken together with the nitrogen to which both are attached to form a 3- to 8-membered ring, which may optionally contain 1-4 heteroatoms selected from N, O, and S and be optionally substituted with one or more R$_{20}$'s;

R$_{20}$ is: (a) halo; (b) (C$_1$-C$_6$)-alkyl, which may be optionally substituted with one or more R$_{21}$'s; (c) —OR$_{26}$; (d) (C$_1$-C$_6$)-alkylthio; (e) cyano; (f) nitro; (g) —NR$_{29}$R$_{30}$; (h) aryl, which may be optionally substituted with one or more R$_{21}$'s; (i) arylalkyl, which may be optionally substituted with one or more R$_{21}$'s; (j) heteroaryl, which may be optionally substituted with one or more R$_{21}$'s; (k) heteroarylalkyl, which may be optionally substituted with one or more R$_{21}$'s; (l) heterocyclyl, which may be optionally substituted with one or more R$_{21}$'s; (m) heterocyclylalkyl, which may be optionally substituted with one or more R$_{21}$'s; (n) halo(C$_1$-C$_6$)alkyl; (o) (C$_2$-C$_6$)-alkenyl; (p) =O; (q) —(C$_2$-C$_6$)-alkynyl; (r) —COR$_{26}$; (s) —S(O)$_p$R$_{26}$; (t) —SO$_2$NHR$_{26}$; (u) —COOR$_{26}$; (v) —NHC(CN)NHR$_{26}$; (w) cycloalkyl, which may be optionally substituted with one or more R$_{21}$'s; (x) cycloalkylalkyl, which may be optionally substituted with one or more R$_{21}$'s; or (y) —CONR$_{26}$R$_{26}$;

R$_{21}$ is: (a) halo; (b) (C$_1$-C$_6$)-alkyl; (c) —OR$_{26}$; (d) (C$_1$-C$_6$)-alkylthio; (e) cyano; (f) nitro; (g) —NR$_{29}$R$_{30}$; (h) aryl; (i) arylalkyl; (j) heteroaryl; (k) heteroarylalkyl; (l) heterocyclyl; (m) heterocyclylalkyl; (n) halo(C$_1$-C$_6$)alkyl; (o) —CONR$_{26}$R$_{26}$; (p) (C$_2$-C$_6$)-alkenyl; (q) =O; (r) (C$_2$-C$_6$)-alkynyl; (s) cycloalkyl; (t) cycloalkylalkyl; (u) —COR$_{26}$; (v) —S(O)$_p$R$_{26}$; (w) —SO$_2$NHR$_{26}$; (x) —COOR$_{26}$; or (y) —NHC(CN)NHR$_{26}$;

R$_{26}$, at each occurrence, is independently:

(a) alkyl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) heteroaryl, which may be optionally substituted with one or more R$_{40}$'s, 11) heterocyclyl, which may be optionally substituted with one or more R$_{40}$'s, 12) halo(C$_1$-C$_6$)alkyl, 13) (C$_2$-C$_6$)-alkenyl, 14) —COOH, 15) —CONR$_{36}$R$_{36}$, 16) =O, 17) (C$_2$-C$_6$)-alkynyl, 18) —COR$_{36}$, 19) —S(O)$_p$R$_{36}$, 20) —SO$_2$NHR$_{36}$, 21) —COOR$_{36}$, 22) —NHC(CN)NHR$_{36}$, and 23) cycloalkyl, which may be optionally substituted with one or more R$_{40}$'s;

(b) aryl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) arylalkyl, which may be optionally substituted with one or more R$_{40}$'s, 11) heteroaryl, which may be optionally substituted with one or more R$_{40}$'s, 12) heteroarylalkyl, which may be optionally substituted with one or more R$_{40}$'s, 13) heterocyclyl, which may be optionally substituted with one or more R$_{40}$'s, 14) heterocyclylalkyl, which may be optionally substituted with one or more R$_{40}$'s, 15) halo(C$_1$-C$_6$)alkyl, 16) —COOH, 17) —CONR$_{36}$R$_{36}$, 18) =O, 19) (C$_2$-C$_6$)-alkynyl, 20) —COR$_{36}$, 21) —S(O)$_p$R$_{36}$, 22) —SO$_2$NHR$_{36}$, 23) —COOR$_{36}$, 24) —NHC(CN)NHR$_{36}$, and 25) cycloalkyl, which may be optionally substituted with one or more R$_{40}$'s;

(c) cycloalkyl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) arylalkyl, which may be optionally substituted with one or more R$_{40}$'s, 11) heteroaryl, which may be optionally substituted with one or more R$_{40}$'s, 12) heteroarylalkyl, which may be optionally substituted with one or more R$_{40}$'s, 13) heterocyclyl, which may be optionally substituted with one or more R$_{40}$'s, 14) heterocyclylalkyl, which may be optionally substituted with one or more R$_{40}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, 25) —NHC(CN)NHR$_{36}$, and 26) cycloalkyl, which may be optionally substituted with one or more R$_{40}$'s;

(d) heteroaryl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) arylalkyl, which may be optionally substituted with one or more R$_{40}$'s, 11) heteroaryl, which may be optionally substituted with one or more R$_{40}$'s, 12) heteroarylalkyl, which may be optionally substituted with one or more R$_{40}$'s, 13) heterocyclyl, which may be optionally substituted with one or more R$_{40}$'s, 14) heterocyclylalkyl, which may be optionally substituted with one or more R$_{40}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, 25) —NHC(CN)NHR$_{36}$, and 26) cycloalkyl, which may be optionally substituted with one or more R$_{40}$'s;

(e) heterocyclyl, other than heteroaryl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) arylalkyl, which may be optionally substituted with one or more R$_{40}$'s, 11) heteroaryl, which may be optionally substituted with one or more R$_{40}$'s, 12) heteroarylalkyl, which may be optionally substituted with one or more R$_{40}$'s, 13) heterocyclyl, which may be optionally substituted with one or more R$_{40}$'s, 14) heterocyclylalkyl, which may be optionally substituted with one or more R$_{40}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, 25) —NHC(CN)NHR$_{36}$, and 26) cycloalkyl, which may be optionally substituted with one or more R$_{40}$'s; or (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, $—[(C=O)O_r]_s$ aryl, $—[(C=O)O_r]_s$alkenyl, $—[(C=O)O_r]_s$alkyl, heterocyclyl, $—CONR_{36}R_{36}$, alkynyl, $—COR_{36}$, $—S(O)_pR_{36}$, $—SO_2NHR_{36}$, $—COOR_{36}$, $—C(CN)NHR_{36}$ or cycloalkyl, wherein the aryl, alkyl, alkenyl, cycloalkyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, $—OH$, alkyl, alkyloxy, alkylthio, cyano, nitro, $—NR_{49}R_{50}$, aryl, arylalkyl, heteroaryl, heteroarylalkyl, heterocyclyl, heterocyclylalkyl, haloalkyl, haloalkyloxy, $—CONR_{49}R_{50}$, alkenyl, arylalkyloxy, $=O$, alkynyl, cycloalkyl, cycloalkylalkyl, $—COR_{49}$, $—S(O)_pR_{49}$, $—SO_2NHR_{49}$, $—COOR_{49}$, or $—NHC(CN)NHR_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

In yet another embodiment, compounds of the present invention are provided wherein:

A is:
(a) heteroaryl, which is substituted with one or more substituents selected from the group consisting of: 1) halo, 2) $(C_1-C_6)$-alkyl, which may be optionally substituted with one or more $R_{20}$'s, 3) $—OR_6$, 4) $(C_1-C_6)$-alkylthio, 5) cyano, 6) nitro, 7) $—NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) $—COR_6$, 16) $=O$, 17) $—S(O)_pR_6$, 18) $—SO_2NHR_6$, 19) $—COOR_6$, 20) $—NHC(CN)NHR_6$, and 21) $—CONR_6R_6$;

(b) heterocyclyl, other than heteroaryl, which is substituted with one or more substituents selected from the group consisting of: 1) halo, 2) $(C_1-C_6)$-alkyl, which may be optionally substituted with one or more $R_{20}$'s, 3) $—OR_6$, 4) $(C_1-C_6)$-alkylthio, 5) cyano, 6) nitro, 7) $—NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) $—COR_6$, 16) $=O$, 17) $—S(O)_pR_6$, 18) $—SO_2NHR_6$, 19) $—COOR_6$, 20) $—NHC(CN)NHR_6$, and 21) $—CONR_6R_6$; or (c) phenyl, which is substituted with one or more substituents selected from the group consisting of: 1) halo, 2) $(C_1-C_6)$-alkyl, which may be optionally substituted with one or more $R_{20}$'s, 3) $—OR_6$, 4) $(C_1-C_6)$-alkylthio, 5) cyano, 6) nitro, 7) $—NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) $—COR_6$, 16) $=O$, 17) $—COOR_6$, 18) $—CONR_6R_6$, 19) $(C_2-C_6)$-alkynyl, which may be optionally substituted with one or more $R_{20}$'s, 20) $(C_2-C_6)$-alkenyl, which may be optionally substituted with one or more $R_{20}$'s, 21) $—OCOR_6$, 22) $—OCOOR_6$, or 23) $—OCONR_6R_6$; or any two adjacent substituents may join together to form a 4- to 8-membered ring, which optionally may contain 1-4 heteroatoms selected from N, O, and S and be optionally substituted with one or more $R_{20}$'s;

B is:
(a) phenyl, which is substituted with one or more substituents selected from the group consisting of: 1) halo, 2) $(C_1-C_6)$-alkyl, which may be optionally substituted with one or more $R_{20}$'s, 3) $—OR_6$, 4) $(C_1-C_6)$-alkylthio, 5) cyano, 6) nitro, 7) $—NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) $—COR_6$, 16) $—S(O)_pR_6$, 17) $—SO_2NHR_6$, 18) $—COOR_6$, and 19) $—NHC(CN)NHR_6$; or (b) heteroaryl, which is substituted with one or more substituents selected from the group consisting of: 1) halo, 2) $(C_1-C_6)$-alkyl, which may be optionally substituted with one or more $R_{20}$'s, 3) $—OR_6$, 4) $(C_1-C_6)$-alkylthio, 5) cyano, 6) nitro, 7) $—NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) $—COR_6$, 16) $—S(O)_pR_6$, 17) $—SO_2NHR_6$, 18) $—COOR_6$, and 19) $—NHC(CN)NHR_6$;

C is:
(a) alkyl, which may be optionally substituted with one or more substituents selected from the group consisting of: 1) halo, 2) $(C_1-C_6)$-alkyl, which may be optionally substituted with one or more $R_{20}$'s, 3) $—OR_6$, 4) $(C_1-C_6)$-alkylthio, 5) cyano, 6) nitro, 7) $—NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) —$S(O)_pR_6$, 15) —$SO_2NHR_6$, 16) —$COOR_6$, and 17) —NHC(CN)$NHR_6$;

(b) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl; or (c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) —$S(O)_pR_6$, 15) —$SO_2NHR_6$, 16) —$COOR_6$, and 17) —NHC(CN)$NHR_6$;

$R_1$ is:
  (a) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) —$SO_2NHR_6$, 19) —$COOR_6$, 20) —NHC(CN)$NHR_6$, 21) —$CONR_6R_6$, and 22) —$CONR_9NR_9R_{10}$;

(b) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) —$SO_2NHR_6$, 19) —$COOR_6$, 20) —NHC(CN)$NHR_6$, 21) —$CONR_6R_6$, and 22) —$CONR_9NR_9R_{10}$; or (c) —C(NH)NHC(O)$OR_6$;

$R_6$, at each occurrence, is independently:
  (a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$; or (f) hydrogen;

or two $R_6$'s are taken together to form a 3- to 9-membered ring, which optionally may contain 1-4 heteroatoms selected from N, O, and S and be optionally substituted with one or more $R_{20}$'s;

$R_9$ and $R_{10}$ are independently: (a) hydrogen; (b) —[(C=O)O$_r$]$_s$aryl, wherein the aryl may be optionally substituted with one or more $R_{20}$'s; (c) —[(C=O)O$_r$]$_s$($C_2$-$C_8$)-alkenyl, wherein the alkenyl may be optionally substituted with one or more $R_{20}$'s; (d) —[(C=O)O$_r$]$_s$($C_1$-$C_8$)-alkyl, wherein the alkyl may be optionally substituted with one or more $R_{20}$'s, (e) heterocyclyl optionally substituted with one or more $R_{20}$'s; (f) —CONR$_{26}$R$_{26}$; (g) —($C_2$-$C_6$)-alkynyl; (h) —COR$_{26}$; (i) —S(O)$_p$R$_{26}$; (j) —SO$_2$NHR$_{26}$; (k) —COOR$_{26}$; or (l) —NHC(CN)NHR$_{26}$;

or $R_9$ and $R_{10}$ are taken together with the nitrogen to which both are attached to form a 3- to 8-membered ring, which may optionally contain 1-4 heteroatoms selected from N, O, and S and may be optionally substituted with one or more $R_{20}$'s;

$R_{20}$ is: (a) halo; (b) ($C_1$-$C_6$)-alkyl, which may be optionally substituted with one or more $R_{21}$'s; (c) —OR$_{26}$; (d) ($C_1$-$C_6$)-alkylthio; (e) cyano; (f) nitro; (g) —NR$_{29}$R$_{30}$; h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) =O; (q) —($C_2$-$C_6$)-alkynyl; (r) —COR$_{26}$; (s) —S(O)$_p$R$_{26}$; (t) —SO$_2$NHR$_{26}$; (u) —COOR$_{26}$; (v) —NHC(CN)NHR$_{26}$; (w) cycloalkyl, which may be optionally substituted with one or more $R_{21}$'s; (x) cycloalkylalkyl, which may be optionally substituted with one or more $R_{21}$'s; or (y) —CONR$_{26}$R$_{26}$;

$R_{21}$ is: (a) halo; (b) ($C_1$-$C_6$)-alkyl; (c) —OR$_{26}$; (d) ($C_1$-$C_6$)-alkylthio; (e) cyano; (f) nitro; (g) —NR$_{29}$R$_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —CONR$_{26}$R$_{26}$; (p) ($C_2$-$C_6$)-alkenyl; (q) =O; (r) ($C_2$-$C_6$)-alkynyl; (s) cycloalkyl; (t) cycloalkylalkyl; (u) —COR$_{26}$; (v) —S(O)$_p$R$_{26}$; (w) —SO$_2$NHR$_{26}$; (x) —COOR$_{26}$; or (y) —NHC(CN)NHR$_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —CONR$_{36}$R$_{36}$, 16) =O, 17) ($C_2$-$C_6$)-alkynyl, 18) —COR$_{36}$, 19) —S(O)$_p$R$_{36}$, 20) —SO$_2$NHR$_{36}$, 21) —COOR$_{36}$, and 22) —NHC(CN)NHR$_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —CONR$_{36}$R$_{36}$, 18) =O, 19) ($C_2$-$C_6$)-alkynyl, 20) —COR$_{36}$, 21) —S(O)$_p$R$_{36}$, 22) —SO$_2$NHR$_{36}$, 23) —COOR$_{36}$, and 24) —NHC(CN)NHR$_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$; or (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —[(C=O)O$_r$]$_s$aryl, —[(C=O)O$_r$]$_s$alkenyl, —[(C=O)O$_r$]$_s$alkyl, heterocyclyl, —CONR$_{36}$R$_{36}$, alkynyl, —COR$_{36}$, —S(O)$_p$R$_{36}$, —SO$_2$NHR$_{36}$, —COOR$_{36}$, or —C(CN)NHR$_{36}$, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and may be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —NR$_{49}$R$_{50}$, aryl, arylalkyl, heteroaryl, heteroarylalkyl, heterocyclyl, heterocyclylalkyl, haloalkyl, haloalkyloxy, —CONR$_{49}$R$_{50}$, alkenyl, arylalkyloxy, =O, alkynyl, cycloalkyl, cycloalkylalkyl, —COR$_{49}$, —S(O)$_p$R$_{49}$, —SO$_2$NHR$_{49}$, —COOR$_{49}$, or —NHC(CN)NHR$_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

In still yet another embodiment, compounds of the present invention are provided wherein:

A is:
(a) heteroaryl, which is substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —COR$_6$, 16) =O, 17) —S(O)$_p$R$_6$, 18) —SO$_2$NHR$_6$, 19) —COOR$_6$, 20) —NHC(CN)NHR$_6$, and 21) —CONR$_6$R$_6$; or (b) phenyl, which is substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —COR$_6$, 16) =O, 17) —COOR$_6$, 18) —CONR$_6$R$_6$, 19) ($C_2$-$C_6$)-alkynyl, which may be optionally substituted with one or more $R_{20}$'s, 20) —OCOR$_6$, 21) —OCOOR$_6$, or 22) —OCONR$_6$R$_6$; or any two adjacent substituents may join together to form a 4- to 8-membered ring, which optionally may contain 1-4 heteroatoms selected from N, O, and S and be optionally substituted with one or more $R_{20}$'s;

B is:
(a) phenyl, which is substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —COR$_6$, 16) —S(O)$_p$R$_6$, 17) —SO$_2$NHR$_6$, 18) —COOR$_6$, and 19) —NHC(CN)NHR$_6$; or (b) heteroaryl, which is substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) —$S(O)_pR_6$, 17) —$SO_2NHR_6$, 18) —$COOR_6$, and 19) —NHC(CN)$NHR_6$;

C is:
(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) —$S(O)_pR_6$, 15) —$SO_2NHR_6$, 16) —$COOR_6$, and 17) —NHC(CN)$NHR_6$; or
(b) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl;

$R_1$ is:
(a) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) —$SO_2NHR_6$, 19) —$COOR_6$, 20) —NHC(CN)$NHR_6$, 21) —$CONR_6R_6$, and 22) —$CONR_9NR_9R_{10}$; or
(b) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) —$SO_2NHR_6$, 19) —$COOR_6$, 20) —NHC(CN)$NHR_6$, 21) —$CONR_6R_6$, and 22) —$CONR_9NR_9R_{10}$;

$R_6$, at each occurrence, is independently:
(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;
(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;
(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;
(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$; or (f) hydrogen;

or two $R_6$'s are taken together to form a 3- to 9-membered ring, which optionally may contain 1-4 heteroatoms selected from N, O, and S and may be optionally substituted with one or more $R_{20}$'s;

$R_9$ and $R_{10}$ are independently: (a) hydrogen; (b) —[(C=O)O$_r$]$_s$aryl, wherein the aryl may be optionally substituted with one or more $R_{20}$'s; (c) —[(C=O)O$_r$]$_s$($C_2$-$C_8$)-alkenyl, wherein the alkenyl may be optionally substituted with one or more $R_{20}$'s; (d) —[(C=O)O$_r$]$_s$($C_1$-$C_8$) alkyl, wherein the alkyl may be optionally substituted with one or more $R_{20}$'s; (e) heterocyclyl optionally substituted with one or more $R_{20}$'s; (f) —CONR$_{26}$R$_{26}$; (g) —($C_2$-$C_6$)-alkynyl; (h) —COR$_{26}$; (i) —S(O)$_p$R$_{26}$; (j) —SO$_2$NHR$_{26}$; (k) —COOR$_{26}$; or (l) —NHC(CN)NHR$_{26}$;

or $R_9$ and $R_{10}$ are taken together with the nitrogen to which both are attached to form a 3- to 8-membered ring, which may optionally contain 1-4 heteroatoms selected from N, O, and S and may be optionally substituted with one or more $R_{20}$'s;

$R_{20}$ is: (a) halo; (b) ($C_1$-$C_6$)-alkyl, which may be optionally substituted with one or more $R_{21}$'s; (c) —OR$_{26}$; (d) ($C_1$-$C_6$)-alkylthio; (e) cyano; (f) nitro; (g) —NR$_{29}$R$_{30}$; h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) =O; (q) —($C_2$-$C_6$)-alkynyl; (r) —COR$_{26}$; (s) —S(O)$_p$R$_{26}$; (t) —SO$_2$NHR$_{26}$; (u) —COOR$_{26}$; (v) —NHC(CN)NHR$_{26}$; (w) cycloalkyl, which may be optionally substituted with one or more $R_{21}$'s; (x) cycloalkylalkyl, which may be optionally substituted with one or more $R_{21}$'s; or (y) —CONR$_{26}$R$_{26}$;

$R_{21}$ is: (a) halo; (b) ($C_1$-$C_6$)-alkyl; (c) —OR$_{26}$; (d) ($C_1$-$C_6$)-alkylthio; (e) cyano; (f) nitro; (g) —NR$_{29}$R$_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —CONR$_{26}$R$_{26}$; (p) ($C_2$-$C_6$)-alkenyl; (q) =O; (r) ($C_2$-$C_6$)-alkynyl; (s) cycloalkyl; (t) cycloalkylalkyl; (u) —COR$_{26}$; (v) —S(O)$_p$R$_{26}$; (w) —SO$_2$NHR$_{26}$; (x) —COOR$_{26}$; or (y) —NHC(CN)NHR$_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —CONR$_{36}$R$_{36}$, 16) =O, 17) ($C_2$-$C_6$)-alkynyl, 18) —COR$_{36}$, 19) —S(O)$_p$R$_{36}$, 20) —SO$_2$NHR$_{36}$, 21) —COOR$_{36}$, and 22) —NHC(CN)NHR$_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —CONR$_{36}$R$_{36}$, 18) =O, 19) ($C_2$-$C_6$)-alkynyl, 20) —COR$_{36}$, 21) —S(O)$_p$R$_{36}$, 22) —SO$_2$NHR$_{36}$, 23) —COOR$_{36}$, and 24) —NHC(CN)NHR$_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8)

—$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$) alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$; or (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —$[(C=O)O_r]_s$aryl, —$[(C=O)O_r]_s$alkenyl, —$[(C=O)O_r]_s$alkyl, heterocyclyl, —$CONR_{36}R_{36}$, alkynyl, —$COR_{36}$, —$S(O)_pR_{36}$, —$SO_2NHR_{36}$, —$COOR_{36}$, or —$C(CN)NHR_{36}$, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and may be optionally substituted with one or more P4's;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, =O, alkynyl, cycloalkyl, cycloalkylalkyl, —$COR_{49}$, —$S(O)_pR_{49}$, —$SO_2NHR_{49}$, —$COOR_{49}$, or —$NHC(CN)NHR_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

In one embodiment, compounds of the present invention are provided wherein:

A is:

(a) heteroaryl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$) alkyl, 15) —$COR_6$, 16) =O, 17) —$S(O)_pR_6$, 18) —$SO_2NHR_6$, 19) —$COOR_6$, 20) —$NHC(CN)NHR_6$, and 21) —$CONR_6R_6$; or (b) phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$) alkyl, 15) —$COR_6$, 16) =O, 17) —$COOR_6$, 18) ($C_2$-$C_6$)-alkynyl, which may be optionally substituted with one or more $R_{20}$'s, 19) —$OCOR_6$, and 20) —$OCOOR_6$; or any two adjacent substituents may join together to form a 4- to 8-membered ring, which optionally may contain 1-4 heteroatoms selected from N, O, and S and be optionally substituted with one or more $R_{20}$'s;

B is:

(a) phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$) alkyl, 15) —$COR_6$, 16) —$S(O)_pR_6$, 17) —$SO_2NHR_6$, 18) —$COOR_6$, and 19) —$NHC(CN)NHR_6$; or (b) heteroaryl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) —$S(O)_pR_6$, 17) —$SO_2NHR_6$, 18) —$COOR_6$, and 19) —NHC(CN)$NHR_6$;

C is alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) —$S(O)_pR_6$, 15) —$SO_2NHR_6$, 16) —$COOR_6$, and 17) —NHC(CN)$NHR_6$;

$R_1$ is heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) —$SO_2NHR_6$, 19) —$COOR_6$, 20) —NHC(CN)$NHR_6$, 21) —$CONR_6R_6$, and 22) —$CONR_9NR_9R_{10}$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

or two $R_6$'s are taken together to form a 3- to 9-membered ring, which optionally may contain 1-4 heteroatoms selected from N, O, and S and may be optionally substituted with one or more $R_{20}$'s;

$R_9$ and $R_{10}$ are independently: (a) hydrogen; (b) —[(C=O)$O_r$]$_s$aryl, wherein the aryl may be optionally substituted with one or more $R_{20}$'s; (c) —[(C=O)$O_r$]$_s$($C_2$-$C_8$)-alkenyl, wherein the alkenyl may be optionally substituted with one or more $R_{20}$'s; (d) —[(C=O)$O_r$]$_s$($C_1$-$C_8$)-alkyl, wherein the alkyl may be optionally substituted with one or more $R_{20}$'s; (e) heterocyclyl optionally substituted with one or more $R_{20}$'s; (f) —CONR$_{26}$R$_{26}$; (g) —($C_2$-$C_6$)-alkynyl; (h) —COR$_{26}$; (i) —S(O)$_p$R$_{26}$; (j) —SO$_2$NHR$_{26}$; (k) —COOR$_{26}$; or (l) —NHC(CN)NHR$_{26}$;

or $R_9$ and $R_{10}$ are taken together with the nitrogen to which both are attached to form a 3- to 8-membered ring, which may optionally contain 1-4 heteroatoms selected from N, O, and S and may be optionally substituted with one or more $R_{20}$'s;

$R_{20}$ is: (a) halo; (b) ($C_1$-$C_6$)-alkyl, which may be optionally substituted with one or more $R_{21}$'s; (c) —OR$_{26}$; (d) ($C_1$-$C_6$)-alkylthio; (e) cyano; (f) nitro; (g) —NR$_{29}$R$_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) =O; (q) —($C_2$-$C_6$)-alkynyl; (r) —COR$_{26}$; (s) —S(O)$_p$R$_{26}$; (t) —SO$_2$NHR$_{26}$; (u) —COOR$_{26}$; (v) —NHC(CN)NHR$_{26}$; (w) cycloalkyl, which may be optionally substituted with one or more $R_{21}$'s; (x) cycloalkylalkyl, which may be optionally substituted with one or more $R_{21}$'s; or (y) —CONR$_{26}$R$_{26}$;

$R_{21}$ is: (a) halo; (b) ($C_1$-$C_6$)-alkyl; (c) —OR$_{26}$; (d) ($C_1$-$C_6$)-alkylthio; (e) cyano; (f) nitro; (g) —NR$_{29}$R$_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —CONR$_{26}$R$_{26}$; (p) ($C_2$-$C_6$)-alkenyl; (q) =O; (r) ($C_2$-$C_6$)-alkynyl; (s) cycloalkyl; (t) cycloalkylalkyl; (u) —COR$_{26}$; (v) —S(O)$_p$R$_{26}$; (w) —SO$_2$NHR$_{26}$; (x) —COOR$_{26}$; or (y) —NHC(CN)NHR$_{26}$;

$R_{26}$, at each occurrence, is independently:
- (a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —CONR$_{36}$R$_{36}$, 16) =O, 17) ($C_2$-$C_6$)-alkynyl, 18) —COR$_{36}$, 19) —S(O)$_p$R$_{36}$, 20) —SO$_2$NHR$_{36}$, 21) —COOR$_{36}$, and 22) —NHC(CN)NHR$_{36}$;
- (b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —CONR$_{36}$R$_{36}$, 18) =O, 19) ($C_2$-$C_6$)-alkynyl, 20) —COR$_{36}$, 21) —S(O)$_p$R$_{36}$, 22) —SO$_2$NHR$_{36}$, 23) —COOR$_{36}$, and 24) —NHC(CN)NHR$_{36}$;
- (c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;
- (d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;
- (e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$; or
- (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, $-[(C=O)O_r]_s$ aryl, $-[(C=O)O_r]_s$alkenyl, $-[(C=O)O_r]_s$alkyl, heterocyclyl, $-CONR_{36}R_{36}$, alkynyl, $-COR_{36}$, $-S(O)_p R_{36}$, $-SO_2NHR_{36}$, $-COOR_{36}$, or $-C(CN)NHR_{36}$, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and may be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, $-OH$, alkyl, alkyloxy, alkylthio, cyano, nitro, $-NR_{49}R_{50}$, aryl, arylalkyl, heteroaryl, heteroarylalkyl, heterocyclyl, heterocyclylalkyl, haloalkyl, haloalkyloxy, $-CONR_{49}R_{50}$, alkenyl, arylalkyloxy, $=O$, alkynyl, cycloalkyl, cycloalkylalkyl, $-COR_{49}$, $-S(O)_pR_{49}$, $-SO_2NHR_{49}$, $-COOR_{49}$, or $-NHC(CN)NHR_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

In another embodiment, compounds of the present invention are provided wherein:

A is:
(a) a nitrogen or oxygen containing heteroaryl, which is substituted with one or more substituents selected from the group consisting of: 1) halo, 2) $(C_1-C_6)$-alkyl, which may be optionally substituted with one or more $R_{20}$'s, 3) $-OR_6$, 4) $(C_1-C_6)$-alkylthio, 5) cyano, 6) nitro, 7) $-NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) $-COR_6$, and 16) $=O$; or
(b) phenyl, which is substituted with one or more substituents selected from the group consisting of: 1) halo, 2) $(C_1-C_6)$-alkyl, which may be optionally substituted with one or more $R_{20}$'s, 3) $-OR_6$, 4) $(C_1-C_6)$-alkylthio, 5) cyano, 6) nitro, 7) $-NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) $-COR_6$, 16) $=O$, 17) $(C_2-C_6)$-alkynyl, which may be optionally substituted with one or more $R_{20}$'s, and 18) $-OCOR_6$; or any two adjacent substituents may join together to form a 4- to 8-membered ring, which optionally may contain 1-4 heteroatoms selected from N, O, and S and be optionally substituted with one or more $R_{20}$'s;

B is:
(a) phenyl, which is substituted with one or more substituents selected from the group consisting of: 1) halo, 2) $(C_1-C_6)$-alkyl, which may be optionally substituted with one or more $R_{20}$'s, 3) $-OR_6$, 4) $(C_1-C_6)$-alkylthio, 5) cyano, 6) nitro, 7) $-NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo$(C_1-C_6)$alkyl; or
(b) a nitrogen containing heteroaryl, which is substituted with one or more substituents selected from the group consisting of: 1) halo, 2) $(C_1-C_6)$-alkyl, which may be optionally substituted with one or more $R_{20}$'s, 3) $-OR_6$, 4) $(C_1-C_6)$-alkylthio, 5) cyano, 6) nitro, 7) $-NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo$(C_1-C_6)$alkyl;

C is alkyl, which may be optionally substituted with one or more substituents selected from the group consisting of: 1) halo, 2) $-OR_6$, 3) $-NR_9R_{10}$, 4) aryl, which may be optionally substituted with one or more $R_{20}$'s, 5) heteroaryl, which may be optionally substituted with one or more $R_{20}$'s, 6) heterocyclyl, which may be optionally substituted with one or more $R_{20}$'s, 7) $-CONR_6R_6$, and 8) $-COOR_6$;

$R_1$ is a nitrogen, sulfur or oxygen containing heteroaryl, which may be optionally substituted with one or more substituents selected from the group consisting of: 1) halo, 2) $(C_1-C_6)$-alkyl, which may be optionally substituted with one or more $R_{20}$'s, 3) $-OR_6$, 4) $(C_1-C_6)$-alkylthio, 5) cyano, 6) nitro, 7) $-NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) $-COR_6$, 16) $=O$, 17) $-S(O)_pR_6$, 18) $-SO_2NHR_6$, 19) $-COOR_6$, 20) $-NHC(CN)NHR_6$, 21) $-CONR_6R_6$, and 22) $-CONR_9NR_9R_{10}$;

$R_6$, at each occurrence, is independently:
(a) alkyl, which may be optionally substituted with one or more substituents selected from the group consisting of: 1) halo, 2) $-OH$, 3) $(C_1-C_6)$-alkyl, which may be optionally substituted with one or more $R_{20}$'s, 4)

—$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —$NHC(CN)NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —$NHC(CN)NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$; or (f) hydrogen;

$R_9$ and $R_{10}$ are independently: (a) hydrogen; (b) —$[(C=O)O_r]_s$aryl, wherein the aryl may be optionally substituted with one or more $R_{20}$'s; (c) —$[(C=O)O_r]_s(C_1$-$C_8)$-alkyl, wherein the alkyl may be optionally substituted with one or more $R_{20}$'s; or (d) heterocyclyl optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) =O; (q) —($C_2$-$C_6$)-alkynyl; (r) —$COR_{26}$; (s) —$S(O)_pR_{26}$; (t) —$SO_2NHR_{26}$; (u) —$COOR_{26}$; (v) —$NHC(CN)NHR_{26}$; (w) cycloalkyl, which may be optionally substituted with one or more $R_{21}$'s; (x) cycloalkylalkyl, which may be optionally substituted with one or more $R_{21}$'s; or (y) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) =O; (r) ($C_2$-$C_6$)-alkynyl; (s) cycloalkyl; (t) cycloalkylalkyl; (u) —$COR_{26}$; (v) —$S(O)_pR_{26}$; (w) —$SO_2NHR_{26}$; (x) —$COOR_{26}$; or (y) —$NHC(CN)NHR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —CONR$_{36}$R$_{36}$, 16) =O, 17) ($C_2$-$C_6$)-alkynyl, 18) —COR$_{36}$, 19) —S(O)$_p$R$_{36}$, 20) —SO$_2$NHR$_{36}$, 21) —COOR$_{36}$, and 22) —NHC(CN)NHR$_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —CONR$_{36}$R$_{36}$, 18) =O, 19) ($C_2$-$C_6$)-alkynyl, 20) —COR$_{36}$, 21) —S(O)$_p$R$_{36}$, 22) —SO$_2$NHR$_{36}$, 23) —COOR$_{36}$, and 24) —NHC(CN)NHR$_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$) alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$; or (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —[(C=O)O$_r$]$_s$aryl, —[(C=O)O$_r$]$_s$alkenyl, —[(C=O)O$_r$]$_s$alkyl, heterocyclyl, —CONR$_{36}$R$_{36}$, alkynyl, —COR$_{36}$, —S(O)$_p$R$_{36}$, —SO$_2$NHR$_{36}$, —COOR$_{36}$, or —C(CN)NHR$_{36}$, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and may be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —NR$_{49}$R$_{50}$, aryl, arylalkyl, heteroaryl, heteroarylalkyl, heterocyclyl, heterocyclylalkyl, haloalkyl, haloalkyloxy, —CONR$_{49}$R$_{50}$, alkenyl, arylalkyloxy, =O, alkynyl, cycloalkyl, cycloalkylalkyl, —COR$_{49}$, —S(O)$_p$R$_{49}$, —SO$_2$NHR$_{49}$, —COOR$_{49}$, or —NHC(CN)NHR$_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

In yet another embodiment, compounds of the present invention are provided wherein:

A is:

(a) a 5- to 10-membered nitrogen or oxygen containing heteroaryl, which is substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$) alkyl, 15) —COR$_6$, and 16) =O; or (b) phenyl, which is substituted with one or more substituents selected from the group consisting of: 1) halo, 2) $(C_1-C_6)$-alkyl, which may be optionally substituted with one or more $R_{20}$'s, 3) —$OR_6$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) —$COR_6$, 16) =O, 17) $(C_2-C_6)$-alkynyl, which may be optionally substituted with one or more $R_{20}$'s, and 18) —$OCOR_6$; or any two adjacent substituents may join together to form a 4- to 8-membered ring, which optionally may contain 1-4 heteroatoms selected from N, O, and S and be optionally substituted with one or more $R_{20}$'s;

B is:
  (a) phenyl, which is substituted with one or more substituents selected from the group consisting of: 1) halo, 2) $(C_1-C_6)$-alkyl, which may be optionally substituted with one or more $R_{20}$'s, 3) —$OR_6$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo$(C_1-C_6)$alkyl; or
  (b) a 6- to 10-membered nitrogen containing heteroaryl, which is substituted with one or more substituents selected from the group consisting of: 1) halo, 2) $(C_1-C_6)$-alkyl, which may be optionally substituted with one or more $R_{20}$'s, 3) —$OR_6$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo$(C_1-C_6)$alkyl;

C is alkyl, which may be optionally substituted with one or more substituents selected from the group consisting of: 1) halo, 2) —$OR_6$, 3) —$NR_9R_{10}$, 4) aryl, which may be optionally substituted with one or more $R_{20}$'s, 5) a nitrogen containing heteroaryl, which may be optionally substituted with one or more $R_{20}$'s, 6) —$CONR_6R_6$, and 7) —$COOR_6$;

$R_1$ is a 5- to 14-membered nitrogen, sulfur or oxygen containing heteroaryl, which may be optionally substituted with one or more substituents selected from the group consisting of: 1) halo, 2) $(C_1-C_6)$-alkyl, which may be optionally substituted with one or more $R_{20}$'s, 3) —$OR_6$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) —$COR_6$, 16) =O, 17) —$S(O)_pR_6$, 18) —$SO_2NHR_6$, 19) —$COOR_6$, 20) —$NHC(CN)NHR_6$, 21) —$CONR_6R_6$, and 22) —$CONR_9NR_9R_{10}$;

$R_6$, at each occurrence, is independently:
  (a) alkyl, which may be optionally substituted with one or more substituents selected from the group consisting of: 1) halo, 2) —OH, 3) $(C_1-C_6)$-alkyl, which may be optionally substituted with one or more $R_{20}$'s, 4) —$OR_{36}$, 5) $(C_1-C_6)$-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo$(C_1-C_6)$alkyl, 13) $(C_2-C_6)$-alkenyl, 14) —COOH, 15) —$CONR_{36}R_{36}$, 16) =O, 17) $(C_2-C_6)$-alkynyl, 18) —$COR_{36}$, 19) —$S(O)_pR_{36}$, 20) —$SO_2NHR_{36}$, 21) —$COOR_{36}$, and 22) —$NHC(CN)NHR_{36}$;
  (b) aryl, which may be optionally substituted with one or more substituents selected from the group consisting of: 1) halo, 2) —OH, 3) $(C_1-C_6)$-alkyl, which may be optionally substituted with one or more $R_{20}$'s, 4) —$OR_{36}$, 5) $(C_1-C_6)$-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo$(C_1-C_6)$alkyl, 16) —COOH, 17) —$CONR_{36}R_{36}$, 18) =O, 19) $(C_2-C_6)$-alkynyl, 20) —$COR_{36}$, 21) —$S(O)_pR_{36}$, 22) —$SO_2NHR_{36}$, 23) —$COOR_{36}$, and 24) —$NHC(CN)NHR_{36}$;
  (c) cycloalkyl, which may be optionally substituted with one or more substituents selected from the group consisting of: 1) halo, 2) —OH, 3) $(C_1-C_6)$-alkyl, which may be optionally substituted with one or more $R_{20}$'s, 4) —$OR_{36}$, 5) $(C_1-C_6)$-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo$(C_1-C_6)$alkyl, 16) $(C_2-C_6)$-alkenyl, 17) —COOH, 18) —$CONR_{36}R_{36}$, 19) =O, 20) $(C_2-C_6)$-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;
  (d) heteroaryl, which may be optionally substituted with one or more substituents selected from the group consisting of: 1) halo, 2) —OH, 3) $(C_1-C_6)$-alkyl, which may be optionally substituted with one or more $R_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) arylalkyl, which may be optionally substituted with one or more R$_{20}$'s, 11) heteroaryl, which may be optionally substituted with one or more R$_{20}$'s, 12) heteroarylalkyl, which may be optionally substituted with one or more R$_{20}$'s, 13) heterocyclyl, which may be optionally substituted with one or more R$_{20}$'s, 14) heterocyclylalkyl, which may be optionally substituted with one or more R$_{20}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(e) heterocyclyl, other than heteroaryl, which may be optionally substituted with one or more substituents selected from the group consisting of: 1) halo, 2) —OH, 3) (C$_1$-C$_6$)-alkyl, which may be optionally substituted with one or more R$_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) arylalkyl, which may be optionally substituted with one or more R$_{20}$'s, 11) heteroaryl, which may be optionally substituted with one or more R$_{20}$'s, 12) heteroarylalkyl, which may be optionally substituted with one or more R$_{20}$'s, 13) heterocyclyl, which may be optionally substituted with one or more R$_{20}$'s, 14) heterocyclylalkyl, which may be optionally substituted with one or more R$_{20}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$; or (f) hydrogen;

or two R$_6$'s are taken together to form a 3- to 9-membered ring, which optionally may contain 1-4 heteroatoms selected from N, O, and S and may be optionally substituted with one or more R$_{20}$'s;

R$_9$ and R$_{10}$ are independently: (a) hydrogen; (b) —[(C=O)O$_r$]$_s$aryl, wherein the aryl may be optionally substituted with one or more R$_{20}$'s; or (c) —[(C=O)O$_r$]$_s$(C$_1$-C$_8$)-alkyl, wherein the alkyl may be optionally substituted with one or more R$_{20}$'s;

or R$_9$ and R$_{10}$ are taken together with the nitrogen to which both are attached to form a 3- to 8-membered ring, which may optionally contain 1-4 heteroatoms selected from N, O, and S and be optionally substituted with one or more R$_{20}$'s;

R$_{20}$ is: (a) halo; (b) (C$_1$-C$_6$)-alkyl, which may be optionally substituted with one or more R$_{21}$'s; (c) —OR$_{26}$; (d) (C$_1$-C$_6$)-alkylthio; (e) cyano; (f) nitro; (g) —NR$_{29}$R$_{30}$; (h) aryl, which may be optionally substituted with one or more R$_{21}$'s; (i) arylalkyl, which may be optionally substituted with one or more R$_{21}$'s; (j) heteroaryl, which may be optionally substituted with one or more R$_{21}$'s; (k) heteroarylalkyl, which may be optionally substituted with one or more R$_{21}$'s; (l) heterocyclyl, which may be optionally substituted with one or more R$_{21}$'s; (m) heterocyclylalkyl, which may be optionally substituted with one or more R$_{21}$'s; (n) halo(C$_1$-C$_6$)alkyl; (o) (C$_2$-C$_6$)-alkenyl; (p) =O; (q) —(C$_2$-C$_6$)-alkynyl; (r) —COR$_{26}$; (s) —S(O)$_p$R$_{26}$; (t) —SO$_2$NHR$_{26}$; (u) —COOR$_{26}$; (v) —NHC(CN)NHR$_{26}$; (w) cycloalkyl, which may be optionally substituted with one or more R$_{21}$'s; (x) cycloalkylalkyl, which may be optionally substituted with one or more R$_{21}$'s; or (y) —CONR$_{26}$R$_{26}$;

R$_{21}$ is: (a) halo; (b) (C$_1$-C$_6$)-alkyl; (c) —OR$_{26}$; (d) (C$_1$-C$_6$)-alkylthio; (e) cyano; (f) nitro; (g) —NR$_{29}$R$_{30}$; (h) aryl; (i) arylalkyl; (j) heteroaryl; (k) heteroarylalkyl; (l) heterocyclyl; (m) heterocyclylalkyl; (n) halo(C$_1$-C$_6$)alkyl; (o) —CONR$_{26}$R$_{26}$; (p) (C$_2$-C$_6$)-alkenyl; (q) =O; (r) (C$_2$-C$_6$)-alkynyl; (s) cycloalkyl; (t) cycloalkylalkyl; (u) —COR$_{26}$; (v) —S(O)$_p$R$_{26}$; (w) —SO$_2$NHR$_{26}$; (x) —COOR$_{26}$; or (y) —NHC(CN)NHR$_{26}$;

R$_{26}$, at each occurrence, is independently:

(a) alkyl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) heteroaryl, which may be optionally substituted with one or more R$_{40}$'s, 11) heterocyclyl, which may be optionally substituted with one or more R$_{40}$'s, 12) halo(C$_1$-C$_6$)alkyl, 13) (C$_2$-C$_6$)-alkenyl, 14) —COOH, 15) —CONR$_{36}$R$_{36}$, 16) =O, 17) (C$_2$-C$_6$)-alkynyl, 18) —COR$_{36}$, 19) —S(O)$_p$R$_{36}$, 20) —SO$_2$NHR$_{36}$, 21) —COOR$_{36}$, and 22) —NHC(CN)NHR$_{36}$;

(b) aryl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) arylalkyl, which may be optionally substituted with one or more R$_{40}$'s, 11) heteroaryl, which may be optionally substituted with one or more R$_{40}$'s, 12) heteroarylalkyl, which may be optionally substituted with one or more R$_{40}$'s, 13) heterocyclyl, which may be optionally substituted with one or more R$_{40}$'s, 14) heterocyclylalkyl, which may be optionally substituted with one or more R$_{40}$'s, 15) halo(C$_1$-C$_6$)alkyl, 16) —COOH, 17) —CONR$_{36}$R$_{36}$, 18) =O, 19) (C$_2$-C$_6$)-alkynyl, 20) —COR$_{36}$, 21) —S(O)$_p$R$_{36}$, 22) —SO$_2$NHR$_{36}$, 23) —COOR$_{36}$, and 24) —NHC(CN)NHR$_{36}$;

(c) cycloalkyl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) arylalkyl, which may be optionally substituted with one or more R$_{40}$'s, 11) heteroaryl, which may be optionally substituted with one or more R$_{40}$'s, 12) heteroarylalkyl, which may be optionally substituted with one or more R$_{40}$'s, 13) heterocyclyl, which may be optionally substituted with one or more R$_{40}$'s, 14) heterocyclylalkyl, which may be optionally substituted with one or more R$_{40}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(d) heteroaryl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8)

—$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$) alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —$[(C=O)O_r]_s$aryl, —$[(C=O)O_r]_s$alkenyl, —$[(C=O)O_r]_s$alkyl, heterocyclyl, —$CONR_{36}R_{36}$, alkynyl, —$COR_{36}$, —$S(O)_pR_{36}$, —$SO_2NHR_{36}$, —$COOR_{36}$, or —C(CN)$NHR_{36}$, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and may be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, =O, alkynyl, cycloalkyl, cycloalkylalkyl, —$COR_{49}$, —$S(O)_pR_{49}$, —$SO_2NHR_{49}$, —$COOR_{49}$, or —NHC(CN)$NHR_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

In still yet another embodiment, compounds of the present invention are provided wherein:

A is:

(a) a 6-membered nitrogen containing heteroaryl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, and 16) =O; or (b) phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$) alkyl, 15) —$COR_6$, 16) =O, and 17) —$OCOR_6$; or any two adjacent substituents may join together to form a 4- to 8-membered ring, which optionally may contain 1-4 heteroatoms selected from N, O, and S and be optionally substituted with one or more $R_{20}$'s;

B is:

(a) phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl; or (b) a 6-membered nitrogen containing heteroaryl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl;

C is alkyl, which may be optionally substituted with one or more substituents selected from the group consisting of: 1) halo, 2) phenyl, which may be optionally substituted with one or more $R_{20}$'s, or 3) a 5- or 6-membered nitrogen containing heteroaryl, which may be optionally substituted with one or more $R_{20}$'s;

$R_1$ is a 5- to 14-membered nitrogen or sulfur containing heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —S(O)$_p$$R_6$, 18) —$SO_2NHR_6$, 19) —$COOR_6$, 20) —NHC(CN)NHR$_6$, 21) —$CONR_6R_6$, and 22) —$CONR_9NR_9R_{10}$;

$R_6$, at each occurrence, is independently:
(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —S(O)$_p$$R_{36}$, 20) —$SO_2NHR_{36}$, 21) —$COOR_{36}$, and 22) —NHC(CN)NHR$_{36}$;
(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —S(O)$_p$$R_{36}$, 22) —$SO_2NHR_{36}$, 23) —$COOR_{36}$, and 24) —NHC(CN)NHR$_{36}$;
(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —S(O)$_p$$R_{36}$, 23) —$SO_2NHR_{36}$, 24) —$COOR_{36}$, and 25) —NHC(CN)NHR$_{36}$;
(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —S(O)$_p$$R_{36}$, 23) —$SO_2NHR_{36}$, 24) —$COOR_{36}$, and 25) —NHC(CN)NHR$_{36}$;
(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —S(O)$_p$$R_{36}$, 23) —$SO_2NHR_{36}$, 24) —$COOR_{36}$, and 25) —NHC(CN)NHR$_{36}$; or
(f) hydrogen;

$R_9$ and $R_{10}$ are independently: (a) hydrogen; or (b) —[(C=O)O$_r$]$_s$($C_1$-$C_8$)-alkyl, wherein the alkyl may be optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) =O; (q) —($C_2$-$C_6$)-alkynyl; (r) —$COR_{26}$; (s) —$S(O)_p R_{26}$; (t) —$SO_2 NHR_{26}$; (u) —$COOR_{26}$; (v) —$NHC(CN)NHR_{26}$; (w) cycloalkyl, which may be optionally substituted with one or more $R_{21}$'s; (x) cycloalkylalkyl, which may be optionally substituted with one or more $R_{21}$'s; or (y) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) =O; (r) ($C_2$-$C_6$)-alkynyl; (s) cycloalkyl; (t) cycloalkylalkyl; (u) —$COR_{26}$; (v) —$S(O)_p R_{26}$; (w) —$SO_2 NHR_{26}$; (x) —$COOR_{26}$; or (y) —$NHC(CN)NHR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_p R_{36}$, 20) —$SO_2 NHR_{36}$, 21) —$COOR_{36}$, and 22) —$NHC(CN)NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_p R_{36}$, 22) —$SO_2 NHR_{36}$, 23) —$COOR_{36}$, and 24) —$NHC(CN)NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_p R_{36}$, 23) —$SO_2 NHR_{36}$, 24) —$COOR_{36}$, and 25) —$NHC(CN)NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_p R_{36}$, 23) —$SO_2 NHR_{36}$, 24) —$COOR_{36}$, and 25) —$NHC(CN)NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_p R_{36}$, 23) —$SO_2 NHR_{36}$, 24) —$COOR_{36}$, and 25) —$NHC(CN)NHR_{36}$; or (f) hydrogen;

$R_{29}$ and $R_{30}$ are independently hydrogen, —$[(C=O)O_r]_s$aryl, —$[(C=O)O_r]_s$alkenyl, —$[(C=O)O_r]_s$alkyl, heterocyclyl, —$CONR_{36}R_{36}$, alkynyl, —$COR_{36}$, —$S(O)_p R_{36}$, —$SO_2 NHR_{36}$, —$COOR_{36}$, or —$C(CN)NHR_{36}$, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and may be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, =O, alkynyl, cycloalkyl, cycloalkylalkyl, —$COR_{49}$, —$S(O)_p R_{49}$, —$SO_2 NHR_{49}$, —$COOR_{49}$, or —$NHC(CN)NHR_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

In one embodiment, compounds of the present invention are provided wherein:

A is:
- (a) pyridyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, and 16) =O;
- (b) phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, and 15) —$COR_6$;

B is phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl;

C is alkyl, which may be optionally substituted with one or more substituents selected from the group consisting of: 1) phenyl, which may be optionally substituted with one or more $R_{20}$'s, or 2) a 5- or 6-membered nitrogen containing heteroaryl, which may be optionally substituted with one or more $R_{20}$'s;

$R_1$ is a 5- to 14-membered nitrogen containing heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$COOR_6$, 18) —$CONR_6R_6$, and 19) —$CONR_9NR_9R_{10}$;

$R_6$, at each occurrence, is independently:
- (a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)NHR$_{36}$;
- (b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)NHR$_{36}$;
- (c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)NHR$_{36}$;
- (d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$) alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$; or (f) hydrogen;

$R_9$ and $R_{10}$ are independently: (a) hydrogen; or (b) —[(C=O)O$_r$]$_s$($C_1$-$C_8$)-alkyl, wherein the alkyl may be optionally substituted with one or more $R_{20}$'s;

$R_{20}$ is: (a) halo; (b) ($C_1$-$C_6$)-alkyl, which may be optionally substituted with one or more $R_{21}$'s; (c) —OR$_{26}$; (d) ($C_1$-$C_6$)-alkylthio; (e) cyano; (f) nitro; (g) —NR$_{29}$R$_{30}$, h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) —($C_2$-$C_6$)-alkynyl; (q) —COR$_{26}$; (r) —COOR$_{26}$; (s) cycloalkyl, which may be optionally substituted with one or more $R_{21}$'s; (t) cycloalkylalkyl, which may be optionally substituted with one or more $R_{21}$'s; or (u) —CONR$_{26}$R$_{26}$;

$R_{21}$ is: (a) halo; (b) ($C_1$-$C_6$)-alkyl; (c) —OR$_{26}$; (d) ($C_1$-$C_6$)-alkylthio; (e) cyano; (f) nitro; (g) —NR$_{29}$R$_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —CONR$_{26}$R$_{26}$; (p) ($C_2$-$C_6$)-alkenyl; (q) ($C_2$-$C_6$)-alkynyl; (r) cycloalkyl; (s) cycloalkylalkyl; (t) —COR$_{26}$; or (u) —COOR$_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —CONR$_{36}$R$_{36}$, 16) =O, 17) ($C_2$-$C_6$)-alkynyl, 18) —COR$_{36}$, 19) —S(O)$_p$R$_{36}$, 20) —SO$_2$NHR$_{36}$, 21) —COOR$_{36}$, and 22) —NHC(CN)NHR$_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —CONR$_{36}$R$_{36}$, 18) =O, 19) ($C_2$-$C_6$)-alkynyl, 20) —COR$_{36}$, 21) —S(O)$_p$R$_{36}$, 22) —SO$_2$NHR$_{36}$, 23) —COOR$_{36}$, and 24) —NHC(CN)NHR$_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$; or (f) hydrogen;

$R_{29}$ and $R_{30}$ are independently hydrogen or —[(C=O)O$_r$]$_s$ alkyl, wherein the alkyl may be optionally substituted with one or more $R_{40}$'s;

$R_{36}$, at each occurrence, is independently alkyl, aryl, heteroaryl or heterocyclyl, other than heteroaryl, wherein the alkyl, aryl, heteroaryl or heterocyclyl may be optionally substituted with one or more $R_{40}$'s;

$R_{40}$ is halo, —OH, alkyl, alkyloxy, alkylthio, cyano, nitro, aryl, arylalkyl, heteroaryl, heteroarylalkyl, heterocyclyl, heterocyclylalkyl, haloalkyl, haloalkyloxy, alkenyl, arylalkyloxy, =O, alkynyl, cycloalkyl or cycloalkylalkyl;

r is 0 to 2;

s is 0 to 1; and p is 1 or 2.

In another embodiment, compounds of the present invention are provided wherein:

A is:

(a) pyridyl, which is substituted with one or more substituents selected from the group consisting of: 1) halo, 2) ($C_1$-$C_6$)-alkyl, 3) —OR$_6$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo($C_1$-$C_6$)alkyl, and 14) —COR$_6$;

(b) phenyl, which is substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, and 15) —COR$_6$;

B is phenyl, which is substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl;

C is methylphenyl, which may be optionally substituted with one or more $R_{20}$'s;

$R_1$ is a 5- to 14-membered nitrogen containing heteroaryl, which may be optionally substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —COR$_6$, 16) =O, 17) —COOR$_6$, 18) —CONR$_6$R$_6$, and 19) —CONR$_9$NR$_9$R$_{10}$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, 4) —OR$_{36}$, 5) ($C_1$-$C_6$)-alkylthio, 6) cyano, 7) nitro, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) ($C_2$-$C_6$)-alkenyl, 13) —COOH, 14) ($C_2$-$C_6$)-alkynyl, 15) —COR$_{36}$ and 16) —COOR$_{36}$; or (b) hydrogen;

$R_9$ and $R_{10}$ are independently: (a) hydrogen; or (b) —[(C=O)O$_r$]$_s$($C_1$-$C_8$)-alkyl, wherein the alkyl may be optionally substituted with one or more $R_{20}$'s;

$R_{20}$ is: (a) halo; (b) ($C_1$-$C_6$)-alkyl; (c) —OR$_{26}$; (d) ($C_1$-$C_6$)-alkylthio; (e) cyano; (f) nitro; (g) aryl, which may be optionally substituted with one or more $R_{21}$'s; (h) arylalkyl, which may be optionally substituted with one or more $R_{21}$'s; (i) heteroaryl, which may be optionally substituted with one or more $R_{21}$'s; (j) heteroarylalkyl, which may be optionally substituted with one or more $R_{21}$'s; (k) heterocyclyl, which may be optionally substituted with one or more $R_{21}$'s; (l) heterocyclylalkyl, which may be optionally substituted with one or more $R_{21}$'s; (m) halo($C_1$-$C_6$)alkyl; (n) ($C_2$-$C_6$)-alkenyl; (o) —($C_2$-$C_6$)-alkynyl; (p) —COR$_{26}$; (q) —COOR$_{26}$; (r) cycloalkyl, which may be optionally substituted with one or more $R_{21}$'s; or (s) cycloalkylalkyl, which may be optionally substituted with one or more $R_{21}$'s;

$R_{21}$ is: (a) halo; (b) ($C_1$-$C_6$)-alkyl; (c) —OR$_{26}$; (d) ($C_1$-$C_6$)-alkylthio; (e) cyano; (f) nitro; (g) aryl; (h) arylalkyl; (i) heteroaryl; (j) heteroarylalkyl; (k) heterocyclyl; (l) heterocyclylalkyl; (m) halo($C_1$-$C_6$)alkyl; (n) ($C_2$-$C_6$)-alkenyl; (o) ($C_2$-$C_6$)-alkynyl; (p) cycloalkyl; (q) cycloalkylalkyl; (r) —COR$_{26}$; or (s) —COOR$_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, 4) —OR$_{36}$, 5) ($C_1$-$C_6$)-alkylthio, 6) cyano, 7) nitro, 8) aryl, which may be optionally substituted with one or more $R_{40}$'s, 9) heteroaryl, which may be optionally substituted with one or more $R_{40}$'s, 10) heterocyclyl, which may be optionally substituted with one or more $R_{40}$'s, 11) halo($C_1$-$C_6$)alkyl, 12) ($C_2$-$C_6$)-alkenyl, 13) —COOH, 14) ($C_2$-$C_6$)-alkynyl, 15) —$COR_{36}$, or 16) —$COOR_{36}$; or (b) hydrogen;

$R_{36}$, at each occurrence, is independently alkyl, aryl or heteroaryl, wherein the alkyl, aryl or heteroaryl may be optionally substituted with one or more $R_{40}$'s; and $R_{40}$ is halo, —OH, alkyl, alkyloxy, alkylthio, cyano, nitro, aryl, arylalkyl, heteroaryl, heteroarylalkyl, heterocyclyl, heterocyclylalkyl, haloalkyl, haloalkyloxy, alkenyl, arylalkyloxy, alkynyl, cycloalkyl or cycloalkylalkyl.

In yet another embodiment, compounds of the present invention are provided wherein:

A is:

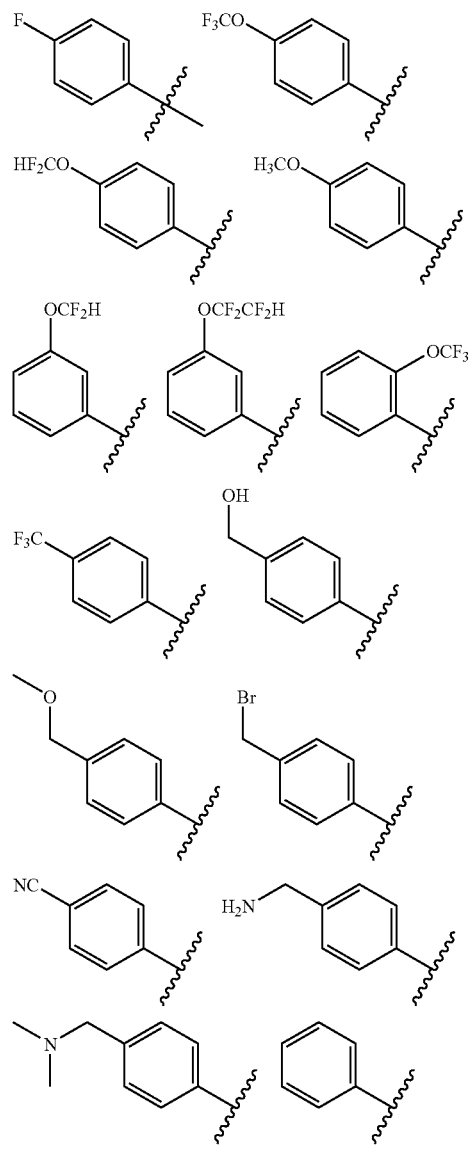

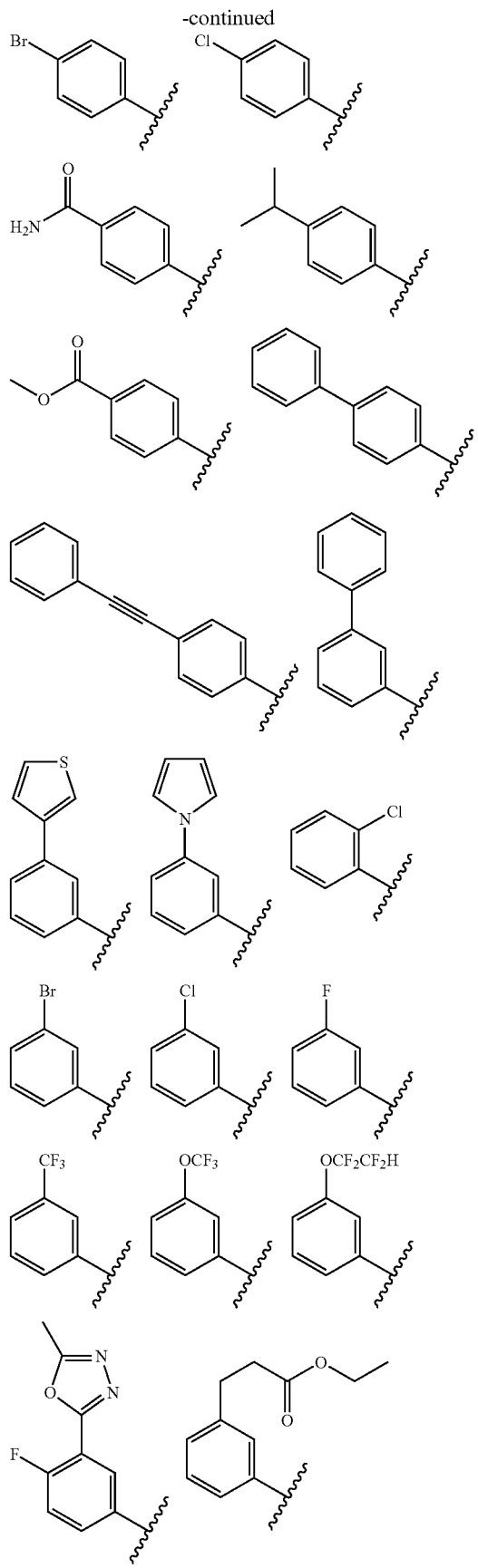

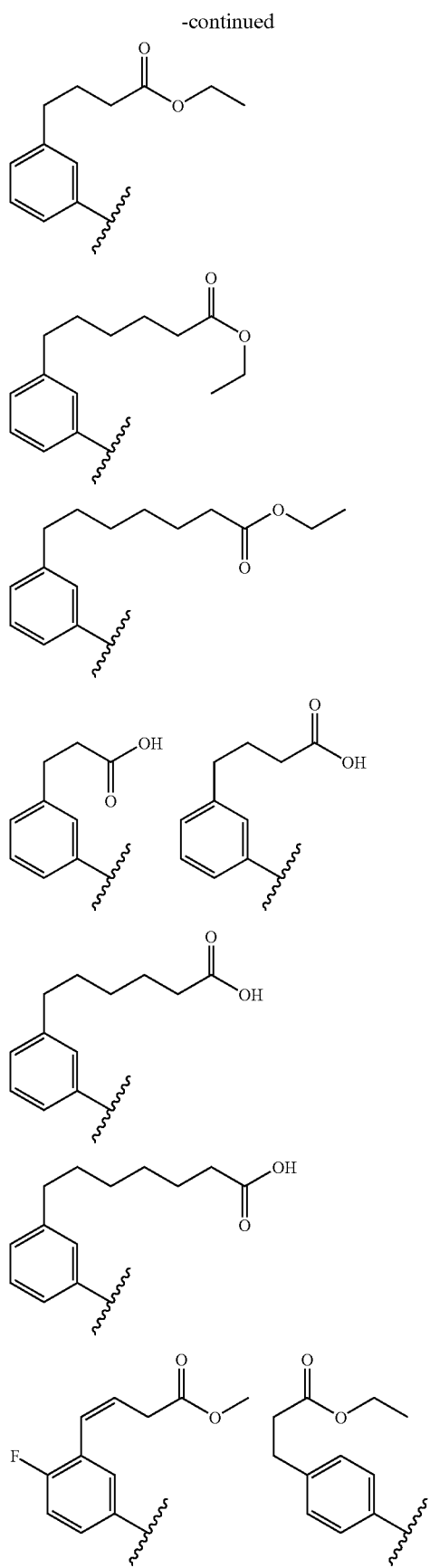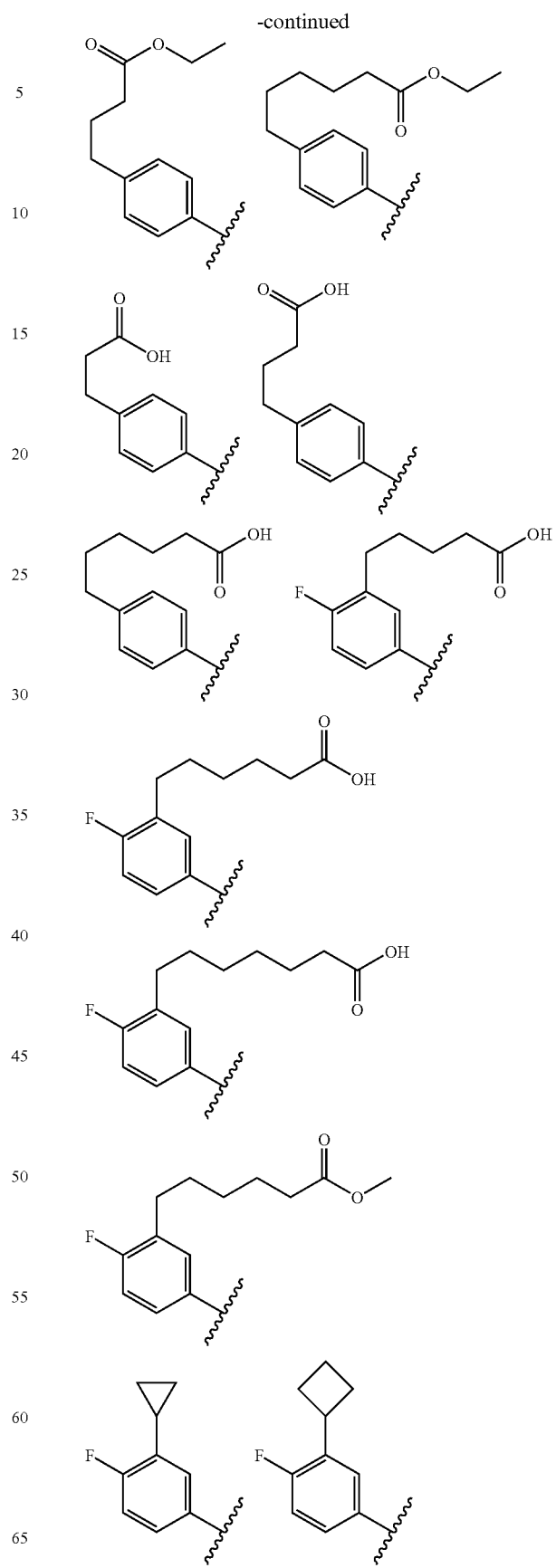

-continued
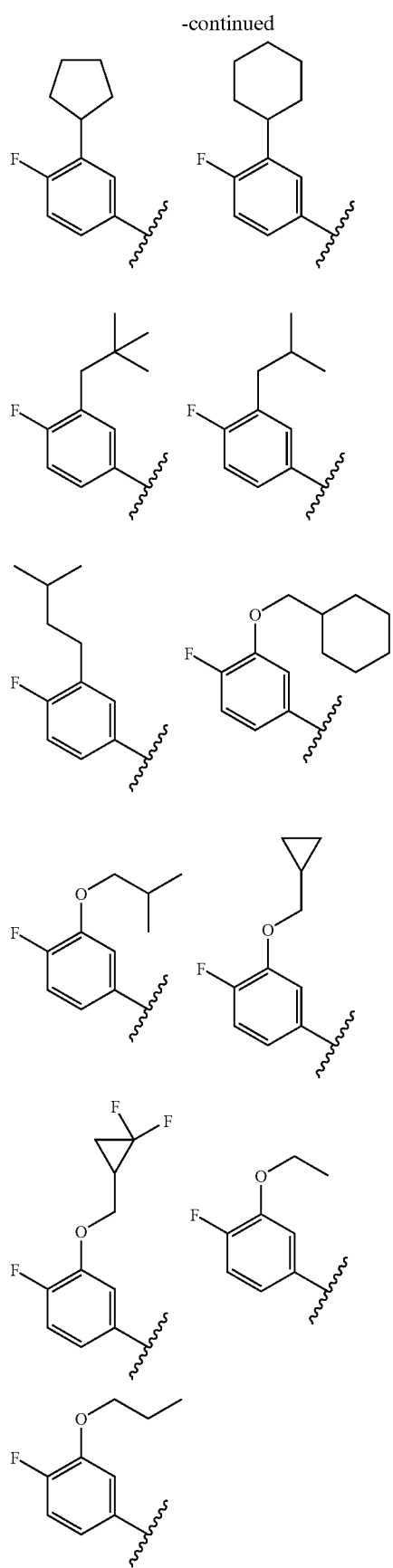
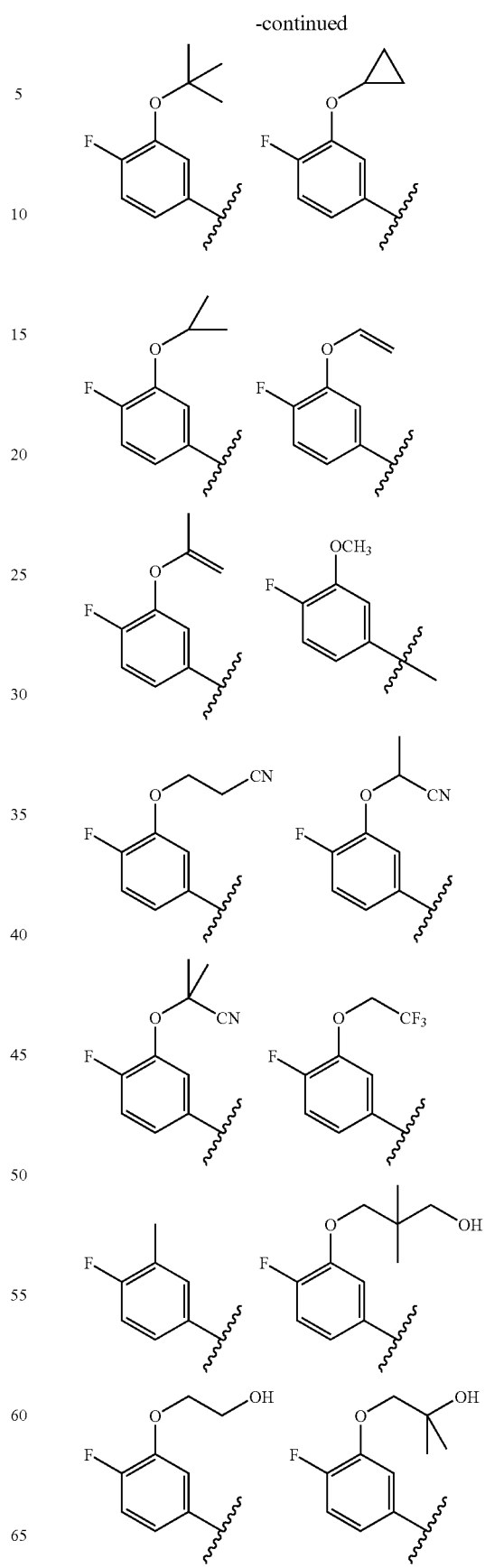

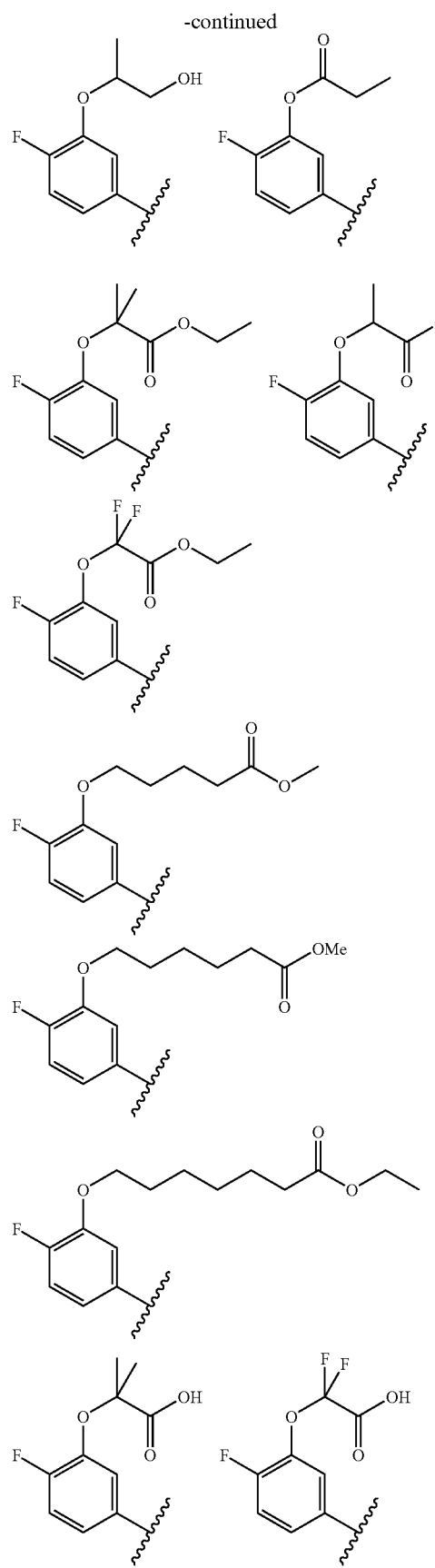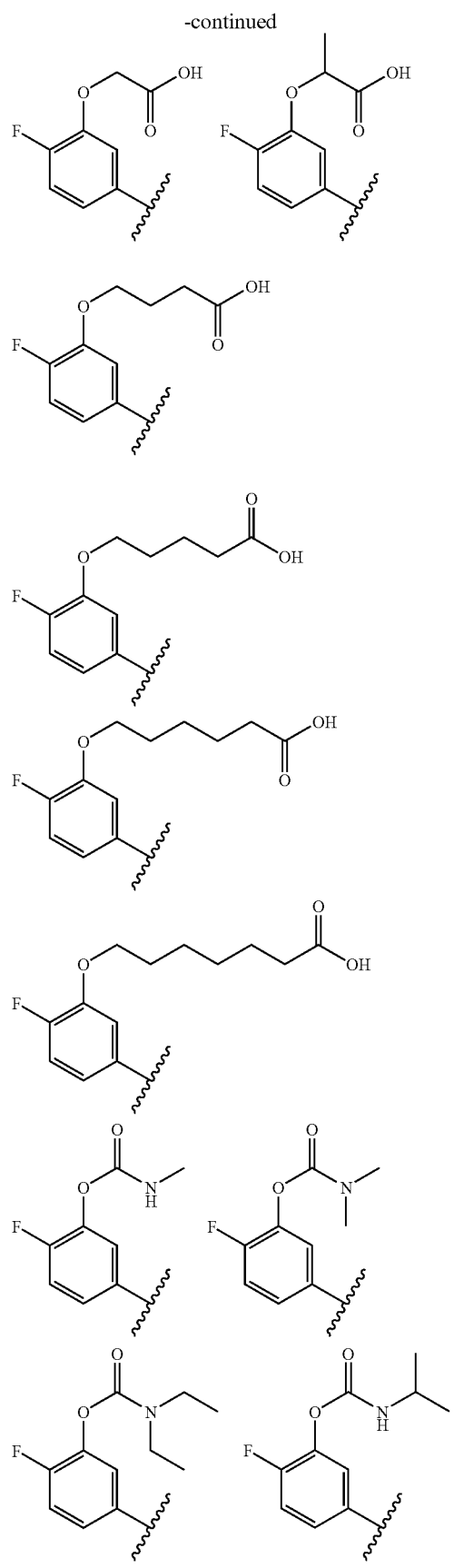

-continued
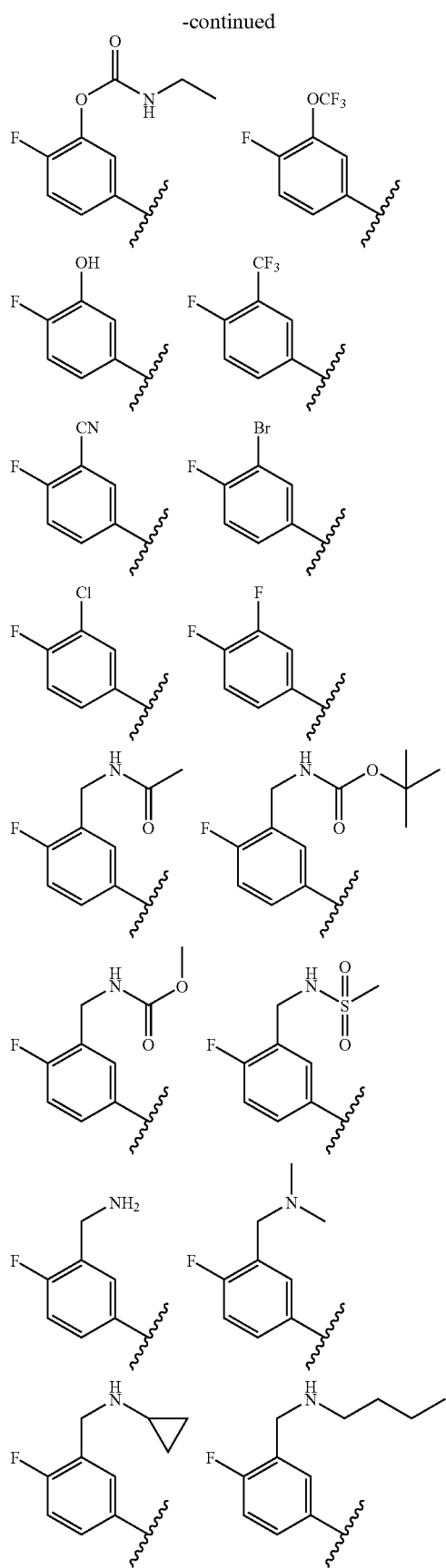
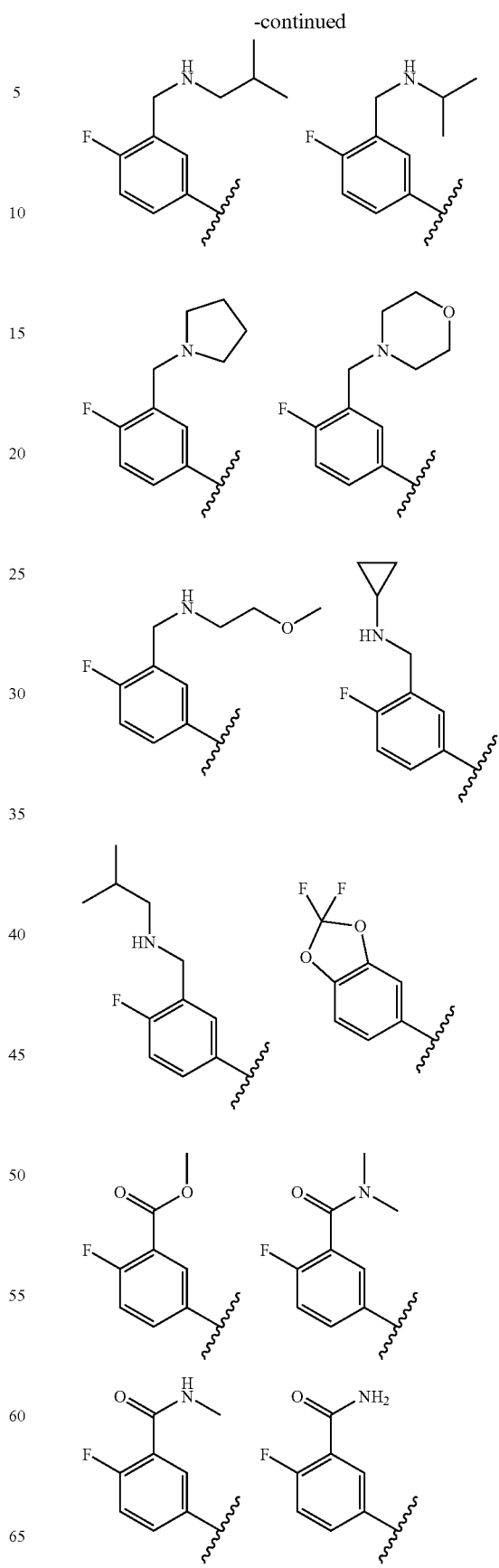

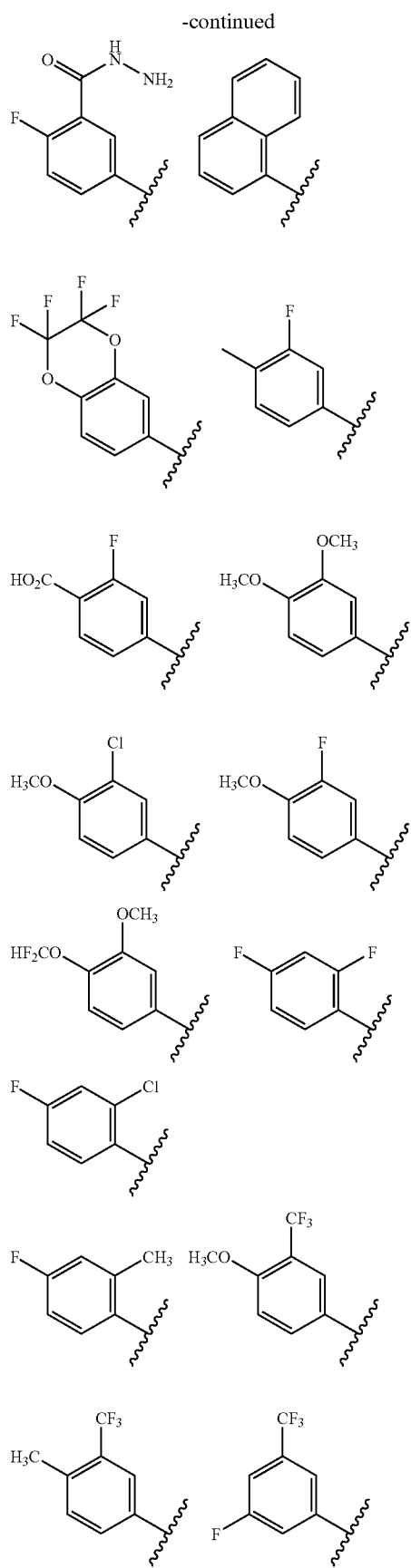
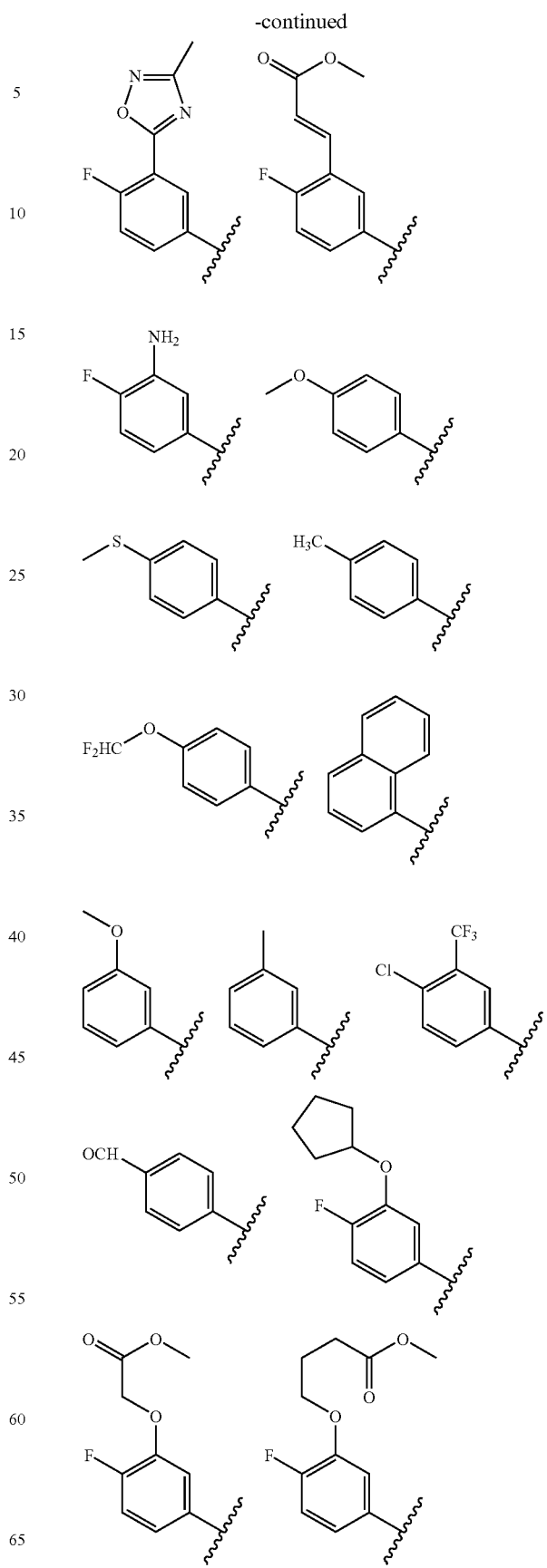

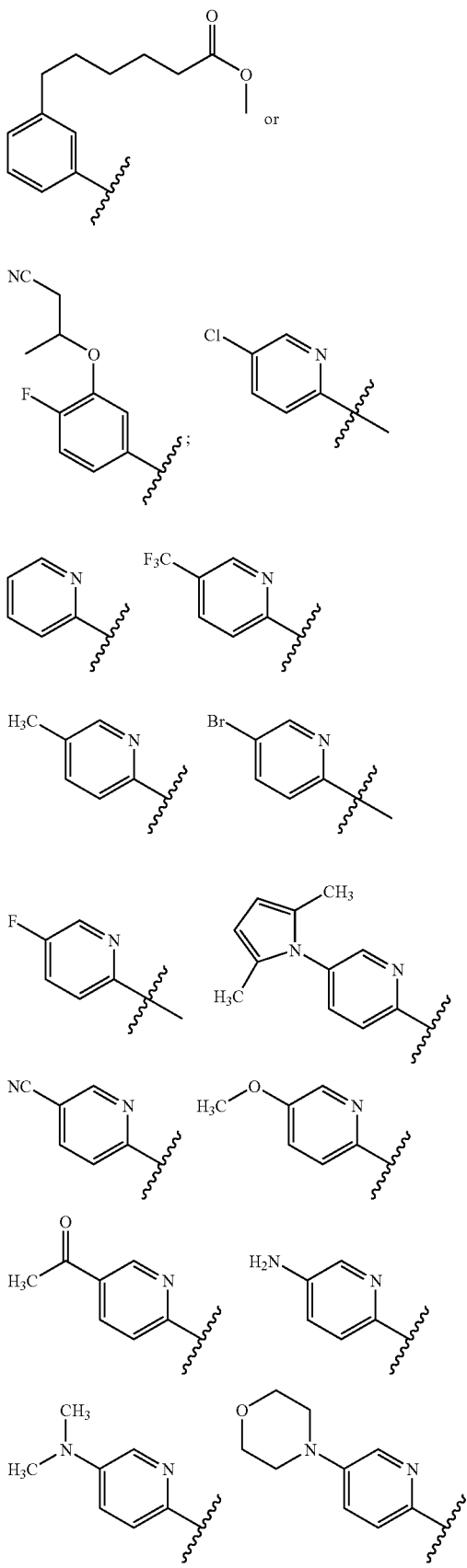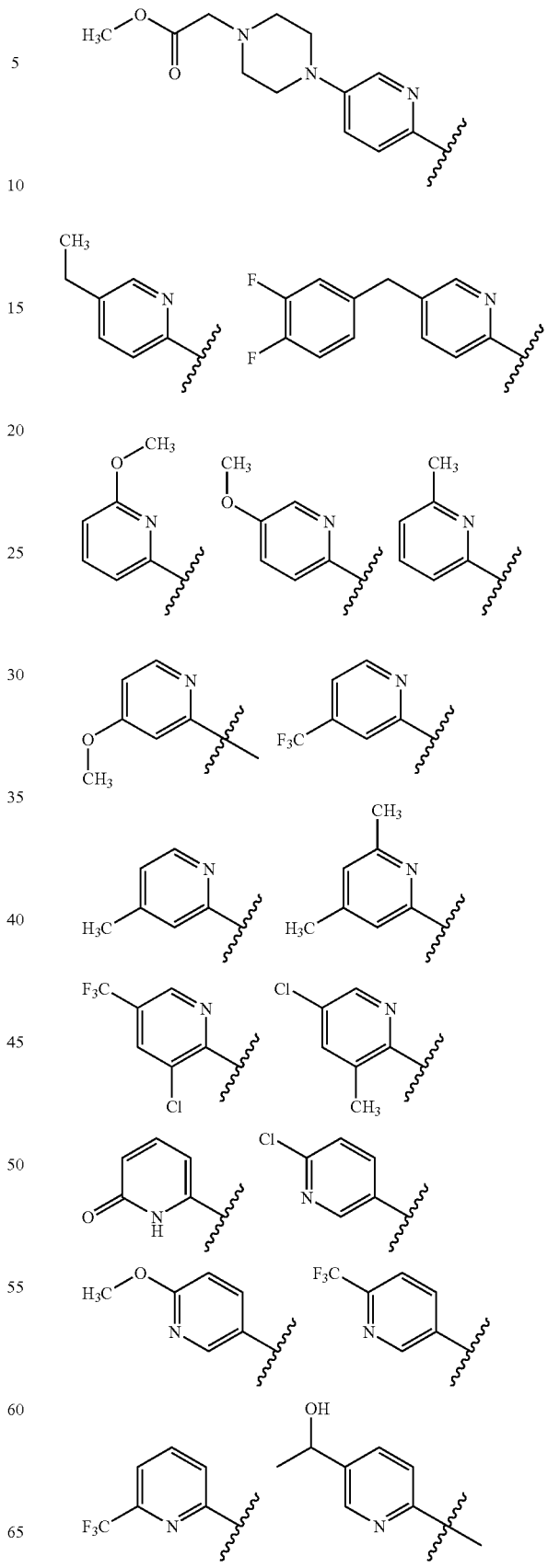

-continued
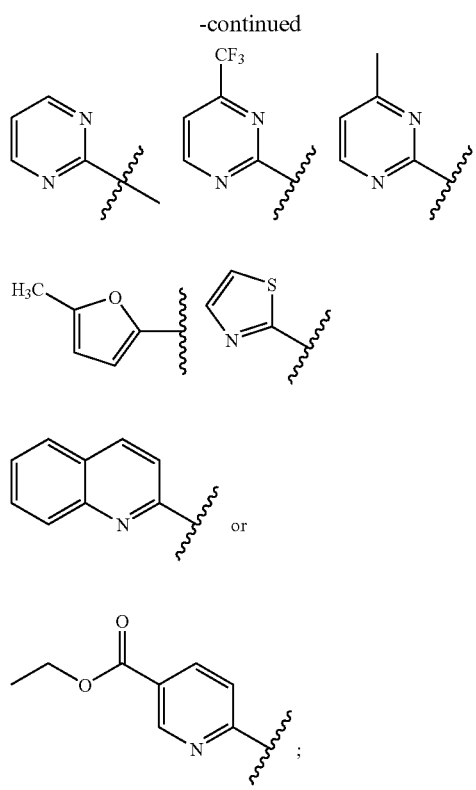
B is:
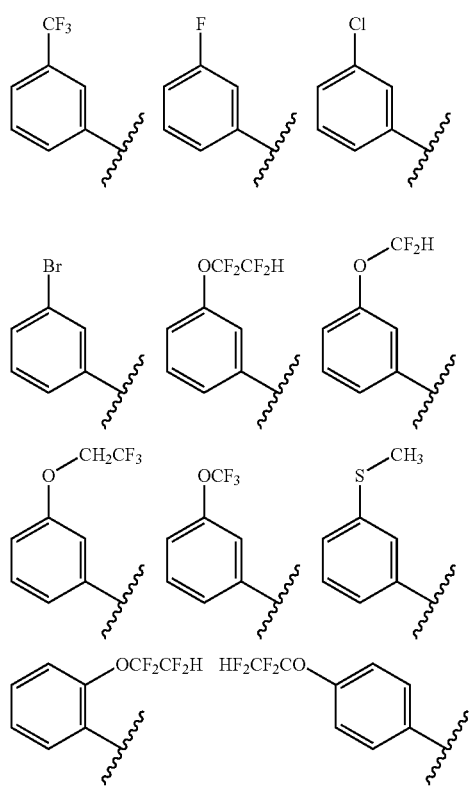
-continued
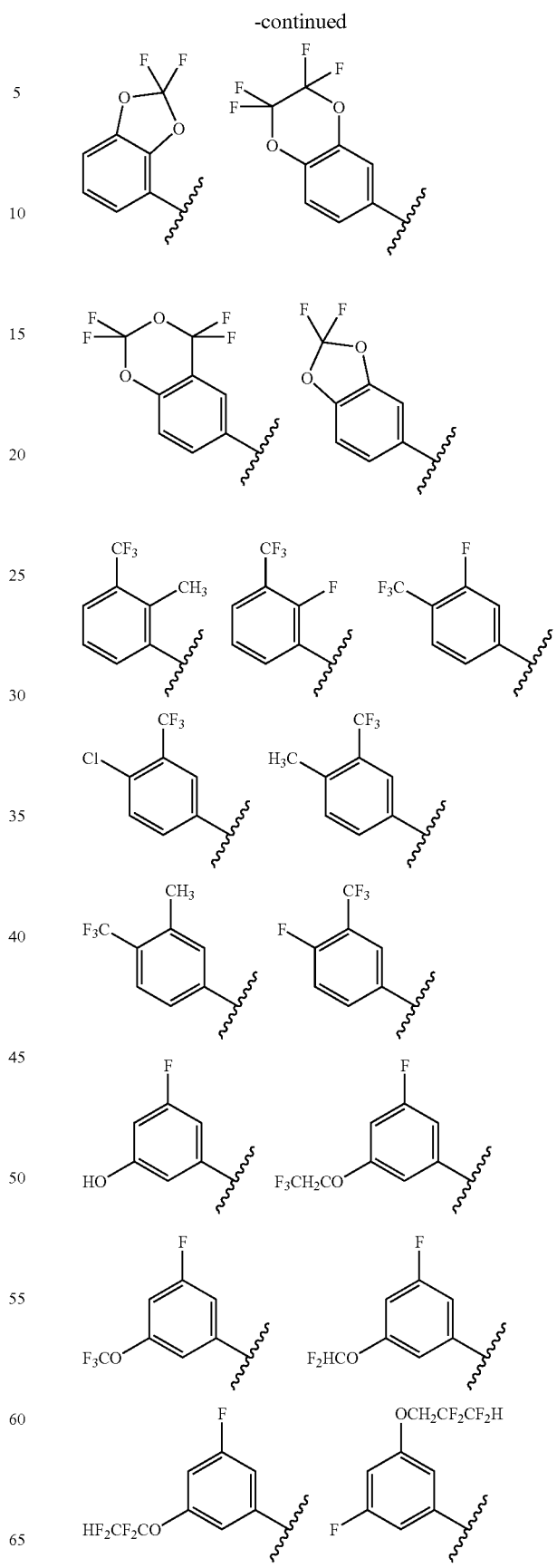

-continued
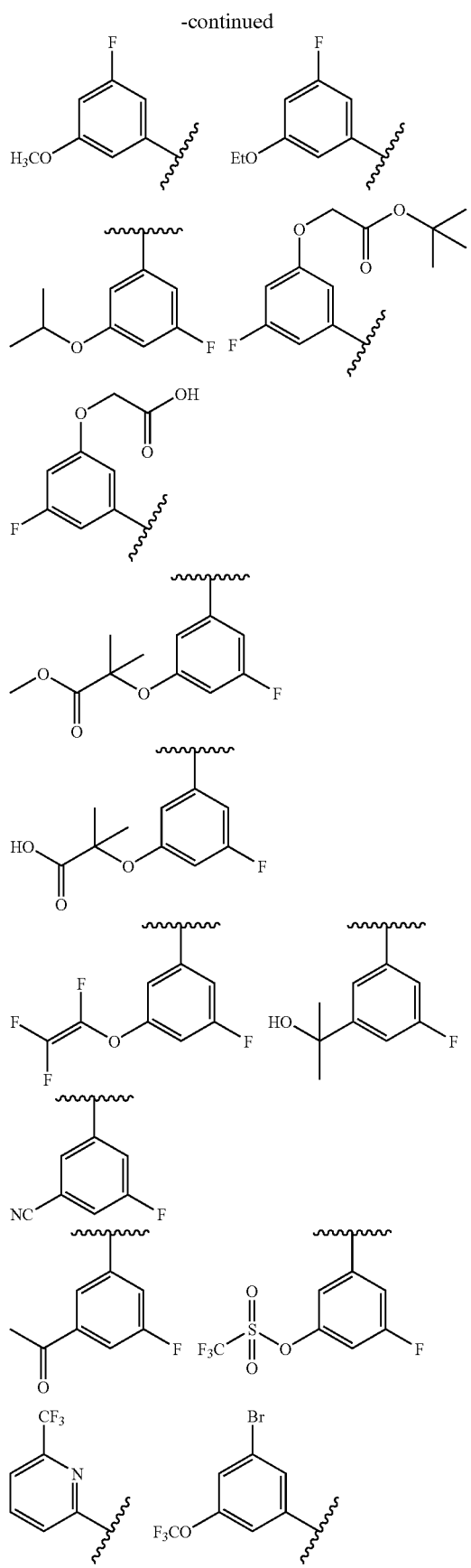
-continued
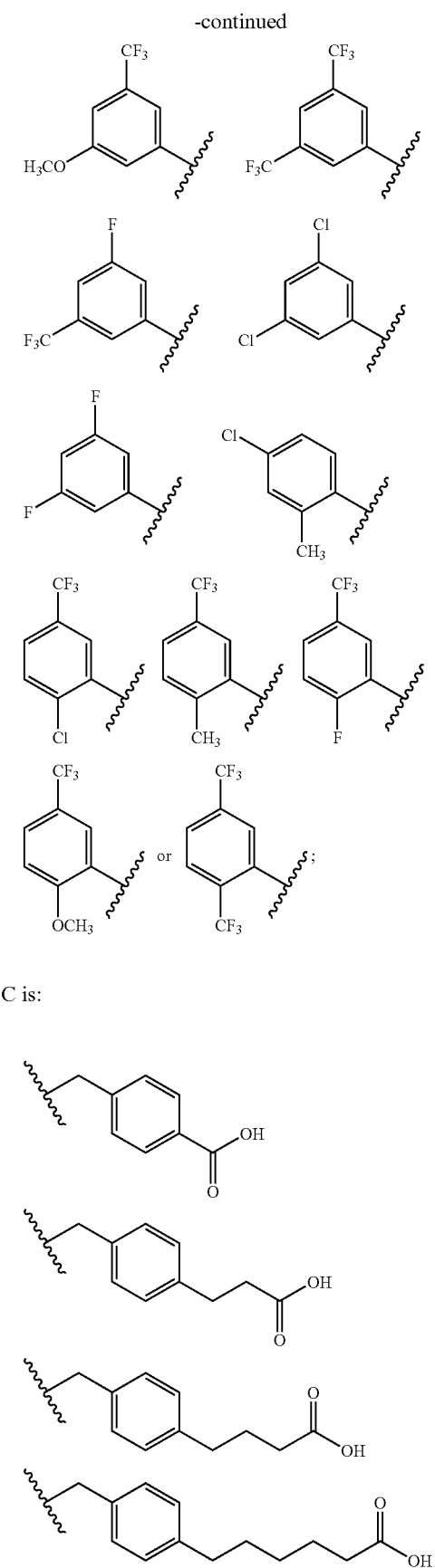
C is:

-continued
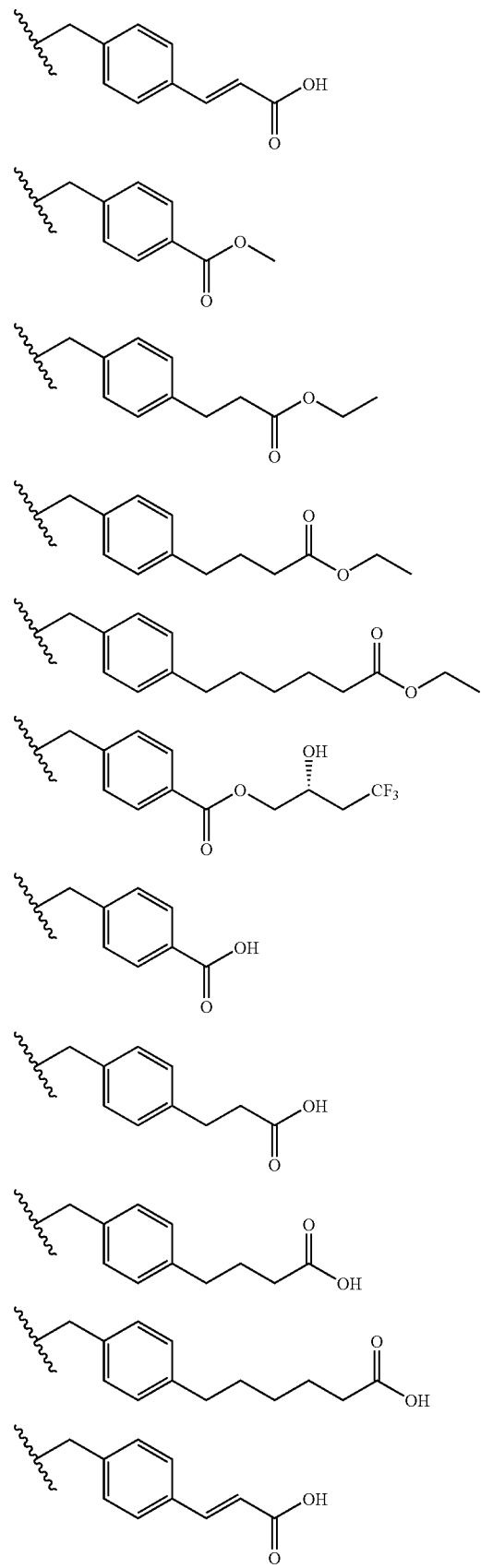
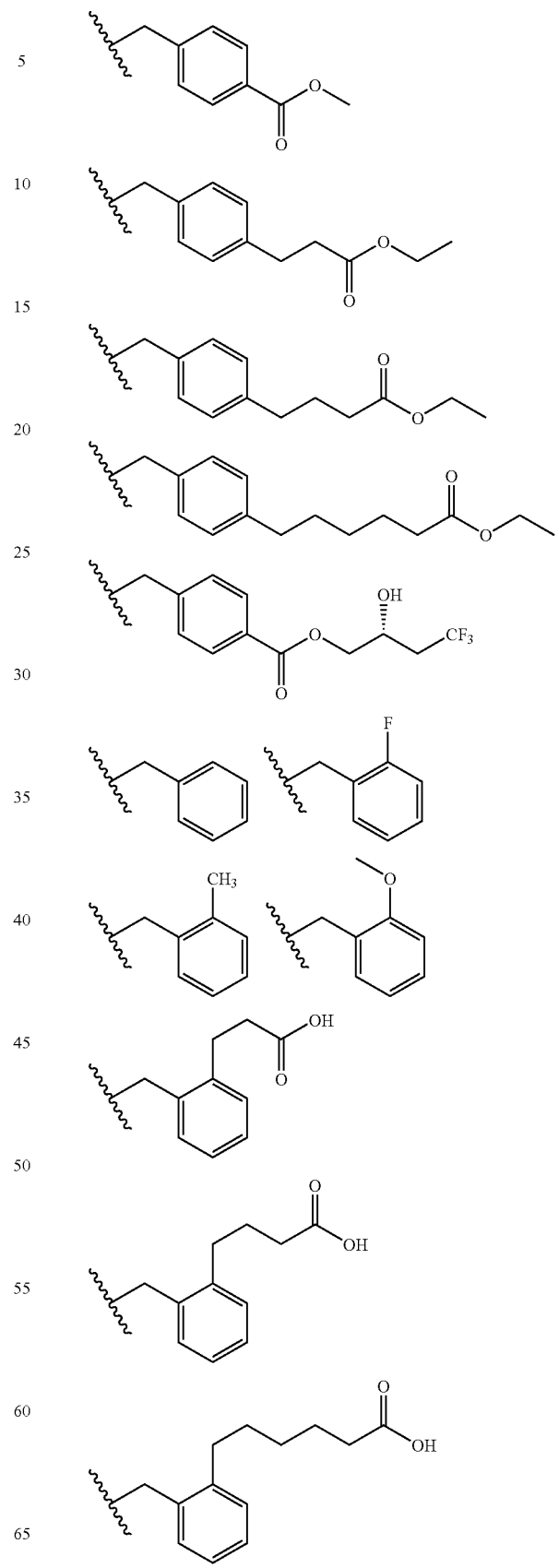

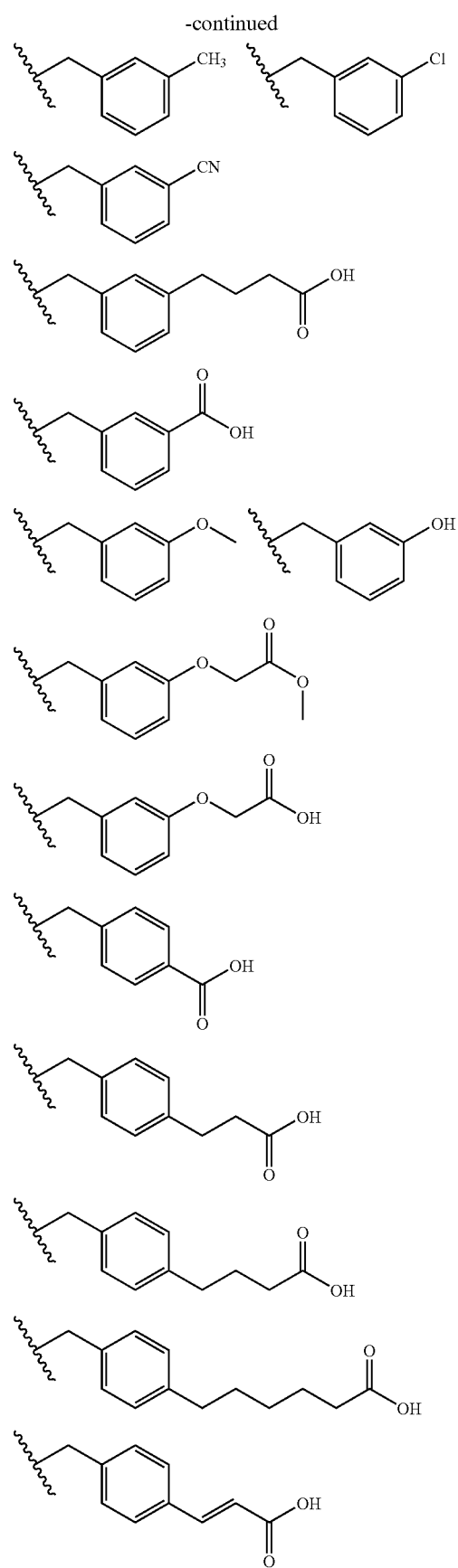
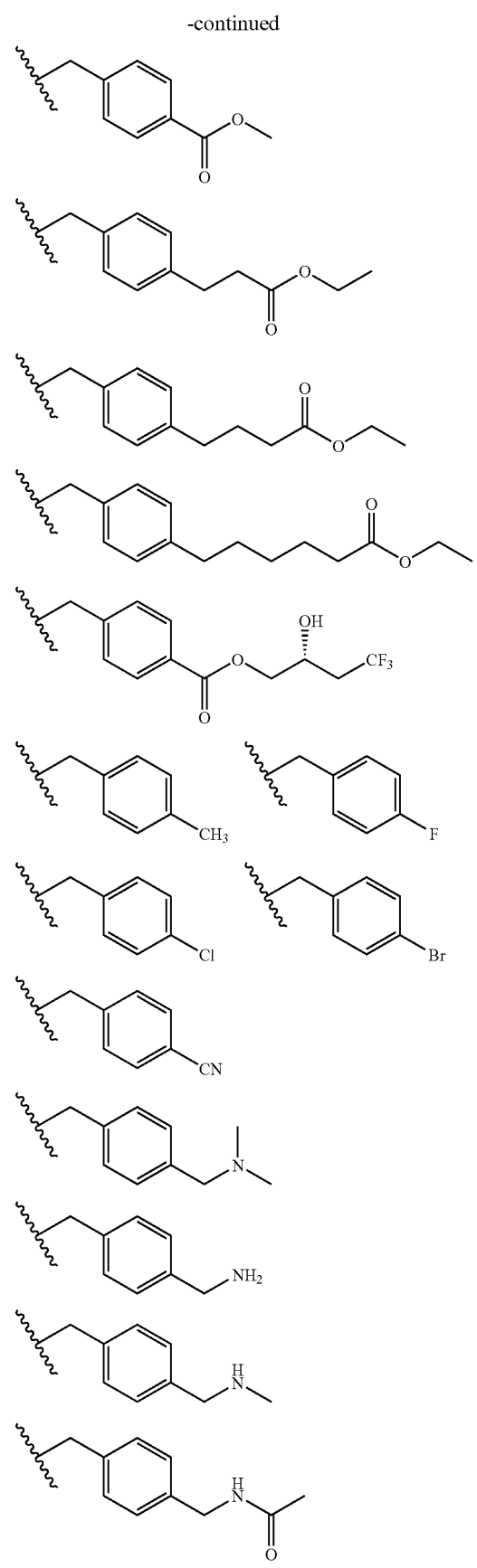

-continued
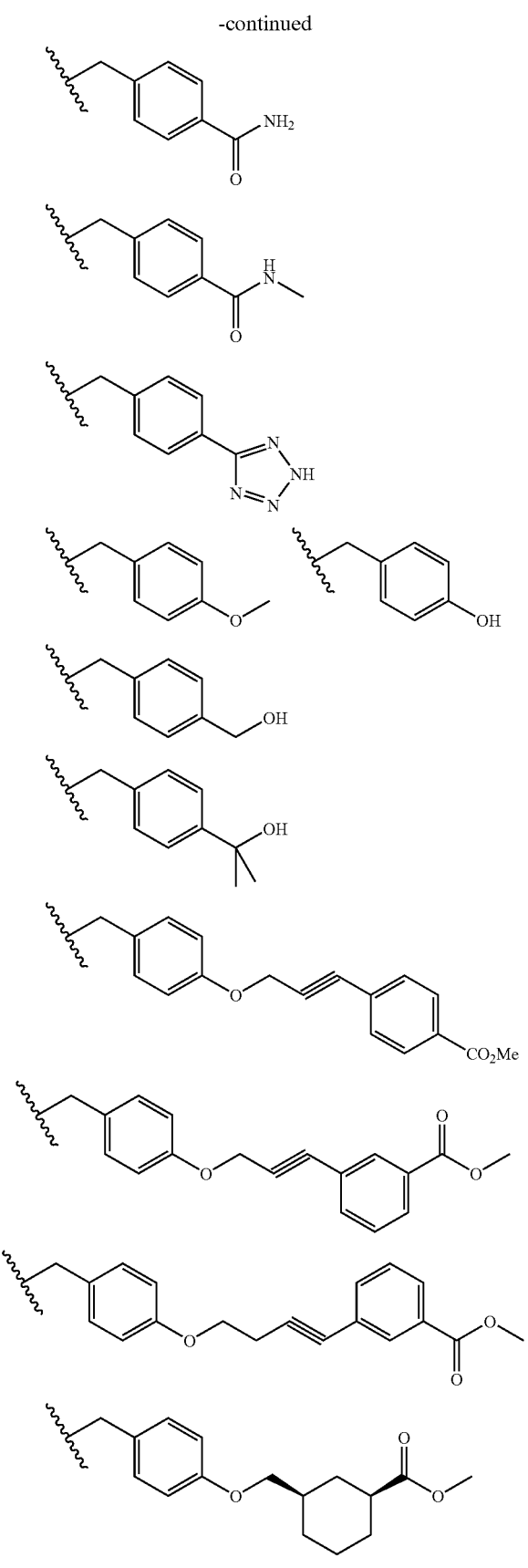
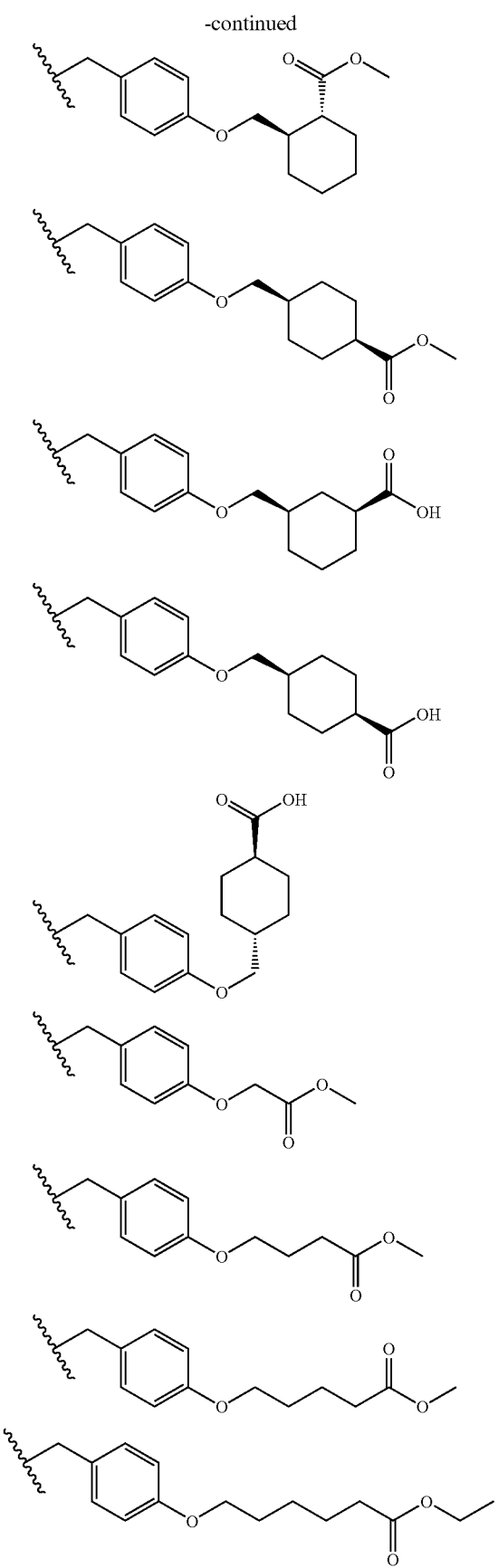

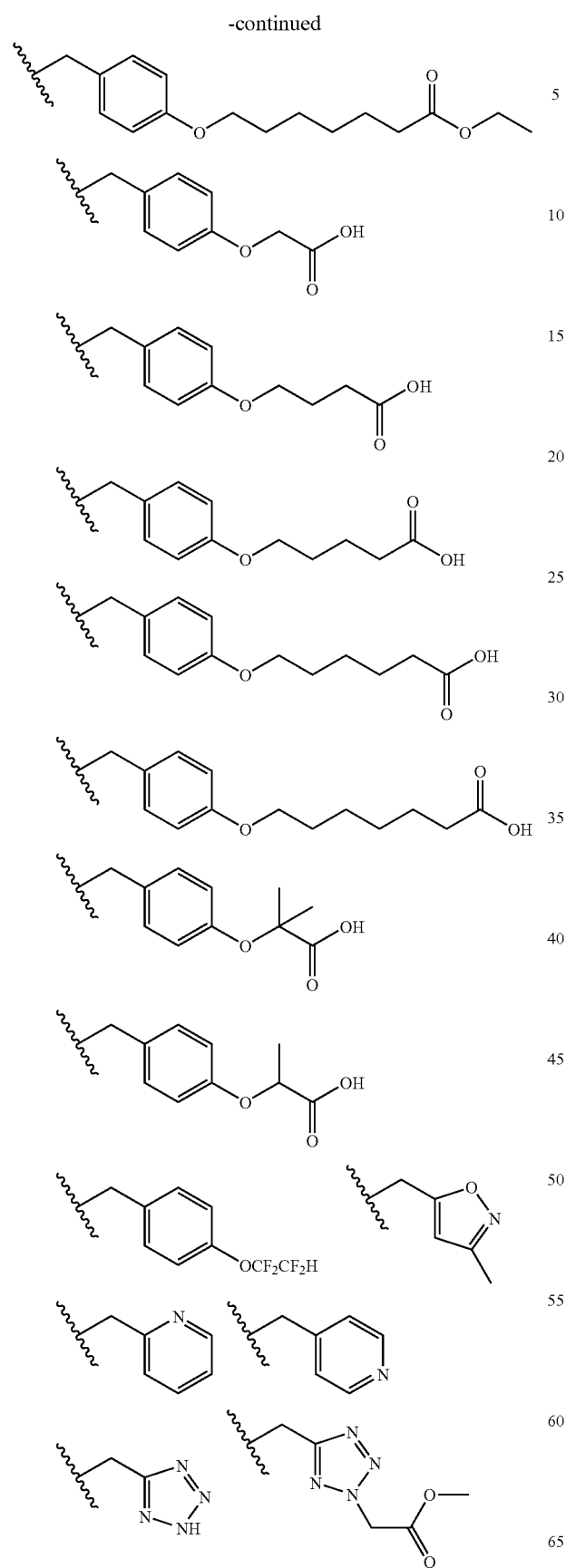
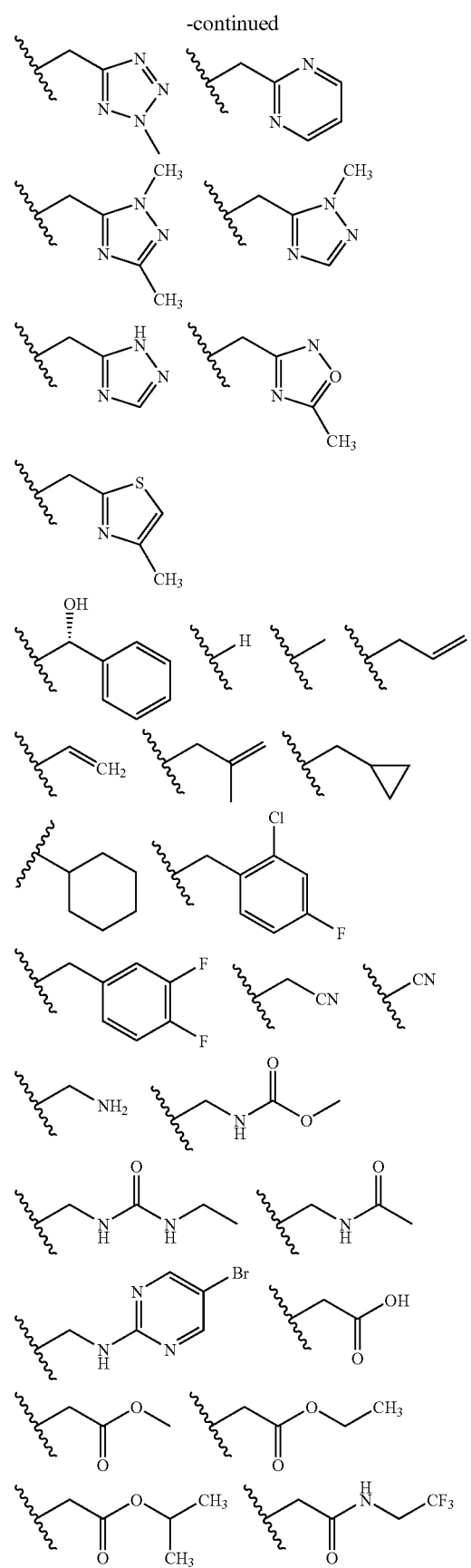

-continued
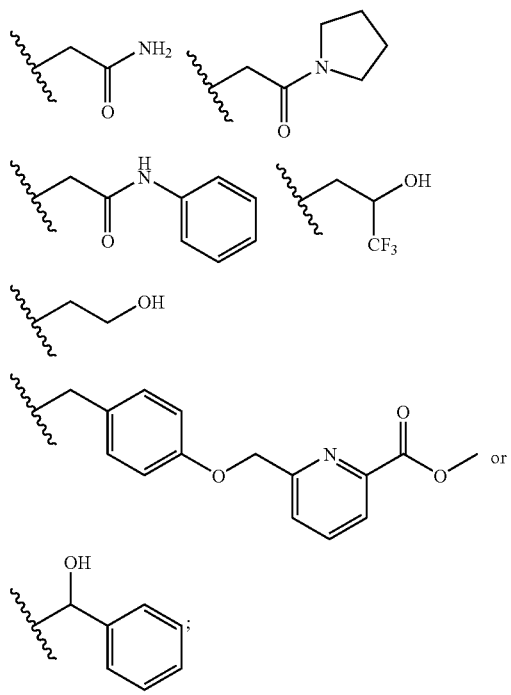
R₁ is:
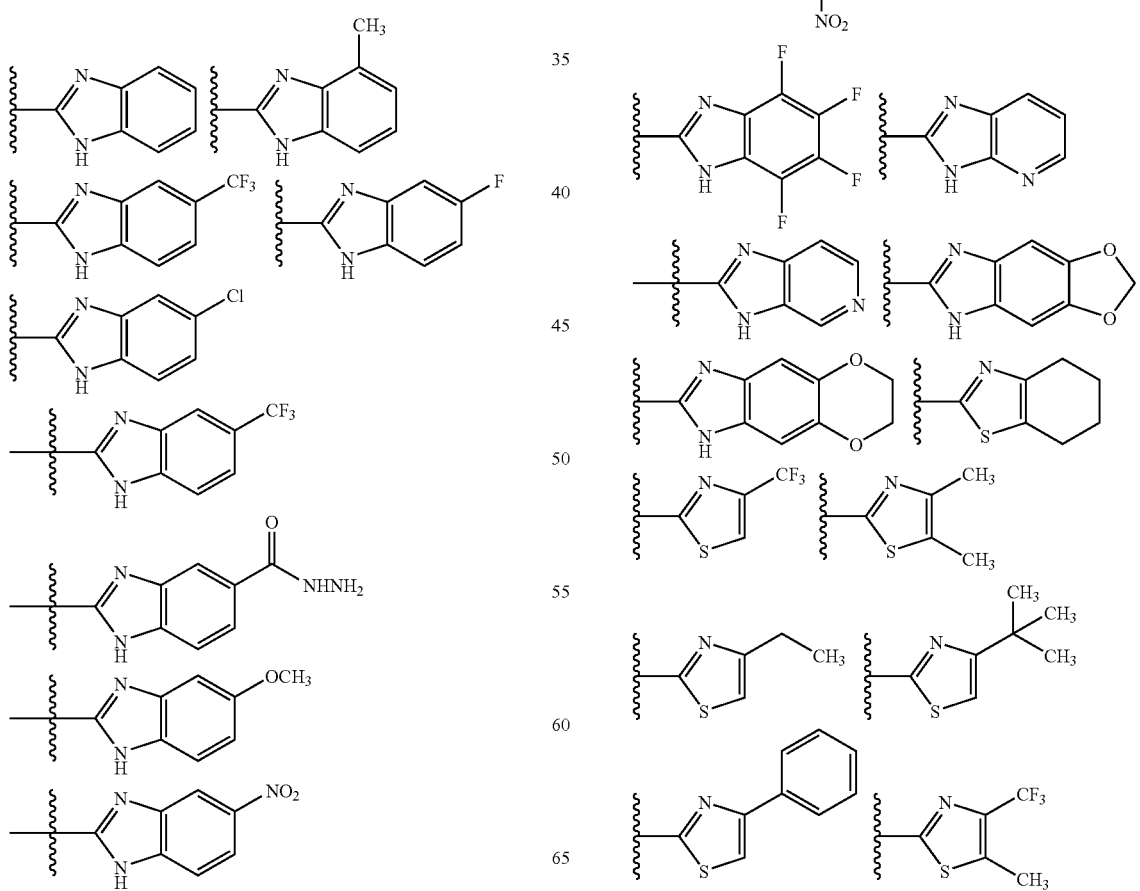

-continued
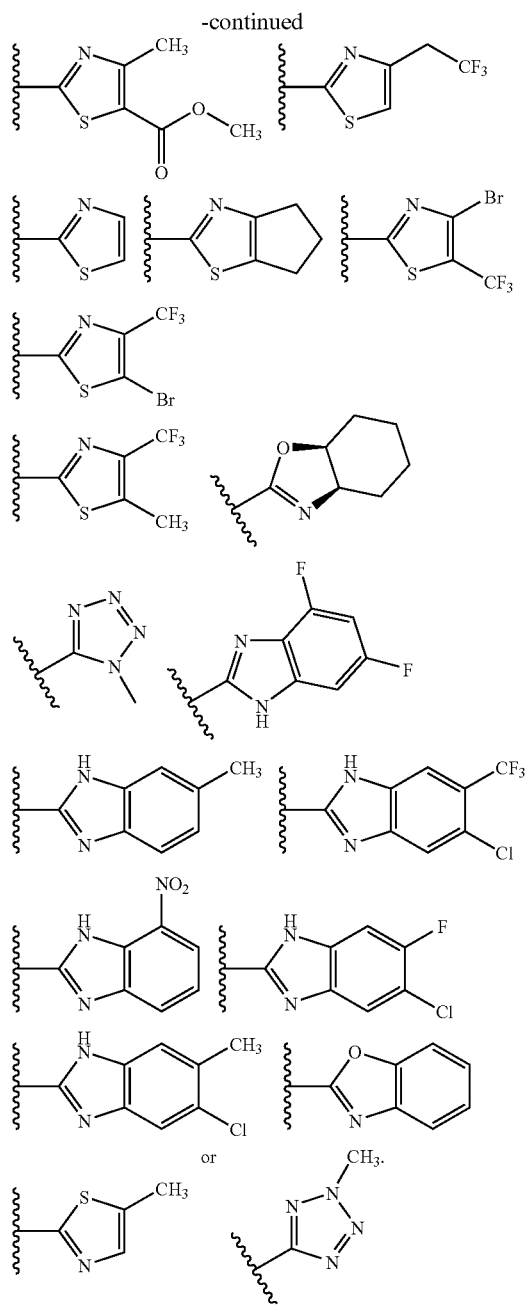
Also in accordance with the present invention, compounds are provided wherein:
A is:
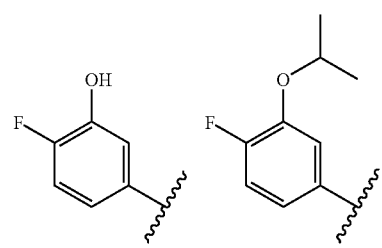
B is:
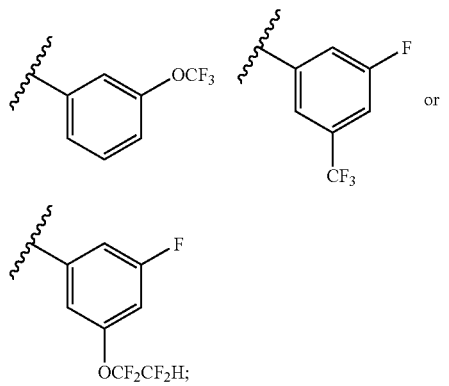
C is:
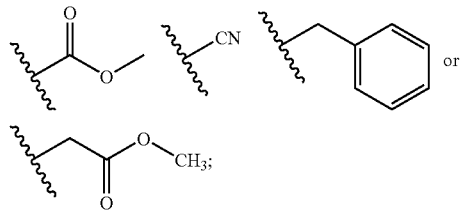
$R_1$ is:
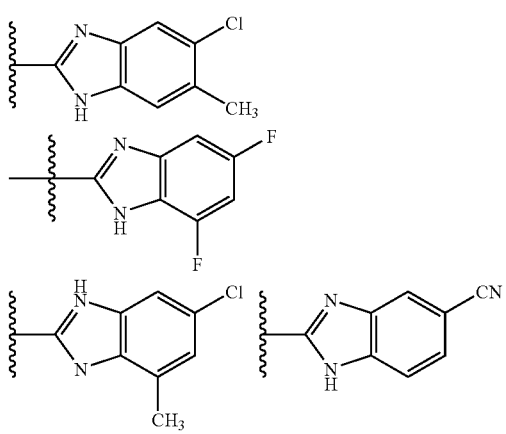

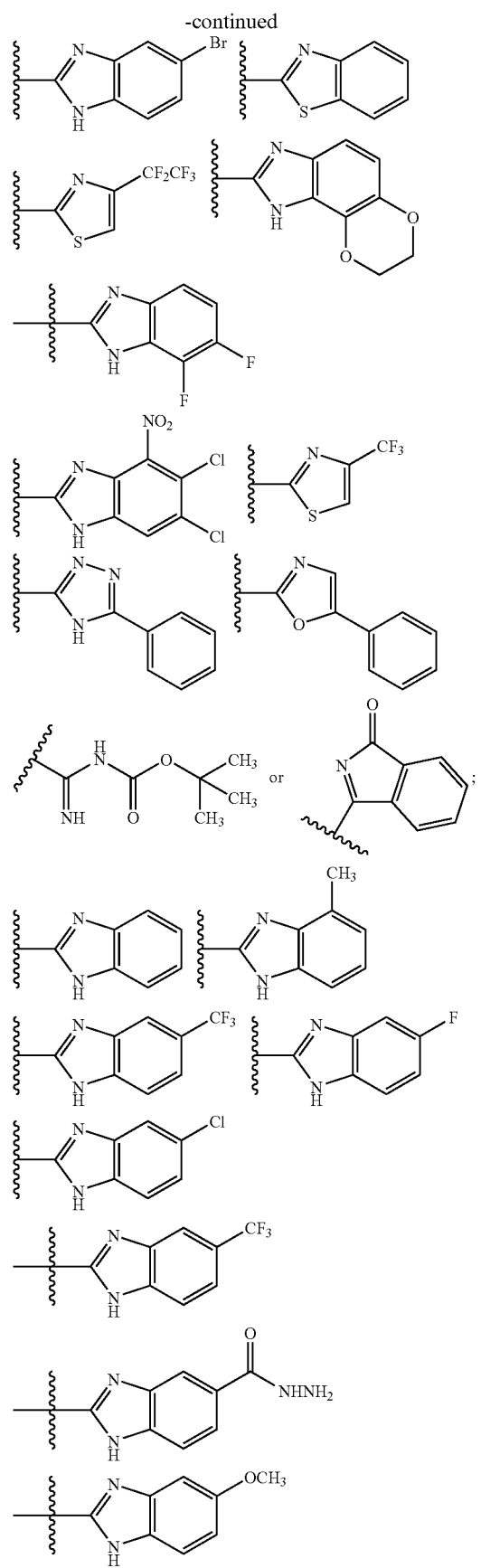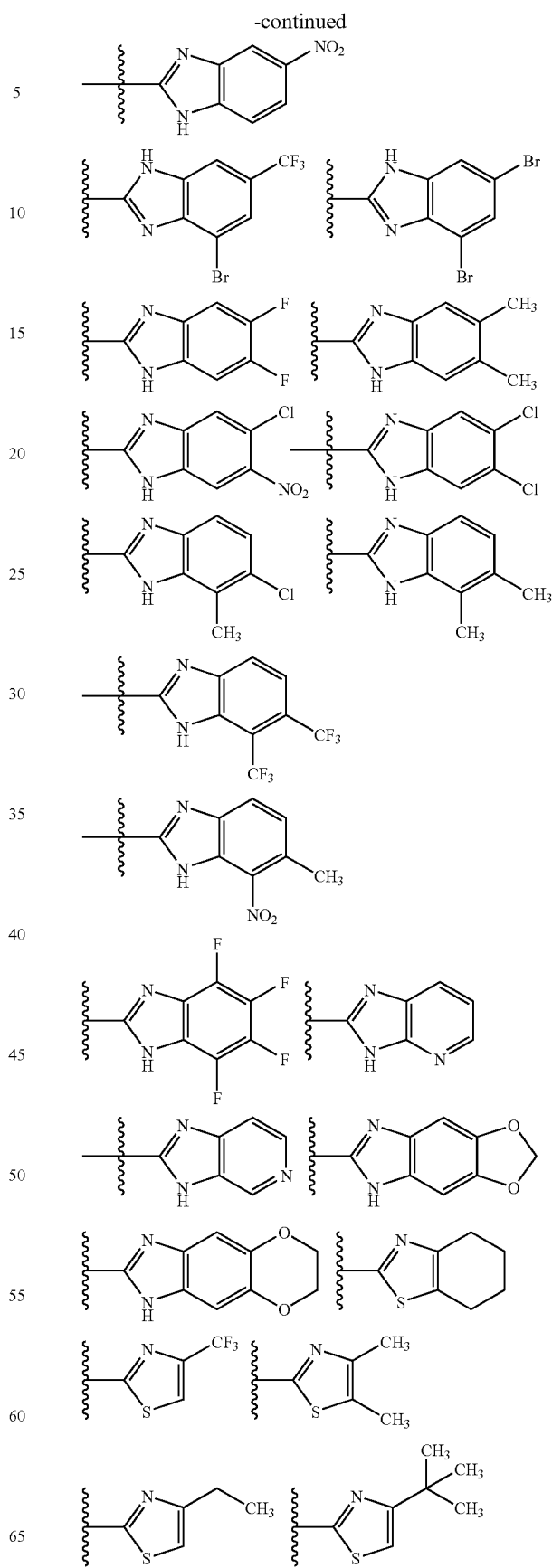

In another embodiment, compounds of the present invention are selected from the compounds exemplified in the examples.

In yet another embodiment, pharmaceutical compositions comprised of compounds of the present invention alone or in combination with a pharmaceutically acceptable carrier and/or at least one additional therapeutic agent.

In still yet another embodiment, methods of inhibiting the cholesteryl ester transfer protein comprising administering to a mammal in need of treatment a compound and/or pharmaceutical composition of the present invention are provided.

In one embodiment, methods for treating, preventing or slowing the progression of Alzheimer's, atherosclerosis, venous thrombosis, coronary artery disease, coronary heart disease, coronary vascular disease, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia in a mammal (including a human being either male or female) by administering to a mammal in need of such treatment an atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia treating, preventing or slowing amount of a compound and/or pharmaceutical composition of the present invention are provided.

In another embodiment, methods for treating, preventing or slowing the progression of atherosclerosis in a mammal by administering to a mammal in need of such treatment an atherosclerotic treating, preventing or slowing amount of a compound and/or pharmaceutical composition of the present invention are provided.

In another embodiment, methods for treating, preventing or slowing the progression of peripheral vascular disease in a mammal by administering to a mammal in need of such treatment a peripheral vascular disease treating, preventing or slowing amount of a compound and/or pharmaceutical composition of the present invention are provided.

In yet another embodiment, methods for treating, preventing or slowing the progression of dyslipidemia in a mammal by administering to a mammal in need of such treatment a dyslipidemia treating, preventing or slowing amount of a compound and/or pharmaceutical composition of the present invention are provided.

In still yet another embodiment, methods for treating, preventing or slowing the progression of hyperbetalipoproteinemia in a mammal by administering to a mammal in need of such treatment a hyperbetalipoproteinemia treating, preventing or slowing amount of a compound and/or pharmaceutical composition of the present invention are provided.

In one embodiment, methods for treating, preventing or slowing the progression of hypoalphalipoproteinemia in a mammal by administering to a mammal in need of such treatment a hypoalphalipoproteinemia treating, preventing or slowing amount of a compound and/or pharmaceutical composition of the present invention are provided.

In another embodiment, methods for treating, preventing or slowing the progression of hypercholesterolemia in a mammal by administering to a mammal in need of such treatment a hypercholesterolemia treating, preventing or slowing amount of a compound and/or pharmaceutical composition of the present invention are provided.

In yet another embodiment, methods for treating, preventing or slowing the progression of hypertriglyceridemia in a mammal by administering to a mammal in need of such treatment a hypertriglyceridemia treating, preventing or slowing amount of a compound and/or pharmaceutical composition of the present invention are provided.

In still yet another embodiment, methods for treating, preventing or slowing the progression of familial-hypercholesterolemia in a mammal by administering to a mammal in need of such treatment a familial-hypercholesterolemia treating, preventing or slowing amount of a compound and/or pharmaceutical composition of the present invention are provided.

In one embodiment, methods for treating, preventing or slowing the progression of cardiovascular disorders in a mammal by administering to a mammal in need of such treatment a cardiovascular disorder treating, preventing or slowing amount of a compound and/or pharmaceutical composition of the present invention are provided.

In another embodiment, methods for treating, preventing or slowing the progression of angina in a mammal by administering to a mammal in need of such treatment an angina treating, preventing or slowing amount of a compound and/or pharmaceutical composition of the present invention are provided.

In yet another embodiment, methods for treating, preventing or slowing the progression of ischemia in a mammal by administering to a mammal in need of such treatment an ischemic disease treating, preventing or slowing amount of a compound and/or pharmaceutical composition of the present invention are provided.

In still yet another embodiment, methods for treating, preventing or slowing the progression of cardiac ischemia in a mammal by administering to a mammal in need of such treatment a cardiac ischemic treating, preventing or slowing amount of a compound and/or pharmaceutical composition of the present invention are provided.

In one embodiment, methods for treating, preventing or slowing the progression of stroke in a mammal by administering to a mammal in need of such treatment a stroke treating, preventing or slowing amount of a compound and/or pharmaceutical composition of the present invention are provided.

In one embodiment, methods for treating, preventing or slowing the progression of a myocardial infarction in a mammal by administering to a mammal in need of such treatment a myocardial infarction treating, preventing or slowing amount of a compound and/or pharmaceutical composition of the present invention are provided.

In another embodiment, methods for treating, preventing or slowing the progression of reperfusion injury in a mammal by administering to a mammal in need of such treatment a reperfusion injury treating, preventing or slowing amount of a compound and/or pharmaceutical composition of the present invention are provided.

In another embodiment, methods for treating, preventing or slowing the progression of angioplastic restenosis in a mammal by administering to a mammal in need of such treatment an angioplastic restenosis treating, preventing or slowing amount of a compound and/or pharmaceutical composition of the present invention are provided.

In yet another embodiment, methods for treating, preventing or slowing the progression of hypertension in a mammal by administering to a mammal in need of such treatment a hypertension treating, preventing or slowing amount of a compound and/or pharmaceutical composition of the present invention are provided.

In yet another embodiment, methods for treating, preventing or slowing the progression of the ascular complications of diabetes in a mammal by administering to a mammal in need of such treatment a vascular complications of diabetes treating, preventing or slowing amount of a compound and/or pharmaceutical composition of the present invention are provided.

In still yet another embodiment, methods for treating, preventing or slowing the progression of obesity in a mammal by administering to a mammal in need of such treatment an obesity treating, preventing or slowing amount of a compound and/or pharmaceutical composition of the present invention are provided.

In one embodiment, methods for treating, preventing or slowing the progression of endotoxemia in a mammal by administering to a mammal in need of such treatment an endotoxemia treating, preventing or slowing amount of a compound and/or pharmaceutical composition of the present invention are provided.

In another embodiment, methods for treating, preventing or slowing the progression of a disease requiring cholesteryl ester transfer protein inhibitor therapy comprising administering, concurrently or sequentially, to a mammal in need of treatment, prevention or slowing a therapeutically effective amount of a compound of the present invention and at least one additional therapeutic agent.

In yet another embodiment, methods of inhibiting remnant lipoprotein production comprising administering to a mammal a compound and/or pharmaceutical composition of the present invention are provided.

In still yet another embodiment, methods of raising HDL cholesterol in a mammal comprising administering to a mammal in need of treatment a compound and/or pharmaceutical composition of the present invention are provided.

Synthesis

Generally, compounds of the present invention may be prepared by methods such as those illustrated in the following Schemes A to P. Exemplary compounds of the present invention were prepared by the methods illustrated in the examples set forth below. Solvents, temperatures, pressures, and other reaction conditions may readily be selected by one of ordinary skill in the art. Starting materials are commercially available or readily prepared by one of ordinary skill in the art. Combinatorial techniques may be employed in the preparation of compounds, for example, where the intermediates possess groups suitable for these techniques.

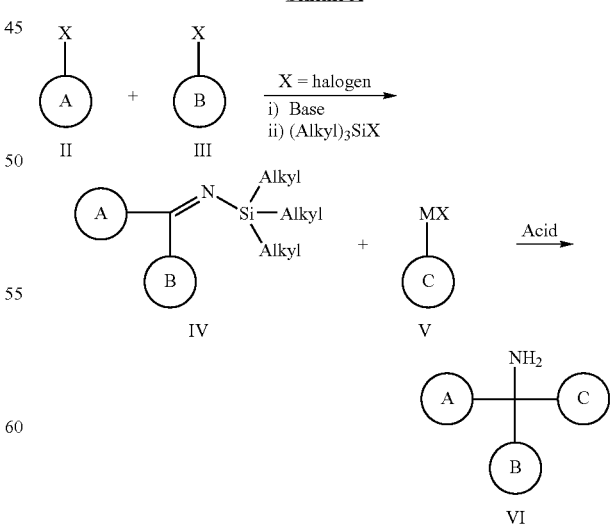

As illustrated in Scheme A, a substituted reagent of Formula II, wherein the composition of A is as described under Formula Ia & Ib, with the requirement that at least one of the substituents (X) attached to the reagent of Formula II is a nitrile group or a halogen group, such as bromine, can be combined with a reagent of Formula III, wherein the composition of B is as described under Formula Ia & Ib, with the requirement that at least one of the substituents (X) attached to the reagent of Formula III is a halide group, such as bromine, or a nitrile group, followed by treatment with a base, such as nBuLi. To the imine intermediate of Formula IV can be added a metal halide (MX) reagent, such as an alkyl lithium complex, a magnesium bromide complex or a magnesium chloride complex, or a zinc bromide or zinc chloride complex, of Formula V, where the metal halide complex is made from a reagent wherein the composition of C is as described under Formula Ia & Ib, followed by treatment with acid, such as HCl, to remove the silyl group, to yield the racemic intermediate of Formula VI. As will be described in the proceeding schemes, the racemic intermediate of Formula VI will allow for the generation of compounds of Formula Ia or Ib via the routes to be described.

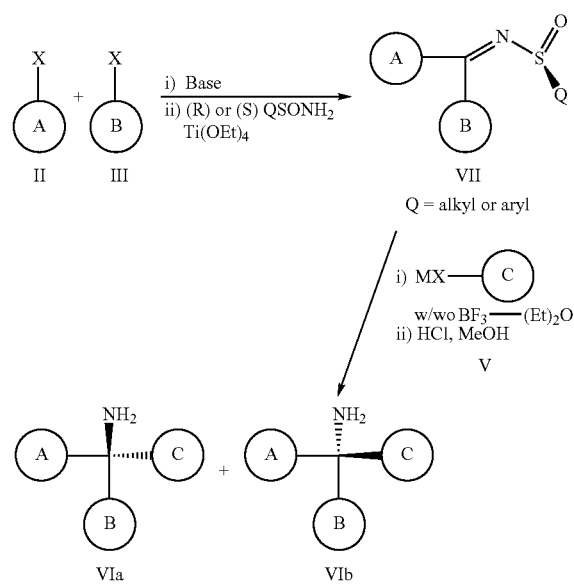

As illustrated in Scheme B, a substituted reagent of Formula II, wherein the composition of A is as described under Formula Ia & Ib, with the requirement that at least one of the substituents (X) attached to the reagent of Formula II is a nitrile group or a halogen group, such as bromine, can be combined with a reagent of Formula III, wherein the composition of B is as described under Formula Ia & Ib, with the requirement that at least one of the substituents (X) attached to the reagent of Formula III is a halide group, such as bromine, or a nitrile group, followed by treatment with a base, such as nBuLi. Alternatively, a substituted reagent of Formula II, wherein the composition of A is as described under Formula Ia & Ib, with the requirement that at least one of the substituents (X) attached to the reagent of Formula II is an aldehyde group or a halogen group, such as bromine, can be combined with a reagent of Formula III, wherein the composition of B is as described under Formula Ia & Ib, with the requirement that at least one of the substituents (X) attached to the reagent of Formula III is a halide group, such as bromine, or an aldehyde group, followed by treatment with a base, such as nBuLi, followed by treatment with an oxidizing agent such as, $MnO_2$ or Jones' Reagent. The resulting mixture can then be treated with a substituted sulfinamide reagent, such as (R)-4-methylbenzenesulfinamide or (R)-4-methylbenzenesulfinamide or (S)-2-methylpropane-2-sulfinamide or (R)-2-methylpropane-2-sulfinamide, along with $Ti(OEt)_4$, to yield a the sulfinyl imide intermediate of Formula VII. To the sulfinyl imide intermediate of Formula VII can be added a metal halide reagent (MX), such as a magnesium bromide complex or a magnesium chloride complex, or a zinc bromide or zinc chloride complex, of Formula V, where the metal halide complex is made from a reagent wherein the composition of C is as described under Formula Ia & Ib, with or without a Lewis acid, such as $BF_3 \blacksquare (Et)_2O$, followed by treatment with acid, such as HCl, to hydrolyze the sulfinamide, to yield the intermediates of Formula VIa and VIb. By application of substituted sulfinamide reagent, such as (R)-4-methylbenzenesulfinamide or (R)-4-methylbenzenesulfinamide or (S)-2-methylpropane-2-sulfinamide or (R)-2-methylpropane-2-sulfinamide one skilled in the art can enrich the formation of the (R) antipode (Formula VIa) versus the (S) antipode (Formula VIb) or the (S) antipode (Formula VIb) versus the (R) antipode (Formula VIa), respectively. As will be described in the proceeding schemes, the intermediate of Formula VIa and VIb will allow for the generation of compounds of Formula Ia or Ib via the routes to be described.

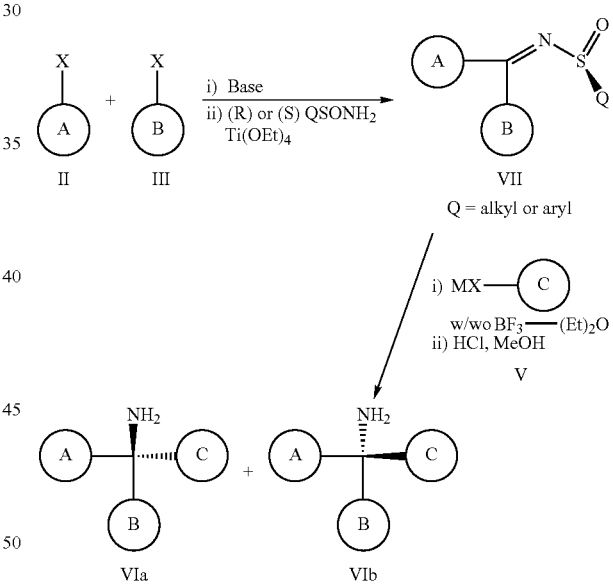

As illustrated in Scheme C, a substituted reagent of Formula II, wherein the composition of A is as described under Formula Ia & Ib, with the requirement that at least one of the substituents (X) attached to the reagent of Formula II is an alkyl ester group, such as a methyl or an ethyl ester, can be combined with a reagent of Formula III, wherein the composition of B is as described under Formula Ia & Ib, with the requirement that at least one of the substituents (X) attached to the reagent of Formula III is a halide group, such as bromine, followed by treatment with a base, such as nBuLi. The resulting mixture can then be treated with a substituted sulfinamide reagent, such as (R)-4-methylbenzenesulfinamide or (R)-4-methylbenzenesulfinamide or (S)-2-methylpropane-2-sulfinamide or (R)-2-methylpropane-2-sulfinamide, along with Ti(OEt)$_4$, to yield a the sulfonylimide intermediate of Formula VII. In addition, as illustrated in Scheme C, a substituted reagent of Formula II, wherein the composition of A is as described under Formula Ia & Ib, with the requirement that at least one of the substituents (X) attached to the reagent of Formula II is a halide group, such as bromine, can be combined with a reagent of Formula III, wherein the composition of B is as described under Formula Ia & Ib, with the requirement that at least one of the substituents (X) attached to the reagent of Formula III is an alkyl ester group, such as a methyl or an ethyl ester, followed by treatment with a base, such as nBuLi. The resulting mixture can then be treated with a substituted sulfinamide reagent, such as (R)-4-methylbenzenesulfinamide or (R)-4-methylbenzenesulfinamide or (S)-2-methylpropane-2-sulfinamide or (R)-2-methylpropane-2-sulfinamide, along with Ti(OEt)$_4$, to yield a the sulfinyl imide intermediate of Formula VII. To the sulfinyl imide intermediate of Formula VII can be added a metal halide reagent, such as an alkyl lithium complex, a magnesium bromide or a magnesium chloride complex, or a zinc bromide or zinc chloride complex, of Formula V, where the metal halide complex is made from a reagent wherein the composition of C is as described under Formula Ia & Ib, with or without a Lewis acid, such as BF$_3$·(Et)$_2$O, followed by treatment with acid, such as HCl, to hydrolyze the sulfinamide, to yield the intermediates of Formula VIa and VIb. By application of substituted sulfinamide reagent, such as (R)-4-methylbenzenesulfinamide or (R)-4-methylbenzenesulfinamide or (S)-2-methylpropane-2-sulfinamide or (R)-2-methylpropane-2-sulfinamide one skilled in the art can enrich the formation of the (R) antipode (Formula VIa) versus the (S) antipode (Formula VIb) or the (S) antipode (Formula VIb) versus the (R) antipode (Formula VIa), respectively. As will be described in the proceeding schemes, the intermediate of Formula VIa and VIb will allow for the generation of compounds of Formula Ia or Ib via the routes to be described.

Scheme D

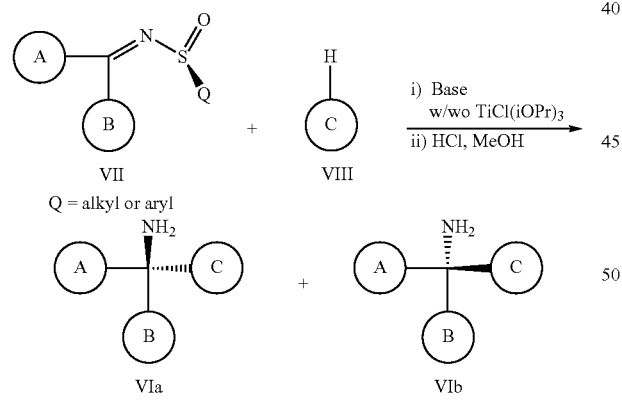

As illustrated in Scheme D, to the sulfinyl imide intermediate of Formula VII can be added a base, such as LDA or nBuLi, with or with out the addition of TiCl(iOPr)$_3$, and a reagent of Formula VIII, wherein the composition of C is as described under Formula Ia & Ib, with the requirement that at least one of the substituents attached to the reagent of Formula VIII is a hydrogen that can be deprotonated to yield a reactive anion species, followed by treatment with acid, such as HCl, to hydrolyze the sulfinamide, to yield the intermediates of Formula VIa and VIb. By application of substituted sulfinamide reagent, such as (R)-4-methylbenzenesulfinamide or (R)-4-methylbenzenesulfinamide or (S)-2-methylpropane-2-sulfinamide or (R)-2-methylpropane-2-sulfinamide one skilled in the art can enrich the formation of the (R) antipode (Formula VIa) versus the (S) antipode (Formula VIb) or the (S) antipode (Formula VIb) versus the (R) antipode (Formula VIa), respectively. As will be described in the proceeding schemes, the intermediate of Formula VIa and VIb will allow for the generation of compounds of Formula Ia or Ib via the routes to be described.

Scheme E

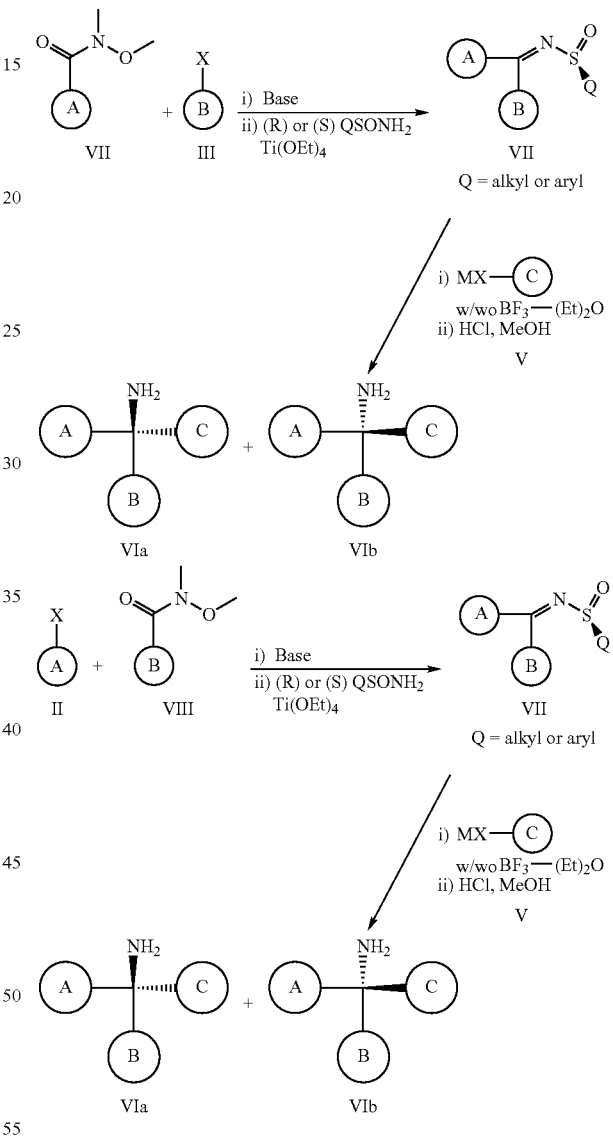

As illustrated in Scheme E, a substituted reagent of Formula VII, wherein the composition of A is as described under Formula Ia & Ib, with the requirement that at least one of the substituents attached to the reagent of Formula XIX is a N-methoxy-N-methylacetamide group, can be combined with a reagent of Formula III, wherein the composition of B is as described under Formula Ia & Ib, with the requirement that at least one of the substituents (X) attached to the reagent of Formula III is a halide group, such as bromine, followed by treatment with a base, such as nBuLi. The resulting mixture can then be treated with a substituted sulfinamide reagent, such as (R)-4-methylbenzenesulfinamide or (R)-4-methylbenzenesulfinamide or (S)-2-methylpropane-2-sulfinamide or (R)-2-methylpropane-2-sulfinamide, along with Ti(OEt)$_4$, to yield a the sulfinyl imide intermediate of Formula VII. To the sulfinyl imide intermediate of Formula VII can be added a metal halide reagent (MX), such as a magnesium bromide complex or a magnesium chloride complex, or a zinc bromide or zinc chloride complex, of Formula V, where the metal pane-2-sulfinamide one skilled in the art can enrich the formation of the (R) antipode (Formula VIa) versus the (S) antipode (Formula VIb) or the (S) antipode (Formula VIb) versus the (R) antipode (Formula VIa), respectively. As will be described in the proceeding schemes, the penultimate intermediate of Formula VIa and VIb will allow for the generation of compounds of Formula Ia or Ib via the routes to be described.

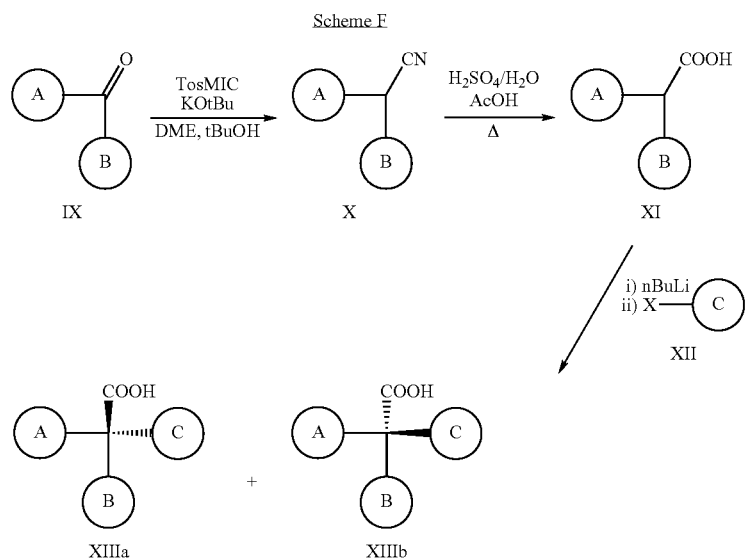

halide complex is made from a reagent wherein the composition of C is as described under Formula Ia & Ib, with or without a Lewis acid, such as BF$_3$■(Et)$_2$O, followed by treatment with acid, such as HCl, to hydrolyze the sulfinamide, to yield the intermediates of Formula VIa and VIb. In addition, a substituted reagent of Formula II, wherein the composition of A is as described under Formula Ia & Ib, with the requirement that at least one of the substituents attached to the reagent of Formula II is a halide group, such as bromine, can be combined with a reagent of Formula II, wherein the composition of B is as described under Formula Ia & Ib, with the requirement that at least one of the substituents (X) attached to the reagent of Formula VIII, is a N-methoxy-N-methylacetamide group, followed by treatment with a base, such as nBuLi. The resulting mixture can then be treated with a substituted sulfinamide reagent, such as (R)-4-methylbenzenesulfinamide or (R)-4-methylbenzenesulfinamide or (S)-2-methylpropane-2-sulfinamide or (R)-2-methylpropane-2-sulfinamide, along with Ti(OEt)$_4$, to yield a the sulfinyl imide intermediate of Formula VII. To the sulfinyl imide intermediate of Formula VII can be added a metal halide reagent (MX), such as a magnesium bromide complex or a magnesium chloride complex, or a zinc bromide or zinc chloride complex, of Formula V, where the metal halide complex is made from a reagent wherein the composition of C is as described under Formula Ia & Ib, with or without a Lewis acid, such as BF$_3$■(Et)$_2$O, followed by treatment with acid, such as HCl, to hydrolyze the sulfinamide, to yield the penultimate intermediates of Formula VIa and VIb. By application of substituted sulfinamide reagent, such as (R)-4-methylbenzenesulfinamide or (R)-4-methylbenzenesulfinamide or (S)-2-methylpropane-2-sulfinamide or (R)-2-methylpro- As illustrated in Scheme A and Scheme F, a substituted reagent of Formula II, wherein the composition of A is as described under Formula Ia & Ib, with the requirement that at least one of the substituents (X) attached to the reagent of Formula II is a nitrile group or a halogen group, such as bromine, can be combined with a reagent of Formula III, wherein the composition of B is as described under Formula Ia & Ib, with the requirement that at least one of the substituents (X) attached to the reagent of Formula III is a halide group, such as bromine, or a nitrile group, followed by treatment with a base, such as nBuLi, followed by treatment with aqueous acid, such as 1N HCl, to form a benzophenone intermediate of Formula IX. Alternatively, a substituted reagent of Formula II, wherein the composition of A is as described under Formula Ia & Ib, with the requirement that at least one of the substituents (X) attached to the reagent of Formula II is an aldehyde group or a halogen group, such as bromine, can be combined with a reagent of Formula III, wherein the composition of B is as described under Formula Ia & Ib, with the requirement that at least one of the substituents (X) attached to the reagent of Formula III is a halide group, such as bromine, or an aldehyde group, followed by treatment with a base, such as nBuLi, followed by treatment with aqueous acid, such as 1N HCl, to form a benzophenone intermediate of Formula IX. Alternately, as illustrated in Scheme C and Scheme F, a substituted reagent of Formula II, wherein the composition of A is as described under Formula Ia & Ib, with the requirement that at least one of the substituents (X) attached to the reagent of Formula II is an alkyl ester group, such as a methyl or an ethyl ester, can be combined with a reagent of Formula III, wherein the composition of B is as described under Formula Ia & Ib, with the requirement that at least one of the substituents (X) attached to the reagent of Formula III is a halide group, such as bromine, followed by treatment with a base, such as nBuLi, followed by treatment with aqueous acid, to yield a benzophenone intermediate of Formula IX. In addition, as illustrated in Scheme C and Scheme F, a substituted reagent of Formula II, wherein the composition of A is as described under Formula Ia & Ib, with the requirement that at least one of the substituents (X) attached to the reagent of Formula II is a halide group, such as bromine, can be combined with a reagent of Formula III, wherein the composition of B is as described under Formula Ia & Ib, with the requirement that at least one of the substituents (X) attached to the reagent of Formula III is an alkyl ester group, such as a methyl or an ethyl ester, followed by treatment with a base, such as nBuLi, followed by treatment with aqueous acid, to yield a benzophenone intermediate of Formula IX. As illustrated in Scheme E and Scheme F, a substituted reagent of Formula VII, wherein the composition of A is as described under Formula Ia & Ib, with the requirement that at least one of the substituents attached to the reagent of Formula VII is a N-methoxy-N-methylacetamide group, can be combined with a reagent of Formula III, wherein the composition of B is as described under Formula Ia & Ib, with the requirement that at least one of the substituents (X) attached to the reagent of Formula III is a halide group, followed by treatment with a base, such as nBuLi, followed by treatment with aqueous acid, to yield a benzophenone intermediate of Formula IX, or a substituted reagent of Formula II, wherein the composition of A is as described under Formula Ia & Ib, with the requirement that at least one of the substituents attached to the reagent of Formula II is a halide group, such as bromine, can be combined with a reagent of Formula VIII, wherein the composition of B is as described under Formula Ia & Ib, with the requirement that at least one of the substituents (X) attached to the reagent of Formula VIII, is a N-methoxy-N-methylacetamide group, followed by treatment with a base, such as nBuLi, followed by treatment with aqueous acid, to yield a benzophenone intermediate of Formula IX. Numerous alternate approaches well known to one skilled in the art can also be employed to generate a benzophenone intermediate of Formula IX.

As illustrated in Scheme F, an intermediate benzophenone of Formula IX can be treated with an agent such as 1-(isocyanomethylsulfonyl)-4-methylbenzene (TosMIC) and a base, such as potassium tert-butoxide, to yield an intermediate of Formula X. Hydrolysis of an intermediate of Formula X can be accomplished by treatment with an acid, such as aqueous $H_2SO_4$ and acetic acid, to yield an intermediate of Formula XI. An intermediate of Formula XI can be treated with a base, such as n-butyl lithium, followed by an alkyl halide reagent of Formula XII, where X is a halide, such as chlorine, bromine or iodine and the composition of C is as described under Formula Ia and Ib, to yield an intermediate of Formula XIIIa and XIIIb, which are key intermediates for the synthesis of compounds of Formula Ia and Ib.

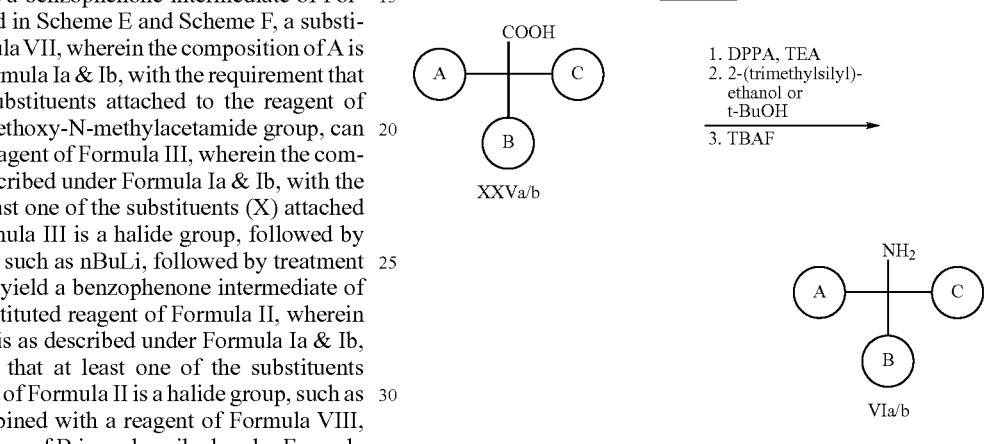

As illustrated in Scheme G, an intermediate of Formula XIIIa/b can be treated with an agent such as diphenylphosphoryl azide (DPPA) in the presence of a base, such as triethyl amine (TEA), followed by treatment with an agent, such as 2-(trimethylsilyl)ethanol or tert-butyl alcohol and eventual cleavage of the resulting intermediate carbamate by treatment with agents such as tetrabutylammonium fluoride (TBAF) or trifluoroacetic acid, to yield the advanced intermediate of Formula VIa/b, which is a key intermediate for the synthesis of compounds of Formula Ia and Ib.

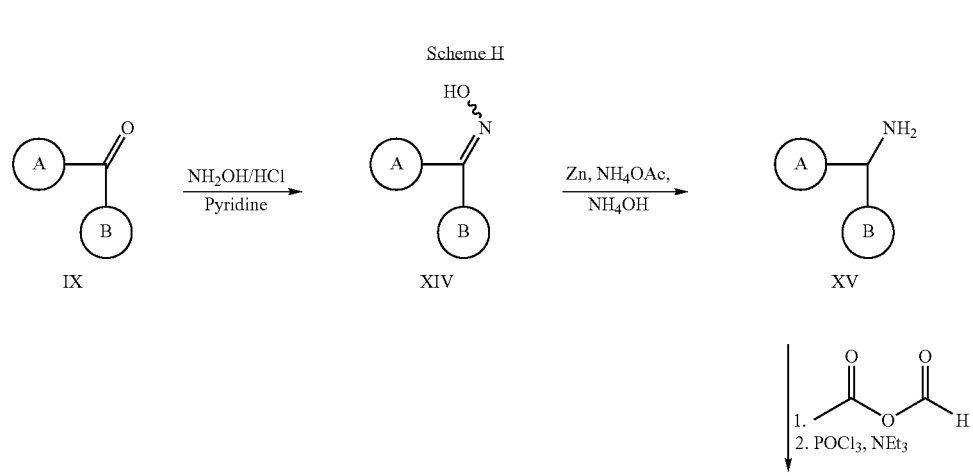

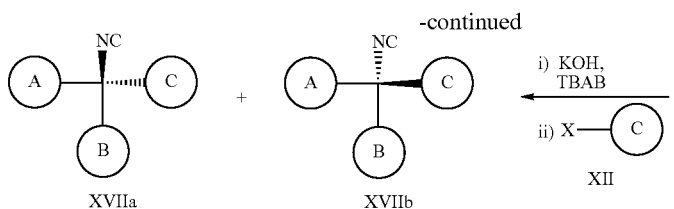
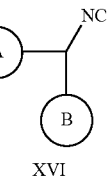

As illustrated in Scheme H, an intermediate of Formula IX, made as described in Scheme F, can be treated with a reagent such as $NH_2OH$, in the presence of an acid such as HCl, followed by treatment with a base such as pyridine, to yield an intermediate of Formula XIV. An intermediate of Formula XIV can be treated with a reducing agent such as zinc, along with $NH_4OAc$ and $NH_4OH$, to yield an intermediate of Formula XV. An intermediate of Formula XV can be treated with a formylating agent, such as acetic formic anhydride, followed by dehydration through treatment with an agent such as $POCl_3$, to yield the isonitrile intermediate of Formula XVI. The isonitrile intermediate of Formula XVI can be treated with a base, such as aqueous KOH, along with tetrabutylammonium bromide, followed by an alkyl halide reagent of Formula XII where the composition of C is as described under Formula Ia and Ib, and the X can be a halide, such as chlorine, bromine or iodine, to yield intermediates of Formula XVIIa and XVIIb, which are key intermediates for the synthesis of compounds of Formula Ia and Ib. The formation of an intermediate of Formula XVIIa or XVIIb from an intermediate of Formula XVI, as described above, can also be performed in the presence of a chiral catalyst such as, but not limited to, N-benzylcinchoninium chloride or N-benzylcinchonidinium chloride, to enrich the formation of the intermediate of Formula XVIIa over the intermediate of Formula XVIIb or to enrich the formation of the intermediate of Formula XVIIb over the intermediate of Formula XVIIa as needed to make compounds of Formula Ia and Ib.

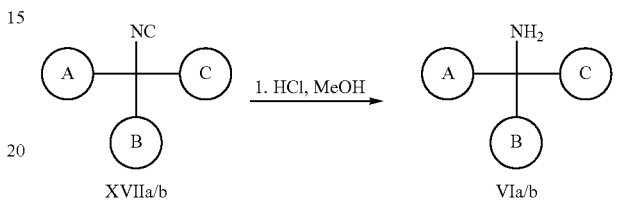

As illustrated in Scheme I, an intermediate of Formula XVIIa/b can be converted to an intermediate of Formula VIa/b by treatment with an acid such as HCl in methanol. As described in earlier schemes, and intermediate of Formula VIa/b is a key intermediate for the synthesis of compounds of Formula Ia and Ib.

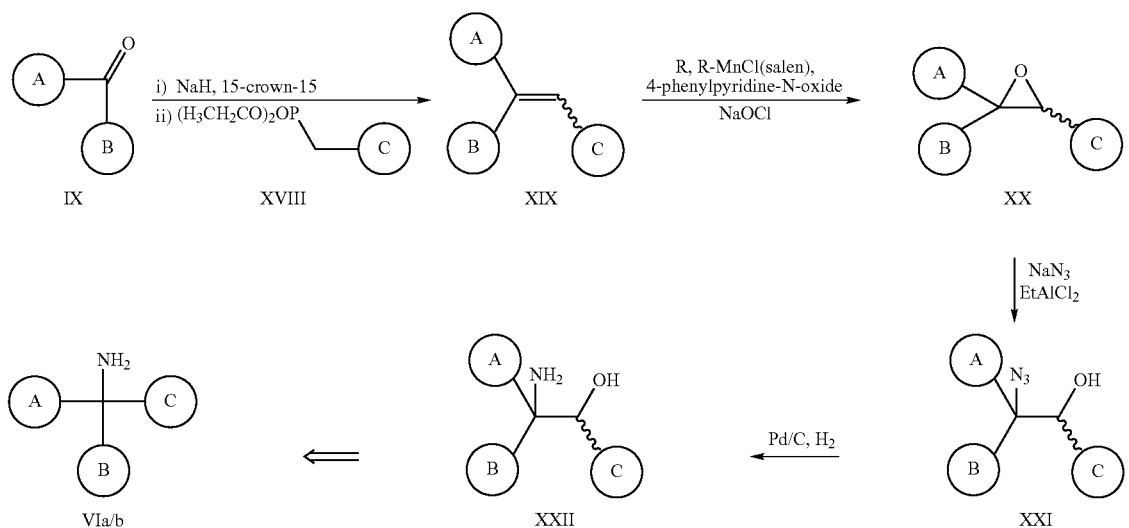

As illustrated in Scheme J, an intermediate of Formula IX, made as described in Schemes F, can be reacted with a reagent of Formula XVIII, where the composition of C is as described under Formula Ia and Ib, to yield a styrene intermediate of Formula XIX. A reagent of Formula XVIII can be derived from a variety of commercially available intermediates or can readily be made by one skilled in the art. A styrene intermediate of Formula XIX can be treated with an expoxidizing agent, such as sodium chlorite in the presence of 4-phenylpyridine-N-oxide, with or without a chiral catalyst such as, (1R,2R)-(−)-[1,2-cyclohexanediamino-N,N'-bis(3,5-di-t-butyl-salicylidene)]manganese (III) chloride, (R,R-MnCl (salen)), to obtain an oxirane intermediate of Formula XX. Treatment of the oxirane intermediate of Formula XX with an agent such as NaN₃, in the presence of a Lewis acid such as ethylaluminum dichloride, yields the azide intermediate of Formula XXI. Reduction of the azide intermediate of Formula XXI can be achieved over palladium on charcoal in the presence of H₂ gas to generate the advanced intermediate of Formula XXII. An intermediate of Formula XXII is embodied by the intermediate of Formula VIa/b which is a key intermediate on route to the synthesis of compounds of Formula Ia and Ib.

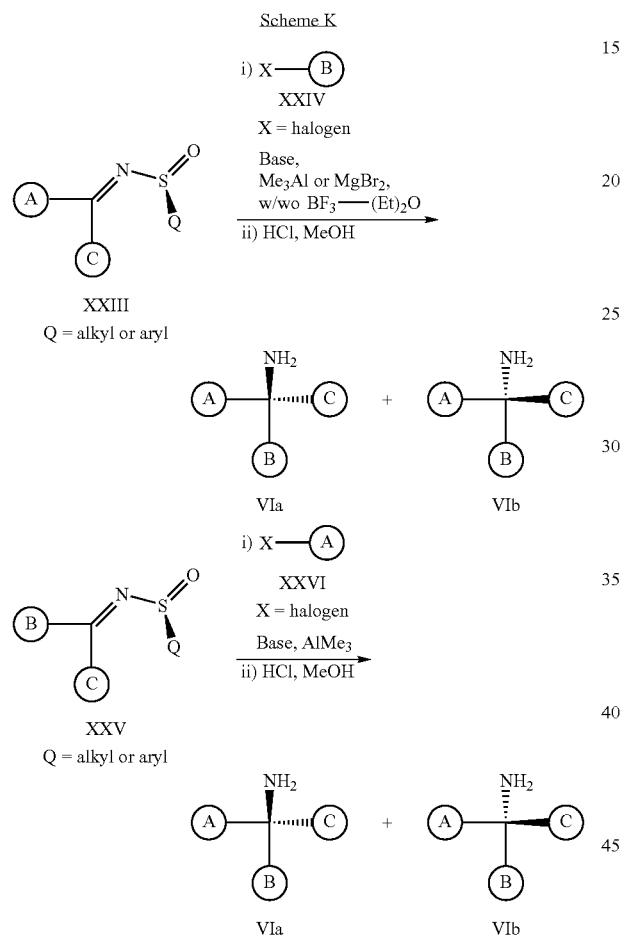

As illustrated in Scheme K, by applications of routes described in Schemes A, B, C and E for the synthesis of an intermediate of Formula VII, one skilled in the art can make intermediates of Formula XXIII and XXV, where the definition of A, B and C are as defined for Formula Ia and Ib. An intermediate of Formula XXIII can be reacted with an intermediate of Formula XXIV, where X is a halogen, such as bromine, iodine or chlorine, and the definition of C is as described for Formula Ia and Ib, in the presence of a base, such as n-butyl lithium or tert-butyl lithium, along with a metalating agent such as, (CH₃)₃Al or MgBr₂, followed by hydrolysis of the sulfinamide, to yield the intermediate of Formula VIa and VIb, which is a key intermediate on route to compounds of Formula Ia and Ib. An intermediate of Formula XXV can be reacted with an intermediate of Formula XXVI, where X is a halogen, such as bromine, iodine or chlorine, and the definition of A is as described for Formula Ia and Ib, in the presence of a base, such as n-butyl lithium or tert-butyl lithium, along with a chelating agent such as, (CH₃)₃Al, followed by hydrolysis of the sulfinamide, to yield the intermediate of Formula VIa and VIb, which is a key intermediate on route to compounds of Formula Ia and Ib.

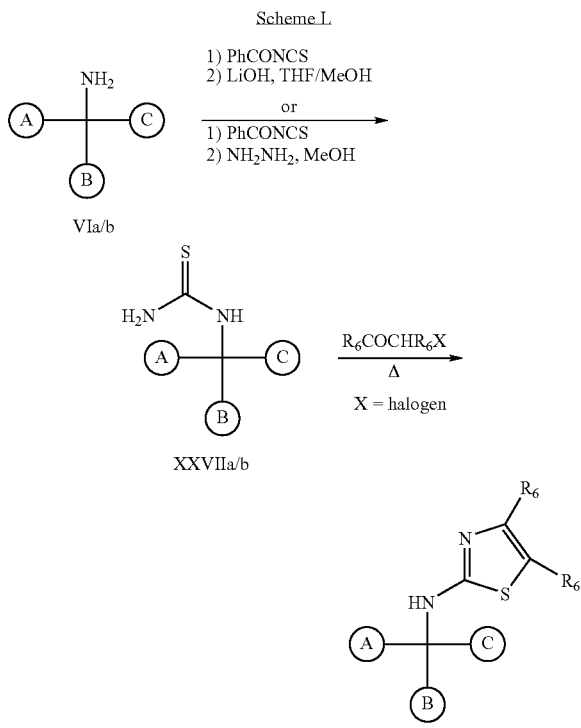

As illustrated in Scheme E, an advanced intermediate of Formula VIa/b can be treated with benzoyl isothiocyanate, followed by a base, such as LiOH or hydrazine, in MeOH/THF or MeOH, to yield the thiourea intermediate of Formula XXVIIa/b. Treatment of the thiourea intermediate of Formula XXVIIa/b, with a reagent of Formula R₆COCHR₆X, where R₆ is as described for Formula Ia and Ib, and X can be a halogen, such as bromine, chlorine or iodine, followed by heating, yields a compound of Formula XVIIIa/b, which is a compound of Formula Ia and Ib.

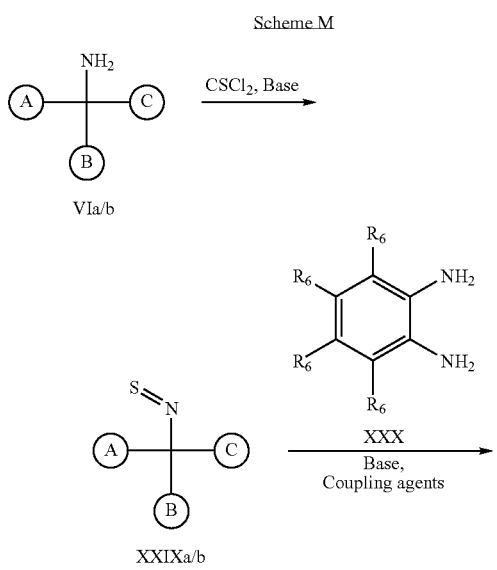

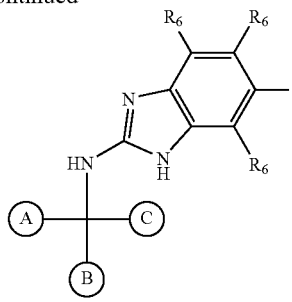

XXXIa/b

As illustrated in Scheme M, an advanced intermediate of Formula VIa/b can be treated with $CSCl_2$ and a base, such as $NaHCO_3$, to yield an isothiocyanate intermediate of Formula XXIXa/b. The isothiocyanate intermediate of Formula XXIXa/b can be reacted with a benzene-1,2-diamine reagent of Formula XXX, where $R_6$ is as described for Formula Ia and Ib, in the presence of a coupling agent, such as EDCI, DCC or other agents known to one skilled in the art for facilitating amide bond formation, to yield a compound of Formula XXXIa/b, which is a compound of Formula Ia and Ib.

Scheme N

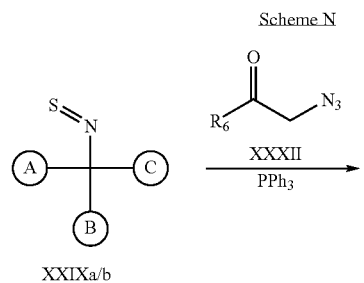

XXIXa/b

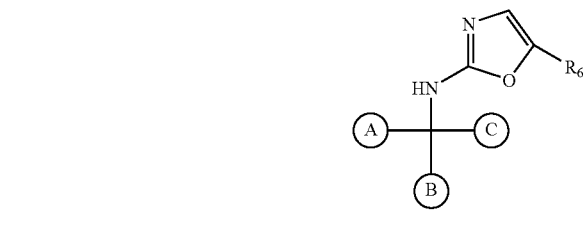

XXXIIIa/b

As illustrated in Scheme N, an advanced intermediate of Formula XXIXa/b can be treated with a 1-azidopropan-2-one reagent of Formula XXXII, where $R_6$ is as described for Formula Ia and Ib, in the presence of $PPh_3$, to yield a compound of Formula XXXIIIa/b, which is a compound of Formula Ia and Ib.

Scheme O

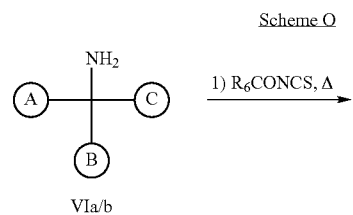

VIa/b

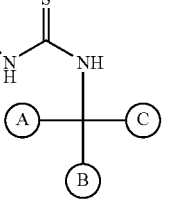 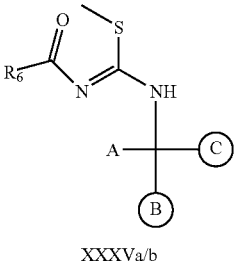

XXXIVa/b    XXXVa/b

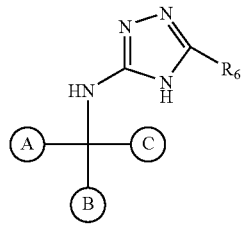

XXXVIa/b

As illustrated in Scheme O, an advanced intermediate of Formula VIa/b can be treated with an isothiocyanate of Formula $R_6CONCS$, where $R_6$ is as defined under Formula Ia and Ib, with heating, to generate an intermediate of Formula XXXIVa/b. An intermediate of Formula XXXIVa/b can be treated with a alkylhalide, such as $CH_3I$, to generate an thioether intermediate of Formula XXXVa/b. An intermediate of Formula XXXVa/b can be treated with $AgNO_3$, along with a base, such as triethyl amine (TEA), followed by hydrazine and heating, to generate a compound of Formula XXXVIa/b, which is a compound of Formula Ia and Ib.

Scheme P

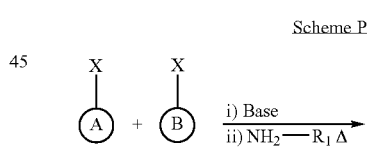

XXXVII

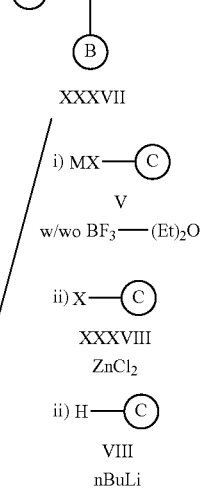

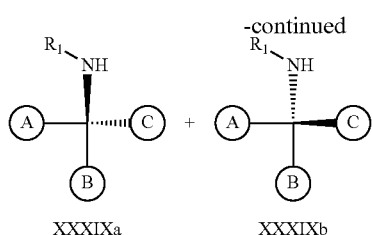

XXXIXa  XXXIXb

As illustrated in Schemes P, A, B, C and E, a substituted reagent of Formula II, wherein the composition of A is as described under Formula Ia & Ib, with the requirement that at least one of the substituents (X) attached to the reagent of Formula II is a halogen, such as Bromine, Chlorine or Iodine or a nitrile group, can be combined with a reagent of Formula III, wherein the composition of B is as described under Formula Ia & Ib, with the requirement that at least one of the substituents (X) attached to the reagent of Formula III is a halogen, such as Bromine, Chlorine or Iodine or a nitrile group, followed by treatment with a base, such as nBuLi, followed by treatment with a reagent of Formula $NH_2$—$R_1$, where the definition of $R_1$ is as described under Formula Ia and Ib, to yield the intermediate of Formula XXXVII. Reagents of Formula $NH_2$—$R_1$, can readily be made by one skilled in the art or are readily available from commercial sources. To the intermediate of Formula XXXVII can be added a metal halide reagent, such as an alkyl lithium complex, a magnesium bromide or a magnesium chloride complex, or a zinc bromide or zinc chloride complex, of Formula V, where the metal halide complex is made from a reagent wherein the composition of C is as described under Formula Ia & Ib, with or without a Lewis acid, such as $BF_3$■$(Et)_2O$, to yield compounds of Formula XXXIXa and XXXIXb, which are compounds of Formula Ia and Ib. Alternatively, an intermediate of Formula XXXVII can be treated with a reactive anion species of Formula XXXVIII, where X represents a leaving group such as, but not limited to, trimethylsilyl and C represents a stabilized anion species, wherein the composition of C is a definition under Formula Ia and Ib, along with a metal species, such as $ZnCl_2$, to yield to yield compounds of Formula XXXIXa and XXXIXb, which are compounds of Formula Ia and Ib. Alternatively, to an intermediate of Formula XXXVII can be added a base, such as LDA or nBuLi, with or with out the addition of $TiCl(iOPr)_3$, and a reagent of Formula VIII, wherein the composition of C is as described under Formula Ia & Ib, with the requirement that at least one of the substituents attached to the reagent of Formula VIII is a hydrogen that can be deprotonated to yield a reactive anion species, to yield compounds of Formula XXXIXa and XXXIXb, which are compounds of Formula Ia and Ib.

The above schemes give an overview of several general processes for the synthesis of compounds of Formula Ia and Ib. Additional compounds of Formula Ia and Ib can readily be made by one of ordinary skill in the art by further modification of functional groups at positions A, B, C or $R_1$ of compounds of Formula Ia and Ib made by the processes illustrated in the included schemes. The Examples that follow described numerous applications of the routes described in Schemes A-O as well as additional routes to compounds of Formula Ia and Ib achieved through modification of functional groups at positions A, B, C or $R_1$ of compounds of Formula Ia and Ib.

Utility

Compounds of the present invention have been shown to inhibit cholesterol ester transfer protein (CETP) by greater than 30% at two different concentrations of less than 100 uM, preferably with a potency less than 5 uM, more preferably with a potency less than 500 nM. Compounds of the invention were also found to inhibit cholesterol ester transfer activity using in vitro assays that contained up to 96% plasma, and to inhibit plasma cholesterol ester transfer activity in animals. Accordingly, compounds within the scope of the present invention inhibit the CETP protein, and as such are expected to be useful in the treatment, prevention, and/or slowing of the progression of various disorders.

For example, the compounds of the present invention, their prodrugs and the salts of such compounds and prodrugs can be adapted to therapeutic use as agents that inhibit cholesterol ester transfer protein activity in mammals, particularly humans. Thus, the compounds of the present invention are expected to be useful in elevating plasma HDL cholesterol, its associated components, and the functions performed by them in mammals, particularly humans. By virtue of their expected activity, these agents are also expected to reduce VLDL cholesterol, LDL cholesterol and their associated components in mammals, particularly humans. Hence, these compounds are expected to be useful for the treatment and correction of the various dyslipidemias observed to be associated with the development and incidence of atherosclerosis and cardiovascular disease, including hypoalphalipoproteinemia, hyperbetalipoproteinemia, hypertriglyceridemia, and familial-hypercholesterolemia (see U.S. Pat. No. 6,489,478, incorporated herein by reference).

Further, introduction of a functional CETP gene into an animal lacking CETP (mouse) results in reduced HDL levels (Agellon, L. B. et al., J. Biol. Chem., 266:10796-10801 (1991) and, increased susceptibility to atherosclerosis. (Marotti, K. R. et al., Nature, 364:73-75 (1993)). Also, inhibition of CETP activity with an inhibitory antibody raises HDL-cholesterol in hamster (Evans, G. F. et al., J. Lipid Research, 35:1634-1645 (1994)) and rabbit (Whitlock, M. E. et al., J. Clin. Invest., 84:129-137 (1989)). Suppression of increased plasma CETP by intravenous injection with antisense oligodeoxynucleotides against CETP mRNA reduced atherosclerosis in cholesterol-fed rabbits (Sugano, M. et al., J. Biol. Chem., 273:5033-5036 (1998)). Importantly, human subjects deficient in plasma CETP, due to a genetic mutation possess markedly elevated plasma HDL-cholesterol levels and apolipoprotein A-I, the major apoprotein component of HDL. In addition, most demonstrate markedly decreased plasma LDL cholesterol and apolipoprotein B (the major apolipoprotein component of LDL. (Inazu, A. et al., N. Engl. J. Med., 323: 1234-1238 (1990).)

Given the negative correlation between the levels of HDL cholesterol and HDL associated lipoproteins, and the positive correlation between triglycerides, LDL cholesterol, and their associated apolipoproteins in blood with the development of cardiovascular, cerebral vascular and peripheral vascular diseases, the compounds of the present invention, their prodrugs and the salts of such compounds and prodrugs, by virtue of their pharmacologic action, are expected to be useful for the treatment, prevention, the arrestment and/or regression of atherosclerosis and its associated disease states. These include cardiovascular disorders (e.g., angina, cardiac ischemia and myocardial infarction), complications due to cardiovascular disease therapies (e.g., reperfusion injury and angioplastic restenosis), hypertension, stroke, and atherosclerosis associated with organ transplantation.

Because of the beneficial effects widely associated with elevated HDL levels, an agent which inhibits CETP activity in humans, by virtue of its HDL increasing ability, also provides valuable avenues for therapy in a number of other disease areas as well.

Accordingly, given the ability of the compounds of the present invention, their prodrugs and the salts of such compounds and prodrugs to alter lipoprotein composition via inhibition of cholesterol ester transfer, they are expected to be useful in the treatment, prevention and/or slowing of the progression of vascular complications associated with diabetes. Hyperlipidemia is present in most subjects with diabetes mellitus (Howard, B. V., J. Lipid Res., 28:613 (1987)). Even in the presence of normal lipid levels, diabetic subjects experience a greater risk of cardiovascular disease (Kannel, W. B. et al., Diabetes Care, 2:120 (1979)). CETP-mediated cholesteryl ester transfer is known to be abnormally increased in both insulin-dependent (Bagdade, J. D. et al., Eur. J. Clin. Invest., 21:161 (1991)) and non-insulin dependent diabetes (Bagdade. J. D. et al., Atherosclerosis 104:69 (1993)). It has been suggested that the abnormal increase in cholesterol transfer results in changes in lipoprotein composition, particularly for VLDL and LDL, that are more atherogenic (Bagdade, J. D. et al., J. Lipid Res., 36:759 (1995)). These changes would not necessarily be observed during routine lipid screening. Thus, it is expected that the present invention will be useful in reducing the risk of vascular complications as a result of the diabetic condition.

In addition, the compounds of the present invention are expected to be useful in the treatment of obesity. In both humans (Radeau, T. et al., J. Lipid Research, 36(12):2552-2561 (1995)) and nonhuman primates (Quinet, E. et al., J. Clin. Inv., 87(5):1559-1566 (1991)) mRNA for CETP is expressed at high levels in adipose tissue. The adipose message increases with fat feeding (Martin, L. J. et al., J. Lipid Research, 34(3):437-446 (1993)), and is translated into functional transfer protein and through secretion contributes significantly to plasma CETP levels. In human adipocytes the bulk of cholesterol is provided by plasma LDL and HDL (Fong, B. S. et al., Biochimica et Biophysica Acta, 1004(1): 53-60 (1989)). The uptake of HDL cholesteryl ester is dependent in large part on CETP (Benoist, F. et al., J. Biol. Chem., 272(38):23572-23577 (1997)). This ability of CETP to stimulate HDL cholesteryl uptake, coupled with the enhanced binding of HDL to adipocytes in obese subjects (Jimenez, J. G. et al., Int. J. Obesity, 13(5):699-709 (1989)), suggests a role for CETP, not only in generating the low HDL phenotype for these subjects, but in the development of obesity itself by promoting cholesterol accumulation. Inhibitors of CETP activity that block this process therefore serve as useful adjuvants to dietary therapy in causing weight reduction.

CETP inhibitors are useful in the treatment of inflammation due to Gram-negative sepsis and septic shock. For example, the systemic toxicity of Gram-negative sepsis is in large part due to endotoxin, a lipopolysaccharide (LPS) released from the outer surface of the bacteria, which causes an extensive inflammatory response. Lipopolysaccharide can form complexes with lipoproteins (Ulevitch, R. J. et al., J. Clin. Invest., 67:827-837 (1981)). In vitro studies have demonstrated that binding of LPS to HDL substantially reduces the production and release of mediators of inflammation (Ulevitch, R. J. et al., J. Clin. Invest., 62:1313-1324 (1978)). In vivo studies show that transgenic mice expressing human apo-Al and elevated HDL levels are protected from septic shock (Levine, D. M. et al., Proc. Natl. Acad. Sci., 90:12040-12044 (1993)). Importantly, administration of reconstituted HDL to humans challenged with endotoxin resulted in a decreased inflammatory response (Pajkrt, D. et al., J. Exp. Med., 184:1601-1608 (1996)). The CETP inhibitors, by virtue of the fact that they raise HDL levels, attenuate the development of inflammation and septic shock.

Thus, the present invention provides methods for the prevention or treatment of one or more of the aforementioned disorders, comprising the step of administering to a subject in need thereof an effective amount of at least one compound of the present invention, its prodrug and the salt of such compound and prodrugs. Other therapeutic agents such as those described below may be employed with the inventive compounds in the present methods. In the methods of the present invention, such other therapeutic agent(s) may be administered prior to, simultaneously with or following the administration of the compound(s) of the present invention.

In addition, the compounds of the present invention are expected to be useful in the inhibition of remnant lipoprotein production (Okamoto et al., WO 2005/030185).

CETP Assay

CETP inhibition can be determined at a specific concentration of test compound in any of the assays described herein. Potencies are more generally calculated by determining $IC_{50}$ values using these assays.

CETP Scintillation Proximity Assay

Compounds of the present invention inhibit CETP-dependent cholesterol ester transfer from HDL to LDL as described here. Dilutions of compounds in DMSO (1 µl) are added to BD plates (#353232). To this is added 20 µl of a mixture containing $^3$H-CE/HDL (0.15 µl), biotinylated LDL (~5 µg protein/ml final concentration) and unlabeled HDL (16 µg/ml final concentration) in a buffer containing 50 mM HEPES, pH 7.4, 150 mM NaCl and 0.05% sodium azide. Reactions are initiated by the addition of 10 µl of buffer containing purified human recombinant CETP, and incubated at 37° C. At the end of the reaction, 60 µl of LEADseeker beads (#RPNQ0261, 2 mg/ml in buffer containing 1 mg/ml BSA and 0.05 mg protein/ml HDL) are added, the plates are covered and subsequently read. Background activity is determined in a set of wells that receive buffer but no CETP. The level of inhibition is determined by comparing the readings in wells that contain compound to the readings in control wells containing DMSO.

Plasma Cholesterol Ester Transfer Assay

Compounds of the present invention were also tested for the ability to inhibit cholesterol ester transfer activity in plasma as described here. Dilutions of compounds in DMSO (1 µl) are added to 384-well polypropylene plates. To each well is added 29 ul of human plasma containing 0.15 ul $^3$H-CE/HDL. The reaction is incubated at 37° C. and terminated by the addition of 6 ul of precipitation reagent (2:1:1 of water:1M $MgCl_2$:2% Dextralip 50), to precipitate LDL and VLDL. After 10 minutes at room temperature, 15 µl of the reaction is transferred to filter plates (Millipore, #MHVBN45) pre-wetted with 100 ul phosphate buffered saline. The plates are centrifuged (1800 rpm) at room temperature for 10 minutes, and 50 ul Microscint-20 is added. The plates are then sealed and read. Background activity is determined with plasma samples incubated at 4° C. The level of inhibition is determined by comparing the readings in wells that contain compound to the readings in control wells containing DMSO.

In Vivo Cholesterol Ester Transfer Activity

Compounds of the present invention have further been shown to inhibit plasma cholesterol ester transfer activity in mice that are dually transgenic for human CETP and apoB-100 (hCETP/apoB-100) as described here.

Mice (commercially available from Taconic) are fasted for two hours and plasma obtained before dosing. The animals are then dosed with vehicle or compound (p.o.). The vehicle may vary as needed to dissolve the compound, while at the same time having no, or minimal, activity on plasma cholesterol ester transfer activity. Plasma samples are collected again at various times after dosing and assayed for cholesterol ester transfer activity.

To measure CETP activity in plasma samples obtained from animals treated with compounds, the following methodology is employed. To a sample of plasma (typically between 9 and 30 ul), 1 µl of diluted $^3$H-CE/HDL is added (0.15 µl $^3$H-CE/HDL and 0.85 ul assay buffer) to label endogenous HDL. Assay buffer contains 50 mM HEPES, pH 7.4, and 150 mM NaCl. The reaction is incubated at 37° C., and LDL/VLDL precipitated with 3 µl of precipitation reagent (4:1:1 of water:0.5M $MgCl_2$:1% Dextralip 50). The tubes are centrifuged for 15-30 minutes at 10,000×g (10° C.), the supernatants discarded, and the pellets dissolved in 140 µl of 2% SDS. Half of the SDS solution (70 µl) is transferred to scintillation tubes, scintillation fluid is added, and radioactivity measured in a scintillation counter. Background activity is determined for each sample with an aliquot incubated at 4° C. Plasma cholesterol ester transfer inhibition is calculated by comparing the transfer activity in a plasma sample obtained after dosing to the transfer activity in the plasma sample obtained from the same animal before dosing. All data are background subtracted.

The in vivo assay described above (with appropriate modifications within the skill in the art) may be used to determine the activity of other lipid or triglyceride controlling agents as well as the compounds of this invention. The assays set forth above also provide a means whereby the activities of the compounds of the present invention, their prodrugs and the salts of such compounds and prodrugs (or the other agents described herein) can be compared to each other and with the activities of other known compounds. The results of these comparisons are useful for determining dosage levels in mammals, including humans, for the treatment of the above described disease/conditions.

HDL Cholesterol Protocol

The ability of CETP inhibitors to increase HDL cholesterol (HDL-C) can be shown in mammalian subjects via methods known to one of ordinary skill in the art (see Evans, G. F. et al., J. Lipid Research, 35:1634-1645 (1994)). For example, compounds of the present invention have been shown to be efficacious in the elevation of HDL-C in golden syrian hamsters. The hamsters are fed a moderate fat diet containing variable amounts of coconut oil and cholesterol to alter their HDL-C and LDL-C levels. The moderately fat-fed hamsters are fasted and bled to determine baseline HDL-C levels, then dosed orally with compound for three days in an appropriate vehicle. The animals are fasted and bled again on the third day of dosing, and the results are compared to the baseline HDL-C levels. The compounds increase HDL-C in this model in a dose-dependent manner, demonstrating their usefulness to alter plasma lipids.

Antiobesity Protocol

The ability of CETP inhibitors to cause weight loss can be assessed in obese human subjects with body mass index (BMI)$\geq$30 kg/$m_2$. Doses of inhibitor are administered sufficient to result in an increase of $\geq$25% in HDL cholesterol levels. BMI and body fat distribution, defined as waist (W) to hip (H) ratio (WHR), are monitored during the course of the 3-6 month studies, and the results for treatment groups compared to those receiving placebo.

The above assays can of course be varied by those skilled in the art.

The present invention also provides pharmaceutical compositions comprising at least one of the compounds of the present invention, their prodrugs and the salts of such compounds and prodrugs capable of preventing, treating, and/or slowing the progression of one or more of the aforementioned disorders in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the present invention may be administered by any suitable means, for example, orally, such as in the form of tablets, capsules, granules or powders; sublingually; bucally; parenterally, such as by subcutaneous, intravenous, intramuscular, or intrastemal injection or infusion techniques (e.g., as sterile injectable aqueous or non aqueous solutions or suspensions); nasally such as by inhalation spray; topically, such as in the form of a cream or ointment; or rectally such as in the form of suppositories; in dosage unit formulations containing non toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of present invention may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non toxic, parenterally acceptable diluents or solvents, such as mannitol, 1,3 butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.001 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The compounds of the present invention may be employed alone or in combination with each other and/or other suitable therapeutic agents useful in the treatment of the aforementioned disorders or other disorders.

For example, they may be used in combination with a HMG-CoA reductase inhibitor, a cholesterol synthesis inhibitor, a cholesterol absorption inhibitor, another CETP inhibitor, a MTP/Apo B secretion inhibitor, a PPAR modulator and other cholesterol lowering agents such as a fibrate, niacin, an ion-exchange resin, an antioxidant, an ACAT inhibitor, and a bile acid sequestrant. Other pharmaceutical agents would also include the following: a bile acid reuptake inhibitor, an ileal bile acid transporter inhibitor, an ACC inhibitor, an antihypertensive (such as NORVASC®), a selective estrogen receptor modulator, a selective androgen receptor modulator, an antibiotic, an antidiabetic (such as metformin, a PPARγ activator, a sulfonylurea, insulin, an aldose reductase inhibitor (ARI) and a sorbitol dehydrogenase inhibitor (SDI)), aspirin (acetylsalicylic acid) and niacin and combinations thereof.

Any HMG-CoA reductase inhibitor may be used in the combination aspect of this invention. The term HMG-CoA reductase inhibitor refers to compounds which inhibit the bioconversion of hydroxymethylglutaryl-coenzyme A to mevalonic acid catalyzed by the enzyme HMG-CoA reductase. Such inhibition is readily determined by those skilled in the art according to standard assays (e.g., Meth. Enzymol., 71:455-509 (1981) and references cited therein). A variety of these compounds are described and referenced below however other HMG-CoA reductase inhibitors will be known to those skilled in the art. U.S. Pat. No. 4,231,938 (the disclosure of which is hereby incorporated by reference) discloses certain compounds isolated after cultivation of a microorganism belonging to the genus *Aspergillus*, such as Iovastatin. Also, U.S. Pat. No. 4,444,784 (the disclosure of which is hereby incorporated by reference) discloses synthetic derivatives of the aforementioned compounds, such as simvastatin. Also, U.S. Pat. No. 4,739,073 (the disclosure of which is incorporated by reference) discloses certain substituted indoles, such as fluvastatin. Also, U.S. Pat. No. 4,346,227 (the disclosure of which is incorporated by reference) discloses ML-236B derivatives, such as pravastatin. Also, EP-491226A (the disclosure of which is incorporated by reference) discloses certain pyridyldihydroxyheptenoic acids, such as cerivastatin. In addition, U.S. Pat. No. 5,273,995 (the disclosure of which is incorporated by reference) discloses certain 6-[2-(substituted-pyrrol-1-yl)-alkyl]pyran-2-ones such as atorvastatin and any pharmaceutically acceptable form thereof (i.e. LIPITOR®). Additional HMG-CoA reductase inhibitors include rosuvastatin and pitavastatin. Statins also include such compounds as rosuvastatin disclosed in U.S. Pat. No. RE37,314 E, pitavastatin disclosed in EP 304063 B1 and U.S. Pat. No. 5,011,930; mevastatin, disclosed in U.S. Pat. No. 3,983,140; velostatin, disclosed in U.S. Pat. Nos. 4,448,784 and 4,450,171; compactin, disclosed in U.S. Pat. No. 4,804,770; dalvastatin, disclosed in European Patent Application Publication No. 738510 A2; fluindostatin, disclosed in European Patent Application Publication No. 363934 A1; and dihydrocompactin, disclosed in U.S. Pat. No. 4,450,171.

Any PPAR modulator may be used In the combination aspect of this invention. The term PPAR modulator refers to compounds which modulate peroxisome proliferator activator receptor (PPAR) activity in mammals, particularly humans. Such modulation is readily determined by those skilled in the art according to standard assays known in the literature. It is believed that such compounds, by modulating the PPAR receptor, regulate transcription of key genes involved in lipid and glucose metabolism such as those in fatty acid oxidation and also those involved in high density lipoprotein (HDL) assembly (for example, apolipoprotein AI gene transcription), accordingly reducing whole body fat and increasing HDL cholesterol. By virtue of their activity, these compounds also reduce plasma levels of triglycerides, VLDL cholesterol, LDL cholesterol and their associated components such as apolipoprotein B in mammals, particularly humans, as welt as increasing HDL cholesterol and apolipoprotein AI. Hence, these compounds are useful for the treatment and correction of the various dyslipidemias observed to be associated with the development and incidence of atherosclerosis and cardiovascular disease, including hypoalphalipoproteinemia and hypertriglyceridemia. A variety of these compounds are described and referenced below, however, others will be known to those skilled in the art. International Publication Nos. WO 02/064549 and WO 02/064130, U.S. patent application Ser. No. 10/720,942, and U.S. patent application 60/552,114 disclose certain compounds which are PPARα activators.

Any other PPAR modulator may be used in the combination aspect of this invention. In particular, modulators of PPARβ and/or PPARγ may be useful in combination with compounds of the present invention. An example PPAR inhibitor is described in U.S. 2003/0225158 as {5-Methoxy-2-methyl-4-[4-(4-trifluoromethyt-benzy]oxy)-benzylsulfany]-phenoxy}-acetic acid.

Any MTP/Apo B (microsomal triglyceride transfer protein and or apolipoprotein B) secretion inhibitor may be used in the combination aspect of this invention. The term MTP/Apo B secretion inhibitor refers to compounds which inhibit the secretion of triglycerides, cholesteryl ester, and phospholipids. Such inhibition is readily determined by those skilled in the art according to standard assays (e.g., Wetterau, J. R., Science, 258:999 (1992)). A variety of these compounds are described and referenced below however other MTP/Apo B secretion inhibitors will be known to those skilled in the art, including implitapride (Bayer) and additional compounds such as those disclosed in WO 96/40640 and WO 98/23593, (two exemplary publications). For example, the following MTP/Apo B secretion inhibitors are particularly useful: 4'-trifluoromethyl-biphenyl-2-carboxylic acid [2-(1H-[1,2,4,]triazol-3-ylmethyl)-1,2,3,4-tetrahydro-isoquinolin-6-yl]-amide; 4'-trifluoromethyl-biphenyl-2-carboxylic acid [2-(2-acetylamino-ethyl)-1,2,3,4-tetrahydro-isoquinolin-6-yl]-amide; (2-{6-[(4'-trifluoromethyl-biphenyl-2-carbonyl) -amino]-3, 4-dihydro-1H-isoquinolin-2-yl}-ethyl)-carbamic acid methyl ester; 4'-trifluoromethyl-biphenyl-2-carboxylic acid [2-(1H-imidazol-2-ylmethyl)-1,2,3,4-tetrahydro-isoquinolin-6-yl]-amide; 4'-trifluoromethyl-biphenyl-2-carboxylic acid [2-(2,2-diphenyl-ethyl)-1,2,3,4-tetrahydro-isoquinolin-6-yl]-amide; 4'-trifluoromethyl-biphenyl-2-carboxylic acid [2-(2-ethoxy-ethyl)-1,2,3,4-tetrahydro-isoquinolin-6-yl]-amide; (S)-N-{2-[benzyl(methyl)amino]-2-oxo-1-phenylethyl}-1-methyl-5-[4'-(trifluoromethyl)[1,1'-biphenyl]-2-carboxamide]-1H-indole-2-carboxamide; (S)-2-[(4'-trifluoromethyl-biphenyl-2-carbonyl)-amino]-quinoline-6-carboxylic acid (pentylcarbamoyl-phenyl-methyl)-amide; 1H-indole-2-carboxamide, 1-methyl-N-[(1S)-2-[methyl (phenylmethyl)amino]-2-oxo-1-phenylethyl]-5-[[[4'-(trifluoromethyl)[1,1'-biphenyl]-2-yl]carbonyl]amino]; and N-[(1S)-2-(benzylmethylamino)-2-oxo-1-phenylethyl]-1-methyl-5-[[[4'-(trifluoromethyl)[1,1'-biphenyl]-2-yl]carbonyl]amino]-1H-indole-2-carboxamide.

Any HMG-CoA synthase inhibitor may be used in the combination aspect of this invention. The term HMG-CoA synthase inhibitor refers to compounds which inhibit the biosynthesis of hydroxymethylglutaryl-coenzyme A from acetyl-coenzyme A and acetoacetyl-coenzyme A, catalyzed by the enzyme HMG-CoA synthase. Such inhibition is readily determined by those skilled in the art according to standard assays (Meth. Enzymol., 35:155-160 (1975); Meth. Enzymol., 110:19-26 (1985) and references cited therein). A variety of these compounds are described and referenced below, however other HMG-CoA synthase inhibitors will be known to those skilled in the art. U.S. Pat. No. 5,120,729 discloses certain beta-lactam derivatives. U.S. Pat. No. 5,064, 856 discloses certain spiro-lactone derivatives prepared by culturing a microorganism (MF5253). U.S. Pat. No. 4,847, 271 discloses certain oxetane compounds such as 11-(3-hydroxymethyl-4-oxo-2-oxetayl)-3,5,7-trimethyl-2,4-undecadienoic acid derivatives.

Any compound that decreases HMG-CoA reductase gene expression may be used in the combination aspect of this invention. These agents may be HMG-CoA reductase transcription inhibitors that block the transcription of DNA or translation inhibitors that prevent or decrease translation of mRNA coding for HMG-CoA reductase into protein. Such compounds may either affect transcription or translation directly, or may be biotransformed to compounds that have the aforementioned activities by one or more enzymes in the cholesterol biosynthetic cascade or may lead to the accumulation of an isoprene metabolite that has the aforementioned activities. Such compounds may cause this effect by decreasing levels of SREBP (sterol receptor binding protein) by inhibiting the activity of site-1 protease (SIP) or agonizing the oxysterol receptor or SCAP. Such regulation is readily determined by those skilled in the art according to standard assays (Meth. Enzymol., 110:9-19 (1985)). Several compounds are described and referenced below, however other inhibitors of HMG-CoA reductase gene expression will be known to those skilled in the art. U.S. Pat. No. 5,041,432 discloses certain 15-substituted lanosterol derivatives. Other oxygenated sterols that suppress synthesis of HMG-CoA reductase are discussed by E. I. Mercer (Prog. Lip. Res., 32:357-416 (1993)).

Any compound having activity as a CETP inhibitor can serve as the second compound in the combination therapy aspect of the present invention. The term CETP inhibitor refers to compounds that inhibit the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). A variety of CETP inhibitors will be known to those skilled in the art, for example, those disclosed in U.S. Pat. Nos. 6,140,343 and 6,197,786. CETP inhibitors disclosed in these patents include compounds, such as [2R,4S] 4-[(3,5-bis-trifluoromethylbenzyl)methoxycarbonylamino]-2-ethyl-6-trifluoromethyl-3,4-dihydro-2H-quinoline-1-carboxylic acid ethyl ester (torcetrapib). CETP inhibitors are also described in U.S. Pat. No. 6,723,752, which includes a number of CETP inhibitors including (2R)-3-{[3-(4-chloro-3-ethyl-phenoxy)-phenyl]-[[3-(1,1,2,2-tetrafluoroethoxy) phenyl]methyl]amino}-1,1,1-trifluoro-2-propanol. Moreover, CETP inhibitors included herein are also described in U.S. patent application Ser. No. 10/807,838 and PCT Publication No. WO 2006/090250. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in J. Antibiot., 49(8):815-816 (1996), and Bioorg. Med. Chem. Lett., 6:1951-1954 (1996), respectively.

Any squalene synthetase inhibitor may be used in the combination aspect of this invention. The term squalene synthetase inhibitor refers to compounds which inhibit the condensation of 2 molecules of farnesylpyrophosphate to form squalene, catalyzed by the enzyme squalene synthetase. Such inhibition is readily determined by those skilled in the art according to standard assays (Meth. Enzymol., 15:393-454 (1969) and Meth. Enzymol., 110:359-373 (1985) and references contained therein). A variety of these compounds are described in and referenced below however other squalene synthetase inhibitors will be known to those skilled in the art. U.S. Pat. No. 5,026,554 discloses fermentation products of the microorganism MF5465 (ATCC 74011) including zaragozic acid. A summary of other patented squalene synthetase inhibitors has been compiled (Curr. Op. Ther. Patents, 861-864 (1993)).

Any squalene epoxidase inhibitor may be used in the combination aspect of this invention. The term squalene epoxidase inhibitor refers to compounds which inhibit the bioconversion of squalene and molecular oxygen into squalene-2,3-epoxide, catalyzed by the enzyme squalene epoxidase. Such inhibition is readily determined by those skilled in the art according to standard assays (Biochim. Biophys. Acta, 794: 466-471 (1984)). A variety of these compounds are described and referenced below, however other squalene epoxidase inhibitors will be known to those skilled in the art. U.S. Pat. Nos. 5,011,859 and 5,064,864 disclose certain fluoro analogs of squalene. EP publication 395,768 A discloses certain substituted allylamine derivatives. PCT publication WO 93/12069 A discloses certain amino alcohol derivatives. U.S. Pat. No. 5,051,534 discloses certain cyclopropyloxy-squalene derivatives.

Any squalene cyclase inhibitor may be used as the second component in the combination aspect of this invention. The term squalene cyclase inhibitor refers to compounds which inhibit the bioconversion of squalene-2,3-epoxide to lanosterol, catalyzed by the enzyme squalene cyclase. Such inhibition is readily determined by those skilled in the art according to standard assays (FEBS Lett., 244:347-350 (1989)). In addition, the compounds described and referenced below are squalene cyclase inhibitors, however other squalene cyclase inhibitors will also be known to those skilled in the art. PCT publication WO 94/10150 discloses certain 1,2,3,5,6,7,8,8a-octahydro-5,5,8(beta)-trimethyl-6-isoquinolineamine derivatives, such as N-trifluoroacetyl-1,2,3,5,6,7,8,8a-octahydro-2-allyl-5,5,8(beta)-trimethyl-6(beta)-isoquinolineamine. French patent publication 2697250 discloses certain beta,beta-dimethyl-4-piperidine ethanol derivatives such as 1-(1,5,9-trimethyldecyl)-beta,beta-dimethyl-4-piperidineethanol.

Any combined squalene epoxidase/squalene cyclase inhibitor may be used as the second component in the combination aspect of this invention. The term combined squalene epoxidase/squalene cyclase inhibitor refers to compounds that inhibit the bioconversion of squalene to lanosterol via a squalene-2,3-epoxide intermediate. In some assays it is not possible to distinguish between squalene epoxidase inhibitors and squalene cyclase inhibitors, however, these assays are recognized by those skilled in the art. Thus, inhibition by combined squalene epoxidase/squalene cyclase inhibitors is readily determined by those skilled in art according to the aforementioned standard assays for squalene cyclase or squalene epoxidase inhibitors. A variety of these compounds are described and referenced below, however other squalene epoxidase/squalene cyclase inhibitors will be known to those skilled in the art. U.S. Pat. Nos. 5,084,461 and 5,278,171 disclose certain azadecalin derivatives. EP publication 468,434 discloses certain piperidyl ether and thioether derivatives such as 2-(1-piperidyl)pentyl isopentyl sulfoxide and 2-(1-piperidyl)ethyl ethyl sulfide. PCT publication WO 94/01404 discloses certain acyl-piperidines such as 1-(1-oxopentyl-5-phenylthio)-4-(2-hydroxy-1-methyl)-ethyl)piperidine. U.S. Pat. No. 5,102,915 discloses certain cyclopropyloxy-squalene derivatives.

The compounds of the present invention may also be administered in combination with naturally occurring compounds that act to lower plasma LDL cholesterol levels or raise plasma HDL levels via a pathway distinct from CETP inhibitors. These naturally occurring compounds are commonly called nutraceuticals and include, for example, garlic extract and niacin. Niacin is a particularly attractive secondary agent for combination with a CETP inhibitor as it also raises HDL cholesterol levels. Furthermore, niacin lowers LDL cholesterol and triglycerides. Therefore, a combination of niacin and a CETP inhibitor would not only provide the potential for enhanced HDL-raising efficacy, it would yield a very favorable shift in the overall cardiovascular risk profile by decreasing LDL cholesterol and triglycerides. Niacin is commercially available in various dosage forms. Immediate release niacin may be purchase over-the-counter in pharmacies or health-food stores. A slow-release form of niacin is available and is known as Niaspan. Niacin may also be combined with other therapeutic agents such as iovastatin, an HMG-CoA reductase inhibitor. This combination therapy with iovastatin is known as ADVICOR™ (Kos Pharmaceuticals Inc.). In long term clinical trials, niacin either as monotherapy or in combination with HMG-CoA reductase inhibitors has been shown to reduce cardiovascular events, cardiovascular deaths and all cause mortality.

Any cholesterol absorption inhibitor can be used as an additional component in the combination aspect of the present invention. The term cholesterol absorption inhibition refers to the ability of a compound to prevent cholesterol contained within the lumen of the intestine from entering into the intestinal cells and/or passing from within the intestinal cells into the lymph system and/or into the blood stream. Such cholesterol absorption inhibition activity is readily determined by those skilled in the art according to standard assays (e.g., J. Lipid Res., 34:377-395 (1993)). Cholesterol absorption inhibitors are known to those skilled in the art and are described, for example, in PCT WO 94/00480. An example of a recently approved cholesterol absorption inhibitor is ZETIA™ (ezetimibe) (Schering-Plough/Merck).

Any ACAT inhibitor may be used in the combination therapy aspect of the present invention. The term ACAT inhibitor refers to compounds that inhibit the intracellular esterification of dietary cholesterol by the enzyme acyl CoA: cholesterol acyltransferase. Such inhibition may be determined readily by one of skill in the art according to standard assays, such as the method of Heider et al. described in J. Lipid Research, 24:1127 (1983). A variety of these compounds are known to those skilled in the art, for example, U.S. Pat. No. 5,510,379 discloses certain carboxysulfonates, while WO 96/26948 and WO 96/10559 both disclose urea derivatives having ACAT inhibitory activity. Examples of ACAT inhibitors include compounds such as Avasimibe (Pfizer), CS-505 (Sankyo) and Eflucimibe (Ell Lilly and Pierre Fabre).

A lipase inhibitor may be used in the combination therapy aspect of the present invention. A lipase inhibitor is a compound that inhibits the metabolic cleavage of dietary triglycerides or plasma phospholipids into free fatty acids and the corresponding glycerides (e.g. EL, HL, etc.). Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a glyceride and fatty acid. In the intestine, the resultant free fatty acids and monoglycerides are incorporated into bile acid-phospholipid micelles, which are subsequently absorbed at the level of the brush border of the small intestine. The micelles eventually enter the peripheral circulation as chylomicrons. Such lipase inhibition activity is readily determined by those skilled in the art according to standard assays (e.g., Meth. Enzymol., 286:190-231). Pancreatic lipase mediates the metabolic cleavage of fatty acids from triglycerides at the 1- and 3-carbon positions. The primary site of the metabolism of ingested fats is in the duodenum and proximal jejunum by pancreatic tipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions. Such pancreatic lipase inhibition activity is readily determined by those skilled in the art according to standard assays (e.g., Meth. Enzymol., 286:190-231).

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams et al., Gastroenterology, 92:125 (1987). Such gastric lipase inhibition activity is readily determined by those skilled in the art according to standard assays (e.g., Meth. Enzymol., 286:190-231).

A variety of gastric and/or pancreatic lipase inhibitors are known to one of ordinary skill in the art. Preferred lipase inhibitors are those inhibitors that are selected from the group consisting of lipstatin, tetrahydrolipstatin (orlistat), valilactone, esterastin, ebelactone A, and ebelactone B. The compound tetrahydrolipstatin is especially preferred. The lipase inhibitor, N-3-trifluoromethylphenyl-N'-3-chloro-4'-trifluoromethylphenylurea, and the various urea derivatives related thereto, are disclosed in U.S. Pat. No. 4,405,644. The lipase inhibitor, esteracin, is disclosed in U.S. Pat. Nos. 4,189,438 and 4,242,453. The lipase inhibitor, cyclo-O,O'-[(1,6-hexanediyl)-bis-(iminocarbonyl)]dioxime, and the various bis(iminocarbonyl)dioximes related thereto may be prepared as described in Petersen et al., Liebig's Annalen, 562:205-229 (1949).

A variety of pancreatic lipase inhibitors are described herein below. The pancreatic lipase inhibitors lipstatin, (2S,3S,5S,7Z,10Z)-5-[(S)-2-formamido-4-methyl-valeryloxy]-2-hexyl-3-hydroxy-7,10-hexadecanoic acid lactone, and tetrahydrolipstatin (orlistat), (2S,3S,5S)-5-[(S)-2-formamido-4-methyl-valeryloxy]-2-hexyl-3-hydroxy-hexadecanoic 1,3 acid lactone, and the variously substituted N-formylleucine derivatives and stereoisomers thereof, are disclosed In U.S. Pat. No. 4,598,089. For example, tetrahydrolipstatin is prepared as described in, e.g., U.S. Pat. Nos. 5,274,143; 5,420,305; 5,540,917; and 5,643,874. The pancreatic lipase inhibitor, FL-386, 1-[4-(2-methylpropyl)cyclohexyl]-2-[(phenylsulfonyl)oxy]ethanone, and the variously substituted sulfonate derivatives related thereto, are disclosed in U.S. Pat. No. 4,452,813. The pancreatic lipase inhibitor, WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151. The pancreatic lipase inhibitor, valilactone, and a process for the preparation thereof by the microbial cultivation of *Actinomycetes* strain MG147-CF2, are disclosed in Kitahara, et al., J. Antibiotics, 40(11): 1647-1650 (1987). The pancreatic lipase inhibitors, ebelactone A and ebelactone B, and a process for the preparation thereof by the microbial cultivation of *Actinomycetes* strain MG7-G1, are disclosed in Umezawa et al., J. Antibiotics, 33:1594-1596 (1980). The use of ebelactones A and B in the suppression of monoglyceride formation is disclosed in Japanese Kokai 08-143457, published Jun. 4, 1996.

Other compounds that are marketed for hyperlipidemia, including hypercholesterolemia and which are intended to help prevent or treat atherosclerosis include bile acid sequestrants, such as Welchol®, Colestid®, LoCholest® and Questran®; and fibric acid derivatives, such as Atromid® Lopid® and Tricot®.

Diabetes can be treated by administering to a patient having diabetes (especially Type II), insulin resistance, impaired glucose tolerance, metabolic syndrome, or the like, or any of the diabetic complications such as neuropathy, nephropathy, retinopathy or cataracts, a therapeutically effective amount of a compound of the present invention in combination with other agents (e.g., insulin) that can be used to treat diabetes. This includes the classes of anti-diabetic agents (and specific agents) described herein.

Any glycogen phosphorylase inhibitor can be used as the second agent in combination with a compound of the present invention. The term glycogen phosphorylase inhibitor refers to compounds that inhibit the bioconversion of glycogen to glucose-1-phosphate which is catalyzed by the enzyme glycogen phosphorylase. Such glycogen phosphorylase inhibition activity is readily determined by those skilled in the art according to standard assays (e.g., J. Med. Chem., 41:2934-2938 (1998)). A variety of glycogen phosphorylase inhibitors are known to those skilled in the art including those described in WO 96/39384 and WO 96/39385.

Any aldose reductase inhibitor can be used in combination with a compound of the present invention. The term aldose reductase inhibitor refers to compounds that inhibit the bioconversion of glucose to sorbitol, which is catalyzed by the enzyme aldose reductase. Aldose reductase inhibition is readily determined by those skilled in the art according to standard assays (e.g., J. Malone, "Red Cell Sorbitol, an Indicator of Diabetic Control", Diabetes, 29:861-864 (1980)). A variety of aldose reductase inhibitors are known to those skilled in the art, such as those described in U.S. Pat. No. 6,579,879, which includes 6-(5-chloro-3-methylbenzofuran-2-sulfonyl)-2H-pyridazin-3-one.

Any sorbitol dehydrogenase inhibitor can be used in combination with a compound of the present invention. The term sorbitol dehydrogenase inhibitor refers to compounds that inhibit the bioconversion of sorbitol to fructose which is catalyzed by the enzyme sorbitol dehydrogenase. Such sorbitol dehydrogenase inhibitor activity is readily determined by those skilled in the art according to standard assays (e.g., Analyt. Biochem., 280:329-331 (2000)). A variety of sorbitol dehydrogenase inhibitors are known, for example, U.S. Pat. Nos. 5,728,704 and 5,866,578 disclose compounds and a method for treating or preventing diabetic complications by inhibiting the enzyme sorbitol dehydrogenase.

Any glucosidase inhibitor can be used in combination with a compound of the present invention. A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom. Such glucosidase inhibition activity is readily determined by those skilled in the art according to standard assays (e.g., Biochemistry, 8:4214 (1969)). A generally preferred glucosidase inhibitor includes an amylase inhibitor. An amylase inhibitor is a glucosidase inhibitor that inhibits the enzymatic degradation of starch or glycogen into maltose. Such amylase inhibition activity is readily determined by those skilled in the art according to standard assays (e.g., Meth. Enzymol., 1:149 (1955)). The inhibition of such enzymatic degradation is beneficial in reducing amounts of bioavailable sugars, including glucose and maltose, and the concomitant deleterious conditions resulting therefrom.

A variety of glucosidase inhibitors are known to one of ordinary skill in the art and examples are provided below. Preferred glucosidase inhibitors are those inhibitors that are selected from the group consisting of acarbose, adiposine, voglibose, miglitol, emiglitate, camiglibose, tendamistate, trestatin, pradimicin-Q and salbostatin. The glucosidase inhibitor, acarbose, and the various amino sugar derivatives related thereto are disclosed in U.S. Pat. Nos. 4,062,950 and 4,174,439 respectively. The glucosidase inhibitor, adiposine, is disclosed in U.S. Pat. No. 4,254,256. The glucosidase inhibitor, voglibose, 3,4-dideoxy-4-[[2-hydroxy-1-(hydroxymethyl)ethyl]amino]-2-C-(hydroxymethyl)-D-epi-inositol and the various N-substituted pseudo-aminosugars related thereto, are disclosed in U.S. Pat. No. 4,701,559. The glucosidase inhibitor, miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436. The glucosidase inhibitor, emiglitate, ethyl p-[2-[(2R,3R,4R,5S)-3,4,5-trihydroxy-2-(hydroxymethyl)piperidino]ethoxy]-benzoate, the various derivatives related thereto and pharmaceutically acceptable acid addition salts thereof, are disclosed in U.S. Pat. No. 5,192,772. The glucosidase inhibitor, MDL-25637, 2,6-dideoxy-7-O-β-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765. The glucosidase inhibitor, camiglibose, methyl 6-deoxy-6-[(2R,3R,4R,5S)-3,4,5-trihydroxy-2-(hydroxymethyl)piperidino]-(α-D-glucopyranoside sesquihydrate, the deoxy-nojirimycin derivatives related thereto, the various pharmaceutically acceptable salts thereof and synthetic methods for the preparation thereof, are disclosed in U.S. Pat. Nos. 5,157,116 and 5,504,078. The glycosidase inhibitor, salbostatin and the various pseudosaccharides related thereto, are disclosed In U.S. Pat. No. 5,091,524.

A variety of amylase inhibitors are known to one of ordinary skill in the art. The amylase inhibitor, tendamistat and the various cyclic peptides related thereto, are disclosed in U.S. Pat. No. 4,451,455. The amylase inhibitor AI-3688 and the various cyclic polypeptides related thereto are disclosed in U.S. Pat. No. 4,623,714. The amylase inhibitor, trestatin, consisting of a mixture of trestatin A, trestatin B and trestatin C and the various trehalose-containing aminosugars related thereto are disclosed in U.S. Pat. No. 4,273,765.

Additional anti-diabetic compounds, which can be used as the second agent in combination with a compound of the present invention, include, for example, the following: biguanides (e.g., metformin), insulin secretagogues (e.g., sulfonylureas and glinides), glitazones, non-glitazone PPARγ agonists, PPARβ agonists, inhibitors of DPP-IV, inhibitors of PDE5, inhibitors of GSK-3, glucagon antagonists, inhibitors of f-1,6-BPase(Metabasis/Sankyo), GLP-1/analogs (AC 2993, also known as exendin-4), insulin and insulin mimetics (Merck natural products). Other examples would include PKC-β inhibitors and AGE breakers.

The compounds of the present invention can be used in combination with anti-obesity agents. Any anti-obesity agent can be used as the second agent in such combinations and examples are provided herein. Such anti-obesity activity is readily determined by those skilled in the art according to standard assays known in the art.

Suitable anti-obesity agents include phenylpropanolamine, ephedrine, pseudoephedrine, phentermine, $β_3$ adrenergic receptor agonists, apolipoprotein-B secretion/microsomal triglyceride transfer protein (apo-B/MTP) inhibitors, MCR-4-agonists, cholecystokinin-A (CCK-A) agonists, monoamine reuptake inhibitors (e.g., sibutramine), sympathomimetic agents, serotoninergic agents, cannabinoid receptor (CB-1) antagonists (e.g., rimonabant described in U.S. Pat. No. 5,624,941 (SR-141,716A), purine compounds, such as those described in U.S. Patent Publication No. 2004/0092520; pyrazolo[1,5-a][1,3,5]triazine compounds, such as those described in U.S. Non-Provisional patent application Ser. No. 10/763,105; and bicyclic pyrazolyl and imidazolyl compounds, such as those described in U.S. Provisional Application No. 60/518,280, dopamine agonists (e.g., bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (e.g., tetrahydrolipstatin, i.e. orlistat), bombesin agonists, anorectic agents (e.g., a bombesin agonist), Neuropeptide-Y antagonists, thyroxine, thyromimetic agents, dehydroepiandrosterones or analogs thereof, glucocorticoid receptor agonists or antagonists, orexin receptor antagonists, urocortin binding protein antagonists, glucagon-like peptide-1 receptor agonists, ciliary neurotrophic factors (e.g., Axokine™), human agouti-related proteins (AGRP), ghrelin receptor antagonists, histamine 3 receptor antagonists or inverse agonists, neuromedin U receptor agonists, and the like. Rimonabant (SR-141,716A also known under the trade name Acomplia™ available from Sanofi-Aventis) can be prepared as described in U.S. Pat. No. 5,624,941. Other suitable CB-1 antagonists include those described in U.S. Pat. Nos. 5,747,524, 6,432,984 and 6,518,264; U.S. Patent Publication Nos. US2004/0092520, US2004/0157839, US2004/0214855, and US2004/0214838; U.S. patent application Ser. No. 10/971,599; and PCT Patent Publication Nos. WO 02/076949, WO 03/1075660, WO 04/048317, WO 04/013120, and WO 04/012671.

Preferred apolipoprotein-B secretion/microsomal triglyceride transfer protein (apo-B/MTP) inhibitors for use as anti-obesity agents are gut-selective MTP inhibitors, such as dirlotapide described in U.S. Pat. No. 6,720,351; 4-(4-(4-(4-((2-((4-methyl-4H-1,2,4-triazol-3-ylthio)methyl)-2-(4-chlorophenyl)-1,3-dioxolan-4-yl)methoxy)phenyl)piperazin-1-yl)phenyl)-2-sec-butyl-2H-1,2,4-triazol-3(4H)-one (R103757) described in U.S. Pat. Nos. 5,521,186 and 5,929,075; and implitapide (BAY 13-9952) described in U.S. Pat. No. 6,265,431. As used herein, the term "gut-selective" means that the MTP Inhibitor has a higher exposure to the gastrointestinal tissues versus systemic exposure.

Any thyromimetic can be used as the second agent in combination with a compound of the present Invention. Such thyromimetic activity is readily determined by those skilled in the art according to standard assays (e.g., Atherosclerosis, 126: 53-63 (1996)). A variety of thyromimetic agents are known to those skilled in the art, for example those disclosed in U.S. Pat. Nos. 4,766,121; 4,826,876; 4,910,305; 5,061,798; 5,284,971; 5,401,772; 5,654,468; and 5,569,674. Other antiobesity agents include sibutramine which can be prepared as described in U.S. Pat. No. 4,929,629 and bromocriptine which can be prepared as described in U.S. Pat. Nos. 3,752,814 and 3,752,888.

The compounds of the present invention can also be used in combination with other antihypertensive agents. Any antihypertensive agent can be used as the second agent in such combinations and examples are provided herein. Such antihypertensive activity is readily determined by those skilled in the art according to standard assays (e.g., blood pressure measurements).

Examples of presently marketed products containing antihypertensive agents include calcium channel blockers, such as Cardizem®, Adalat®, Calan®, Cardene®, Covera®, Dilacor®, DynaCirc®, Procardia XL®, Sular®, Tiazac®, Vascor®, Verelan®, Isoptin®, Nimotop®, Norvasc®, and Plendile; angiotensin converting enzyme (ACE) inhibitors, such as Accupril®, Altace®, Captopril®, Lotensin®, Mavik®, Monopril®, Prinivil®, Univasc®, Vasotec® and Zestril®.

Amlodipine and related dihydropyridine compounds are disclosed in U.S. Pat. No. 4,572,909, as potent anti-ischemic and antihypertensive agents. U.S. Pat. No. 4,879,303 discloses amlodipine benzenesulfonate salt (also termed amlodipine besylate). Amlodipine and amlodipine besylate are potent and long lasting calcium channel blockers. As such, amlodipine, amlodipine besylate, amlodipine maleate and other pharmaceutically acceptable acid addition salts of amlodipine have utility as antihypertensive agents and as antiischemic agents. Amlodipine besylate is currently sold as Norvasc®.

Calcium channel blockers which are within the scope of this invention include, but are not limited to: bepridil, which may be prepared as disclosed in U.S. Pat. No. 3,962,238 or U.S. Re. Pat. No. 30,577; clentiazem, which may be prepared as disclosed in U.S. Pat. No. 4,567,175; diltiazem, fendiline, which may be prepared as disclosed in U.S. Pat. No. 3,262,977; gallopamil, which may be prepared as disclosed in U.S. Pat. No. 3,261,859; mibefradil, which may be prepared as disclosed in U.S. Pat. No. 4,808,605; prenylamine, which may be prepared as disclosed in U.S. Pat. No. 3,152,173; semotiadil, which may be prepared as disclosed in U.S. Pat. No. 4,786,635; terodiline, which may be prepared as disclosed in U.S. Pat. No. 3,371,014; verapamil, which may be prepared as disclosed in U.S. Pat. No. 3,261,859; aranipine, which may be prepared as disclosed in U.S. Pat. No. 4,572,909; barnidipine, which may be prepared as disclosed in U.S. Pat. No. 4,220,649; benidipine, which may be prepared as disclosed in European Patent Application Publication No. 106,275; cilnidipine, which may be prepared as disclosed in U.S. Pat. No. 4,672,068; efonidipine, which may be prepared as disclosed in U.S. Pat. No. 4,885,284; elgodipine, which may be prepared as disclosed in U.S. Pat. No. 4,952,592; felodipine, which may be prepared as disclosed in U.S. Pat. No. 4,264,611; isradipine, which may be prepared as disclosed in U.S. Pat. No. 4,466,972; lacidipine, which may be prepared as disclosed in U.S. Pat. No. 4,801,599; lercanidipine, which may be prepared as disclosed in U.S. Pat. No. 4,705,797; manidipine, which may be prepared as disclosed in U.S. Pat. No. 4,892,875; nicardipine, which may be prepared as disclosed in U.S. Pat. No. 3,985,758; nifedipine, which may be prepared as disclosed in U.S. Pat. No. 3,485,847; nilvadipine, which may be prepared as disclosed in U.S. Pat. No. 4,338,322; nimodipine, which may be prepared as disclosed in U.S. Pat. No. 3,799,934; nisoldipine, which may be prepared as disclosed in U.S. Pat. No. 4,154,839; nitrendipine, which may be prepared as disclosed in U.S. Pat. No. 3,799,934; cinnarizine, which may be prepared as disclosed in U.S. Pat. No. 2,882,271; flunarizine, which may be prepared as disclosed in U.S. Pat. No. 3,773,939; lidoflazine, which may be prepared as disclosed in U.S. Pat. No. 3,267,104; lomerizine, which may be prepared as disclosed in U.S. Pat. No. 4,663,325; bencyclane, which may be disclosed in Hungarian Patent No. 151,865; etafenone, which may be prepared as disclosed in German Patent No. 1,265,758; and perhexiline, which may be prepared as disclosed in British Patent No. 1,025,578.

Angiotensin Converting Enzyme Inhibitors (ACE-Inhibitors) which are within the scope of this invention include, but are not limited to: alacepril, which may be prepared as disclosed in U.S. Pat. No. 4,248,883; benazepril, which may be prepared as disclosed in U.S. Pat. No. 4,410,520; captopril, which may be prepared as disclosed in U.S. Pat. Nos. 4,046,889 and 4,105,776; ceronapril, which may be prepared as disclosed in U.S. Pat. No. 4,462,790; delapril, which may be prepared as disclosed in U.S. Pat. No. 4,385,051; enalapril, which may be prepared as disclosed in U.S. Pat. No. 4,374,829; fosinopril, which may be prepared as disclosed in U.S. Pat. No. 4,337,201; imadapril, which may be prepared as disclosed in U.S. Pat. No. 4,508,727; lisinopril, which may be prepared as disclosed in U.S. Pat. No. 4,555,502; moveltopril, which may be prepared as disclosed in Belgian Patent No. 893,553; perindopril, which may be prepared as disclosed in U.S. Pat. No. 4,508,729; quinapril, which may be prepared as disclosed in U.S. Pat. No. 4,344,949; ramipril, which may be prepared as disclosed in U.S. Pat. No. 4,587,258; spirapril, which may be prepared as disclosed in U.S. Pat. No. 4,470,972; temocapril, which may be prepared as disclosed in U.S. Pat. No. 4,699,905; and trandolapril, which may be prepared as disclosed in U.S. Pat. No. 4,933,361.

Angiotensin-II receptor antagonists (A-II antagonists) which are within the scope of this invention include, but are not limited to: candesartan, which may be prepared as disclosed in U.S. Pat. No. 5,196,444; eprosartan, which may be prepared as disclosed in U.S. Pat. No. 5,185,351; irbesartan, which may be prepared as disclosed in U.S. Pat. No. 5,270,317; losartan, which may be prepared as disclosed in U.S. Pat. No. 5,138,069; and valsartan, which may be prepared as disclosed in U.S. Pat. No. 5,399,578.

Beta-adrenergic receptor blockers (beta- or β-blockers) which are within the scope of this invention include, but are not limited to: acebutolol, which may be prepared as disclosed in U.S. Pat. No. 3,857,952; alprenolol, which may be prepared as disclosed in Netherlands Patent Application No. 6,605,692; amosulalol, which may be prepared as disclosed in U.S. Pat. No. 4,217,305; arotinolol, which may be prepared as disclosed in U.S. Pat. No. 3,932,400; atenolol, which may be prepared as disclosed in U.S. Pat. No. 3,663,607 or U.S. Pat. No. 3,836,671; befunolol, which may be prepared as disclosed in U.S. Pat. No. 3,853,923; betaxolol, which may be prepared as disclosed in U.S. Pat. No. 4,252,984; bevantolol, which may be prepared as disclosed in U.S. Pat. No. 3,857,981; bisoprolol, which may be prepared as disclosed in U.S. Pat. No. 4,171,370; bopindolol, which may be prepared as disclosed in U.S. Pat. No. 4,340,541; bucumolol, which may be prepared as disclosed in U.S. Pat. No. 3,663,570; bufetolol, which may be prepared as disclosed in U.S. Pat. No. 3,723,476; bufuralol, which may be prepared as disclosed in U.S. Pat. No. 3,929,836; bunitrolol, which may be prepared as disclosed in U.S. Pat. Nos. 3,940,489 and 3,961,071; buprandolol, which may be prepared as disclosed in U.S. Pat. No. 3,309,406; butiridine hydrochloride, which may be prepared as disclosed in French Patent No. 1,390,056; butofilolol, which may be prepared as disclosed in U.S. Pat. No. 4,252,825; carazolol, which may be prepared as disclosed in German Patent No. 2,240,599; carteolol, which may be prepared as disclosed in U.S. Pat. No. 3,910,924; carvedilol, which may be prepared as disclosed in U.S. Pat. No. 4,503,067; celiprolol, which may be prepared as disclosed in U.S. Pat. No. 4,034,009; cetamolol, which may be prepared as disclosed in U.S. Pat. No. 4,059,622; cloranolol, which may be prepared as disclosed in German Patent No. 2,213,044; dilevalol, which may be prepared as disclosed in Clifton et al., J. Med. Chem., 25:670 (1982); epanolol, which may be prepared as disclosed in European Patent Publication Application No. 41,491; indenolol, which may be prepared as disclosed in U.S. Pat. No. 4,045,482; labetalol, which may be prepared as disclosed in U.S. Pat. No. 4,012,444; levobunolol, which may be prepared as disclosed in U.S. Pat. No. 4,463,176; mepindolol, which may be prepared as disclosed in Seeman et al., Heir. Chim. Acta, 54:241 (1971); metipranolol, which may be prepared as disclosed in Czechoslovakian Patent Application No. 128,471; metoprolol, which may be prepared as disclosed in U.S. Pat. No. 3,873,600; moprolol, which may be prepared as disclosed in U.S. Pat. No. 3,501,7691; nadolol, which may be prepared as disclosed in U.S. Pat. No. 3,935,267; nadoxolol, which may be prepared as disclosed in U.S. Pat. No. 3,819,702; nebivalol, which may be prepared as disclosed in U.S. Pat. No. 4,654,362; nipradilol, which may be prepared as disclosed in U.S. Pat. No. 4,394,382; oxprenolol, which may be prepared as disclosed in British Patent No. 1,077,603; perbutolol, which may be prepared as disclosed in U.S. Pat. No. 3,551,493; pindolol, which may be prepared as disclosed in Swiss Patent Nos. 469,002 and 472,404; practolol, which may be prepared as disclosed in U.S. Pat. No. 3,408,387; pronethalol, which may be prepared as disclosed in British Patent No. 909,357; propranolol, which may be prepared as disclosed in U.S. Pat. Nos. 3,337,628 and 3,520,919; sotalol, which may be prepared as disclosed in Uloth et al., J. Med. Chem., 9:88 (1966); sufinalol, which may be prepared as disclosed in German Pat. No. 2,728,641; talindol, which may be prepared as disclosed in U.S. Pat. Nos. 3,935,259 and 4,038,313; tertatolol, which may be prepared as disclosed in U.S. Pat. No. 3,960,891; tilisolol, which may be prepared as disclosed in U.S. Pat. No. 4,129,565; timolol, which may be prepared as disclosed in U.S. Pat. No. 3,655,663; toliprolol, which may be prepared as disclosed in U.S. Pat. No. 3,432,545; and xibenolol, which may be prepared as disclosed in U.S. Pat. No. 4,018,824.

Alpha-adrenergic receptor blockers (alpha- or α-blockers) which are within the scope of this invention include, but are not limited to: amosulalol, which may be prepared as disclosed in U.S. Pat. No. 4,217,307; arotinolol, which may be prepared as disclosed in U.S. Pat. No. 3,932,400; dapiprazole, which may be prepared as disclosed in U.S. Pat. No. 4,252,721; doxazosin, which may be prepared as disclosed in U.S. Pat. No. 4,188,390; fenspiride, which may be prepared as disclosed in U.S. Pat. No. 3,399,192; indoramin, which may be prepared as disclosed in U.S. Pat. No. 3,527,761; labetolol; naftopidil, which may be prepared as disclosed in U.S. Pat. No. 3,997,666; nicergoline, which may be prepared as disclosed in U.S. Pat. No. 3,228,943; prazosin, which may be prepared as disclosed in U.S. Pat. No. 3,511,836; tamsulosin, which may be prepared as disclosed in U.S. Pat. No. 4,703,063; tolazoline, which may be prepared as disclosed in U.S. Pat. No. 2,161,938; trimazosin, which may be prepared as disclosed in U.S. Pat. No. 3,669,968; and yohimbine, which may be isolated from natural sources according to methods well known to those skilled in the art.

The term "vasodilator," where used herein, is meant to include cerebral vasodilators, coronary vasodilators and peripheral vasodilators. Cerebral vasodilators within the scope of this invention include, but are not limited to: bencyclane; cinnarizine; citicoline, which may be isolated from natural sources as disclosed in Kennedy et al., J. Am. Chem. Soc., 77:250 (1955) or synthesized as disclosed in Kennedy, J. Biol. Chem., 222:185 (1956); cyclandelate, which may be prepared as disclosed in U.S. Pat. No. 3,663,597; ciclonicate, which may be prepared as disclosed in German Patent No. 1,910,481; diisopropylamine dichloroacetate, which may be prepared as disclosed in British Patent No. 862,248; eburnamonine, which may be prepared as disclosed in Hermann et al., J. Am. Chem. Soc., 101:1540 (1979); fasudil, which may be prepared as disclosed in U.S. Pat. No. 4,678,783; fenoxedil, which may be prepared as disclosed in U.S. Pat. No. 3,818,021; flunarizine, which may be prepared as disclosed in U.S. Pat. No. 3,773,939; ibudilast, which may be prepared as disclosed in U.S. Pat. No. 3,850,941; ifenprodil, which may be prepared as disclosed in U.S. Pat. No. 3,509,164; lomerizine, which may be prepared as disclosed in U.S. Pat. No. 4,663,325; nafronyl, which may be prepared as disclosed in U.S. Pat. No. 3,334,096; nicametate, which may be prepared as disclosed in Blicke et al., J. Am. Chem. Soc., 64:1722 (1942); nicergoline, which may be prepared as disclosed above; nimodipine, which may be prepared as disclosed in U.S. Pat. No. 3,799,934; papaverine, which may be prepared as reviewed in Goldberg, Chem. Prod. Chem. News, 17, 371 (1954); pentifylline, which may be prepared as disclosed in German Patent No. 860,217; tinofedrine, which may be prepared as disclosed in U.S. Pat. No. 3,563,997; vincamine, which may be prepared as disclosed in U.S. Pat. No. 3,770,724; vinpocetine, which may be prepared as disclosed in U.S. Pat. No. 4,035,750; and viquidil, which may be prepared as disclosed in U.S. Pat. No. 2,500,444.

Coronary vasodilators within the scope of this invention include, but are not limited to: amotriphene, which may be prepared as disclosed in U.S. Pat. No. 3,010,965; bendazol, which may be prepared as disclosed in J. Chem. Soc. 1958, 2426; benfurodil hemisuccinate, which may be prepared as disclosed in U.S. Pat. No. 3,355,463; benziodarone, which may be prepared as disclosed in U.S. Pat. No. 3,012,042; chloracizine, which may be prepared as disclosed in British Patent No. 740,932; chromonar, which may be prepared as disclosed in U.S. Pat. No. 3,282,938; clobenfural, which may be prepared as disclosed in British Patent No. 1,160,925; clonitrate, which may be prepared from propanediol according to methods well known to those skilled in the art, e.g., see Annalen, 1870, 155, 165; cloricromen, which may be prepared as disclosed in U.S. Pat. No. 4,452,811; dilazep, which may be prepared as disclosed in U.S. Pat. No. 3,532,685; dipyridamole, which may be prepared as disclosed in British Patent No. 807,826; droprenilamine, which may be prepared as disclosed in German Patent No. 2,521,113; efloxate, which may be prepared as disclosed in British Patent Nos. 803,372 and 824,547; erythrityl tetranitrate, which may be prepared by nitration of erythritol according to methods well-known to those skilled in the art; etafenone, which may be prepared as disclosed in German Patent No. 1,265,758; fendiline, which may be prepared as disclosed in U.S. Pat. No. 3,262,977; floredil, which may be prepared as disclosed in German Pat. No. 2,020,464; ganglefene, which may be prepared as disclosed in U.S.S.R. Patent No. 115,905; hexestrol, which may be prepared as disclosed in U.S. Pat. No. 2,357,985; hexobendine, which may be prepared as disclosed in U.S. Pat. No. 3,267,103; itramin tosylate, which may be prepared as disclosed in Swedish Patent No. 168,308; khellin, which may be prepared as disclosed in Baxter et al., J. Chem. Soc., 1949, S 30; lidoflazine, which may be prepared as disclosed in U.S. Pat. No. 3,267,104; mannitol hexanitrate, which may be prepared by the nitration of mannitol according to methods well-known to those skilled in the art; medibazine, which may be prepared as disclosed in U.S. Pat. No. 3,119,826; nitroglycerin; pentaerythritol tetranitrate, which may be prepared by the nitration of pentaerythritol according to methods well-known to those skilled in the art; pentrinitrol, which may be prepared as disclosed in German Patent No. 638,422-3; perhexilline, which may be prepared as disclosed above; pimefylline, which may be prepared as disclosed in U.S. Pat. No. 3,350,400; prenylamine, which may be prepared as disclosed in U.S. Pat. No. 3,152,173; propatyl nitrate, which may be prepared as disclosed in French Patent No. 1,103,113; trapidil, which may be prepared as disclosed in East German Patent No. 55,956; tricromyl, which may be prepared as disclosed in U.S. Pat. No. 2,769,015; trimetazidine, which may be prepared as disclosed in U.S. Pat. No. 3,262,852; trolnitrate phosphate, which may be prepared by nitration of triethanolamine followed by precipitation with phosphoric acid according to methods well-known to those skilled in the art; visnadine, which may be prepared as disclosed in U.S. Pat. Nos. 2,816,118 and 2,980,699.

Peripheral vasodilators within the scope of this invention include, but are not limited to: aluminum nicotinate, which may be prepared as disclosed in U.S. Pat. No. 2,970,082; bamethan, which may be prepared as disclosed in Corrigan et al., J. Am. Chem. Soc., 67:1894 (1945); bencyclane, which may be prepared as disclosed above; betahistine, which may be prepared as disclosed in Walter et al., J. Am. Chem. Soc., 63:2771 (1941); bradykinin, which may be prepared as disclosed in Hamburg et al., Arch. Biochem. Biophys., 76:252 (1958); brovincamine, which may be prepared as disclosed in U.S. Pat. No. 4,146,643; bufeniode, which may be prepared as disclosed in U.S. Pat. No. 3,542,870; buflomedil, which may be prepared as disclosed in U.S. Pat. No. 3,895,030; butalamine, which may be prepared as disclosed in U.S. Pat. No. 3,338,899; cetiedil, which may be prepared as disclosed in French Patent No. 1,460,571; ciclonicate, which may be prepared as disclosed in German Patent No. 1,910,481; cinepazide, which may be prepared as disclosed in Belgian Patent No. 730,345; cinnarizine, which may be prepared as disclosed above; cyclandelate, which may be prepared as disclosed above; diisopropylamine dichloroacetate, which may be prepared as disclosed above; eledoisin, which may be prepared as disclosed in British Patent No. 984,810; fenoxedil, which may be prepared as disclosed above; flunarizine, which may be prepared as disclosed above; heproni- cate, which may be prepared as disclosed in U.S. Pat. No. 3,384,642; ifenprodil, which may be prepared as disclosed above; iloprost, which may be prepared as disclosed in U.S. Pat. No. 4,692,464; inositol niacinate, which may be prepared as disclosed in Badgett et al., J. Am. Chem. Soc., 69:2907 (1947); isoxsuprine, which may be prepared as disclosed in U.S. Pat. No. 3,056,836; kallidin, which may be prepared as disclosed in Biochem. Biophys. Res. Commun., 6:210 (1961); kallikrein, which may be prepared as disclosed in German Patent No. 1,102,973; moxisylyte, which may be prepared as disclosed in German Patent No. 905,738; nafronyl, which may be prepared as disclosed above; nicametate, which may be prepared as disclosed above; nicergoline, which may be prepared as disclosed above; nicofuranose, which may be prepared as disclosed in Swiss Patent No. 366,523; nylidrin, which may be prepared as disclosed in U.S. Pat. Nos. 2,661,372 and 2,661,373; pentifylline, which may be prepared as disclosed above; pentoxifylline, which may be prepared as disclosed in U.S. Pat. No. 3,422,107; piribedil, which may be prepared as disclosed in U.S. Pat. No. 3,299, 067; prostaglandin $E_1$, which may be prepared by any of the methods referenced in the Merck Index, Twelfth Edition, Budaveri, Ed., New Jersey, p. 1353 (1996); suloctidil, which may be prepared as disclosed in German Patent No. 2,334, 404; tolazoline, which may be prepared as disclosed in U.S. Pat. No. 2,161,938; and xanthinol niacinate, which may be prepared as disclosed in German Patent No. 1,102,750.

The term "diuretic," within the scope of this invention, is meant to include diuretic benzothiadiazine derivatives, diuretic organomercurials, diuretic purines, diuretic steroids, diuretic sulfonamide derivatives, diuretic uracils and other diuretics such as amanozine, which may be prepared as disclosed in Austrian Patent No. 168,063; amiloride, which may be prepared as disclosed in Belgian Patent No. 639,386; arbutin, which may be prepared as disclosed in Tschitschibabin, Annalen, 1930, 479, 303; chlorazanil, which may be prepared as disclosed in Austrian Patent No. 168,063; ethacrynic acid, which may be prepared as disclosed in U.S. Pat. No. 3,255, 241; etozolin, which may be prepared as disclosed in U.S. Pat. No. 3,072,653; hydracarbazine, which may be prepared as disclosed in British Patent No. 856,409; isosorbide, which may be prepared as disclosed in U.S. Pat. No. 3,160,641; mannitol; metochalcone, which may be prepared as disclosed in Freudenberg et al., Ber., 90:957 (1957); muzolimine, which may be prepared as disclosed in U.S. Pat. No. 4,018, 890; perhexiline, which may be prepared as disclosed above; ticrynafen, which may be prepared as disclosed in U.S. Pat. No. 3,758,506; triamterene which may be prepared as disclosed in U.S. Pat. No. 3,051,230; and urea.

Diuretic benzothiadiazine derivatives within the scope of this invention include, but are not limited to: althiazide, which may be prepared as disclosed in British Patent No. 902,658; bendroflumethiazide, which may be prepared as disclosed in U.S. Pat. No. 3,265,573; benzthiazide, McManus et al., 136th Am. Soc. Meeting (Atlantic City, September 1959), Abstract of papers, pp 13-O; benzylhydrochlorothiazide, which may be prepared as disclosed in U.S. Pat. No. 3,108,097; buthiazide, which may be prepared as disclosed in British Patent Nos. 861,367 and 885,078; chlorothiazide, which may be prepared as disclosed in U.S. Pat. Nos. 2,809,194 and 2,937,169; chlorthalidone, which may be prepared as disclosed in U.S. Pat. No. 3,055,904; cyclopenthiazide, which maybe prepared as disclosed in Belgian Patent No. 587,225; cyclothiazide, which may be prepared as disclosed in Whitehead et al., J. Org. Chem., 26:2814 (1961); epithiazide, which may be prepared as disclosed in U.S. Pat. No. 3,009,911; ethiazide, which may be prepared as disclosed in British Patent No. 861,367; fenquizone, which may be prepared as disclosed in U.S. Pat. No. 3,870,720; indapamide, which may be prepared as disclosed in U.S. Pat. No. 3,565,911; hydrochlorothiazide, which may be prepared as disclosed in U.S. Pat. No. 3,164, 588; hydroflumethiazide, which may be prepared as disclosed in U.S. Pat. No. 3,254,076; methyclothiazide, which may be prepared as disclosed in Close et al., J. Am. Chem. Soc., 82:1132 (1960); meticrane, which may be prepared as disclosed in French Patent Nos. M2790 and 1,365,504; metolazone, which may be prepared as disclosed in U.S. Pat. No. 3,360,518; paraflutizide, which may be prepared as disclosed in Belgian Patent No. 620,829; polythiazide, which may be prepared as disclosed in U.S. Pat. No. 3,009,911; quinethazone, which may be prepared as disclosed in U.S. Pat. No. 2,976,289; teclothiazide, which may be prepared as disclosed in Close et al., J. Am. Chem. Soc., 82:1132 (1960); and trichlormethiazide, which may be prepared as disclosed in deStevens et al., Experientia, 16:113 (1960).

Diuretic sulfonamide derivatives within the scope of this invention include, but are not limited to: acetazolamide, which may be prepared as disclosed in U.S. Pat. No. 2,980, 679; ambuside, which may be prepared as disclosed in U.S. Pat. No. 3,188,329; azosemide, which may be prepared as disclosed in U.S. Pat. No. 3,665,002; bumetanide, which may be prepared as disclosed in U.S. Pat. No. 3,634,583; butazolamide, which may be prepared as disclosed in British Patent No. 769,757; chloraminophenamide, which may be prepared as disclosed in U.S. Pat. Nos. 2,809,194, 2,965,655 and 2,965,656; clofenamide, which may be prepared as disclosed in Olivier, Rec. Trav. Chim., 1918, 37, 307; clopamide, which may be prepared as disclosed in U.S. Pat. No. 3,459,756; clorexolone, which may be prepared as disclosed in U.S. Pat. No. 3,183,243; disulfamide, which may be prepared as disclosed in British Patent No. 851,287; ethoxolamide, which may be prepared as disclosed in British Patent No. 795,174; furosemide, which may be prepared as disclosed in U.S. Pat. No. 3,058,882; mefruside, which may be prepared as disclosed in U.S. Pat. No. 3,356,692; methazolamide, which may be prepared as disclosed in U.S. Pat. No. 2,783,241; piretanide, which may be prepared as disclosed in U.S. Pat. No. 4,010,273; torasemide, which may be prepared as disclosed in U.S. Pat. No. 4,018,929; tripamide, which may be prepared as disclosed in Japanese Patent No. 73 05,585; and xipamide, which may be prepared as disclosed in U.S. Pat. No. 3,567,777.

Osteoporosis is a systemic skeletal disease, characterized by low bone mass and deterioration of bone tissue, with a consequent increase in bone fragility and susceptibility to fracture, in the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5-20% of patients dying within one year, and over 50% of survivors being incapacitated. The elderly are at greatest risk of osteoporosis, and the problem is therefore predicted to increase significantly within the aging of the population. Worldwide fracture incidence is forecasted to increase three-fold over the next 60 years, and one study has estimated that there will be 4.5 million hip fractures worldwide in 2050. Women are at greater risk of osteoporosis than men. Women experience a sharp acceleration of bone loss during the five years following menopause. Other factors that increase the risk include smoking, alcohol abuse, a sedentary lifestyle and low calcium intake.

Those skilled in the art will recognize that anti-resorptive agents (for example progestins, polyphosphonates, bisphosphonate(s), estrogen agonists/antagonists, estrogen, estrogen/progestin combinations, Premarin®, estrone, estriol or 17α- or 17β-ethynyl estradiol) may be used in conjunction with the compounds of the present invention.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, ethynodiol diacetate, etonogestrel, flurogestone acetate, gestaclone, gestodene, gestonorone caproate, gestrinone, haloprogesterone, hydroxyprogesterone caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenproprionate, progesterone, quingestanol acetate, quingestrone, and tigestol. Preferred progestins are medroxyprogestrone, norethindrone and norethynedrel.

Exemplary bone resorption inhibiting polyphosphonates include polyphosphenates of the type disclosed in U.S. Pat. No. 3,683,080. Preferred polyphosphonates are geminal diphosphonates (also referred to as bis-phosphonates). Tiludronate disodium is an especially preferred polyphosphonate. Ibandronic acid is an especially preferred polyphosphonate. Alendronate and resindronate are especially preferred polyphosphonates. Zoledronic acid is an especially preferred polyphosphonate. Other preferred polyphosphonates are 6-amino-1-hydroxy-hexylidene-bisphosphonic acid and 1-hydroxy-3(methylpentylamino)-propylidene-bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonic acid, N-(2-hydroxyethyl) amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the compounds of this invention may be combined with a mammalian estrogen agonist/antagonist. Any estrogen agonist/antagonist may be used in the combination aspect of this invention. The term estrogen agonist/antagonist refers to compounds which bind with the estrogen receptor, inhibit bone turnover and/or prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. Such activities are readily determined by those skilled in the art of standard assays including estrogen receptor binding assays, standard bone histomorphometric and densitometer methods (Eriksen E. F. et al., Bone Histomorphometry, Raven Press, New York, pp. 1-74 (1994); Grier S. J. et al., "The Use of Dual-Energy X-Ray Absorptiometry In Animals", Inv. Radiol., 31(1):50-62 (1996); Wahner H. W. et al., The Evaluation of Osteoporosis: Dual Energy X-Ray Absorptiometry in Clinical Practice., Martin Dunitz Ltd., London, pp. 1-296 (1994)). A variety of these compounds are described and referenced below. Another preferred estrogen agonist/antagonist is 3-(4-{1,2-diphenyl-but-1-enyl)-phenyl)-acrylic acid, which is disclosed in Willson et al., Endocrinology, 138:3901-3911 (1997). Another preferred estrogen agonist/antagonist is tamoxifen: (ethanamine,2-(-4-(1,2-diphenyl-1-butenyl)phenoxy)-N,N-dimethyl, (Z)-2-, 2-hydroxy-1,2,3-propanetricarboxylate(1:1)) and related compounds which are disclosed in U.S. Pat. No. 4,536,516. Another related compound is 4-hydroxy tamoxifen, which is disclosed in U.S. Pat. No. 4,623,660. A preferred estrogen agonist/antagonist is raloxifene: (methanone, (6-hydroxy-2-(4-hydroxyphenyl)benzo[b]thien-3-yl)(4-(2-(1-piperidinyl)ethoxy)phenyl)hydrochloride) which is disclosed in U.S. Pat. No. 4,418,068. Another preferred estrogen agonist/antagonist is toremifene: (ethanamine, 2-(4-(4-chloro-1,2-diphenyl-1-butenyl)phenoxy)-N,N-dimethyl-, (Z)-, 2-hydroxy-1,2,3-propanetricarboxylate (1:1) which is disclosed in U.S. Pat. No. 4,996,225. Another preferred estrogen agonist/antagonist is centchroman: 1-(2-((4-(-methoxy-2,2, dimethyl-3-phenyl-chroman-4-yl)-phenoxy)-ethyl)-pyrrolidine, which is disclosed in U.S. Pat. No. 3,822,287. Also preferred is levormeloxifene.

Another preferred estrogen agonist/antagonist is idoxifene: (E)-1-(2-(4-(1-(4-iodo-phenyl)-2-phenyl-but-1-enyl)-phenoxy)-ethyl)-pyrrolidinone, which is disclosed in U.S.

Pat. No. 4,839,155. Another preferred estrogen agonist/antagonist is 2-(4-methoxy-phenyl)-3-[4-(2-piperidin-1-yl-ethoxy)-phenoxy]-benzo[b]thiophen-6-ol which is disclosed in U.S. Pat. No. 5,488,058. Another preferred estrogen agonist/antagonist is 6-(4-hydroxy-phenyl)-5-(4-(2-piperidin-1-yl-ethoxy)-benzyl)-naphthalen-2-ol, which is disclosed in U.S. Pat. No. 5,484,795. Another preferred estrogen agonist/antagonist is (4-(2-(2-aza-bicyclo[2.2.1]hept-2-yl)-ethoxy)-phenyl)-(6-hydroxy-2-(4-hydroxyphenyl)-benzo[b]thiophen-3-yl)-methanone which is disclosed, along with methods of preparation, in PCT Publication No. WO 95/10513. Other preferred estrogen agonist/antagonists include the compounds, TSE-424 (Wyeth-Ayerst Laboratories) and arazoxifene.

Other preferred estrogen agonist/antagonists include compounds as described in U.S. Pat. No. 5,552,412. Especially preferred compounds described therein are: cis-6-(4-fluoro-phenyl)-5-(4-(2-piperidin-1-yl-ethoxy)-phenyl)-5,6,7,8-tetrahydronaphthalene-2-ol; (−)-cis-6-phenyl-5-(4-(2-pyrrolidin-1-yl-ethoxy)-phenyl)-5,6,7,8-tetrahydronaphthalene-2-ol (also known as lasofoxifene); cis-6-phenyl-5-(4-(2-pyrrolidin-1-yl-ethoxy)-phenyl)-5,6,7,8-tetrahydronaphthalene-2-ol; cis-1-(6'-pyrrolodinoethoxy-3'-pyridyl)-2-phenyl-6-hydroxy-1,2,3,4-tetrahydronaphthalene; 1-(4'-pyrrolidinoethoxyphenyl)-2-(4"-fluorophenyl)-6-hydroxy-1,2,3,44etrahydroisoquinoline; cis-6-(4-hydroxyphenyl)-5-(4-(2-piperidin-1-yl-ethoxy)-phenyl)-5,6,7,8-tetrahydronaphthalene-2-ol; and 1-(4'-pyrrolidinolethoxyphenyl)-2-phenyl-6-hydroxy-1,2,3,4-tetrahydroisoquinoline.

Other estrogen agonist/antagonists are described in U.S. Pat. No. 4,133,814, which discloses derivatives of 2-phenyl-3-aroyl-benzothiophene and 2-phenyl-3-aroylbenzothiophene-1-oxide.

Other anti-osteoporosis agents, which can be used as the second agent in combination with a compound of the present invention, include, for example, the following: parathyroid hormone (PTH) (a bone anabolic agent); parathyroid hormone (PTH) secretagogues (see, e.g., U.S. Pat. No. 6,132,774), particularly calcium receptor antagonists; calcitonin; vitamin D and vitamin D analogs.

Any selective androgen receptor modulator (SARM) can be used in combination with a compound of the present invention. A selective androgen receptor modulator (SARM) is a compound that possesses androgenic activity and which exerts tissue-selective effects. SARM compounds can function as androgen receptor agonists, partial agonists, partial antagonists or antagonists. Examples of suitable SARMs include compounds such as cyproterone acetate, chlormadinone, flutamide, hydroxyflutamide, bicalutamide, nilutamide, spironolactone, 4-(trifluoromethyl)-2(1H)-pyrrolidino[3,2-g]quinoline derivatives, 1,2-dihydropyridino [5,6-g]quinoline derivatives and piperidino[3,2-g]quinolinone derivatives.

Cypterone, also known as (1b,2b)-6-chloro-1,2-dihydro-1,7-hydroxy-3'H-cyclopropa[1,2]pregna-1,4,6-triene-3,20-dione is disclosed in U.S. Pat. No. 3,234,093. Chlormadinone, also known as 17-(acetyloxy)-6-chloropregna-4-,6-diene-3,20-dione, in its acetate form, acts as an anti-androgen and is disclosed in U.S. Pat. No. 3,485,852. Nilutamide, also known as 5,5-dimethyl-3-[4-nito-3-(trifluoromethyl)phenyl]-2,4-imidazolidinedione and by the trade name Nilandron® is disclosed in U.S. Pat. No. 4,097,578. Flutamide, also known as 2-methyl-N-[4-nitro-3-(trifluoromethyl)phenyl]propanamide and the trade name Eulexin® is disclosed in U.S. Pat. 3,847,988. Bicalutamide, also known as 4'-cyano-a',a',a'-trifluoro-3-(4-fluorophenylsulfonyl)-2-hydroxy-2-methylpropiono-m-toluidide and the trade name Casodex® is disclosed in EP-100172. The enantiomers of biclutamide are discussed by Tucker et al., J. Med. Chem., 31:885-887 (1988). Hydroxyflutamide, a known androgen receptor antagonist in most tissues, has been suggested to function as a SARM for effects on IL-6 production by osteoblasts as disclosed in Hofbauer et al., J. Bone Miner. Res., 14:1330-1337 (1999). Additional SARMs have been disclosed in U.S. Pat. No. 6,017,924; WO 01/16108, WO 01/16133, WO 01/16139, WO 02/00617, WO 02/163 10, U.S. Patent Application Publication No. US 2002/0099096, U.S. Patent Application Publication No. US 2003/0022868, WO 03/011302 and WO 03/011824.

Any compound having activity as an LXR modulator can serve as the second compound in the combination therapy aspect of the present invention. The term LXR modulator refers to compounds that modulate the liver X receptor (LXR), which has been identified as a regulator of cellular and whole body cholesterol metabolism. Such LXR modulation activity is readily determined by those skilled in the art according to standard assays (e.g., U.S. Pat. No. 6,140,343). A variety of LXR modulators will be known to those skilled in the art, for example, those disclosed in U.S. Patent Application Publication Nos. 2003/01814206, 2005/0080111, and 2005/0245515.

All of the above referenced patents and patent applications are hereby incorporated by reference herein.

The combinations can be co-formulated or in the form of kits packaged to provide appropriate dosages for co-administration.

The above other therapeutic agents, when employed in combination with the compounds of the present invention, may be used, for example, in those amounts indicated in the Physicians' Desk Reference (PDR) or as otherwise determined by one of ordinary skill in the art.

The following examples further illustrate the present invention, but of course, should not be construed as in any way limiting its scope.

The following abbreviations are used herein:
ee=enantiomeric excess
DMF=dimethylformamide
EtOAc=ethyl acetate
LDA=lithium diisopropylamide
Hünig's Base=N,N-diisopropylethylamine
Me=methyl
RT=retention time
TFA=trifluoroacetic acid
THF=tetrahydrofuran
TLC=thin layer chromatography
TMS=trimethylsilyl
t-Bu=tert-butyl
MeI=methyl iodide
$(BOC)_2O$=di-tert-butyl dicarbonate
TEA=triethylamine
n-BuLi=n-butyllithium
rt=room temperature
LC=liquid chromatography
Ph=phenyl
EtOH=ethanol
DCE=dichloroethane
DMSO=dimethylsulfoxide
MS=molecular sieves
MS(ES)=Electro-Spray Mass Spectrometry
sat=saturated
AcOH=acetic acid
MeOH=methanol Et₂O=diethyl ether
Ac=acetyl
h=hours
Et=ethyl
EDCI=water soluble dicarbonyl diimide, 1-(3-dimethylaminopropyl)-3-ethylcarbodiimide hydrochloride
TBAF=tetrabutylammonium fluoride
DMA=dimethylacetamide
DME=1,2-dimethoxyethane
HRMS=high resolution mass spectrometry
TBME=MTBE=methyl tert-butyl ether (i.e., 2-methoxy-2-methyl-propane)
PyBroP=Bromo-tris-pyrrolidino-phosphonium hexafluorophosphate
DEA=diethylamine
IPA=isopropylamine
TMSCl=trimethylsilylchloride
TMSCN=trimethylsilylcyanide
MS=mass spectrum
NMR=nuclear magnetic resonance
TMSI=trimethylsilyliodide
PPA=polyphosphoric acid
LDA=lithium diisopropylamine
UV=ultraviolet
DCM=dichloromethane
DMAC=N,N-dimethylacetamide
DAST=diethylaminosulfurtrifluoride
HPLC=high performance liquid chromatography
BnMgBr=benzyl magnesium bromide Specifically exemplified compounds of Formula Ia and Ib are listed along with structure, name, HPLC retention time, molecular mass and the procedure employed to make such examples, in the proceeding text and in the tables set forth below. The absolute configuration of chiral examples was determined by converting intermediate amines to the Mosher's amides and obtaining an X-ray of crystalline material as described in example 12, Procedure 12. The NMR spectra of the single intermediate sulfinyl amide diastereomers had diagnostic NMR shifts for the pyridyl protons which were used to assign the quarternary chiral center in the absence of specific Mosher amide examples. Enantiomerically pure intermediate amines were obtained by separation of the racemic mixtures using SFC.

EXAMPLE 1

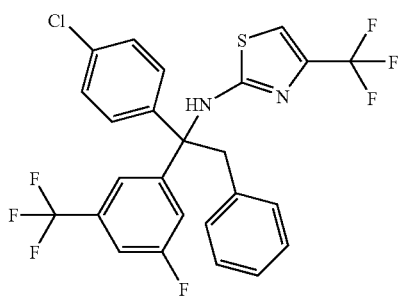

N-(1-(5-chloropyridin-2-yl)-1-(3-fluoro-5-(trifluoromethyl)phenyl)-2-phenylethyl)-4-(trifluoromethyl)thiazol-2-amine Procedure 1

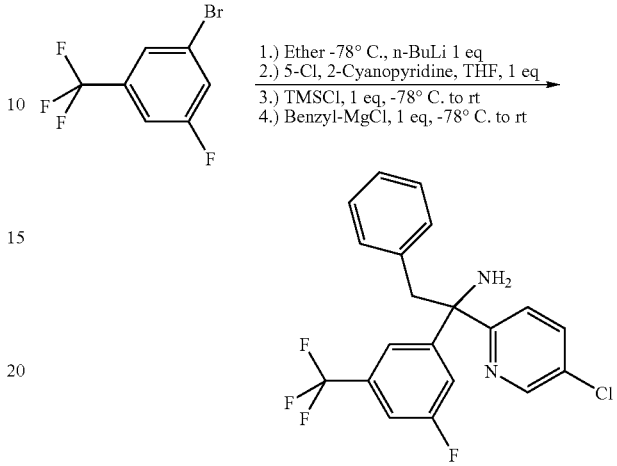

A dry 250 mL round bottomed flask was equipped a stirring bar and fitted to an adapter connected to the vacuum line. The flask was dried under vacuum and then purged several times with nitrogen. Under a stream of nitrogen, 1-bromo-3-fluoro-5-(trifluoromethyl)benzene (2.5 g, 10.3 mmoles) was added to the flask and dissolved in anhydrous ether (100 mL). The flask was fitted with a septum which was connected to the nitrogen line via a 16 gauge 1½ PrecisionGlide® needle. The stirring solution was cooled to −78° C. for 10 minutes, n-BuLi (1.6M in hexanes, 6.4 mL. 10.3 mmoles) was added drop wise. After 15 minutes, a solution of 5-chloro-2-cyanopyridine (1.42 g, 10.3 mmoles) in anhydrous THF (10 mL) was added from a syringe. The reaction was stirred for 2 hours at −78° C. and trimethylchlorosilane (1.41 mL, 10.3 mmoles) was added. The reaction vessel was removed from the acetone/dry ice bath and the reaction was allowed to warm up to room temperature. After 30 minutes, the reaction vessel was cooled to −78° C., Benzylmagnesium chloride (2.0M in THF, 5.15 mL, 10.3 mmoles) was added and the reaction was allowed to slowly warm to room temperature for 2 h. The reaction was quenched with H₂O (10 mL). The crude product was poured into 200 mL ethyl acetate in a 1000 mL separatory funnel. The light brown solution was washed with saturated aqueous NH₄Cl (3×100 mL), then with water (2×100 mL). The organic layer was dried over Na₂SO₄, filtered and concentrated in vacuo. The crude residue was purified by column chromatography on silica gel ISCO with 95-75% hexanes in ethylacetate to yield 1-(5-chloropyridin-2-yl)-1-(3-fluoro-5-(trifluoromethyl)phenyl)-2-phenylethanamine 994 mg (24% yield). LC-MS (methanol) [M+1]=394. ¹H NMR (500 MHz, CDCl₃) δ ppm 8.58 (1H, d, J=2.75 Hz), 7.57-7.64 (2H, m), 7.45 (2H, d, J=8.25 Hz), 7.09 -7.24 (4H, m), 6.81 (2H, d, J=6.60 Hz), 3.93 (1H, d, J=13.20 Hz), 3.46 (1H, d, J=13.20 Hz), 1.87 (2H, broad s).

Alternate benzylzinc bromide procedure:

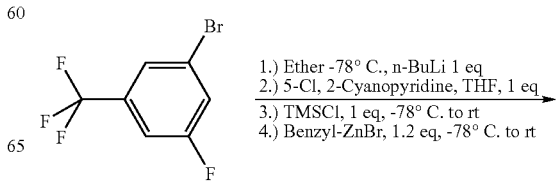

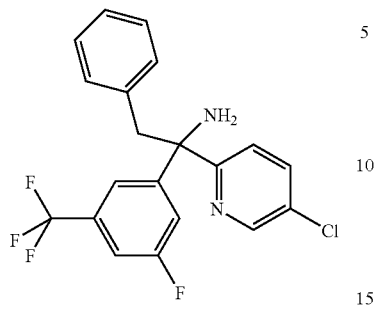

A dry 200 mL round bottomed flask was equipped a stirring bar and fitted to an adapter connected to the vacuum line. The flask was dried under vacuum and then purged several times with nitrogen. Under a stream of nitrogen, 1-bromo-3-fluoro-5-(trifluoromethyl)benzene (972 mg, 4 mmoles) was added to the flask and dissolved in anhydrous ether (75 mL). The flask was fitted with a septum which was connected to the nitrogen line via a 16 gauge 1½ PrecisionGlide® needle. The stirring solution was cooled to −78° C. for 10 minutes, n-BuLi (1.6M in hexanes, 2.25 mL. 3.6 mmoles) was added drop wise. After 15 minutes, a solution of 5-chloro-2-cyanopyridine (552 mg, 4 mmoles) in anhydrous THF (5 mL) was added from a syringe. The reaction was stirred for 2 hours at −78° C. and trimethylchlorosilane (550 μL, 4 mmoles) was added. The reaction vessel was removed from the acetone/dry ice bath and the reaction was allowed to warm up to room temperature. After 30 minutes, the reaction vessel was cooled to −78° C., Benzylzinc chloride (0.5M in THF, 9.6 mL, 4.8 mmoles) was added and the reaction was allowed to slowly warm to room temperature for 3 h. The reaction was quenched with H₂O (10 mL). The crude product was poured into 200 mL ethyl acetate in a 1000 mL separatory funnel. The light brown solution was washed with saturated aqueous NH₄Cl (3×100 mL), then with water (2×100 mL). The organic layer was dried over Na₂SO₄, filtered and concentrated in vacuo. The crude residue was purified on SCX column (10 g, high load, 0.65 mmole/g) to yield 1-(5-chloropyridin-2-yl)-1-(3-fluoro-5-(trifluoromethyl)phenyl)-2-phenylethanamine 890 mg (56% yield). LC-MS (methanol) [M+1]=394.

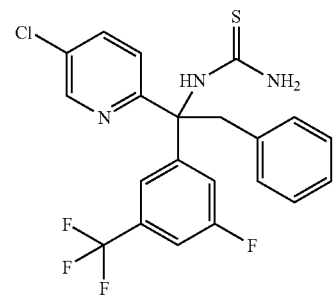

1-(5-chloropyridin-2-yl)-1-(3-fluoro-5-(trifluoromethyl)phenyl)-2-phenylethanamine (0.267 g, 0.678 mmol) was dissolved in anhydrous dichloromethane (8.5 mL). Benzoylisothiocyanate (109 mL, 0.813 mmol) was added and the reaction was refluxed for 2 hours. The reaction was concentrated and crude mixture was purified by ISCO chromatography (12 g column) using hexanes/EtOAc (0-30% over 18 min) to give benzyl 1-(5-chloropyridin-2-yl)-1-(3-fluoro-5-(trifluoromethyl)phenyl)-2-phenylethylcarbamothioylcarbamate as a white foam (269 mg, 71% yield). LCMS: 4.2 min [M+1] 558.2 (4 min gradient, MeOH/H₂O 0.1% TFA); 1H NMR (400 MHz, CDCl₃) δ ppm 3.64 (d, J=13.18 Hz, 1H), 5.14 (d, J=13.18 Hz, 1H), 6.73 (d, J=6.59 Hz, 2H), 7.04-7.14 (m, 4H), 7.22-7.28 (m, 1H), 7.32 (d, J=9.67 Hz, 1H), 7.48-7.56 (m, 3H), 7.61 (t, J=7.47 Hz, 1H), 7.68 (dd, J=8.57, 2.42 Hz, 1H), 7.87 (d, J=7.47 Hz, 2H), 8.49 (d, J=1.76 Hz, 1H), 8.94 (s, 1H), 12.68 (s, 1H).

To benzyl 1-(5-chloropyridin-2-yl)-1-(3-fluoro-5-(trifluoromethyl)phenyl)-2-phenylethylcarbamothioylcarbamate (269 mg, 0.483 mmol) in Methanol/THF (2 mL/2 mL) was added LiOH (2M, 483 mL, 0.966 mmol). The reaction was refluxed for 40 minutes. The solvents were removed and the residue dissolved in EtOAc. The resulting solution was washed with H₂O, brine, dried over MgSO₄ and concentrated. The crude mixture was purified by silica gel ISCO chromatography (12 g column) using hexanes/EtOAc (0-50% over 18 min) to give 1-(1-(5-chloropyridin-2-yl)-1-(3-fluoro-5-(trifluoromethyl)phenyl)-2-phenylethyl)thiourea as a pale yellow foam (169 mg, 78% yield). LCMS: 3.8 min [M+1] 454.2 (4 min gradient, MeOH/H₂O 0.1% TFA); 1H NMR (400 MHz, CDCl₃) δ ppm 5.62 (s, 3H), 6.71 (d, J=7.34 Hz, 3H), 7.11 (d, J=8.56 Hz, 6H), 7.32 (s, 2H), 7.50-7.57 (m, 1H), 7.69 (dd, J=8.56, 2.20 Hz, 1H), 8.28 (s, 1H), 8.64 (s, 1H).

Procedure 2

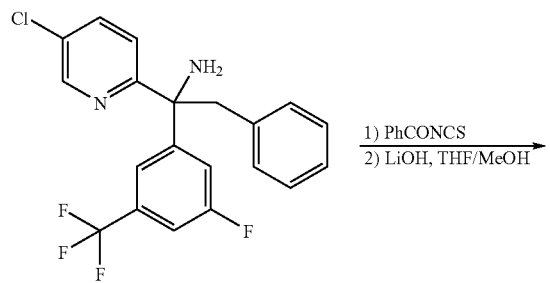

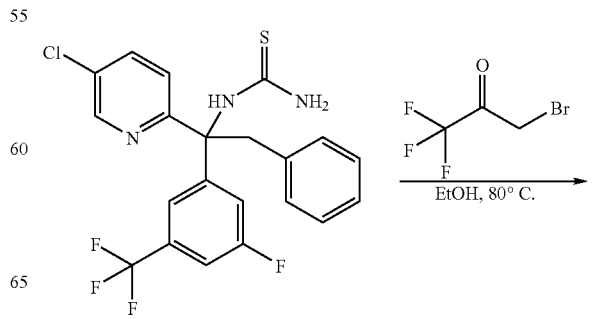

-continued

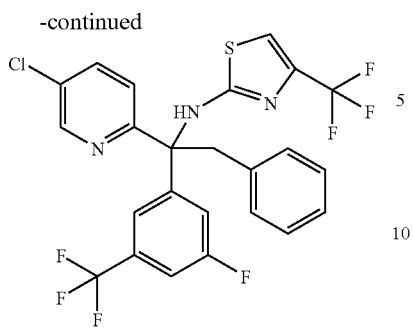

To 1-(1-(5-chloropyridin-2-yl)-1-(3-fluoro-5-(trifluoromethyl)phenyl)-2-phenylethyl)thiourea (15 mg, 0.033 mmol) in ethanol (1 mL) in a two dram vial was added 3-bromo-1,1,1-trifluoropropan-2-one (6.3 mg, 0.033 mmol). The vial was heated in a shaker at 80° C. for 2 hours. The reaction was concentrated and crude mixture was purified by silica gel ISCO chromatography (4 g column) using hexanes/EtOAc (0-25% over 20 min) to give the N-(1-(5-chloropyridin-2-yl)-1-(3-fluoro-5-(trifluoromethyl)phenyl)-2-phenylethyl)-4-(trifluoromethyl)thiazol-2-amine as a white foam (11 mg, 61% yield). LCMS: 4.3 min [M+1] 456.1 (4 min gradient, MeOH/H$_2$O 0.1% TFA); 1H NMR (400 MHz, CDCl$_3$) δ ppm 3.58 (d, J=13.21 Hz, 1H), 4.60 (d, J=12.96 Hz, 1H), 6.46 (d, J=7.58 Hz, 2H), 6.88 (s, 1H), 7.05 (t, J=7.46 Hz, 2H), 7.10-7.15 (m, 2H), 7.24-7.29 (m, 2H), 7.35 (d, J=9.78 Hz, 1H), 7.64-7.71 (m, 2H), 8.01 (s, 1H), 8.31 (d, J=2.20 Hz, 1H).

EXAMPLE 2

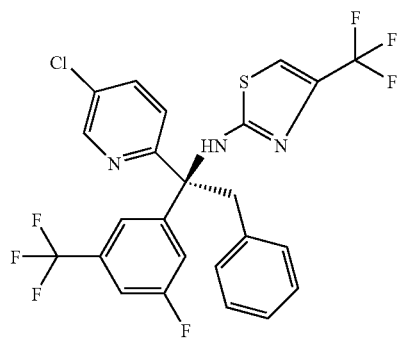

(S)-N-(1-(5-chloropyridin-2-yl)-1-(3-fluoro-5-(trifluoromethyl)phenyl)-2-phenylethyl)-4-(trifluoromethyl)thiazol-2-amine Procedure 3

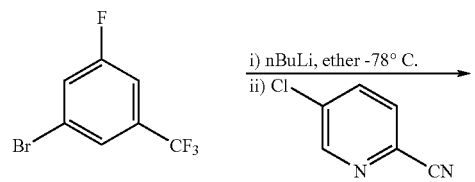

-continued

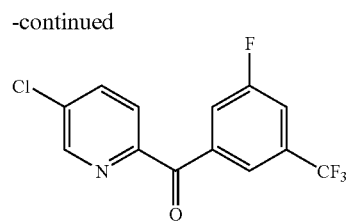

At −78° C. under Ar a dry 250 mL 3 neck flask was charged with 1-bromo-3-fluoro-5-(trifluoromethyl)benzene (4.5 g, 0.018 mol). Dry ether (100 mL) was added and to the stirred solution, nBuLi (9.2 mL, 0.018 mol) was added dropwise via airtight syringe through a rubber septum. The resulting pale orange colored solution was stirred at −78° C. for 30 min. 5-chloropicolinenitrile (2.5 g, 0.018 mol) was then added as a thick slurry in dry ether (approx 10 mL) via wide neck funnel. The resulting solution turned dark red in color and was stirred at −78° C. for 1 hr. LCMS indicated that the reaction was complete and, at −78° C. the reaction mixture was quenched with 1.0M HCl (approx 50 mL). The cooling bath was removed and as the reaction mixture reached ambient temperature, (22° C.), the organic solution turned pale green in color. The solution was transferred to a separation funnel and the organic layer separated. The aqueous phase was washed with EtOAc (20 mL) and the combined organic portions dried over anhydrous Na$_2$SO$_4$, decanted and concentrated yielding a pale brown oil. This was dissolved in hexane (ca 15 mL) and loaded directly onto a silica gel ISCO cartridge (330 g, previously equilibrated with hexanes) and elution at 100 mL/min gradient 0 to 70% EtOAc in hexanes over 45 min. Elution time of the product was 17 to 20 mins and (5-chloropyridin-2-yl)(3-fluoro-5-(trifluoromethyl)phenyl)methanone (4.1 g, 75% yield) was isolated as a pale yellow oil which crystallized on standing. R$_f$ 0.74 (Hexane:EtOAc 4:1) LCMS: 2.03 min [M+1] 304.2 (2 min gradient, MeOH/H$_2$O 0.1% TFA); HPLC: 3.98 min (4 min gradient, MeOH/H$_2$O 0.2% PPA Purity 98%; NMR: 400 MHz $^1$H (CDCl$_3$) 8.69 ppm, 1H, d, J=2.64 Hz; 8.22 ppm, 1H, s; 8.13 ppm, 1H, d, J=8.36 Hz; 8.07 ppm, 1H, brd, J=8.4 Hz; 7.93 ppm, 1H, dd, J=2.2 and J=8.36 Hz; 7.57 ppm, 1H, brd, J=8.4 Hz.

Procedure 4

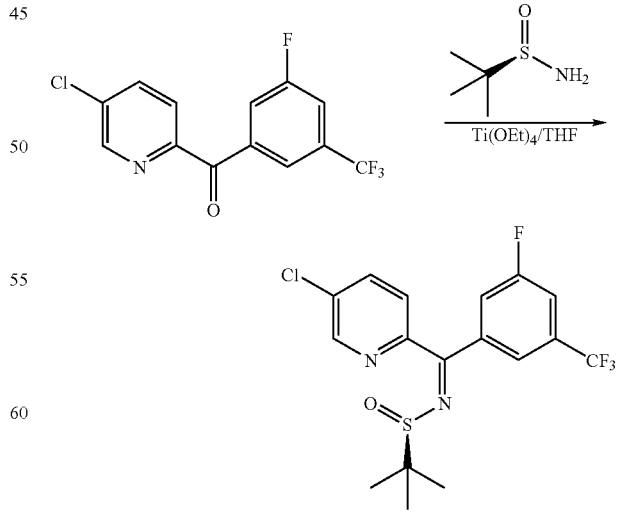

At room temperature, a 50 mL flask fitted with a reflux condenser was charged with (5-chloropyridin-2-yl)(6-(trifluoromethyl)pyridin-2-yl)methanone (0.17 g, 0.60 mmol). Anhydrous THF (10 mL) was added followed by (R+)-2-methylpropane-2-sulfinamide (0.072 g, 0.60 mmol) and Ti(OEt)$_4$ (0.19 mL, 0.90 mol, 1.5 equivalent) in one portion. The pale orange solution was heated to 75° C. for 14 h then allowed to cool to ambient temperature. The solution was concentrated under reduced pressure to half the volume and the resulting orange solution was loaded directly onto a silica gel ISCO (40 g, previously equilibrated with hexanes) and elution at 80 mL/min gradient 0 to 100% EtOAc in hexanes over 20 min. Elution time of the recovered starting material was 10 mins (0.70 g recovered, 41%) and of the product was 12.5 min. (R)-N-((5-chloropyridin-2-yl)(6-(trifluoromethyl)pyridin-2-yl)methylene)-2-methylpropane-2-sulfinamide (40 mg, 31% yield based on recovered starting material) was isolated as a pale yellow oil. R$_f$ 0.5 (Hexane:EtOAc 2:1) LCMS: 1.80 min [M+1] 390.1 (2 min gradient, MeOH/H$_2$O 0.1% TFA); HPLC: 3.50 min (4 min gradient, MeOH/H$_2$O 0.2% PPA); Purity 83%; NMR: 400 MHz $^1$H (CDCl$_3$) (2 sets of peaks attributed to E/Z isomerism) 8.62 ppm, d, J=2.2 Hz; 8.46 ppm, bss; 8.18, 1H, d, J=8.0 Hz; 8.13 ppm, d, J=8.0 Hz; 8.02 ppm, d, J=8.0 Hz; 7.91 ppm, brs; 7.82 ppm, d, J=8.0 Hz; 7.74 ppm, d, J=8.0 Hz; 7.68 ppm, d, J=8.0 Hz; 7.5 ppm, brm; 1.37, s; 1.28, s.

Procedure 5

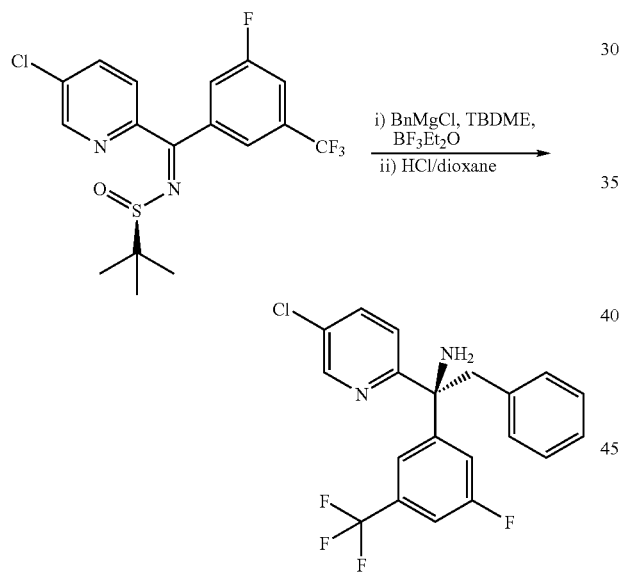

To a solution of (R)-N-((5-chloropyridin-2-yl)(3-fluoro-5-(trifluoromethyl)phenyl)methylene)-2-methylpropane-2-sulfinamide (1.09 g, 2.68 mmol) in anhydrous TBME (45 mL) at −78° C. under argon was added BF$_3$Et$_2$O (0.57 mL, 5.38 mmol). After 5 min, benzylmagnesium grignard (5.38 mL, 5.38 mmol, 1.0M in ether) was added dropwise with stirring. After 40 min, LCMS indicated that the reaction was complete and the cold solution was quenched with saturated NaCl (ca 20 mL), transferred to a separation funnel and the organic phase extracted with EtOAc (3×20 mL). The combined organic portions were dried, decanted, concentrated and purified by silica gel ISCO chromatography. 2×120 g cartridge columns were used 0-60% EtOAc/hexanes over 20 min. A trace amount of minor diastereomer eluted first followed by the major diastereomer (R)-N-((S)-1-(5-chloropyridin-2-yl)-1-(3-fluoro-5-(trifluoromethyl)phenyl)-2-phenylethyl)-2-methylpropane-2-sulfinamide (0.97 g, 72% yield). R$_f$ 0.4 (Hexane:EtOAc 2:1) LCMS: 2.15 min [M+1] 499.1 (2 min gradient, MeOH/H$_2$O 0.1% TFA); HPLC: 4.15 min (4 min gradient, MeOH/H$_2$O 0.2% PPA); Purity 99%; NMR: 400 MHz $^1$H (CDCl$_3$) 8.65 ppm, d, 1H, J=2.6 Hz; 7.62 ppm, dd, 1H, J=2.6 and J=8.8 Hz; 7.36 ppm, 4H, m; 7.29 ppm, 1H, m; 7.24 ppm, 1H, m; 7.14 ppm, 2H, m; 6.99 ppm, 1H, d, J=10.1 Hz; 6.81 ppm, 1H, d, J=6.6 Hz; 4.09 ppm, 1H, d, J=13.2 Hz; 3.69 ppm, 1H, d, J=13.2 Hz; 1.18 ppm, 9H, s.

(R)-N-((S)-1-(5-chloropyridin-2-yl)-1-(3-fluoro-5-(trifluoromethyl)phenyl)-2-phenylethyl)-2-methylpropane-2-sulfinamide (0.765 g, 1.53 mmol) was dissolved in anhydrous MeOH (4 mL). At RT, 4.0M HCl in dioxane (1.5 mL) was added and the reaction mixture stirred for 20 min. The reaction mixture was diluted with EtOAc (50 mL), transferred to a separation funnel and washed with 1.0M NaOH (ca. 20 mL). The organic portion was dried over anhydrous Na$_2$SO$_4$, decanted and concentrated yielding (S)-1-(5-chloropyridin-2-yl)-1-(3-fluoro-5-(trifluoromethyl)phenyl)-2-phenylethanamine as a pale yellow oil, (0.745 g, crude quantitative yield). LCMS: 1.51 min [M+1] 395.2 (2 min gradient, MeOH/H$_2$O 0.1% TFA).

(S)-N-(1-(5-chloropyridin-2-yl)-1-(3-fluoro-5-(trifluoromethyl)phenyl)-2-phenylethyl)-4-(trifluoromethyl)thiazol-2-amine was prepared from (S)-1-(5-chloropyridin-2-yl)-1-(3-fluoro-5-(trifluoromethyl)phenyl)-2-phenylethanamine as described in Procedure 2.

EXAMPLE 3

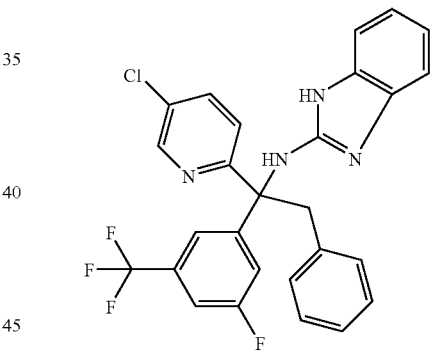

N-(1-(5-chloropyridin-2-yl)-1-(3-fluoro-5-(trifluoromethyl)phenyl)-2-phenylethyl)-1H-benzo[d]imidazol-2-amine Procedure 6

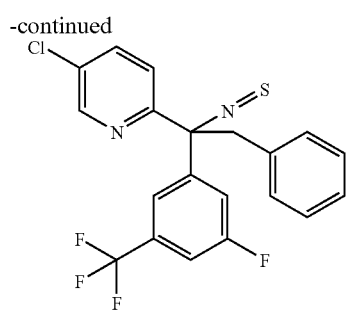

1-(5-chloropyridin-2-yl)-1-(3-fluoro-5-(trifluoromethyl)phenyl)-2-phenylethanamine (0.132 g, 0.335 mmol) in chloroform (1 mL) was added H₂O (1 mL) and NaHCO₃ (84 mg, 1.01 mmol). To this vigorously stirred mixture was added thiophosgene (38.3 μl, 0.502 mmol) dropwise. The reaction was stirred at room temperature for 2 hours and diluted with CHCl₃ and H₂O. The organic layer was separated and washed with brine, dried over MgSO₄ and concentrated. The crude mixture was purified by silica gel ISCO chromatography (12 g column) using hexanes/EtOAc (0-30% over 20 min) to give 5-chloro-2-(1-(3-fluoro-5-(trifluoromethyl)phenyl)-1-isothiocyanato-2-phenylethyl)pyridine as a yellow oil (73 mg, 50% yield). LCMS: 4.3 min [M+1] 437.1 (4 min gradient, MeOH/H₂O 0.1% TFA); 1H NMR (400 MHz, CDCl₃) δ ppm 3.72 (d, J=13.69 Hz, 2H), 4.07 (d, J=13.45 Hz, 2H), 6.89 (dd, J=7.83, 1.47 Hz, 3H), 7.16-7.22 (m, 5H), 7.24 (d, J=1.47 Hz, 1H), 7.37 (dt, J=4.22, 2.17 Hz, 2H), 7.40 (t, J=1.96 Hz, 1H), 7.52 (s, 2H), 7.66 (dd, J=8.31, 2.45 Hz, 2H), 8.65 (d, J=1.96 Hz, 2H).

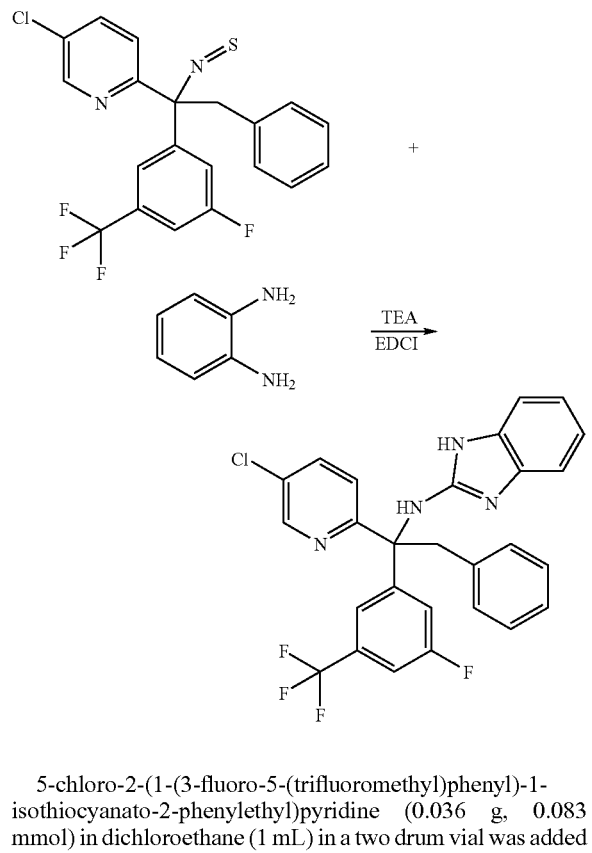

5-chloro-2-(1-(3-fluoro-5-(trifluoromethyl)phenyl)-1-isothiocyanato-2-phenylethyl)pyridine (0.036 g, 0.083 mmol) in dichloroethane (1 mL) in a two drum vial was added phenylenediamine (12 mg, 0.108 mmol) and TEA (13 mL, 0.091 mmol). The reaction was heated at 80° C. for 2 hours. EDCI (24 mg, 0.124 mmol) was added and the reaction was continued to be heated at 80° C. overnight. The reaction was concentrated and the crude mixture was purified by ISCO chromatography (12 g column) using hexanes/EtOAc (0-40% over 25 min) to give N-(1-(5-chloropyridin-2-yl)-1-(3-fluoro-5-(trifluoromethyl)phenyl)-2-phenylethyl)-1H-benzo[d]imidazol-2-amine as a white solid (20 mg, 47% yield). LCMS: 3.2 min [M+1] 511.22 (4 min gradient, MeOH/H₂O 0.1% TFA); 1H NMR (400 MHz, CD₃OD) d ppm 4.01-4.10 (m, 1H), 4.51 (d, J=13.21 Hz, 1H), 6.48 (d, J=7.34 Hz, 2H), 6.93-7.04 (m, 5H), 7.22 (dd, J=5.50, 3.06 Hz, 2H), 7.34 (d, J=8.31 Hz, 1H), 7.51-7.58 (m, 1H), 7.71-7.77 (m, 2H), 7.82 (dd, J=8.56, 2.45 Hz, 1H), 8.41 (d, J=2.45 Hz, 1H).

EXAMPLE 4

N-(1-(5-chloropyridin-2-yl)-1-(3-fluoro-5-(trifluoromethyl)phenyl)-2-phenylethyl)-5-phenyloxazol-2-amine Procedure 7

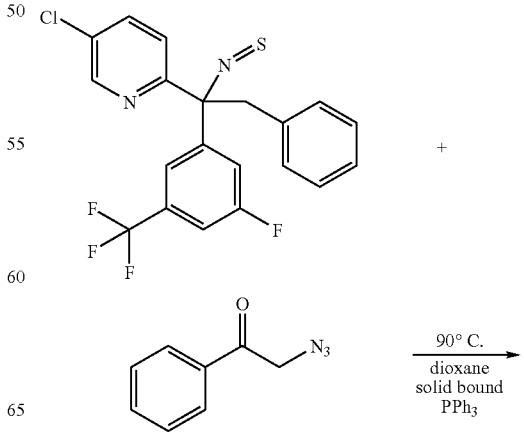

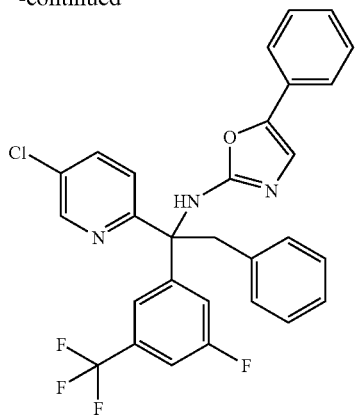

5-chloro-2-(1-(3-fluoro-5-(trifluoromethyl)phenyl)-1-isothiocyanato-2-phenylethyl)pyridine (0.047 g, 0.108 mmol) in dioxane (3 mL) in a two drum vial was added 2-azido-1-phenylethanone (21 mg, 0.129 mmol) and solid bound triphenylphosphine (100 mg, 0.162 mmol). The reaction was heated at 90° C. for 1 hour. The reaction was concentrated and the crude mixture was purified by preparative HPLC (phenominex C18 column, 21×100 mm, 5μ) using MeOH/H₂O (0.1% TFA) to give N-(1-(5-chloropyridin-2-yl)-1-(3-fluoro-5-(trifluoromethyl)phenyl)-2-phenylethyl)-5-phenyloxazol-2-amine as a yellow solid (7 mg, 12% yield). LCMS: 4.1 min [M+1] 538.2 (4 min gradient, MeOH/H₂O 0.1% TFA); 1H NMR (400 MHz, CDCl₃) δ ppm 3.97-4.02 (m, 1H), 4.06-4.13 (m, 1H), 6.52 (d, J=7.58 Hz, 2H), 7.09 (t, J=7.46 Hz, 2H), 7.15 (s, 1H), 7.17 (dd, J=6.36, 1.71 Hz, 3H), 7.23 (d, J=8.56 Hz, 1H), 7.30-7.40 (m, 5H), 7.68-7.73 (m, 2H), 8.50 (d, J=2.20 Hz, 1H).

EXAMPLE 5

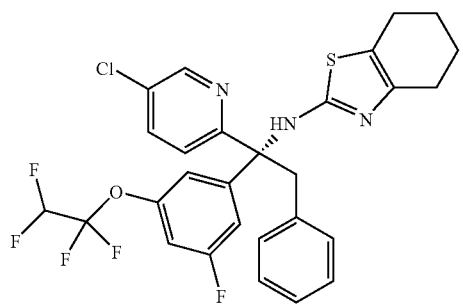

(R)-N-(1-(5-chloropyridin-2-yl)-1-(3-fluoro-5-(1,1,2,2-tetrafluoroethoxy)phenyl)-2-phenylethyl)-4,5,6,7-tetrahydrobenzo[d]thiazol-2-amine Procedure 8

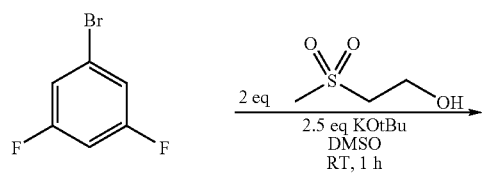

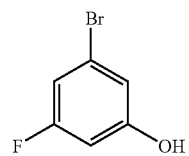

A solution of 1-bromo-3,5-difluorobenzene (20.0 g, 104 mmole) was cooled in a water bath and 2-(methylsulfonyl)ethanol (26.0 g, 207 mmol) in DMSO (100 mL) was added. KOtBu (29.0 g, 260 mmole) was added to this reaction mixture in portions. The reaction mixture turned dark. After the addition was complete, the water bath was removed and the reaction was stirred at room temperature for 1 h. The pH was adjusted to 1 using 1 N HCl, and the reaction was extracted with ether (3×200 mL). The combined organic portions were washed with aqueous 1N NaOH (2×200 mL). The NaOH layer was acidified to pH 1 and extracted with ether (3×200 mL). The combined organic layers were dried over sodium sulfate and filtered. The filtrate solvent volume was concentrated NOT to complete dryness due to volatility of the 3-bromo-5-fluorophenol and was used directly in the next step without further purification. NMR: 400 MHz ¹H (CDCl₃) 6.81 ppm, 1H, dt, J=8.35 Hz and 1.98 Hz; 6.78 ppm, 1H, m; 6.50 ppm, 1H, dt, J=9.67 Hz and 2.20 Hz.

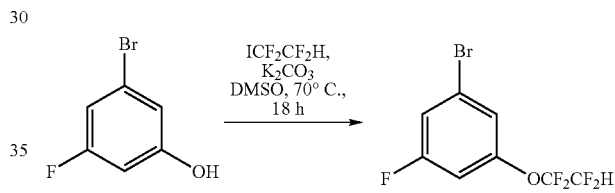

To a solution of 3-bromo-5-fluorophenol (104 mmol crude) and iodo-1,1,2,2,-tetrafluoroethane (28.4 g, 125 mmol) in DMSO (80 mL) was added K₂CO₃ (57.0 g, 420 mmol). The reaction mixture was sealed in a thick walled glass pressure round bottom flask and heated at 70° C. for 18 h. The reaction mixture was allowed to cool to room temperature, diluted with water (500 mL) and extracted with ether (3×200 mL). The combined ether layers were washed with 1N NaOH (2×200 mL), water (2×200 mL) and brine (200 mL). The organic layer was dried over sodium sulfate, filtered and concentrated. The residue was dissolved in ether (150 mL) and filtered through a plug of activated basic alumina. The filtrate was concentrated to give 1-bromo-3-fluoro-5-(1,1,2,2-tetrafluoroethoxy)benzene as a pale yellow oil (27.2 g, 88% for two steps) which was used without further purification LCMS: 1.91 min, [M+1] No Ionizable peak (2 min gradient, MeOH/H₂O 0.1% TFA); HPLC: 3.76 min (4 min gradient, MeOH/H₂O 0.2% PPA) Purity 100%; NMR: 400 MHz ¹H (CDCl₃) 7.19 ppm, 2H, m; 6.92 ppm, 1H, d, J=8.35 Hz; 5.88 ppm, 1H, tt; J=52.95 Hz and J=2.64 Hz.

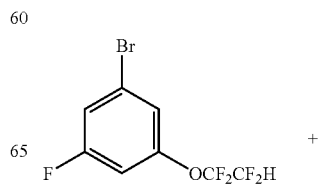

+

149

-continued

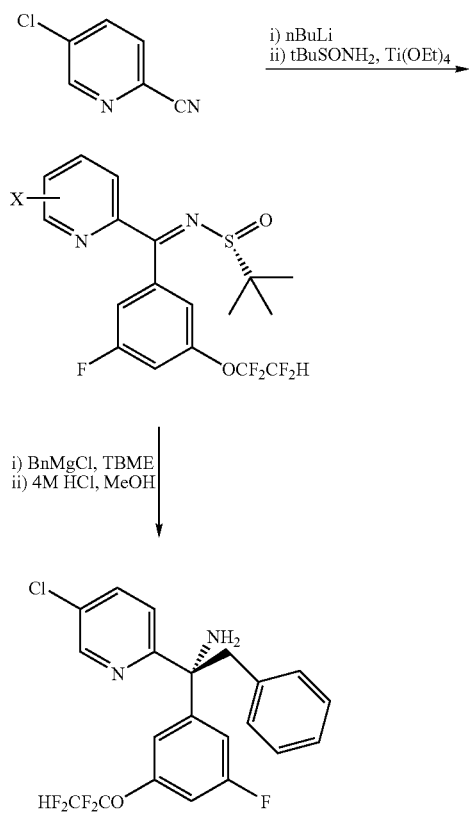

i) nBuLi
ii) tBuSONH₂, Ti(OEt)₄ i) BnMgCl, TBME
ii) 4M HCl, MeOH

Following Procedures 3, 4 and 5, (R)-1-(5-chloropyridin-2-yl)-1-(3-fluoro-5-(1,1,2,2-tetrafluoroethoxy)phenyl)-2-phenylethanamine was prepared and was subjected to the reaction procedures described in Procedure 2 to obtain (R)-N-(1-(5-chloropyridin-2-yl)-1-(3-fluoro-5-(1,1,2,2-tetrafluoroethoxy)phenyl)-2-phenylethyl)-4,5,6,7-tetrahydrobenzo[d]thiazol-2-amine in >95:5 enantiomeric excess. LCMS: 3.46 min, [M+1] 580.31 (4 min gradient, MeOH/H₂O 0.1% TFA).

EXAMPLE 6

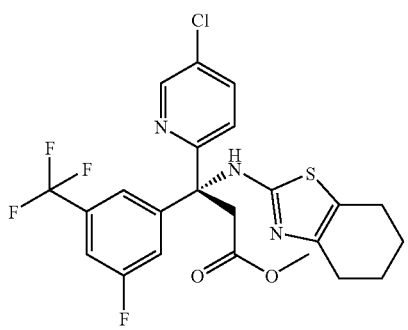

150

(R)-methyl 3-(5-chloropyridin-2-yl)-3-(3-fluoro-5-(trifluoromethyl)phenyl)-3-(4,5,6,7-tetrahydrobenzo[d]thiazol-2-ylamino)propanoate Procedure 9

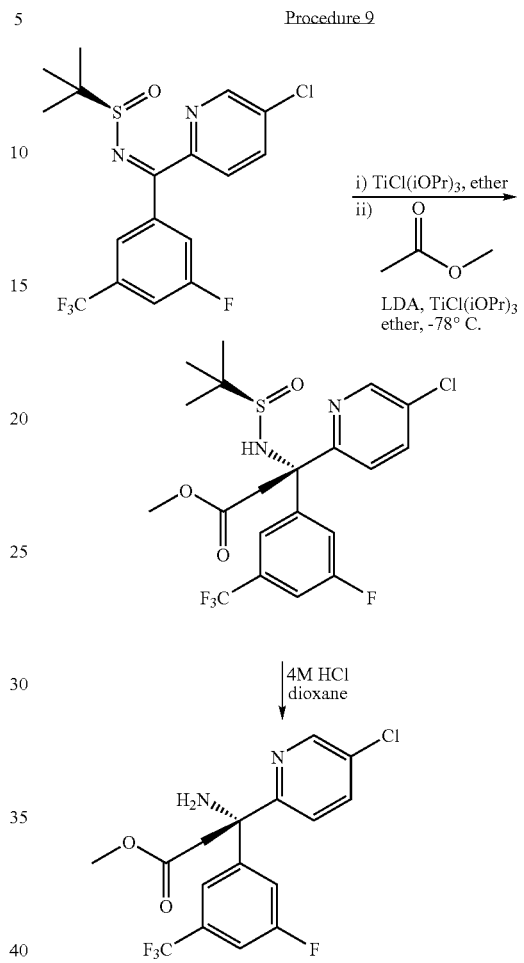

i) TiCl(iOPr)₃, ether
ii)

LDA, TiCl(iOPr)₃
ether, -78° C.

4M HCl
dioxane

The synthesis of (R)-N-((5-chloropyridin-2-yl)(6-(trifluoromethyl)pyridin-2-yl)methylene)-2-methylpropane-2-sulfinamide is described in Procedures 3 and 4. At -78° C. under argon, LDA (3.97 mL, 7.94 mmol, 2.0 M solution in cyclohexane) was added to a solution of methylacetoacetate (0.587 g, 7.95 mmol) in anhydrous ether (40 mL). After 30 min at -78° C., TiCl(iOPr)₃ (11.9 mL, 11.9 mmol, 1.0 M solution in hexanes) was added to the stirred solution. In a separate flask at room temperature, (R)-N-((5-chloropyridin-2-yl)(6-(trifluoromethyl)pyridin-2-yl)methylene)-2-methylpropane-2-sulfinamide (1.61 g, 3.97 mmol) was dissolved in anhydrous ether (40 mL) and TiCl(iOPr)₃ (3.97 mL, 3.97 mmol, 1.0 M solution in hexanes) was added. After 30 mins, the pre-complexed solution was removed via syringe and added to the enolate dropwise at -78° C. under argon. The resulting pale orange solution was stirred at -78° C. for 1 h then quenched by addition of 1.0 M HCl solution (ca. 50 mL). On reaching room temperature, the solution was transferred to a separation funnel and extracted with EtOAc (2×50 mL). The combined organic portion was dried over Na₂SO₄, decanted, concentrated and purified by silica gel ISCO chromatography (120 g column) using hexanes/EtOAc (0-80% over 25 min). The product was isolated as a crude white foam, (1.47 g, 77% yield). NMR analysis of the product showed a diastereomeric ratio of 93:7 by integration. The (S)-methyl 3-(5-chloropyridin-2-yl)-3-(3-fluoro-5-(trifluoromethyl)phenyl)-3-((R)-2-methylpropan-2-ylsulfinamido)propanoate (1.25 g, 2.60 mmol) was dissolved in MeOH (5 mL) and water was added dropwise until turbidity was observed. The solution was kept at 4° C. for 2.5 h then the remaining solution removed by pipet. The crystalline material was azeotroped with ether and dried under vacuum yielding the product as a white crystalline foam, (1.04 g, 83% yield). $R_f$ 0.3 (Hexane:EtOAc 4:1) LCMS: 2.00 min [M+1] 481.1 (2 min gradient, MeOH/H$_2$O 0.1% TFA); HPLC: 3.89 min (4 min gradient, MeOH/H$_2$O 0.2% PPA); Purity 99%; NMR: 400 MHz $^1$H (CDCl$_3$) 8.54 ppm, d, J=2.2 Hz; 7.62 ppm, dd, J=4.0 and J=8.0 Hz; 7.40, 1H, s; 7.37 ppm, 1H, d, J=12.0 Hz; 7.20 ppm, 2H, m; 3.98 ppm, 1H, d, J=20 Hz; 3.73 ppm, 1H, d, J=16.0 Hz; 3.60 ppm, 3H, s; 1.31 ppm, 9H, s.

(S)-methyl 3-(5-chloropyridin-2-yl)-3-(3-fluoro-5-(trifluoromethyl)phenyl)-3-((R)-2-methylpropan-2-ylsulfinamido)propanoate (0.075 g, 0.16 mmol) was dissolved in MeOH (2 mL). At RT, 4.0 M HCl in dioxane (2 mL) was added and the reaction mixture stirred for 30 min. The reaction mixture was diluted with EtOAc (50 mL), transferred to a separation funnel and washed with 1.0 M NaOH (ca. 20 mL). The organic portion was dried over anhydrous Na$_2$SO$_4$, decanted and concentrated yielding a colorless oil, (0.062 g, crude quantitative yield). LCMS: 1.37 min [M+1] 377.1 (2 min gradient, MeOH/H$_2$O 0.1% TFA).

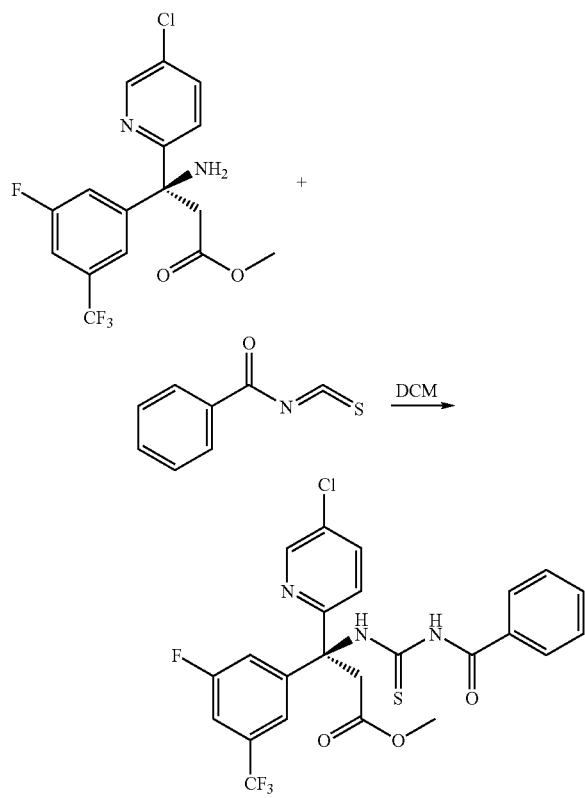

Following Procedure 2, intermediate (S)-methyl 3-(3-benzoylthioureido)-3-(5-chloropyridin-2-yl)-3-(3-fluoro-5-(trifluoromethyl)phenyl)propanoate was prepared. LCMS: 2.06 min [M+1] 540.2 (2 min gradient, MeOH/H$_2$O 0.1% TFA); HPLC: 4.04 min (4 min gradient, MeOH/H$_2$O 0.2% PPA); Purity 100%; NMR: 400 MHz $^1$H (CDCl$_3$) 12.96 ppm, 1H, s; 8.93 ppm, 1H, s; 8.65 ppm, 1H, d, J=2.20 Hz; 7.90 ppm, 2H, d, J=7.47 Hz; 7.62 ppm, 2H, m; 7.50 ppm, 2H, t, J=7.69 Hz; 7.43 ppm, 1H, s; 7.25 ppm, 1H, m; 7.19 ppm, 1H, d, J=7.91 Hz; 7.09 ppm, 1H, d, J=8.35 Hz; 4.90 ppm, 1H, d, J=15.38 Hz; 3.76 ppm, 1H, d, J=15.82 Hz; 3.51 ppm, 3H, s.

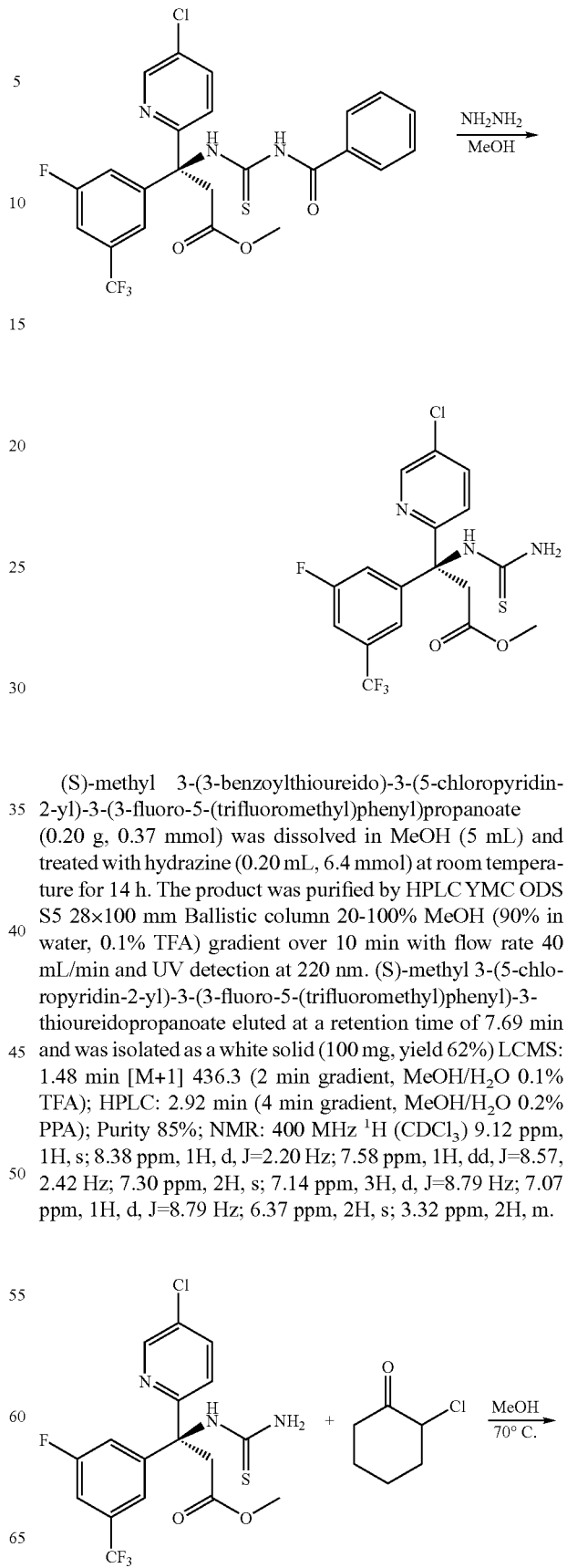

(S)-methyl 3-(3-benzoylthioureido)-3-(5-chloropyridin-2-yl)-3-(3-fluoro-5-(trifluoromethyl)phenyl)propanoate (0.20 g, 0.37 mmol) was dissolved in MeOH (5 mL) and treated with hydrazine (0.20 mL, 6.4 mmol) at room temperature for 14 h. The product was purified by HPLC YMC ODS S5 28×100 mm Ballistic column 20-100% MeOH (90% in water, 0.1% TFA) gradient over 10 min with flow rate 40 mL/min and UV detection at 220 nm. (S)-methyl 3-(5-chloropyridin-2-yl)-3-(3-fluoro-5-(trifluoromethyl)phenyl)-3-thioureidopropanoate eluted at a retention time of 7.69 min and was isolated as a white solid (100 mg, yield 62%) LCMS: 1.48 min [M+1] 436.3 (2 min gradient, MeOH/H$_2$O 0.1% TFA); HPLC: 2.92 min (4 min gradient, MeOH/H$_2$O 0.2% PPA); Purity 85%; NMR: 400 MHz $^1$H (CDCl$_3$) 9.12 ppm, 1H, s; 8.38 ppm, 1H, d, J=2.20 Hz; 7.58 ppm, 1H, dd, J=8.57, 2.42 Hz; 7.30 ppm, 2H, s; 7.14 ppm, 3H, d, J=8.79 Hz; 7.07 ppm, 1H, d, J=8.79 Hz; 6.37 ppm, 2H, s; 3.32 ppm, 2H, m.

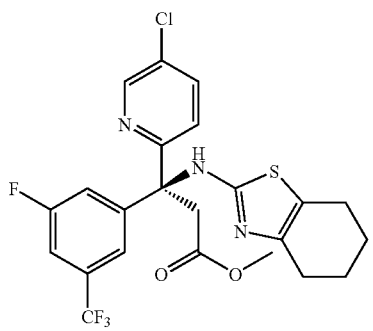

A solution of (S)-methyl 3-(5-chloropyridin-2-yl)-3-(3-fluoro-5-(trifluoromethyl)phenyl)-3-thioureidopropanoate (100 mg, 0.23 mmol) and 2-chloro cyclohexanone (36 mg, 0.28 mmol) in MeOH (5.0 mL) was heated at 70° C. for 18 h. The concentrated reaction mixture was purified by silica gel ISCO chromatography (12 g column) using hexanes/EtOAc (0-30% over 15 min). (S)-methyl 3-(5-chloropyridin-2-yl)-3-(3-fluoro-5-(trifluoromethyl)phenyl)-3-(4,5,6,7-tetrahydrobenzo[d]thiazol-2-ylamino)propanoate was isolated as a clear oil, (13 mg, 11% yield). LCMS: 1.70 min [M+1] 514.3 (2 min gradient, MeOH/H2O 0.1% TFA); HPLC: 3.65 min (4 min gradient, MeOH/H2O 0.2% PPA); Purity 96%; NMR: 400 MHz $^1$H (CDCl$_3$) 8.43 ppm, 1H, d, J=2.20 Hz; 7.55 ppm, 1H, dd, J=8.57, 2.42 Hz; 7.49 ppm, 1H, s; 7.29 ppm, 2H, m; 7.14 ppm, 1H, d, J=7.91 Hz; 3.98 ppm, 1H, d, J=15.82 Hz; 3.70 ppm, 1H, d, J=15.82 Hz; 3.60 ppm, 1H, s; 3.47 ppm, 3H, s; 2.40 ppm, 4H, m; 1.68 ppm, 4H, m.

EXAMPLE 7

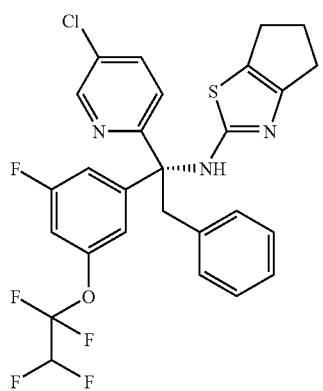

(R)-N-(1-(5-chloropyridin-2-yl)-1-(3-fluoro-5-(1,1,2,2-tetrafluoroethoxy)phenyl)-2-phenylethyl)-5,6-dihydro-4H-cyclopenta[d]thiazol-2-amine Procedure 10

(R)-1-(1-(5-chloropyridin-2-yl)-1-(3-fluoro-5-(1,1,2,2-tetrafluoroethoxy)phenyl)-2-phenylethyl)thiourea was prepared as described for Procedure 8.

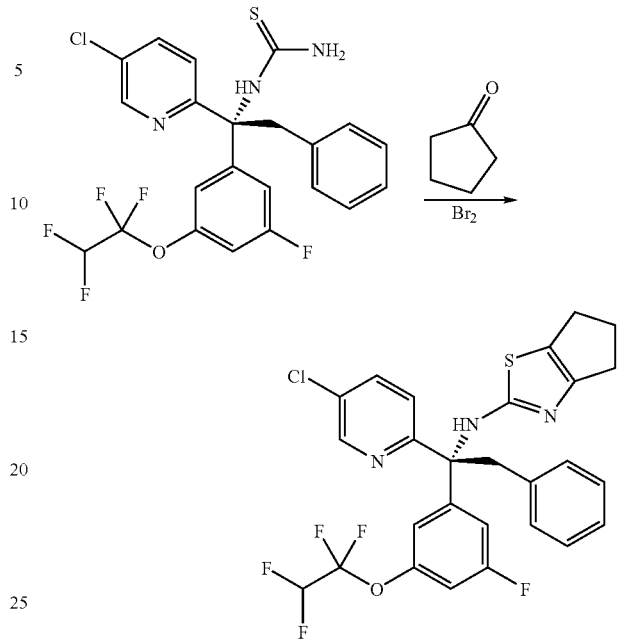

To a solution of cyclopentanone (68 mg, 0.8 mmol) in EtOH (1 ml) was added Br$_2$ (15 mg, 0.09 mmol) at r.t., sealed and stirred for 5 mins. The yellow solution became clear colorless. (R)-1-(1-(5-chloropyridin-2-yl)-1-(3-fluoro-5-(1,1,2,2-tetrafluoroethoxy)phenyl)-2-phenylethyl)thiourea (20 mg, 0.04 mmol) was added to the reaction mixture and the mixture was heated at 75° C. for 16 hrs, then heated at 160° C. under microwave for 30 mins. The reaction mixture was purified by prep HPLC, desired fraction condensed under vacuum to give (R)-N-(1-(5-chloropyridin-2-yl)-1-(3-fluoro-5-(1,1,2,2-tetrafluoroethoxy)phenyl)-2-phenylethyl)-5,6-dihydro-4H-cyclopenta[d]thiazol-2-amine (6 mg, 27% yield). LCMS: 3.67 min [M+1] 566.40 (4 min gradient, MeOH/H$_2$O 0.1% TFA); $^1$H NMR (400 MHz, CD$_3$OD) δ ppm 2.32-2.42 (m, 2H), 2.55-2.66 (m, 2H), 2.69-2.80 (m, 2H), 3.88 (d, J=13.14 Hz, 1H), 4.28 (d, J=13.39 Hz, 1H), 6.27 (t, J=50.0 Hz, 1H), 6.61 (d, J=6.82 Hz, 2H), 6.97-7.09 (m, 4H), 7.24 (s, 1H) 7.34 (ddd, J=9.98, 2.02, 1.89 Hz, 1H), 7.41 (d, J=8.59 Hz, 1H) 7.79 (dd, J=8.59, 2.53 Hz, 1H), 8.38 (d, J=2.02 Hz, 1H).

EXAMPLE 8

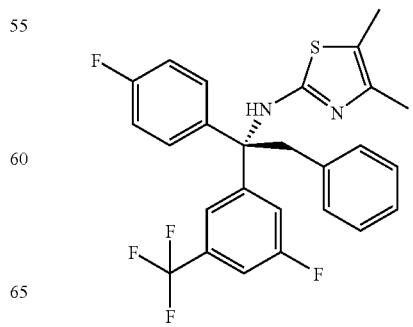

155

(S)-N-(1-(3-fluoro-5-(trifluoromethyl)phenyl)-1-(4-fluorophenyl)-2-phenylethyl)-4,5-dimethylthiazol-2-amine Procedure 11

(S)-1-(1-(3-fluoro-5-(trifluoromethyl)phenyl)-1-(4-fluorophenyl)-2-phenylethyl)thiourea was obtained as described in Procedures 3, 4. (S)-1-(3-fluoro-5-(trifluoromethyl)phenyl)-1-(4-fluorophenyl)-2-phenylethanamine was then converted to (S)-1-(1-(3-fluoro-5-(trifluoromethyl)phenyl)-1-(4-fluorophenyl)-2-phenylethyl)thiourea as described in Procedure 2.

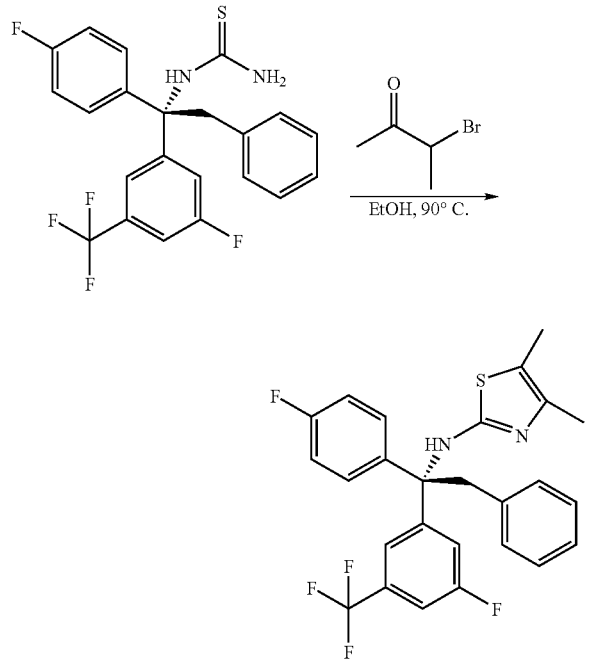

The thiourea (28 mg, 0.064 mmol) in ethanol (0.3 mL) in a two drum vial was added 3-bromobutan-2-one (28 mg, 0.18 mmol). The vial was heated in a shaker at 90° C. for 1 hour. The reaction was concentrated and crude mixture was purified by prep HPLC to give the (S)-N-(1-(3-fluoro-5-(trifluoromethyl)phenyl)-1-(4-fluorophenyl)-2-phenylethyl)4,5-dimethylthiazol-2-amine as a white solid (31 mg, 99% yield). LCMS: 3.63 min [M+1] 498.34 (4 min gradient, MeOH/H$_2$O 0.1% TFA); $^1$H NMR (400 MHz, CDCl$_3$) δ ppm 2.06 (s, 3H), 2.22 (s, 3H), 3.62-3.73 (m, 1H), 3.74-3.85 (m, 1H), 6.57 (d, J=7.58 Hz, 2H), 7.06-7.16 (m, 4H), 7.17-7.23 (m, 2H), 7.24-7.31 (m, 1H), 7.39 (dd, J=8.59, 5.05 Hz, 2H) 11.25(s, 1H).

156

EXAMPLE 9

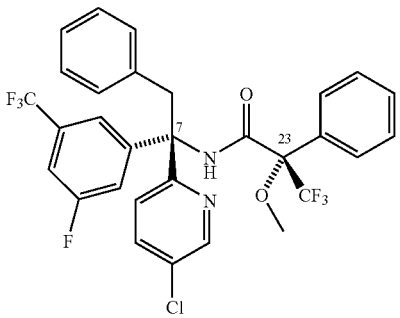

(S)-N-((S)-1-(5-chloropyridin-2-yl)-1-(3-fluoro-5-(trifluoromethyl)phenyl)-2-phenylethyl)-3,3,3-trifluoro-2-methoxy-2-phenylpropanamide Procedure 12

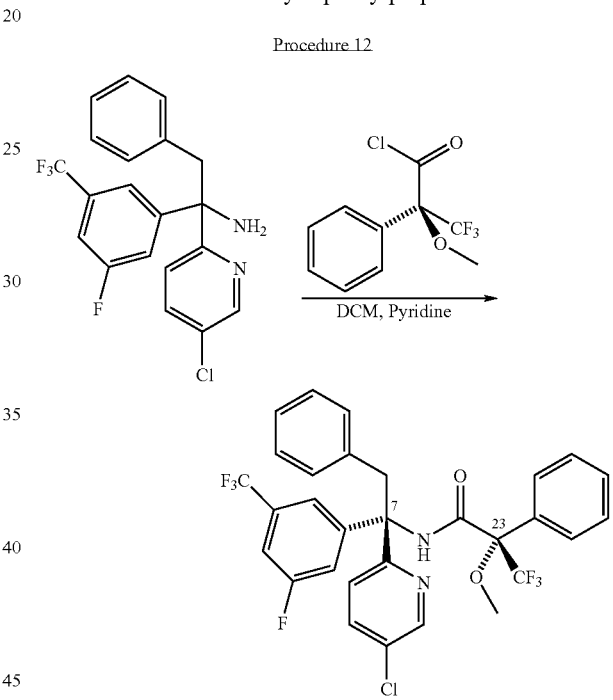

To racemic 1-(5-chloropyridin-2-yl)-1-(3-fluoro-5-(trifluoromethyl)phenyl)-2-phenylethanamine (obtained as described in Example 1, Procedure 1) (55 mg, 0.14 mmol) in DCM (1 mL) was added pyridine (56 μL, 55 mmol) and (R)-3,3,3-trifluoro-2-methoxy-2-phenylpropanoyl chloride (52 μL, 0.22 mmol). The reaction was stirred at room temperature for 14 h and the reaction mixture filtered through a silica plug elution with DCM. (S)-N-((S)-1-(5-chloropyridin-2-yl)-1-(3-fluoro-5-(trifluoromethyl)phenyl)-2-phenylethyl)-3,3,3-trifluoro-2-methoxy-2-phenylpropanamide was crystallized from ether heptane.

| Structure | T | a(Å) | b(Å) | c(Å) | α(°) | β(°) | γ(°) | V(Å$^3$) | Z' | Vm | sg | dcalc | mp(° C.) | R | Renan |
|---|---|---|---|---|---|---|---|---|---|---|---|---|---|---|---|
| 738730 N-1 | 25 | 8.9252(5) | 14.5130(7) | 21.853(1) | | | | 2830.7(3) | 1 | 708 | P2$_1$2$_1$2$_1$ | 1.434 | 160-168 | .060 | .067 |

TABLE 1

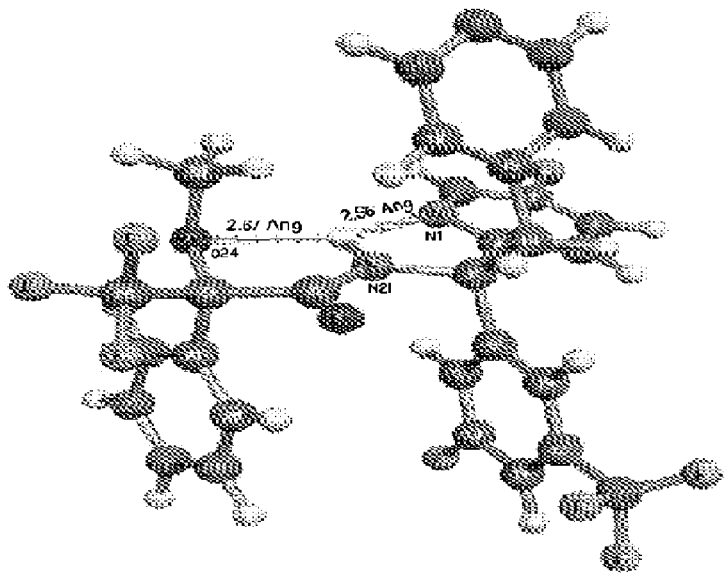

| Ex. No. | Structure | Name | Retention Time Min./ Molecular Mass | Prepared in the manner described in: |
|---|---|---|---|---|
| 10 | 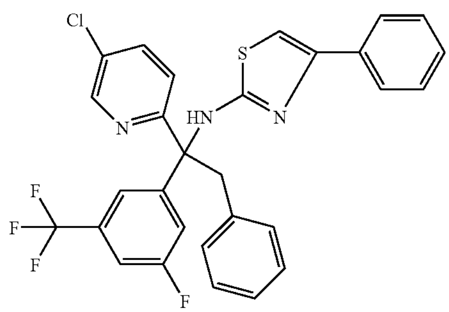 | N-(1-(5-chloropyridin-2-yl)-1-(3-fluoro-5-(trifluoromethyl)phenyl)-2-phenylethyl)-4-phenylthiazol-2-amine | 4.39 LC 554.17 [M + H]$^+$ | Procedure 1 and 2 |
| 11 | 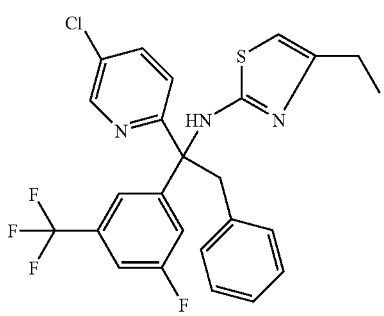 | N-(1-(5-chloropyridin-2-yl)-1-(3-fluoro-5-(trifluoromethyl)phenyl)-2-phenylethyl)-4-ethylthiazol-2-amine | 3.52 LC 506.21 [M + H]$^+$ | Procedure 1 and 2 |
| 12 | 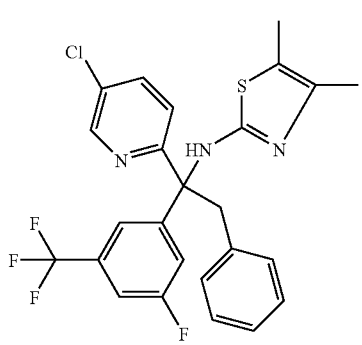 | N-(1-(5-chloropyridin-2-yl)-1-(3-fluoro-5-(trifluoromethyl)phenyl)-2-phenylethyl)-4,5-dimethylthiazol-2-amine | 3.35 LC 506.21 [M + H]$^+$ | Procedure 1 and 2 |

TABLE 1-continued

| | | | | |
|---|---|---|---|---|
| 13 | 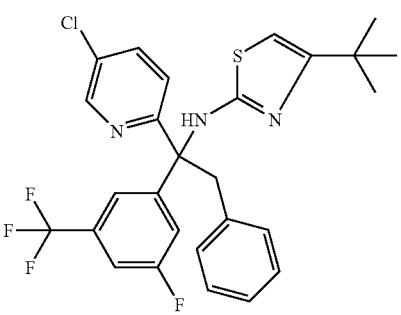 | 4-tert-butyl-N-(1-(5-chloropyridin-2-yl)-1-(3-fluoro-5-(trifluoromethyl)phenyl)-2-phenylethyl)thiazol-2-amine | 3.91 LC 534.23 [M + H]+ | Procedure 1 and 2 |
| 14 | 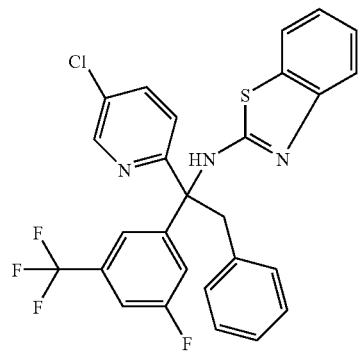 | N-(1-(5-chloropyridin-2-yl)-1-(3-fluoro-5-(trifluoromethyl)phenyl)-2-phenylethyl)benzo[d]thiazol-2-amine | 4.35 LC 528.31 [M + H]+ | Procedure 1 and 2 |
| 15 | 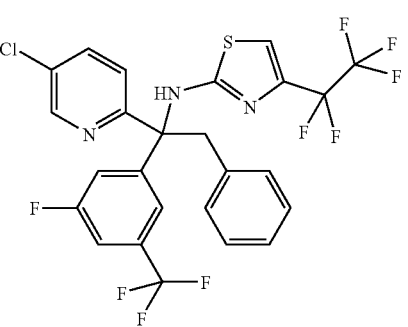 | N-(1-(5-chloropyridin-2-yl)-1-(3-fluoro-5-(trifluoromethyl)phenyl)-2-phenylethyl)-4-(perfluoroethyl)thiazol-2-amine | 4.41 LC 596.21 [M + H]+ | Procedure 1 and 2 |
| 16 | 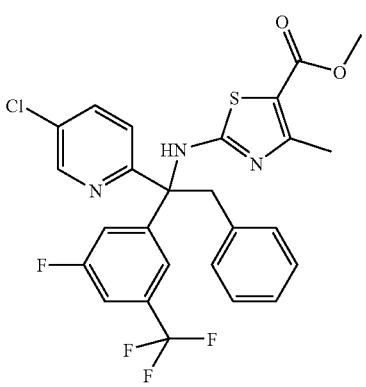 | methyl 2-(1-(5-chloropyridin-2-yl)-1-(3-fluoro-5-(trifluoromethyl)phenyl)-2-phenylethylamino)-4-methylthiazole-5-carboxylate | 4.29 LC 550.22 [M + H]+ | Procedure 1 and 2 |

TABLE 1-continued

| 17 | 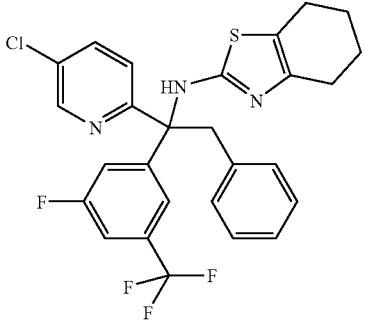 | N-(1-(5-chloropyridin-2-yl)-1-(3-fluoro-5-(trifluoromethyl)phenyl)-2-phenylethyl)-4,5,6,7-tetrahydrobenzo[d]thiazol-2-amine | 3.55 LC 532.23 [M + H]+ | Procedure 1 and 2 |
| 18 | 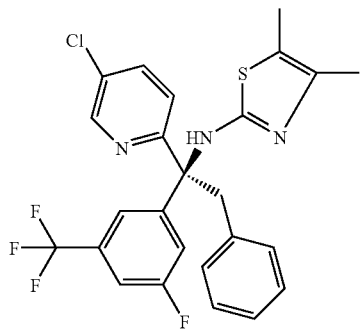 | (S)-N-(1-(5-chloropyridin-2-yl)-1-(3-fluoro-5-(trifluoromethyl)phenyl)-2-phenylethyl)-4,5-dimethylthiazol-2-amine | 3.35 LC 506.21 [M + H]+ | Procedure 3, 4, 5 and 2 |
| 19 | 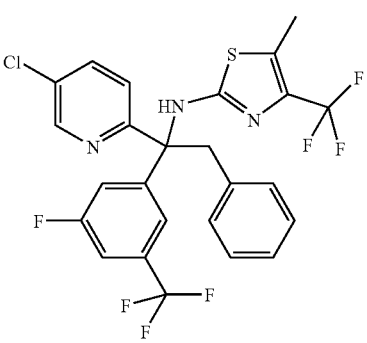 | N-(1-(5-chloropyridin-2-yl)-1-(3-fluoro-5-(trifluoromethyl)phenyl)-2-phenylethyl)-5-methyl-4-(trifluoromethyl)thiazol-2-amine | 4.42 LC 560.21 [M + H]+ | Procedure 1 and 2 |
| 20 | 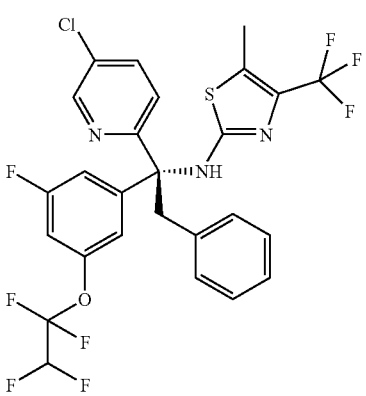 | N-(1-(5-chloropyridin-2-yl)-1-(3-fluoro-5-(trifluoromethyl)phenyl)-2-phenylethyl)-5-methylthiazol-2-amine | 3.37 LC 492.23 [M + H]+ | Procedure 1 and 2 |

TABLE 1-continued

| | | | | |
|---|---|---|---|---|
| 21 | 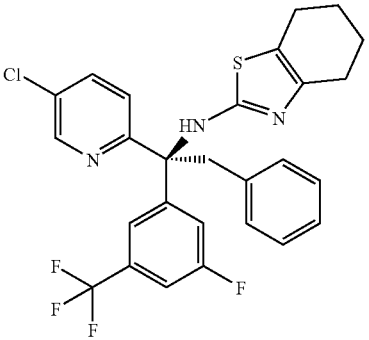 | (S)-N-(1-(5-chloropyridin-2-yl)-1-(3-fluoro-5-(trifluoromethyl)phenyl)-2-phenylethyl)-4,5,6,7-tetrahydrobenzo[d]thiazol-2- | 3.56 LC 532.25 [M + H]$^+$ | Procedure 3, 4, 5 and 2 |
| 22 | 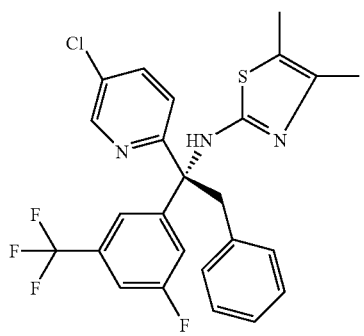 | (R)-N-(1-(5-chloropyridin-2-yl)-1-(3-fluoro-5-(trifluoromethyl)phenyl)-2-phenylethyl)-4,5-dimethylthiazol-2-amine | 3.35 LC 506.21 [M + H]$^+$ | Procedure 3, 4, 5 and 2 |
| 23 | 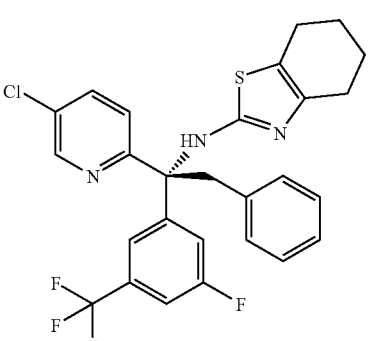 | (R)-N-(1-(5-chloropyridin-2-yl)-1-(3-fluoro-5-(trifluoromethyl)phenyl)-2-phenylethyl)-4,5,6,7-tetrahydrobenzo[d]thiazol-2-amine | 3.52 LC 532.24 [M + H]$^+$ | Procedure 3, 4, 5 and 2 |
| 24 | 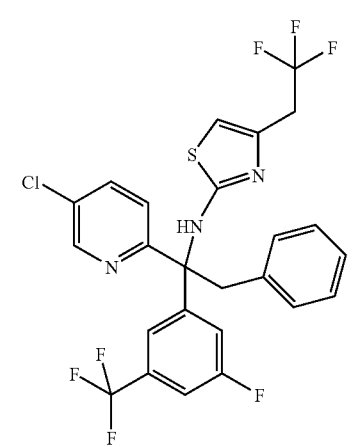 | N-(1-(5-chloropyridin-2-yl)-1-(3-fluoro-5-(trifluoromethyl)phenyl)-2-phenylethyl)-4-(2,2,2-trifluoroethyl)thiazol-2-amine | 4.24 LC 560.21 [M + H]$^+$ | Procedure 1 and 2 |

TABLE 1-continued

| | | | | |
|---|---|---|---|---|
| 25 | 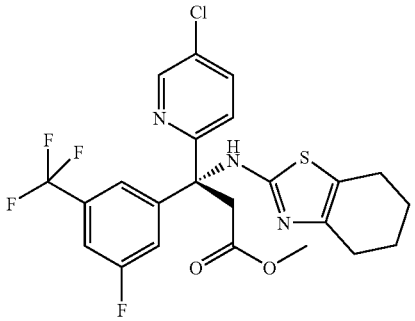 | (R)-methyl 3-(5-chloropyridin-2-yl)-3-(3-fluoro-5-(trifluoromethyl)phenyl)-3-(4,5,6,7-tetrahydrobenzo[d]thiazol-2-ylamino)propanoate | 3.66 LC 514.3 [M + H]$^+$ | Procedure 9 and 2 |
| 26 | 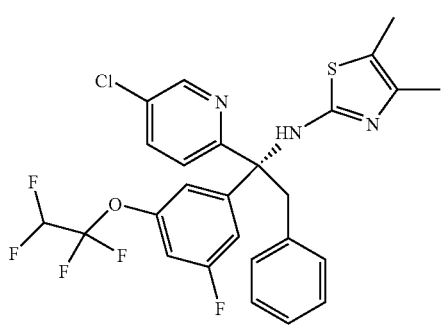 | (R)-N-(1-(5-chloropyridin-2-yl)-1-(3-fluoro-5-(1,1,2,2-tetrafluoroethoxy)phenyl)-2-phenylethyl)-4,5-dimethylthiazol-2-amine | 3.35 LC 554.28 [M + H]$^+$ | Procedure 8 and 2 |
| 27 | 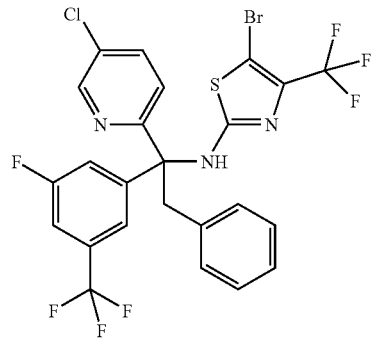 | 5-bromo-N-(1-(5-chloropyridin-2-yl)-1-(3-fluoro-5-(trifluoromethyl)phenyl)-2-phenylethyl)-4-(trifluoromethyl)thiazol-2-amine | 4.52 LC 624.34 [M + H]$^+$ | Procedure 1 and 2 |
| 28 | 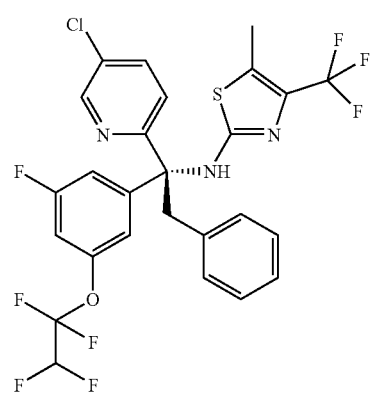 | (R)-N-(1-(5-chloropyridin-2-yl)-1-(3-fluoro-5-(1,1,2,2-tetrafluoroethoxy)phenyl)-2-phenylethyl)-5-methyl-4-(trifluoromethyl)thiazol-2-amine | 4.35 LC 607.94 [M + H]$^+$ | Procedure 8 and 2 |

TABLE 1-continued

| | | | | |
|---|---|---|---|---|
| 29 | [structure] | (R)-N-(1-(3-fluoro-5-(trifluoromethyl)phenyl)-1-(4-fluorophenyl)-2-phenylethyl)-4-(trifluoromethyl)thiazol-2-amine | 4.36 LC 528.95 [M + H]$^+$ | Procedure 3, 4, 5 and 2 |
| 30 | [structure] | (R)-N-(1-(5-chloropyridin-2-yl)-1-(3-fluoro-5-(1,1,2,2-tetrafluoroethoxy)phenyl)-2-phenylethyl)-4-(trifluoromethyl)thiazol-2-amine | 4.26 LC 593.92 [M + H]$^+$ | Procedure 8 and 2 |
| 31 | [structure] | (R)-5-bromo-N-(1-(5-chloropyridin-2-yl)-1-(3-fluoro-5-(1,1,2,2-tetrafluoroethoxy)phenyl)-2-phenylethyl)-4-(trifluoromethyl)thiazol-2-amine | 4.34 LC 672.14 [M + H]$^+$ | Procedure 8 and 2 |

TABLE 2

| Ex. No. | Structure | Name | Retention Time Min./ Molecular Mass | Prepared in the manner described in: |
| --- | --- | --- | --- | --- |
| 32 | 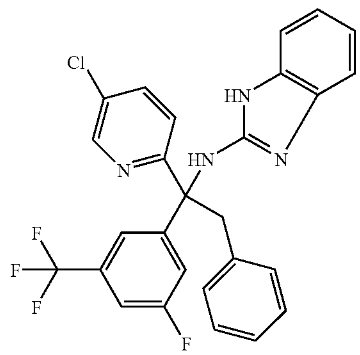 | N-(1-(5-chloropyridin-2-yl)-1-(3-fluoro-5-(trifluoromethyl)phenyl)-2-phenylethyl)-1H-benzo[d]imidazol-2-amine | 3.22 LC 511.22 [M + H]$^+$ | Procedure 1 and 6 |
| 33 | 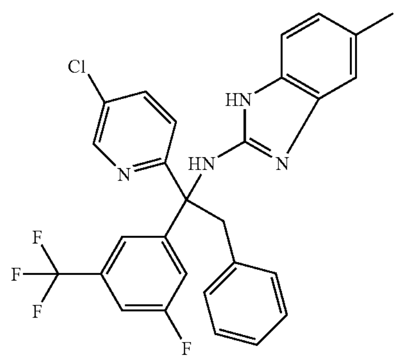 | N-(1-(5-chloropyridin-2-yl)-1-(3-fluoro-5-(trifluoromethyl)phenyl)-2-phenylethyl)-5-methyl-1H-benzo[d]imidazol-2-amine | 5.35 LC 525.30 [M + H]$^+$ | Procedure 1 and 6 |
| 34 | 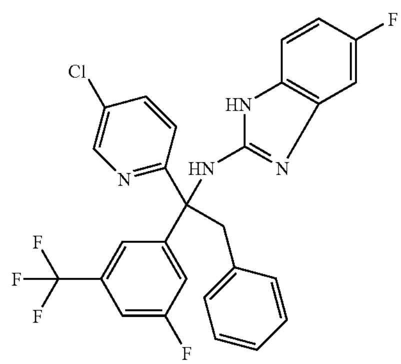 | N-(1-(5-chloropyridin-2-yl)-1-(3-fluoro-5-(trifluoromethyl)phenyl)-2-phenylethyl)-5-fluoro-1H-benzo[d]imidazol-2-amine | 3.27 LC 529.28 [M + H]$^+$ | Procedure 1 and 6 |
| 35 | 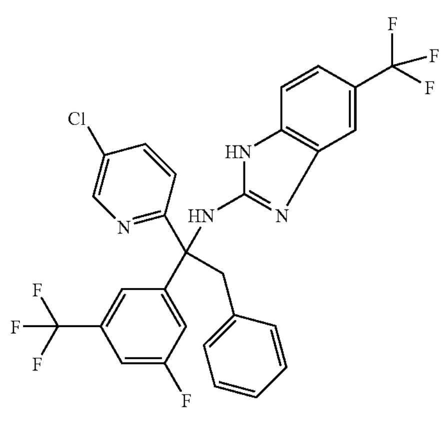 | N-(1-(5-chloropyridin-2-yl)-1-(3-fluoro-5-(trifluoromethyl)phenyl)-2-phenylethyl)-5-(trifluoromethyl)-1H-benzo[d]imidazol-2-amine | 3.52 LC 579.30 [M + H]$^+$ | Procedure 1 and 6 |

TABLE 2-continued

| Ex. No. | Structure | Name | Retention Time Min./ Molecular Mass | Prepared in the manner described in: |
|---|---|---|---|---|
| 36 | 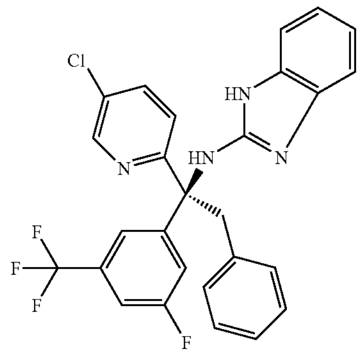 | (S)-N-(1-(5-chloropyridin-2-yl)-1-(3-fluoro-5-(trifluoromethyl)phenyl)-2-phenylethyl)-1H-benzo[d]imidazol-2-amine | 3.22 LC 511.22 [M + H]$^+$ | Procedure 3, 4, 5 and 6 |
| 37 | 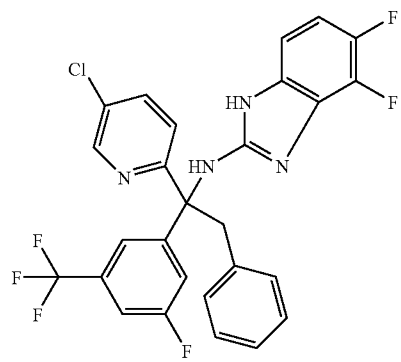 | N-(1-(5-chloropyridin-2-yl)-1-(3-fluoro-5-(trifluoromethyl)phenyl)-2-phenylethyl)-4,5-difluoro-1H-benzo[d]imidazol-2-amine | 3.56 LC 547.28 [M + H]$^+$ | Procedure 1 and 6 |
| 38 | 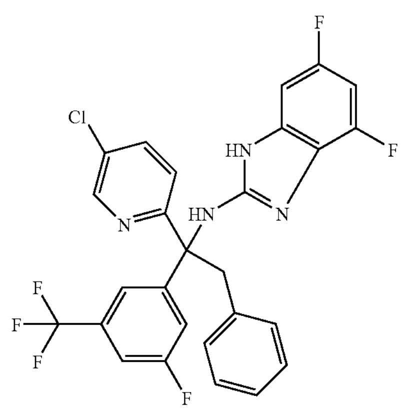 | N-(1-(5-chloropyridin-2-yl)-1-(3-fluoro-5-(trifluoromethyl)phenyl)-2-phenylethyl)-4,6-difluoro-1H-benzo[d]imidazol-2-amine | 3.59 LC 547.27 [M + H]$^+$ | Procedure 1 and 6 |
| 39 | 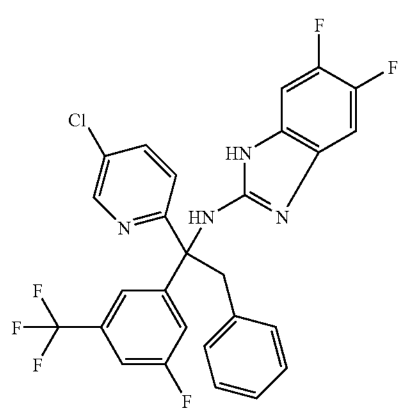 | N-(1-(5-chloropyridin-2-yl)-1-(3-fluoro-5-(trifluoromethyl)phenyl)-2-phenylethyl)-56-difluoro-1H-benzo[d]imidazol-2-amine | 3.43 LC 547.21 [M + H]$^+$ | Procedure 1 and 6 |

TABLE 2-continued

| Ex. No. | Structure | Name | Retention Time Min./ Molecular Mass | Prepared in the manner described in: |
|---|---|---|---|---|
| 40 | 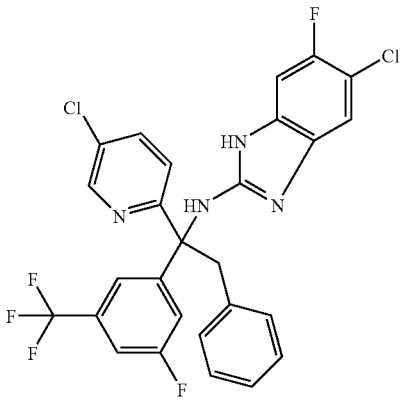 | 5-chloro-N-(1-(5-chloropyridin-2-yl)-1-(3-fluoro-5-(trifluoromethyl)phenyl)-2-phenylethyl)-6-fluoro-1H-benzo[d]imidazol-2-amine | 3.59 LC 563.19 [M + H]+ | Procedure 1 and 6 |
| 41 | 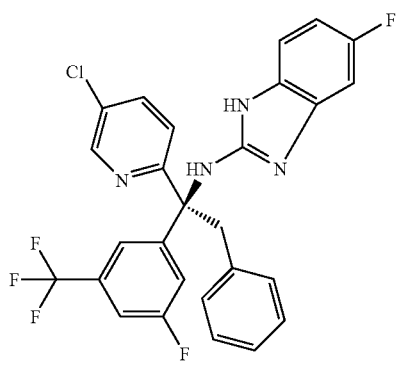 | (S)-N-(1-(5-chloropyridin-2-yl)-1-(3-fluoro-5-(trifluoromethyl) phenyl)-2-phenylethyl)-5-fluoro-1H-benzo[d]imidazol-2-amine | 3.25 LC 529.23 [M + H]+ | Procedure 3, 4, 5 and 6 |
| 42 | 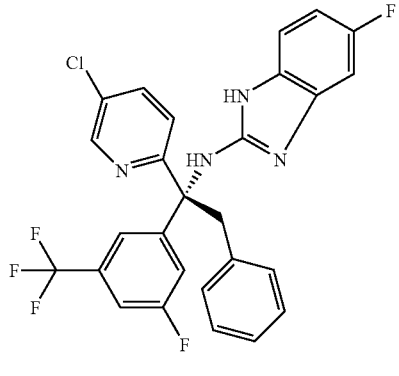 | (R)-N-(1-(5-chloropyridin-2-yl)-1-(3-fluoro-5-(trifluoromethyl) phenyl)-2-phenylethyl)-5-fluoro-1H-benzo[d]imidazol-2-amine | 3.28 LC 529.22 [M + H]+ | Procedure 3, 4, 5 and 6 |
| 43 | 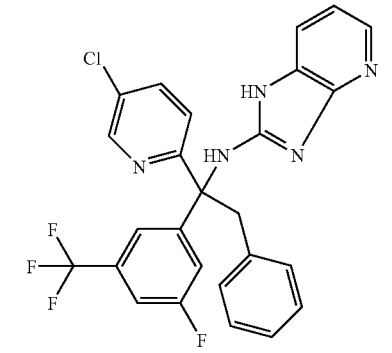 | N-(1-(5-chloropyridin-2-yl)-1-(3-fluoro-5-(trifluoromethyl) phenyl)-2-phenylethyl)-1H-imidazo[4,5-b]pyridin-2-amine | 3.34 LC 512.29 [M + H]+ | Procedure 1 and 6 |

TABLE 2-continued

| Ex. No. | Structure | Name | Retention Time Min./ Molecular Mass | Prepared in the manner described in: |
|---|---|---|---|---|
| 44 | 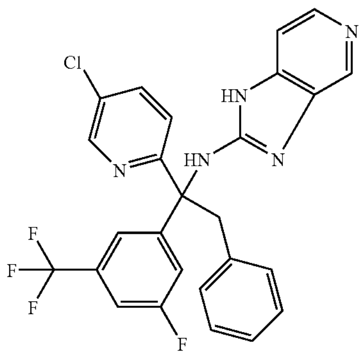 | N-(1-(5-chloropyridin-2-yl)-1-(3-fluoro-5-(trifluoromethyl)phenyl)-2-phenylethyl)-1H-imidazo[4,5-c]pyridin-2-amine | 3.35 LC 512.25 [M + H]$^+$ | Procedure 1 and 6 |
| 45 | 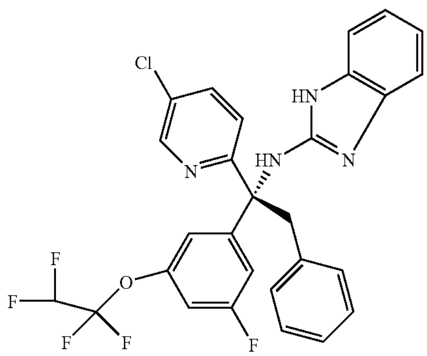 | (R)-N-(1-(5-chloropyridin-2-yl)-1-(3-fluoro-5-(1,1,2,2-tetrafluoroethoxy)phenyl)-2-phenylethyl)-1H-benzo[d]imidazol-2-amine | 3.29 LC 559.29 [M + H]$^+$ | Procedure 8 and 6 |
| 46 | 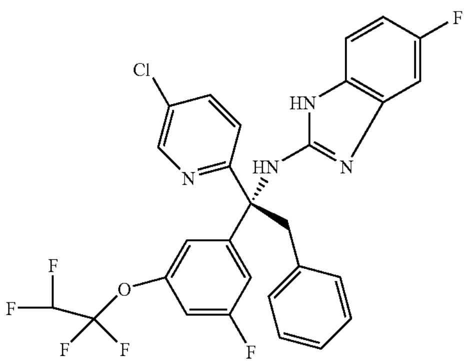 | (R)-N-(1-(5-chloropyridin-2-yl)-1-(3-fluoro-5-(1,1,2,2-tetrafluoroethoxy)phenyl)-2-phenylethyl)-5-fluoro-1H-benzo[d]imidazol-2-amine | 3.30 LC 577.29 [M + H]$^+$ | Procedure 8 and 6 |
| 47 | 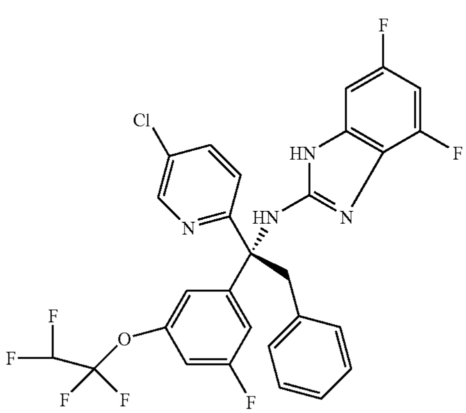 | (R)-N-(1-(5-chloropyridin-2-yl)-1-(3-fluoro-5-(1,1,2,2-tetrafluoroethoxy)phenyl)-2-phenylethyl)-4,6-difluoro-1H-benzo[d]imidazol-2-amine | 3.44 LC 595.35 [M + H]$^+$ | Procedure 8 and 6 |

TABLE 2-continued

| Ex. No. | Structure | Name | Retention Time Min./ Molecular Mass | Prepared in the manner described in: |
|---|---|---|---|---|
| 48 | 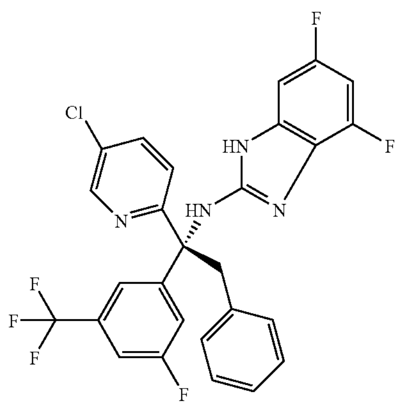 | (R)-N-(1-(5-chloropyridin-2-yl)-1-(3-fluoro-5-(trifluoromethyl)phenyl)-2-phenylethyl)-4,6-difluoro-1H-benzo[d]imidazol-2-amine | 3.59 LC 547.27 [M + H]+ | Procedure 3, 4, 5 and 6 |
| 49 | 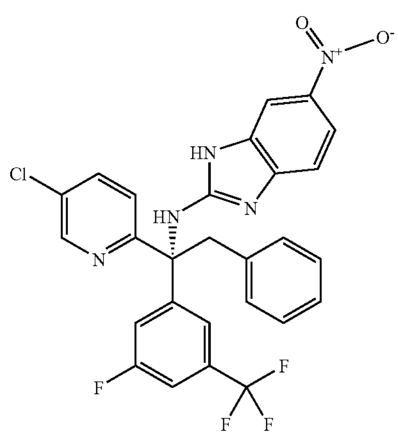 | (R)-N-(1-(5-chloropyridin-2-yl)-1-(3-fluoro-5-(trifluoromethyl)phenyl)-2-phenylethyl)-6-nitro-1H-benzo[d]imidazol-2-amine | 3.70 LC 556.15 [M + H]+ | Procedure 3, 4, 5 and 6 |
| 50 | 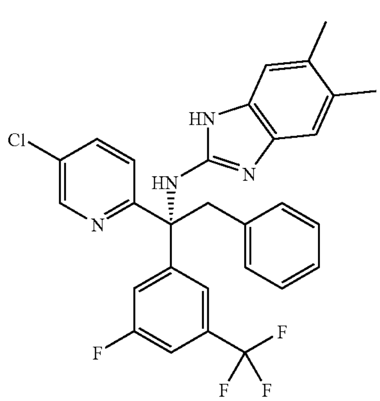 | (R)-N-(1-(5-chloropyridin-2-yl)-1-(3-fluoro-5-(trifluoromethyl)phenyl)-2-phenylethyl)-5,6-dimethyl-1H-benzo[d]imidazol-2-amine | 3.53 LC No obs. [M + H]+ | Procedure 3, 4, 5 and 6 |

TABLE 2-continued

| Ex. No. | Structure | Name | Retention Time Min./ Molecular Mass | Prepared in the manner described in: |
|---|---|---|---|---|
| 51 | 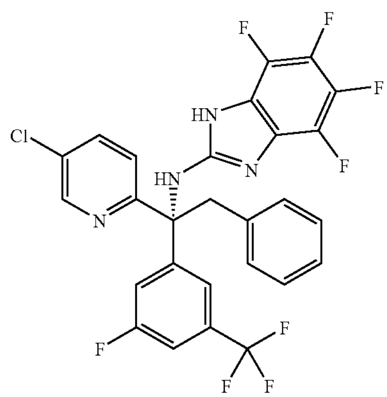 | (R)-N-(1-(5-chloropyridin-2-yl)-1-(3-fluoro-5-(trifluoromethyl)phenyl)-2-phenylethyl)-4,5,6,7-tetrafluoro-1H-benzo[d]imidazol-2-amine | 4.52 LC No obs. [M + H]+ | Procedure 3, 4, 5 and 6 |
| 52 | 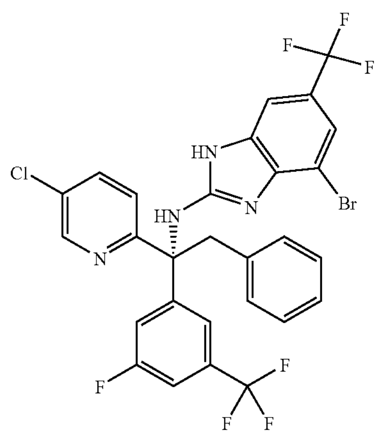 | (R)-4-bromo-N-(1-(5-chloropyridin-2-yl)-1-(3-fluoro-5-(trifluoromethyl)phenyl)-2-phenylethyl)-6-(trifluoromethyl)-1H-benzo[d]imidazol-2-amine | 4.35 LC 659.06 [M + H]+ | Procedure 3, 4, 5 and 6 |
| 53 | 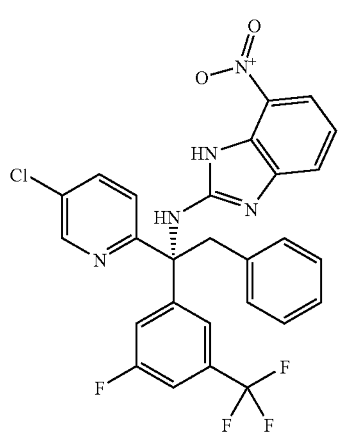 | (R)-N-(1-(5-chloropyridin-2-yl)-1-(3-fluoro-5-(trifluoromethyl)phenyl)-2-phenylethyl)-7-nitro-1H-benzo[d]imidazol-2-amine | 3.89 LC 556.14 [M + H]+ | Procedure 3, 4, 5 and 6 |

TABLE 2-continued

| Ex. No. | Structure | Name | Retention Time Min./ Molecular Mass | Prepared in the manner described in: |
|---|---|---|---|---|
| 54 | 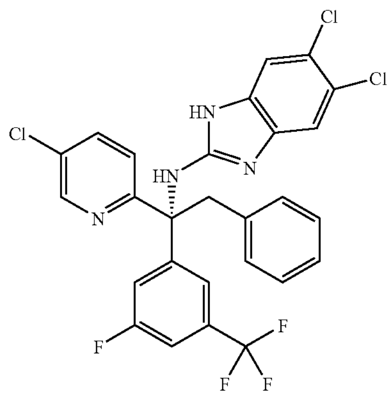 | (R)-5,6-dichloro-N-(1-(5-chloropyridin-2-yl)-1-(3-fluoro-5-(trifluoromethyl)phenyl)-2-phenylethyl)-1H-benzo[d]imidazol-2-amine | 3.76 LC 579.09 [M + H]$^+$ | Procedure 3, 4, 5 and 6 |
| 55 | 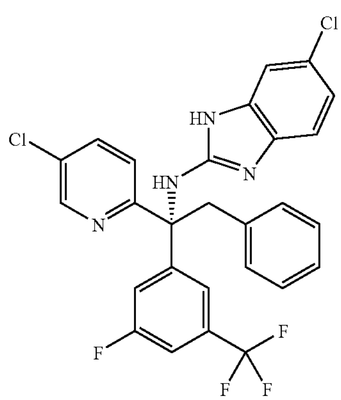 | (R)-6-chloro-N-(1-(5-chloropyridin-2-yl)-1-(3-fluoro-5-(trifluoromethyl)phenyl)-2-phenylethyl)-1H-benzo[d]imidazol-2-amine | 3.43 LC 545.14 [M + H]$^+$ | Procedure 3, 4, 5 and 6 |
| 56 | 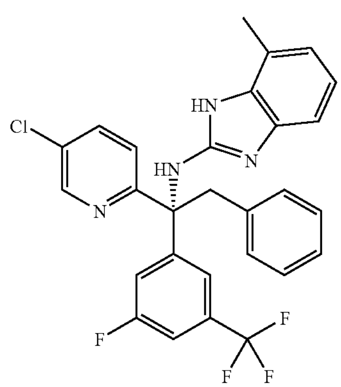 | (R)-N-(1-(5-chloropyridin-2-yl)-1-(3-fluoro-5-(trifluoromethyl)phenyl)-2-phenylethyl)-7-methyl-1H-benzo[d]imidazol-2-amine | 3.36 LC 525.2 [M + H]$^+$ | Procedure 3, 4, 5 and 6 |

TABLE 2-continued

| Ex. No. | Structure | Name | Retention Time Min./ Molecular Mass | Prepared in the manner described in: |
|---|---|---|---|---|
| 57 | 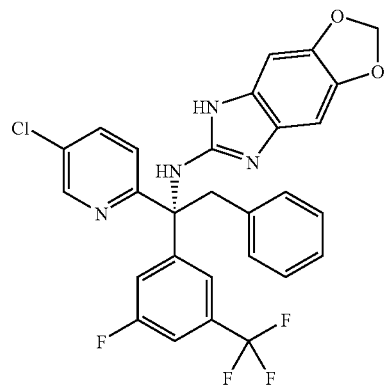 | | 3.27 LC 555.15 [M + H]⁺ | Procedure 3, 4, 5 and 6 |
| 58 | 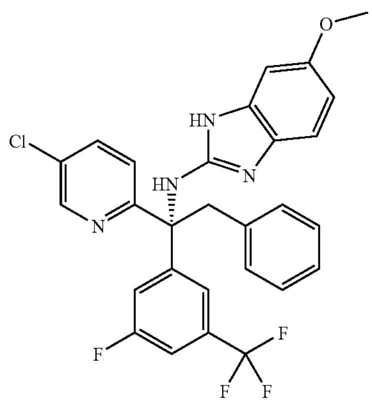 | (R)-N-(1-(5-chloropyridin-2-yl)-1-(3-fluoro-5-(trifluoromethyl)phenyl)-2-phenylethyl)-6-methoxy-1H-benzo[d]imidazol-2-amine | 3.30 LC 541.16 [M + H]⁺ | Procedure 3, 4, 5 and 6 |
| 59 | 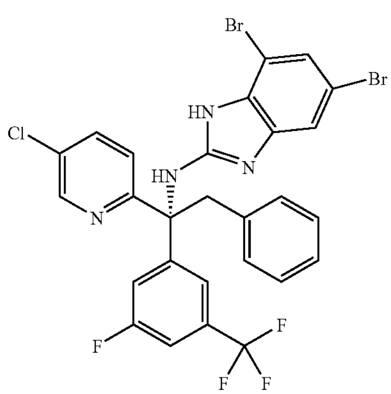 | (R)-5,7-dibromo-N-(1-(5-chloropyridin-2-yl)-1-(3-fluoro-5-(trifluoromethyl)phenyl)-2-phenylethyl)-1H-benzo[d]imidazol-2-amine | 4.15 LC 669.01 [M + H]⁺ | Procedure 3, 4, 5 and 6 |

TABLE 2-continued

| Ex. No. | Structure | Name | Retention Time Min./ Molecular Mass | Prepared in the manner described in: |
| --- | --- | --- | --- | --- |
| 60 | 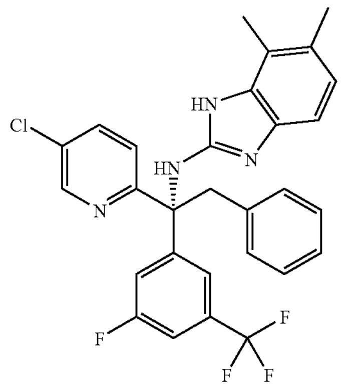 | (R)-N-(1-(5-chloropyridin-2-yl)-1-(3-fluoro-5-(trifluoromethyl)phenyl)-2-phenylethyl)-6,7-dimethyl-1H-benzo[d]imidazol-2-amine | 3.46 LC 539.2 [M + H]$^+$ | Procedure 3, 4, 5 and 6 |
| 61 | 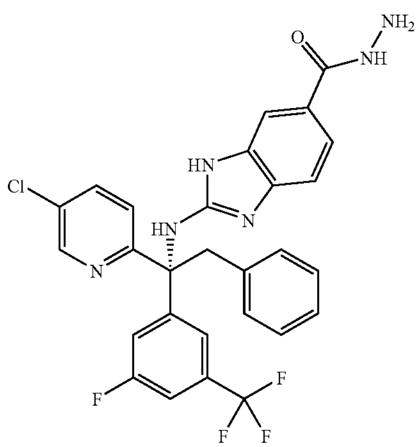 | (R)-2-(1-(5-chloropyridin-2-yl)-1-(3-fluoro-5-(trifluoromethyl)phenyl)-2-phenylethyl)-6,7-3H-benzo[d]imidazole-5-carbohydrazide | 3.46 LC 569.17 [M + H]$^+$ | Procedure 3, 4, 5 and 6 |
| 62 | 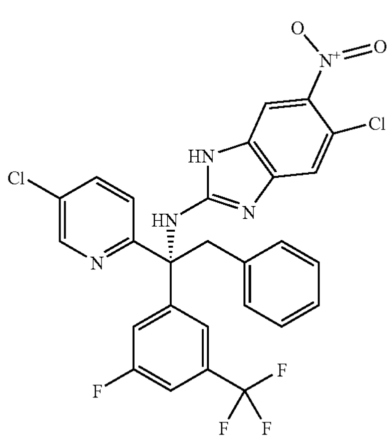 | (R)-5-chloro-N-(1-(5-chloropyridin-2-yl)-1-(3-fluoro-5-(trifluoromethyl)phenyl)-2-phenylethyl)-6-nitro-1H-benzo[d]imidazol-2-amine | 4.16 LC 590.13 [M + H]$^+$ | Procedure 3, 4, 5 and 6 |

TABLE 2-continued

| Ex. No. | Structure | Name | Retention Time Min./ Molecular Mass | Prepared in the manner described in: |
|---|---|---|---|---|
| 63 | 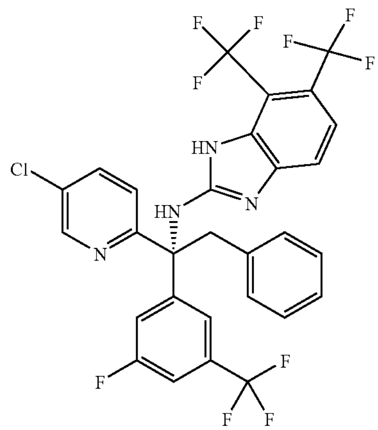 | (R)-N-(1-(5-chloropyridin-2-yl)-1-(3-fluoro-5-(trifluoromethyl)phenyl)-2-phenylethyl)-6,7-bis(trifluoromethyl)-1H-benzo[d]imidazol-2-amine | 4.53 LC 647.19 [M + H]$^+$ | Procedure 3, 4, 5 and 6 |
| 64 | 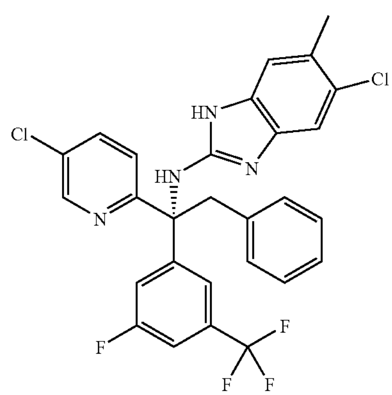 | (R)-5-chloro-N-(1-(5-chloropyridin-2-yl)-1-(3-fluoro-5-(trifluoromethyl)phenyl)-2-phenylethyl)-6-methyl-1H-benzo[d]imidazol-2-amine | 3.54 LC 559.13 [M + H]$^+$ | Procedure 3, 4, 5 and 6 |
| 65 | 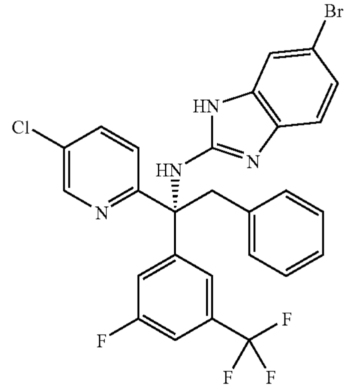 | (R)-6-bromo-N-(1-(5-chloropyridin-2-yl)-1-(3-fluoro-5-(trifluoromethyl)phenyl)-2-phenylethyl)-1H-benzo[d]imidazol-2-amine | 3.47 LC 591.09 [M + H]$^+$ | Procedure 3, 4, 5 and 6 |

TABLE 2-continued

| Ex. No. | Structure | Name | Retention Time Min./ Molecular Mass | Prepared in the manner described in: |
|---|---|---|---|---|
| 66 | 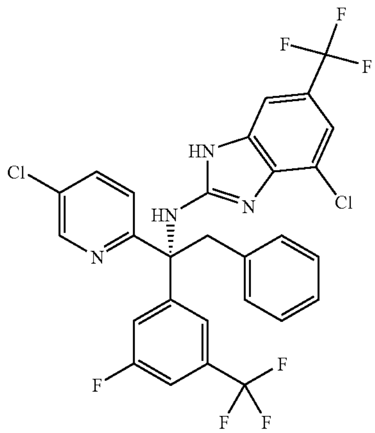 | (R)-4-chloro-N-(1-(5-chloropyridin-2-yl)-1-(3-fluoro-5-(trifluoromethyl)phenyl)-2-phenylethyl)-6-(trifluoromethyl)-1H-benzo[d]imidazol-2-amine | 4.32 LC 613.12 [M + H]$^+$ | Procedure 3, 4, 5 and 6 |
| 67 | 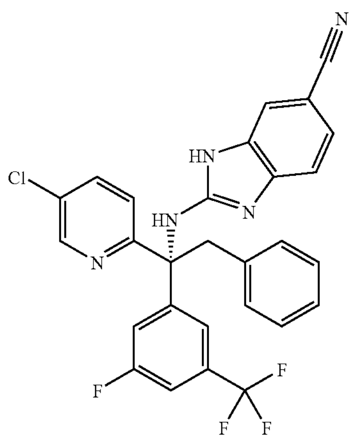 | (R)-2-(1-(5-chloropyridin-2-yl)-1-(3-fluoro-5-(trifluoromethyl)phenyl)-2-phenylethylamino)-3H-benzo[d]imidazole-5-carbonitrile | 3.47 LC 536.16 [M + H]$^+$ | Procedure 3, 4, 5 and 6 |
| 68 | 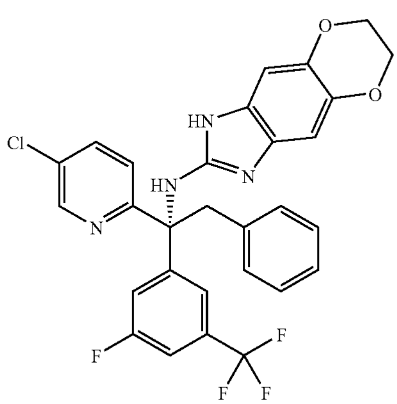 | | 3.29 LC 569.15 [M + H]$^+$ | Procedure 3, 4, 5 and 6 |

TABLE 2-continued

| Ex. No. | Structure | Name | Retention Time Min./ Molecular Mass | Prepared in the manner described in: |
|---|---|---|---|---|
| 69 | 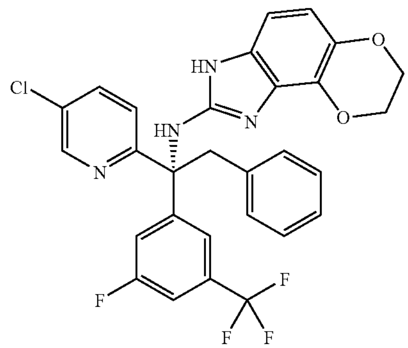 | | 3.30 LC 569.17 [M + H]⁺ | Procedure 3, 4, 5 and 6 |
| 70 | 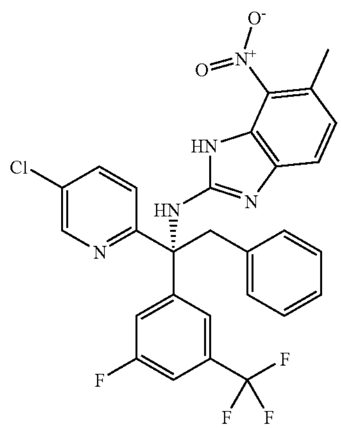 | (R)-N-(1-(5-chloropyridin-2-yl)-1-(3-fluoro-5-(trifluoromethyl)phenyl)-2-phenylethyl)-6-benzo[d]imidazol-2-amine | 3.80 LC 570.17 [M + H]⁺ | Procedure 3, 4, 5 and 6 |
| 71 | 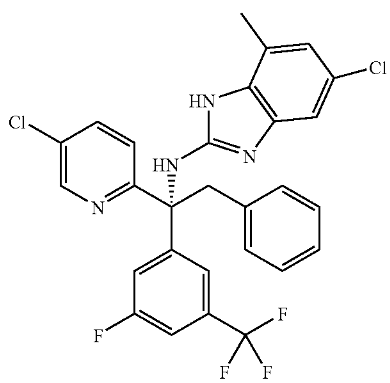 | (R)-5-chloro-N-(1-(5-chloropyridin-2-yl)-1-(3-fluoro-5-(trifluoromethyl)phenyl)-2-phenylethyl)-7-methyl-1H-benzo[d]imidazol-2-amine | 3.56 LC 559.14 [M + H]⁺ | Procedure 3, 4, 5 and 6 |
| 72 | 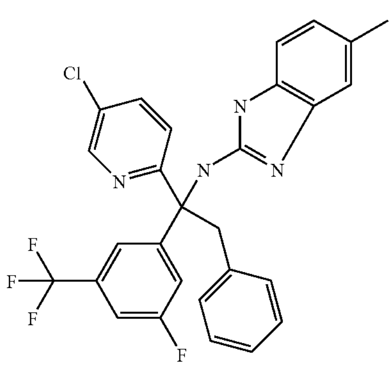 | (R)-2-(1-(5-chloropyridin-2-yl)-1-(3-fluoro-5-(trifluoromethyl)phenyl)-2-phenylethylamino)-3H-benzo[d]imidazole-5-methyl | 5.35 LC 525.30 [M + H]⁺ | Procedure 3, 4, 5 and 6 |

TABLE 3

| Ex. No. | Structure | Name | Retention Time Min./ Molecular Mass | Prepared in the manner described in: |
|---|---|---|---|---|
| 73 | 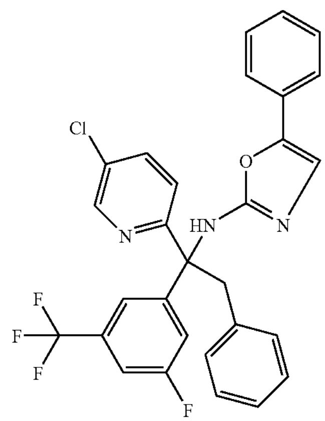 | N-(1-(5-chloropyridin-2-yl)-1-(3-fluoro-5-(trifluoromethyl)phenyl)-2-phenylethyl)-5-phenyloxazol-2-amine | 4.32 LC 538.22 [M + H]$^+$ | Procedure 7 |
| 74 | 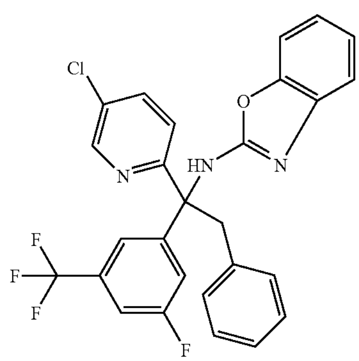 | N-(1-(5-chloropyridin-2-yl)-1-(3-fluoro-5-(trifluoromethyl)phenyl)-2-phenylethyl)benzo[d]oxazol-2-amine | 4.38 LC 512.27 [M + H]$^+$ | Procedure 7 |

TABLE 4

| Ex. No. | Structure | Name | Retention Time Min./ Molecular Mass | Prepared in the manner described in: |
|---|---|---|---|---|
| 75 | 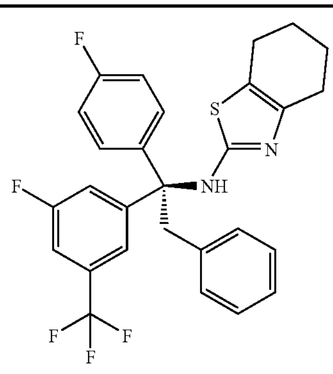 | (R)-N-(1-(3-fluoro-5-(trifluoromethyl)phenyl)-1-(4-fluorophenyl)-2-phenylethyl)-4,5,6,7-tetrahydrobenzo[d]thiazol-2-amine | 3.74 LC 515.05 [M + H]$^+$ | Procedure 11 and 2 |

TABLE 4-continued

| Ex. No. | Structure | Name | Retention Time Min./ Molecular Mass | Prepared in the manner described in: |
|---|---|---|---|---|
| 76 | 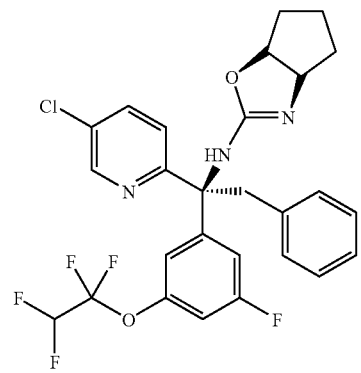 | (R)-N-(1-(3-fluoro-5-(trifluoromethyl)phenyl)-1-(4-fluorophenyl)-2-phenylethyl)-4,5-dimethylthiazol-2-amine | 3.62 LC 489.04 [M + H]$^+$ | Procedure 11 and 2 |

EXAMPLE 77

(3aS,6aS)-N-((S)-1-(5-chloropyridin-2-yl)-1-(3-fluoro-5-(1,1,2,2-tetrafluoroethoxy)phenyl)-2-phenylethyl)-4,5,6,6a-tetrahydro-3aH-cyclopenta[d]oxazol-2-amine

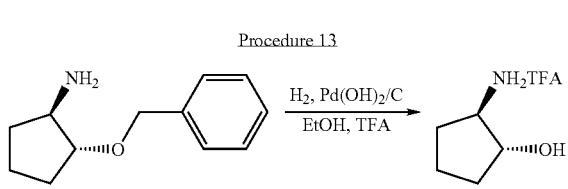

Procedure 13

To a solution of (1R,2R)-2-(benzyloxy)cyclopentanamine (3.5 g, 18.3 mmol) in EtOH (20 mL) was added TFA (1.6 ml, 21.5 mmol), followed by addition of Pd(OH)$_2$/C (20% wt, 627 mg). The reaction mixture was degassed and stirred at ambient temperature under H$_2$ for 3 days, then the solid was removed by filtration and the residue was rinsed with EtOH. The filtrate was concentrated to yield (1R,2R)-2-aminocyclopentanol TFA salt as a yellow oil. (4.3 g, 100%). NMR: 400 MHz $^1$H (DMSO-D6) 7.96 ppm, 2H, m; 3.95 ppm, 1H, m; 3.17 ppm, 1H, m; 2.02 ppm, 1H, m; 1.87 ppm, 1H, m; 1.66 ppm, 2H, m; 1.48 ppm, 2H, m; 1.07 ppm, 1H, m.

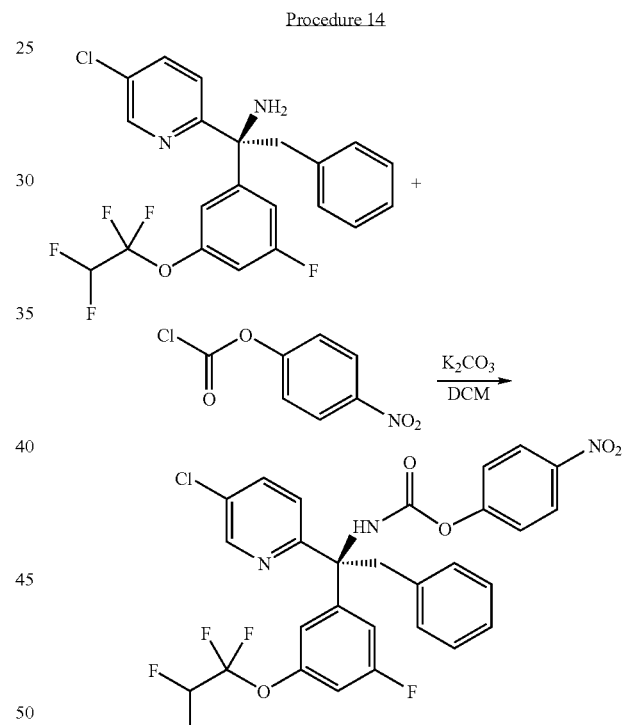

To a solution of (S)-1-(5-chloropyridin-2-yl)-1-(3-fluoro-5-(1,1,2,2-tetrafluoroethoxy)phenyl)-2-phenylethanamine (200 mg, 0.45 mmol) in DCM (2 mL) was added 4-nitrophenyl carbonochloridate (226.9 mg, 1.13 mmol) followed by the addition of K$_2$CO$_3$ (620.6 mg, 4.5 mmol). The reaction mixture was stirred at room temperature for 18 h and filtered through a small silica pad. The filtrate was diluted with DCM (20 mL), washed with saturated NaHCO$_3$ (8×15 mL) till the aqueous layer only showed light yellow color. The organic layer was dried over MgSO$_4$, filtered and concentrated to give (S)-4-nitrophenyl 1-(5-chloropyridin-2-yl)-1-(3-fluoro-5-(1,1,2,2-tetrafluoroethoxy)phenyl)-2-phenylethylcarbamate as a yellow oil (273 mg, crude 100%). This yellow oil was used directly to the next step without further purification. LCMS RT=2.213 min [M+H] 607.94 (Phenomenex Luna C18 column, 4.6×50 mm eluting with 10-90% MeOH/H₂O over 2 minutes containing 0.1% TFA; 5 mL/min, monitoring at 220 nm)

Procedure 15

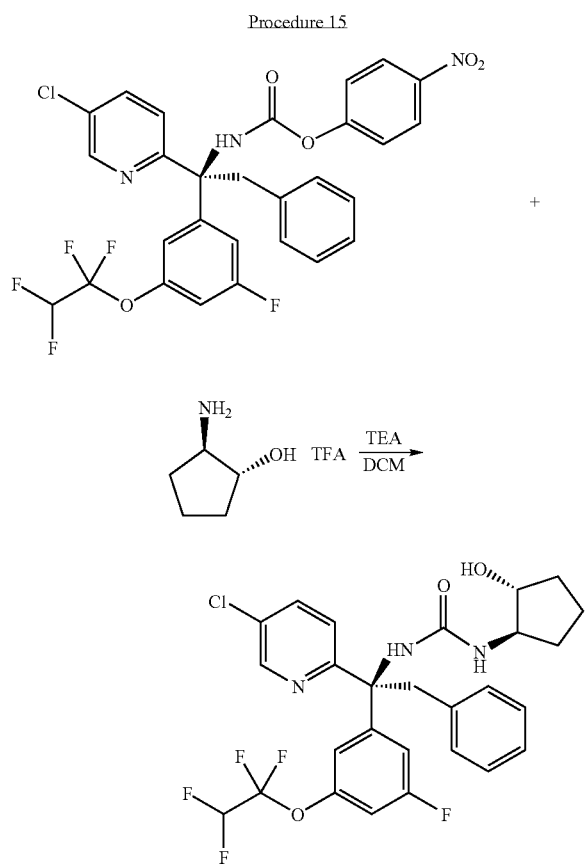

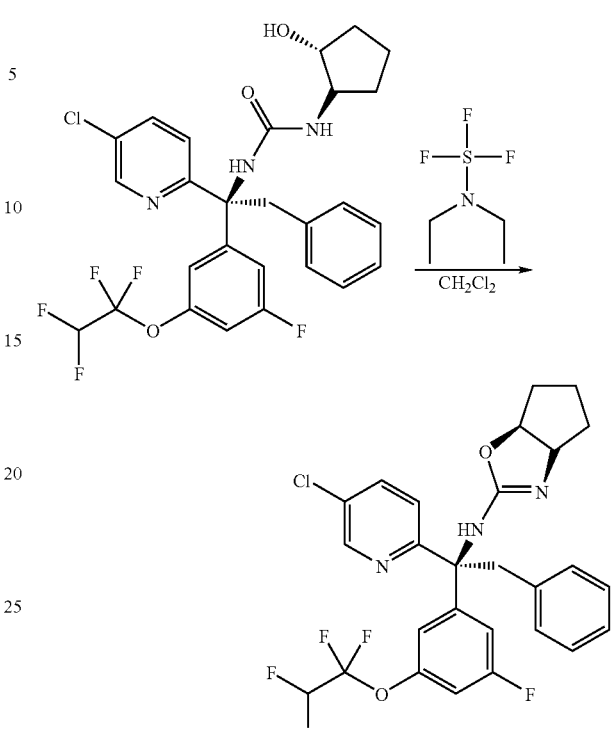

Procedure 16

(1R,2R)-2-aminocyclopentanol TFA salt (107 mg, 0.50 mmol) in DCM (2 mL) was added TEA (140 µL, 1.0 mmol), followed by the addition of crude (S)-4-nitrophenyl 1-(5-chloropyridin-2-yl)-1-(3-fluoro-5-(1,1,2,2-tetrafluoroethoxy)phenyl)-2-phenylethylcarbamate (162 mg, 0.27 mmol). The reaction mixture was stirred at room temperature for 18 h, concentrated and purified by ISCO chromatography (12 g column) using hexanes/EtOAc (0-60%) over 30 min to give 1-((S)-1-(5-chloropyridin-2-yl)-1-(3-fluoro-5-(1,1,2,2-tetrafluoroethoxy)phenyl)-2-phenylethyl)-3-((1R,2R)-2-hydroxycyclopentyl)urea as a pale yellow solid (110 mg, 73% yield). LCMS RT=3.90 min [M+H] 570.24 (Phenomenex Luna C18 column, 4.6×50 mm eluting with 10-90% MeOH/H₂O over 4 minutes containing 0.1% TFA; 4 mL/min, monitoring at 220 nm). NMR: 400 MHz ¹H (CDCl₃) 8.24 ppm, 1H, d, J=2.27 Hz; 7.64 ppm, 1H, dd, J=8.59, 2.27 Hz; 7.20 ppm, 1H, m; 7.12 ppm, 6H, m; 6.87 ppm, 1H, d, J=8.59 Hz; 6.62 ppm, 2H, d, J=7.07 Hz; 5.87 ppm, 1H, tt, J=53.02, 2.56 Hz; 4.91 ppm, 1H, d, J=4.04 Hz; 4.40 ppm, 1H, d, J=12.88 Hz; 3.97 ppm, 1H, q, J=6.57 Hz; 3.66 ppm, 1H, m; 3.55 ppm, 1H, d, J=12.63 Hz; 1.99 ppm, 1H, m; 1.66 ppm, 3H, m; 1.30 ppm, 2H, m.

To a solution of 1-((S)-1-(5-chloropyridin-2-yl)-1-(3-fluoro-5-(1,1,2,2-tetrafluoroethoxy)phenyl)-2-phenylethyl)-3-((1S,2R)-2-hydroxycyclopentyl)urea (9 mg, 0.016 mmol) in CH₂Cl₂ (1 mL) was added DAST (3 mg, 0.02 mmol). The reaction mixture was stirred for 5 min and concentrated under vacuum. The residue was purified by preparative HPLC Shimadzu-Phenomenex Luna 5µ column, 21.2×100 mm eluting with 10-90% CH₃CN (90% in H₂O, 0.1% TFA) gradient over 15 min with flow rate 20 mL/min and UV detection at 220 nm to give (3aS,6aS)-N-((S)-1-(5-chloropyridin-2-yl)-1-(3-fluoro-5-(1,1,2,2-tetrafluoroethoxy)phenyl)-2-phenylethyl)-4,5,6,6a-tetrahydro-3aH-cyclopenta[d]oxazol-2-amine as a white solid (8 mg, 91%). LCMS RT=3.27 min [M+H] 551.94 (Phenomenex Luna C18 column, 4.6×50 mm eluting with 10-90% MeOH/H₂O over 4 minutes containing 0.1% TFA; 4 mL/min, monitoring at 220 nm) NMR: 500 MHz ¹H (CDCl₃) 10.57 ppm, 1H, m; 8.54 ppm, 1H, m,; 7.67 ppm, 1H, m; 7.16 ppm, 5H, m; 7.05 ppm, 1H, m; 6.94 ppm, 1H, m; 6.67 ppm, 2H, m; 5.95 ppm, 1H, t; 5.19 ppm, 1H, t; 4.54 ppm, 1H, t; 3.87 ppm, 2H, m; 2.12 ppm, 1H, m; 1.91 ppm, 1H, m; 1.83 ppm, 1H, m; 1.68 ppm, 2H, m; 1.50 ppm, 1H, m.

EXAMPLE 78

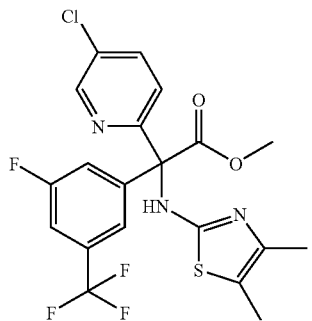

Methyl 2-(5-chloropyridin-2-yl)-2-(4,5-dimethylthiazol-2-ylamino)-2-(3-fluoro-5-(trifluoromethyl)phenyl)acetate

EXAMPLE 79

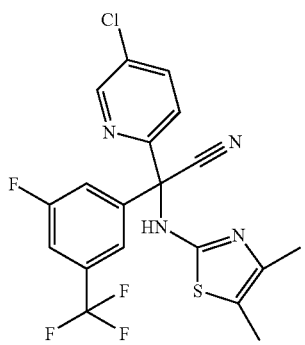

2-(5-chloropyridin-2-yl)-2-(4,5-dimethylthiazol-2-ylamino)-2-(3-fluoro-5-(trifluoromethyl)phenyl)acetonitrile Procedure 17

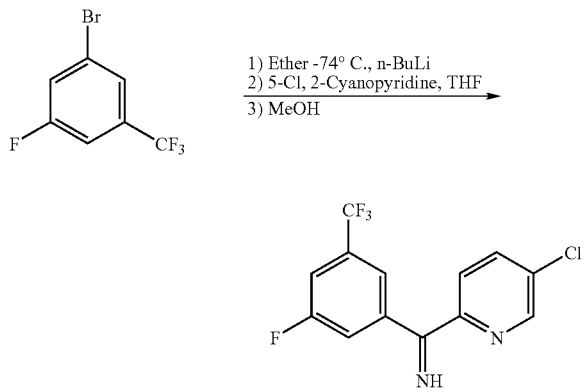

At −74° C. to a solution of 1-bromo-3-fluoro-5-(trifluoromethyl)benzene (11 g, 45.2 mmol) in ether (200 mL) was added dropwise n-BuLi (20 mL, 2.5 M in hexane, 49.8 mmol). The reaction mixture was stirred at −74° C. for 2 h. A solution of 5-Cl-2-cyanopyridine (6.23 g, 45.2 mmol) in THF (100 mL) was added to the reaction mixture via cannulation. The yellow brown reaction solution turned into dark. The reaction mixture was quenched by the addition of dry MeOH at −70° C. and then allowed to warm up to room temperature. The reaction mixture was concentrated to a small volume, filtered and the solid was separated and rinsed with ether. The combined filtrates were concentrated to yield (5-chloropyridin-2-yl)(3-fluoro-5-(trifluoromethyl)phenyl)methanimine as a black oil. LCMS RT=3.913 min [M+H] 303.95 (Phenomenex Luna C18 column, 4.6×50 mm eluting with 10-90% MeOH/H$_2$O over 4 minutes containing 0.1% TFA; 4 mL/min, monitoring at 220 nm)

Procedure 18

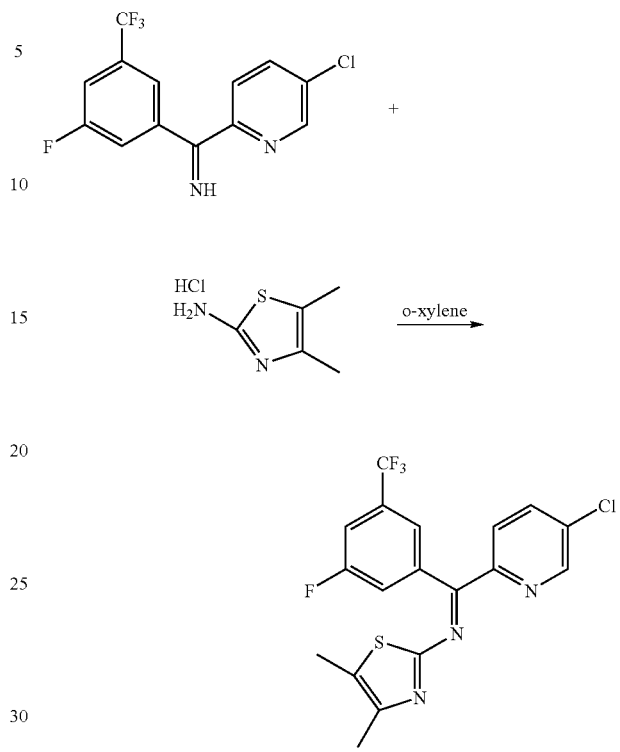

A solution of (5-chloropyridin-2-yl)(3-fluoro-5-(trifluoromethyl)phenyl)methanimine (1.7 g, 5.6 mmol) and 4,5-dimethylthiazol-2-amine HCl salt (900 mg, 5 mmol) in o-xylene (10 mL) was heated at 150° C. for 18 h, then allowed to cool to room temperature. The solvent was removed under reduced pressure and the residue purified by ISCO chromatography (80 g column) using hexanes/EtOAc (0-40%) over 25 min to give (E)-N-((5-chloropyridin-2-yl)(3-fluoro-5-(trifluoromethyl)phenyl)methylene)-4,5-dimethylthiazol-2-amine as a beige solid (910 mg, 44% yield). LCMS RT=4.00 min [M+H] 413.87 (Phenomenex Luna C18 column, 4.6×50 mm eluting with 10-90% MeOH/H$_2$O over 4 minutes containing 0.1% TFA; 4 mL/min, monitoring at 220 nm).

Procedure 19

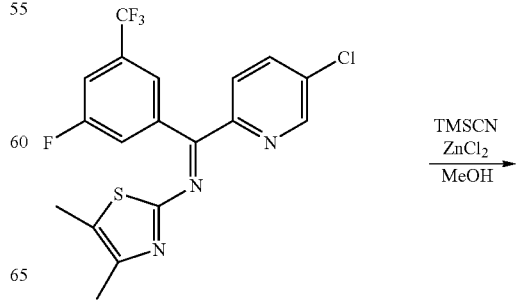

-continued

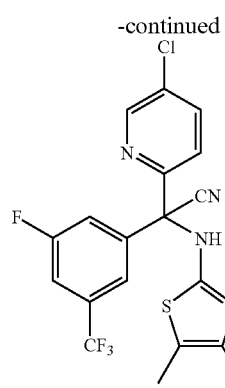

+

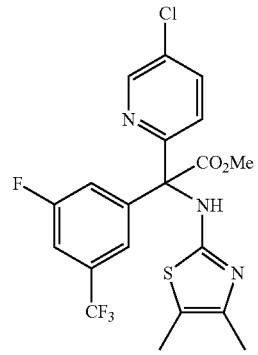

At 0° C. to a solution of N-((5-chloropyridin-2-yl)(3-fluoro-5-(trifluoromethyl)phenyl)methylene)-4,5-dimethylthiazol-2-amine (848 mg, 2.05 mmol) in MeOH (10 mL) was added $ZnCl_2$ (214 mg, 1.43 mmol), followed by the addition of TMSCN (830 μL, 6.19 mmol). The reaction was allowed to slowly warm up to room temperature and heated at 65° C. for 18 h. The reaction mixture was cooled down to room temperature and concentrated. The residue was diluted by addition of DCM. The solid was removed by filtration and the filtrate was concentrated. A portion of the residue was purified by ISCO chromatography (12 g column) using hexanes/EtOAc (0-300%) over 22 min. Methyl 2-(5-chloropyridin-2-yl)-2-(4,5-dimethylthiazol-2-ylamino)-2-(3-fluoro-5-(trifluoromethyl)phenyl)acetate eluted at a retention time of 7-8 min. LCMS RT=3.25 min [M+H] 473.84 (Phenomenex Luna C18 column, 4.6×50 mm eluting with 10-90% MeOH/$H_2O$ over 4 minutes containing 0.1% TFA; 4 mL/min, monitoring at 220 nm). NMR: 400 MHz $^1$H ($CDCl_3$) 7.74 ppm, 1H, s; 7.67 ppm, 1H, dd, J=8.57, 2.42 Hz; 7.56 ppm, 1H, m; 7.30 ppm, 2H, m; 3.76 ppm, 3H, m; 2.09 ppm, 6H, m.

The fractions that eluted at a retention time of 9-10 min were concentrated and the residue was determined to be a mixture of 2-(5-chloropyridin-2-yl)-2-(4,5-dimethylthiazol-2-ylamino)-2-(3-fluoro-5-(trifluoromethyl)phenyl)acetonitrile and impurity. Further purification was accomplished by preparative HPLC Shimadzu-Phenomenex Luna 5μ column, 21.2×100 mm eluting with 40-100% MeOH (90% in $H_2O$, 0.1% TFA) gradient over 10 min with flow rate 20 mL/min and UV detection at 220 nm. 2-(5-chloropyridin-2-yl)-2-(4,5-dimethylthiazol-2-ylamino)-2-(3-fluoro-5-(trifluoromethyl)phenyl)acetonitrile eluted at a retention time of 11.276 min. LCMS RT=3.69 min [M+H] 440.89 (Phenomenex Luna C18 column, 4.6×50 mm eluting with 10-90% MeOH/$H_2O$ over 4 minutes containing 0.1% TFA; 4 mL/min, monitoring at 220 nm). NMR: 400 MHz $^1$H ($CDCl_3$) 8.61 ppm, 1H, d, J=2.64 Hz; 7.80 ppm, 1H, s; 7.74 ppm, 1H, dd, J=8.35, 2.20 Hz; 7.56 ppm, 1H, d, J=8.79 Hz; 7.34 ppm, 1H, d, J=7.91 Hz; 7.27 ppm, 1H, m; 2.15 ppm, 3H, s; 2.08 ppm, 3H, s.

EXAMPLE 80

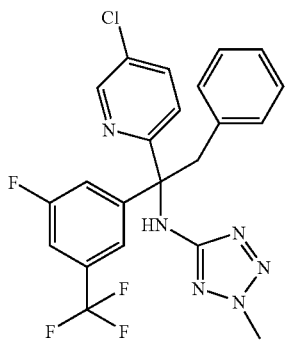

N-(1-(5-chloropyridin-2-yl)-1-(3-fluoro-5-(trifluoromethyl)phenyl)-2-phenylethyl)-2-methyl-2H-tetrazol-5-amine Procedure 20

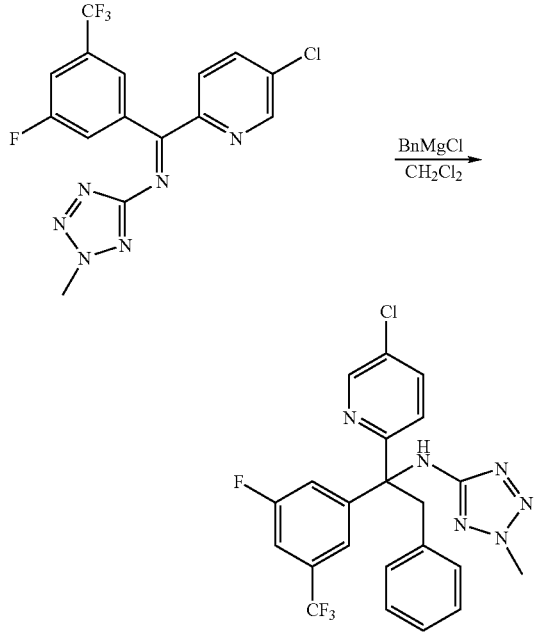

N-((5-chloropyridin-2-yl)(3-fluoro-5-(trifluoromethyl)phenyl)methylene)-1-methyl-1H-tetrazol-5-amine was prepared by method as described in Procedure 18 in 23% yield. LCMS RT=3.65 min [M+H] 384.89 (Phenomenex Luna C18 column, 4.6×50 mm eluting with 10-90% MeOH/$H_2O$ over 4 minutes containing 0.1% TFA; 4 mL/min, monitoring at 220 nm).

At −78° C. to a solution of N-((5-chloropyridin-2-yl)(3-fluoro-5-(trifluoromethyl)phenyl)methylene)-1-methyl-1H-tetrazol-5-amine (135 mg, 0.35 mmol) in $CH_2Cl_2$ (2 mL) was added BnMgCl (0.4 mL, 1 M in ether, 0.4 mol) drop wise. The reaction mixture was stirred at −78° C. for 5 min, then was allowed to slowly warm up to room temperature. After 30 min, the reaction mixture was quenched by saturated $NH_4Cl$, extracted by $CH_2Cl_2$. The organic layer was dried over $MgSO_4$, filtered, and concentrated. The residue was purified by ISCO chromatography (12 g column) using hexanes/

EtOAc (0-20%) over 16 min to give N-(1-(5-chloropyridin-2-yl)-1-(3-fluoro-5-(trifluoromethyl)phenyl)-2-phenylethyl)-1-methyl-1H-tetrazol-5-amine as a yellow solid (26 mg, 16% yield). LCMS RT=4.05 min [M+H] 477.26 (Phenomenex Luna C18 column, 4.6×50 mm eluting with 10-90% MeOH/H$_2$O over 4 minutes containing 0.1% TFA; 4 mL/min, monitoring at 220 nm). NMR: 400 MHz $^1$H (CDCl$_3$) 8.34 ppm, 1H, d, J=2.02 Hz; 7.63 ppm, 2H, m; 7.39 ppm, 1H, d, J=9.85 Hz; 7.25 ppm, 1H, d, J=3.79 Hz; 7.21 ppm, 1H, d, J=8.08 Hz; 7.11 ppm, 2H, m; 7.02 ppm, 2H, t, J=7.33 Hz; 6.42 ppm, 2H, d, J=7.07 Hz; 4.40 ppm, 1H, d, J=13.14 Hz; 4.09 ppm, 3H, s; 3.68 ppm, 1H, d, J=13.14 Hz.

EXAMPLE 81

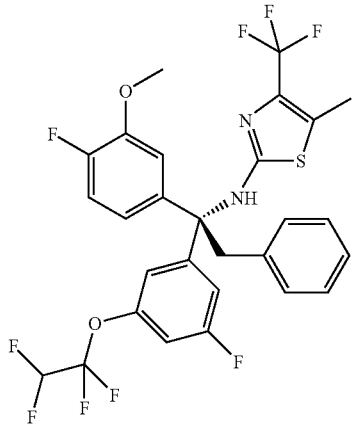

(S)-N-(1-(4-fluoro-3-methoxyphenyl)-1-(3-fluoro-5-(1,1,2,2-tetrafluoroethoxy)phenyl)-2-phenylethyl)-5-methyl-4-(trifluoromethyl)thiazol-2-amine

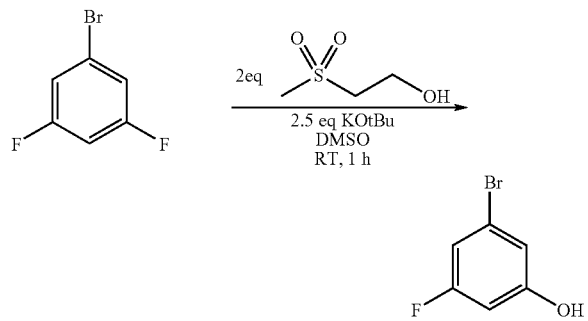

A solution of 1-bromo-3,5-difluorobenzene (20.0 g, 104 mmole) was cooled in a water bath and 2-(methylsulfonyl)ethanol (26.0 g, 207 mmol) in DMSO (100 mL) was added. Potassium 2-methylpropan-2-olate (29.0 g, 260 mmole) was added to this reaction mixture in portions. The reaction mixture turned dark. After the addition was complete, the water bath was removed and the reaction was stirred at room temperature for 1 h. The pH was adjusted to 1 using 1 N HCl, and the reaction mixture was extracted with ether (3×200 mL). The combined organic portions were washed with aqueous 1N NaOH (2×200 mL). The NaOH layer was separated, acidified to pH 1 and extracted with ether (3×200 mL). The combined organic layers were dried over sodium sulfate and filtered. The filtrate solvent volume was concentrated, but NOT to complete dryness, due to volatility of 3-bromo-5-fluorophenol and was used directly in the next step without further purification. NMR: 400 MHz $^1$H (CDCl$_3$) 6.81 ppm, 1H, dt, J=8.35 Hz and 1.98 Hz; 6.78 ppm, 1H, m; 6.50 ppm, 1H, dt, J=9.67 Hz and 2.20 Hz.

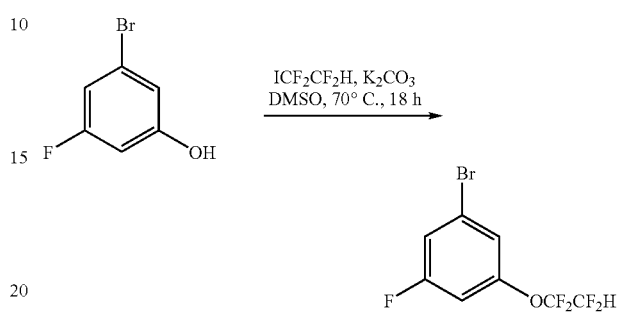

To a solution of 3-bromo-5-fluorophenol (104 mmol crude) and iodo-1,1,2,2,-tetrafluoroethane (28.4 g, 125 mmol) in DMSO (80 mL) was added K$_2$CO$_3$ (57.0 g, 420 mmol). The reaction mixture was sealed in a thick walled glass pressure round bottom flask and heated at 70° C. for 18 h. The reaction mixture was allowed to cool to room temperature, diluted with water (500 mL) and extracted with ether (3×200 mL). The combined ether layers were washed with 1N NaOH (2×200 mL), water (2×200 mL) and saturated NaCl (200 mL). The organic layer was dried over sodium sulfate, filtered and concentrated. The residue was dissolved in ether (150 mL) and filtered through a plug of activated basic alumina. The filtrate was concentrated to give 1-bromo-3-fluoro-5-(1,1,2,2-tetrafluoroethoxy)benzene as a pale yellow oil (27.2 g, 88% for two steps) which was used without further purification LCMS: RT=1.91 min, [M+H] No Ionizable peak (Phenomenex Luna C18 column, 4.6×30 mm eluting with 10-90% MeOH/H$_2$O over 2 minutes containing 0.1% TFA; 5 mL/min, monitoring at 220 nm); NMR: 400 MHz $^1$H (CDCl$_3$) 7.19 ppm, 2H, m; 6.92 ppm, 1H, d, J=8.35 Hz; 5.88 ppm, 1H, tt; J=52.95 Hz and 2.64 Hz.

Procedure 22

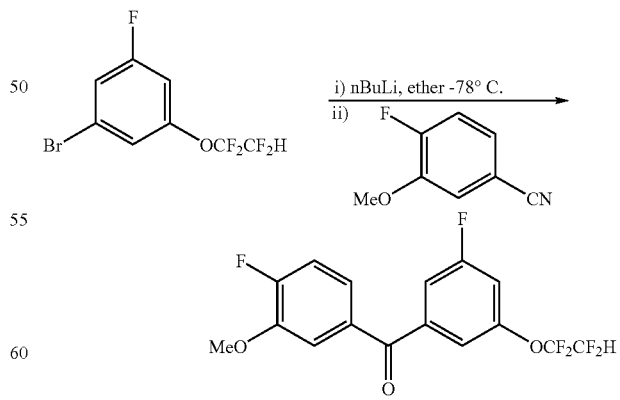

To a solution of 1-bromo-3-fluoro-5-(1,1,2,2-tetrafluoroethoxy)benzene (15 g, 51.7 mmol) in Et$_2$O (100 mL) was added n-BuLi (20.7 mL, 2.5 M, 51.7 mmol) at −75° C. The reaction mixture was allowed to warm up to −60° C., followed by the addition of 4-fluoro-3-methoxy-benzonitrile (7.5 g, 46.6 mmol) in a mixture of THF and Et$_2$O (6 mL/6 mL). The reaction was quenched immediately by addition of H$_2$O. The aqueous portion was extracted with Et$_2$O. The separated organic portion was washed by 1N HCl, concentrated under reduced pressure and purified by ISCO chromatography using hexanes/EtOAc (0-10%) to afford (4-fluoro-3-methoxyphenyl)(3-fluoro-5-(1,1,2,2-tetrafluoroethoxy)phenyl)methanone as white powder (13 g, 71%). LCMS: RT=4.101 min, [M+H] 345.1 (Phenomenex Luna C18 column, 4.6×50 mm eluting with 10-90% MeOH/H$_2$O over 4 minutes containing 0.1% TFA; 4 mL/min, monitoring at 220 nm)

Procedure 23

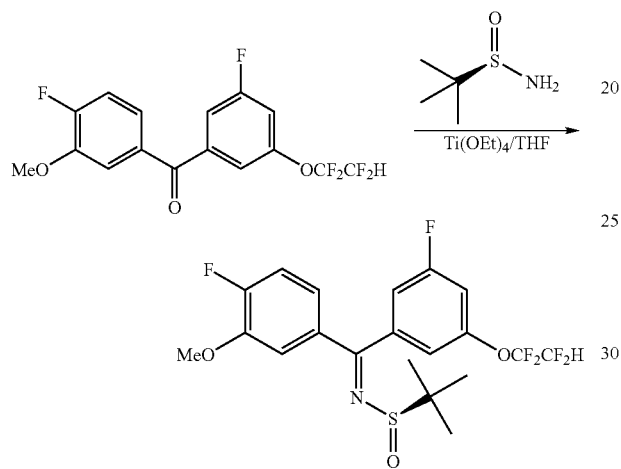

To a solution of (4-fluoro-3-methoxyphenyl)(3-fluoro-5-(1,1,2,2-tetrafluoroethoxy)phenyl)methanone (16 g, 43 mmol) in THF (70 mL) was added Ti(OEt)$_4$ (15 g, 65.9 mmol), followed by the addition of (R)-2-methylpropane-2-sulfinamide (5.86 g, 48.3 mmol). The reaction mixture was heated at reflux for 16 h, allowed to cool to room temperature and quenched by addition of saturated NaCl. The resulting mixture was filtered and the organic solvent was removed under reduced pressure. The residue was purified by ISCO chromatography using hexanes/EtOAc (10-50%) to afford (R)-N-((4-fluoro-3-methoxyphenyl)(3-fluoro-5-(1,1,2,2-tetrafluoroethoxy)phenyl)methylene)-2-methylpropane-2-sulfinamide as an oil (15 g, 75%). LCMS: RT=4.01 min, [M+H] 468.1 (Phenomenex Luna C18 column, 4.6×50 mm eluting with 10-90% MeOH/H$_2$O over 4 minutes containing 0.1% TFA; 4 mL/min, monitoring at 220 nm).

Procedure 24

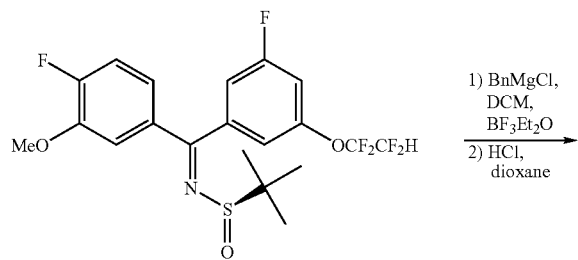

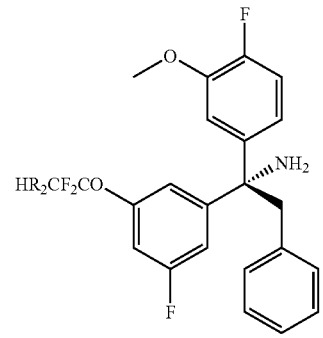

To a solution of (R)-N-((4-fluoro-3-methoxyphenyl)(3-fluoro-5-(1,1,2,2-tetrafluoroethoxy)phenyl)methylene)-2-methylpropane-2-sulfinamide (4.4 g, 9.42 mmol) in CH$_2$Cl$_2$ (190 mL, 0.05 M) at −71° C. was added BF$_3$.Et$_2$O (2.37 mL, 18.8 mmol). The reaction mixture was stirred for 10 min and BnMgCl (25 mL, 1N in Et$_2$O, 26 mmol) was added. The reaction mixture was stirred at −75° C. for an additional 5 min, and quenched by the addition of saturated NH$_4$Cl. The organic portion was separated, washed by H$_2$O, dried over Na$_2$SO$_4$ and filtered. The solvent was then removed under reduced pressure and the residue was purified by ISCO chromatography using hexanes/EtOAc (0-80%) to give (R)-N-(1-(4-fluoro-3-methoxyphenyl)-1-(3-fluoro-5-(1,1,2,2-tetrafluoroethoxy)phenyl)-2-phenylethyl)-2-methylpropane-2-sulfinamide as a mixture of two diastereomers. The mixture (1 to 4 ratio) was then separated by chiral AD column using 20% IPA/hep/0.15 DEA as mobile phase to afford (R)-N-((S)-1-(4-fluoro-3-methoxyphenyl)-1-(3-fluoro-5-(1,1,2,2-tetrafluoroethoxy)phenyl)-2-phenylethyl)-2-methylpropane-2-sulfinamide (0.79 g, 15% yield). LCMS: RT=2.09 min, [M+H] 560.2 (Phenomenex Luna C18 column, 4.6×30 mm eluting with 10-90% MeOH/H$_2$O over 2 minutes containing 0.1% TFA; 5 mL/min, monitoring at 220 nm).

To a solution of (R)-N-((S)-1-(4-fluoro-3-methoxyphenyl)-1-(3-fluoro-5-(1,1,2,2-tetrafluoroethoxy)phenyl)-2-phenylethyl)-2-methylpropane-2-sulfinamide (1.1 g, 2 mmol) in MeOH (50 mL) was added 4N HCl (2.5 mL). The reaction mixture was stirred at room temperature for 20 minutes. The organic solvent was removed under reduced pressure. To the residue was added saturated NaHCO$_3$, and the aqueous portion was extracted with ether. The separated organic portion was dried over MgSO$_4$, filtered and concentrated. The residue was purified by ISCO chromatography (40 g column) using hexanes/EtOAc (0-60%) over 18 min to give (S)-1-(4-fluoro-3-methoxyphenyl)-1-(3-fluoro-5-(1,1,2,2-tetrafluoroethoxy)phenyl)-2-phenylethanamine as a colorless oil (540 mg, 59% yield). LCMS: RT=1.74 min, [M+H]−17=439.3 (Phenomenex Luna C18 column, 4.6×30 mm eluting with 10-90% MeOH/H$_2$O over 2 minutes containing 0.1% TFA; 5 mL/min, monitoring at 220 nm).

207

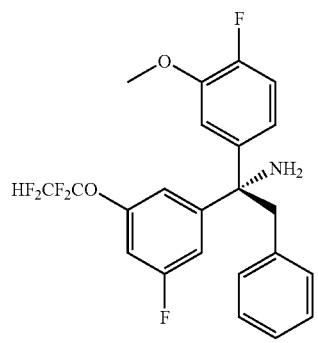

1) benzoyl isothiocyanate, DCM
2) NH₂NH₂, MeOH
3) 3-bromo-1,1,1-trifluorobutan-2-one, EtOH

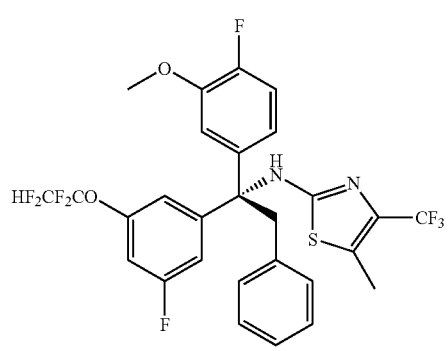

(S)-N-(1-(4-fluoro-3-methoxyphenyl)-1-(3-fluoro-5-(1,1,2,2-tetrafluoroethoxy)phenyl)-2-phenylethyl)-5-methyl-4-(trifluoromethyl)thiazol-2-amine. LCMS: RT=4.352 min [M+H] 621.1 (Phenomenex Luna C18 column, 4.6×50 mm eluting with 10-90% MeOH/H₂O over 4 minutes containing 0.1% TFA; 4 mL/min, monitoring at 220 nm) NMR: 400 MHz ¹H (CDCl₃) 7.09 ppm, 6H, m; 6.91 ppm, 3H, m; 6.65 ppm, 2H, m; 6.42 ppm, 1H, s; 5.88 ppm, 1H, m; 3.75 ppm, 3H, s; 3.71 ppm, 2H, d, J=5.81 Hz; 2.29 ppm, 3H, m.

EXAMPLE 82

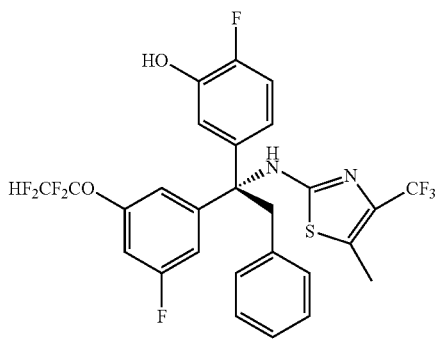

208

(S)-2-fluoro-5-(1-(3-fluoro-5-(1,1,2,2-tetrafluoroethoxy)phenyl)-1-(5-methyl-4-(trifluoromethyl)thiazol-2-ylamino)-2-phenylethyl)phenol Procedure 25

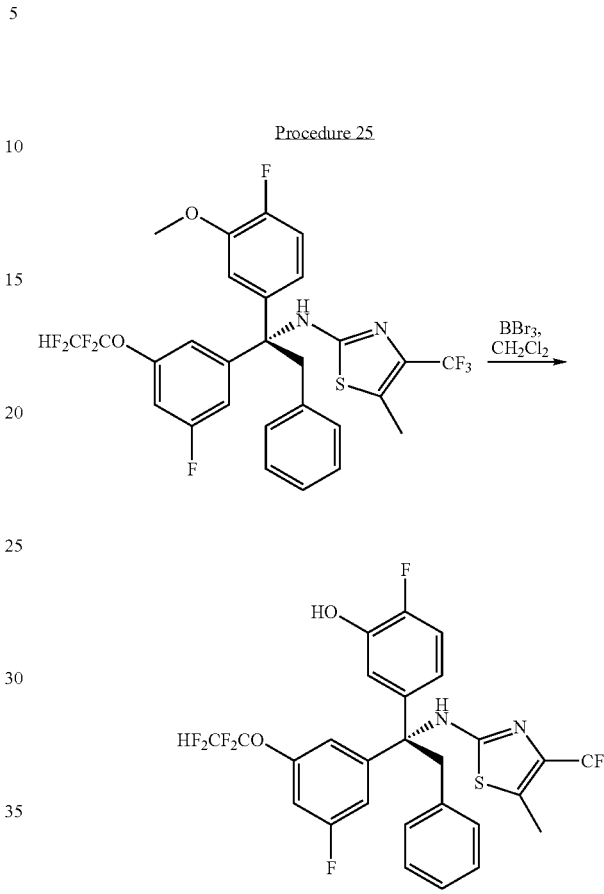

To a solution of (S)-N-(1-(4-fluoro-3-methoxyphenyl)-1-(3-fluoro-5-(1,1,2,2-tetrafluoroethoxy)phenyl)-2-phenylethyl)-5-methyl-4-(trifluoromethyl)thiazol-2-amine (28.5 mg, 0.046 mmol) in CH₂Cl₂ (1 mL) at −76° C. was added BBr₃ (460 μL, 1 M in DCM, 0.46 mmol). The reaction mixture was stirred at −76° C. for 2 h and quenched by the addition of MeOH. The reaction mixture was concentrated and the residue was purified by preparative HPLC Phenomenex Luna AXIA S5 30×100 mm Ballistic column 50-100% MeOH (90% in water, 0.1% TFA) gradient over 10 min with flow rate 40 mL/min and UV detection at 220 nm. (S)-2-fluoro-5-(1-(3-fluoro-5-(1,1,2,2-tetrafluoroethoxy)phenyl)-1-(5-methyl-4-(trifluoromethyl)thiazol-2-ylamino)-2-phenylethyl)phenol eluted at a retention time of 11.09 min and was isolated as a colorless gum (20 mg, 72% yield). LCMS: RT=4.12 min [M+H] 607.2 (Phenomenex Luna C18 column, 4.6×50 mm eluting with 10-90% MeOH/H₂O over 4 minutes containing 0.1% TFA; 4 mL/min, monitoring at 220 nm). NMR: 400 MHz ¹H (CDCl₃) 7.14 ppm, 3H, m; 6.95 ppm, 6H, m; 6.65 ppm, 2H, m; 6.07 ppm, 1H, s; 5.88 ppm, 1H, m; 3.69 ppm, 2H, d, J=1.26 Hz; 3.49 ppm, 1H, s; 2.29 ppm, 3H, q, J=2.19 Hz.

EXAMPLE 83

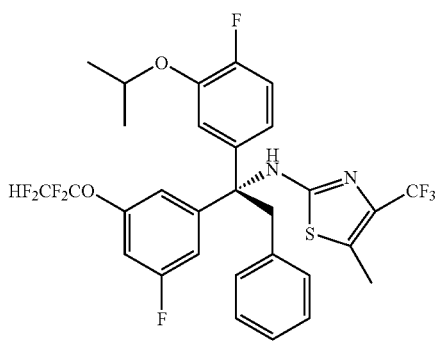

((S)-N-(1-(4-fluoro-3-isopropoxyphenyl)-1-(3-fluoro-5-(1,1,2,2-tetrafluoroethoxy)phenyl)-2-phenylethyl)-5-methyl-4-(trifluoromethyl)thiazol-2-amine Procedure 26

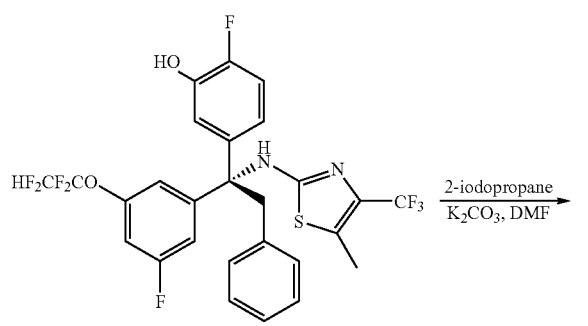

To a solution of (S)-2-fluoro-5-(1-(3-fluoro-5-(1,1,2,2-tetrafluoroethoxy)phenyl)-1-(5-methyl-4-(trifluoromethyl)thiazol-2-ylamino)-2-phenylethyl)phenol (16 mg, 0.026 mmol) in DMF (0.5 mL) was added K₂CO₃ (8 mg, 0.058 mmol), followed by the addition of 2-iodopropane (5 mg, 0.03 mmol). The reaction vessel was sealed and stirred at room temperature for 18 h. The solid was removed by filtration and the filtrate was purified by preparative HPLC Phenomenex AXIA Luna S5 30×75 mm Ballistic column 50-100% ACN (90% in water, 0.1% TFA) gradient over 10 min with flow rate 40 mL/min and UV detection at 220 nm. (S)-N-(1-(4-fluoro-3-isopropoxyphenyl)-1-(3-fluoro-5-(1,1,2,2-tetrafluoroethoxy)phenyl)-2-phenylethyl)-5-methyl-4-(trifluoromethyl)thiazol-2-amine eluted at a retention time of 10.99 min (13 mg, 77% yield). LCMS: RT=4.38 min [M+H] 649.2 (Phenomenex Luna C18 column, 4.6×50 mm eluting with 10-90% MeOH/H₂O over 4 minutes containing 0.1% TFA; 4 mL/min, monitoring at 220 nm). NMR: 400 MHz $^1$H (CDCl₃) 7.18 ppm, 1H, m; 7.11 ppm, 3H, m; 6.97 ppm, 5H, m; 6.59 ppm, 2H, d, J=7.07 Hz; 5.86 ppm, 1H, m; 4.46 ppm, 1H, m; 3.71 ppm, 2H, s; 2.29 ppm, 3H, m; 1.24 ppm, 6H, dd, J=8.84, 6.06 Hz.

EXAMPLE 84

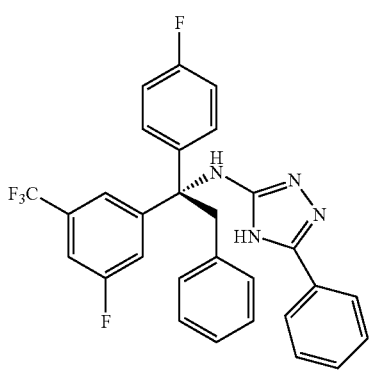

(S)-N-(1-(3-fluoro-5-(trifluoromethyl)phenyl)-1-(4-fluorophenyl)-2-phenylethyl)-5-phenyl-4H-1,2,4-triazol-3-amine Procedure 27

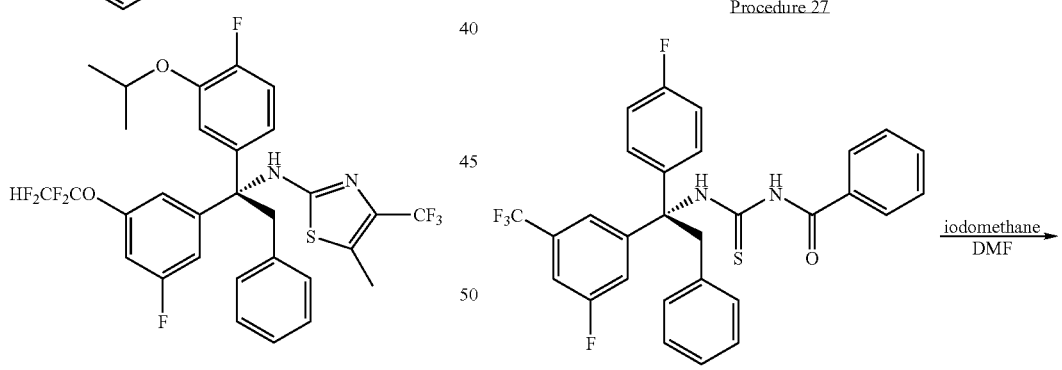

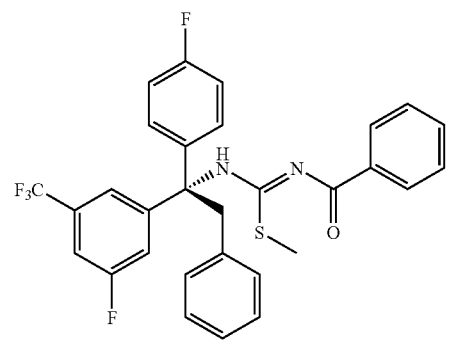

To a solution of (S)-N-(1-(3-fluoro-5-(trifluoromethyl)phenyl)-1-(4-fluorophenyl)-2-phenylethylcarbamothioyl)benzamide (70 mg, 0.13 mmol), prepared by method described in Procedures 22, 23, 24 and 9, in DMF (0.5 mL), was added iodomethane (10 μL, 0.15 mmol). The reaction vessel was sealed and stirred at room temperature for 18 h, followed by the addition of H₂O. The aqueous layer was extracted with EtOAc. The separated organic portion was dried over MgSO₄, filtered and concentrated to give (S,Z)-methyl N'-benzoyl-N-(1-(3-fluoro-5-(trifluoromethyl)phenyl)-1-(4-fluorophenyl)-2-phenylethyl)carbamimidothioate as a white solid (58 mg, 81% yield). LCMS: RT=4.49 min [M+H] 554.92 (Phenomenex Luna C18 column, 4.6×50 mm eluting with 10-90% MeOH/H₂O over 4 minutes containing 0.1% TFA; 4 mL/min, monitoring at 220 nm).

Procedure 28

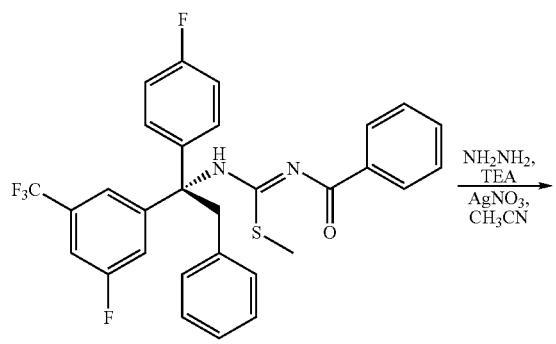

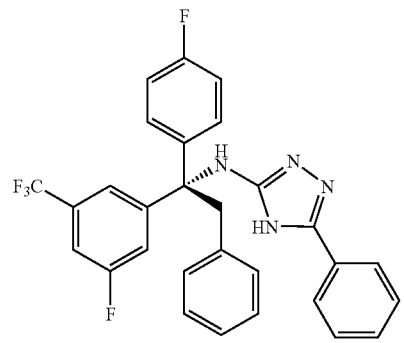

To a solution of (S,Z)-methyl N'-benzoyl-N-(1-(3-fluoro-5-(trifluoromethyl)phenyl)-1-(4-fluorophenyl)-2-phenylethyl)carbamimidothioate (58 mg, 0.1 mmol) and TEA (28 μL, 0.2 mmol) in CH₃CN (1 mL) was added drop wise a solution of AgNO₃ (26 mg, 0.15 mmol) in CH₃CN (1 mL), followed by the addition of NH₂NH₂ (10 μL, 0.1 mmol). The reaction mixture was heated at 60° C. for 1 h and allowed to cool to room temperature. The solid was removed by filtration and the filtrate was concentrated. The residue was purified by ISCO chromatography (4 g column) using hexanes/EtOAc (0-30%) over 10 min to give (S)-N-(1-(3-fluoro-5-(trifluoromethyl)phenyl)-1-(4-fluorophenyl)-2-phenylethyl)-5-phenyl-4H-1,2,4-triazol-3-amine as a white solid (36 mg, 69% yield). LCMS: RT=4.25 min [M+H] 520.97 (Phenomenex Luna C18 column, 4.6×50 mm eluting with 10-90% MeOH/H₂O over 4 minutes containing 0.1% TFA; 4 mL/min, monitoring at 220 nm). NMR: 400 MHz ¹H (CDCl₃) 7.77 ppm, 2H, dd, J=7.83, 1.52 Hz; 7.37 ppm, 4H, m; 7.26 ppm, 4H, m; 7.10 ppm, 3H, m; 6.98 ppm, 2H, m; 6.63 ppm, 2H, d, J=7.33 Hz; 3.97 ppm, 1H, m; 3.85 ppm, 1H, m.

TABLE 5

| Ex. No. | Structure | Name | Retention Time Min./ Molecular Mass | Prepared in the manner described in: |
|---|---|---|---|---|
| 85 | 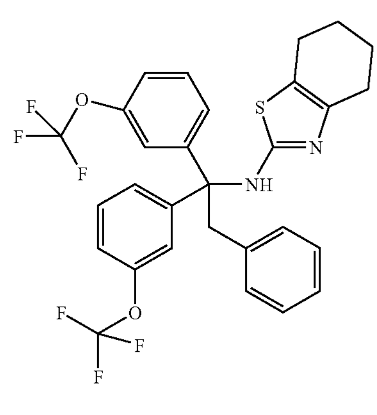 | N-(2-phenyl-1,1-bis(3-(trifluoromethoxy)phenyl)ethyl)-4,5,6,7-tetrahydrobenzo[d]thiazol-2-amine | 3.89 LC (1) 579.32 [M + H]⁺ | Procedures 22, 23, 24, and 9 |

TABLE 5-continued

| Ex. No. | Structure | Name | Retention Time Min./ Molecular Mass | Prepared in the manner described in: |
|---|---|---|---|---|
| 86 | 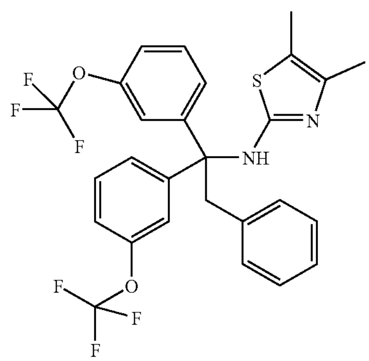 | 4,5-dimethyl-N-(2-phenyl-1,1-bis(3-(trifluoromethoxy)phenyl)ethyl)thiazol-2-amine | 3.77 LC (1) 553.30 [M + H]$^+$ | Procedures 22, 23, 24, 9 and 11 |
| 87 | 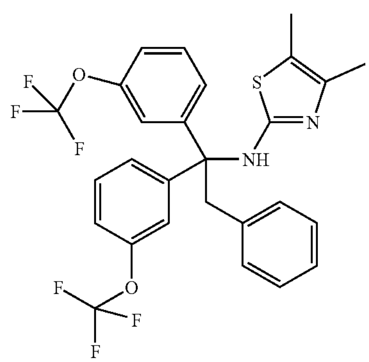 | 5-methyl-N-(2-phenyl-1,1-bis(3-(trifluoromethoxy)phenyl)ethyl)-4-(trifluoromethyl)thiazol-2-amine | 4.50 LC (1) 607.27 [M + H]$^+$ | Procedures 22, 23, 24, 9 and 11 |
| 88 | 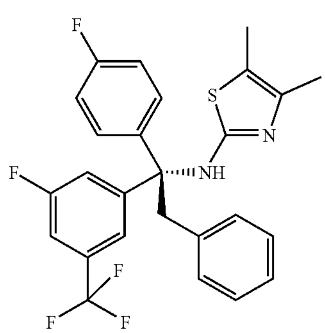 | (S)-N-(1-(3-fluoro-5-(trifluoromethyl)phenyl)-1-(4-fluorophenyl)-2-phenylethyl)-4,5-dimethylthiazol-2-amine | 3.63 LC (1) 489.34 [M + H]$^+$ | Procedures 22, 23, 24, 9 and 11 |
| 89 | 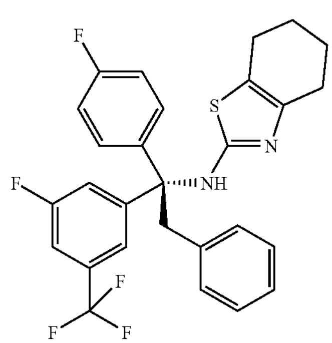 | (S)-N-(1-(3-fluoro-5-(trifluoromethyl)phenyl)-1-(4-fluorophenyl)-2-phenylethyl)-4,5,6,7-tetrahydrobenzo[d]thiazol-2-amine | 3.78 LC (1) 515.35 [M + H]$^+$ | Procedures 22, 23, 24, and 9 |

TABLE 5-continued

| Ex. No. | Structure | Name | Retention Time Min./ Molecular Mass | Prepared in the manner described in: |
|---|---|---|---|---|
| 90 | 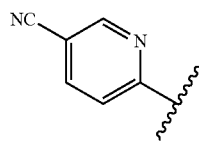 | (S)-N-(1-(3-fluoro-5-(trifluoromethyl)phenyl)-1-(4-fluorophenyl)-2-phenylethyl)-5-methyl-4-(trifluoromethyl)thiazol-2-amine | 4.51 LC (1) 542.96 [M + H]⁺ | Procedures 22, 23, 24, 9 and 11 |
| 91 | 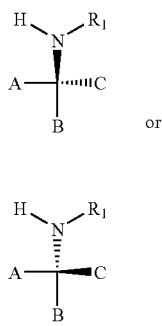 | 4,6-difluoro-N-(2-phenyl-1,1-bis(3-(trifluoromethoxy)phenyl)ethyl)-1H-benzo[d]imidazol-2-amine | 3.85 LC (1) 594.31 [M + H]⁺ | Procedure 22, 23, 24 and 6 |

What is claimed is:

1. A compound of formula Ia or Ib

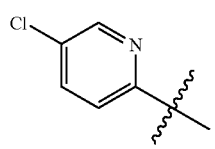

Ia or

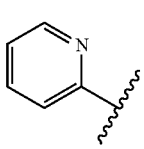

Ib or stereoisomers or pharmaceutically acceptable salt forms thereof, wherein:

A is selected from the group consisting of:

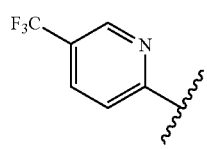 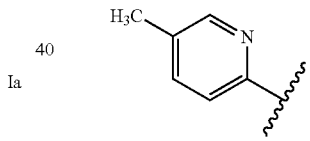 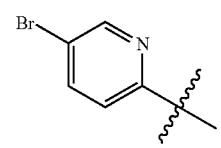

-continued

 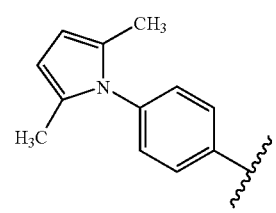

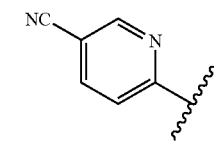 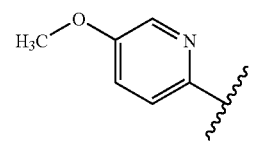

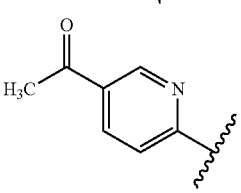 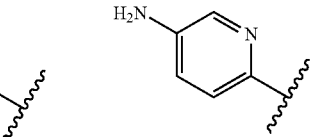

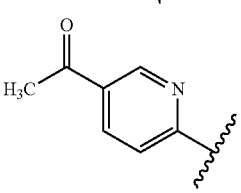 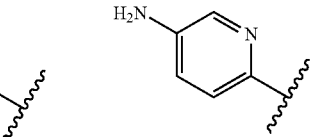

-continued

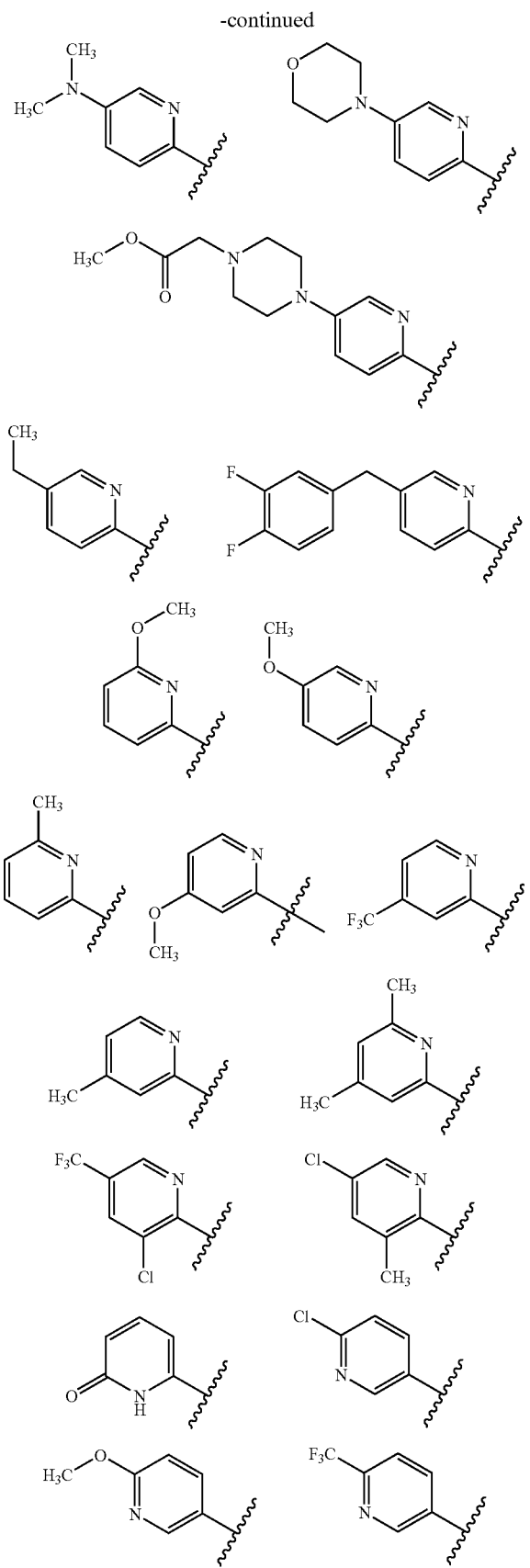

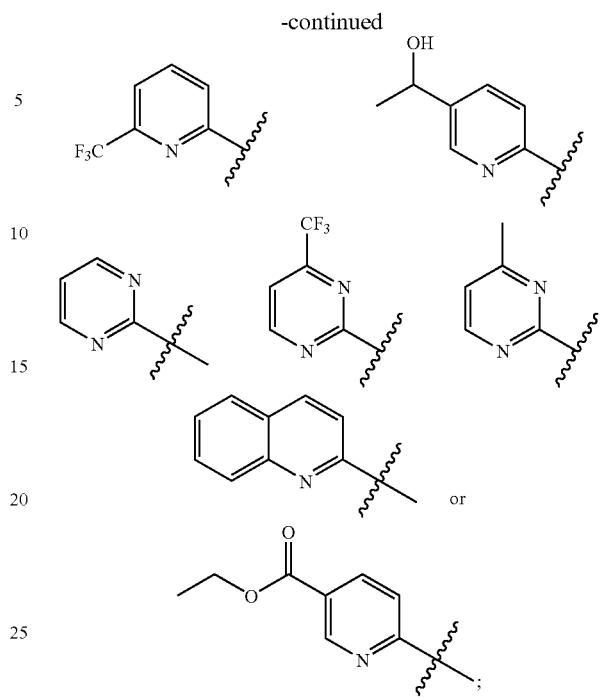

B is:
  phenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) —$S(O)_pR_6$, 17) —$SO_2NHR_6$, 18) —$COOR_6$, 19) —$NHC(CN)NHR_6$, 20) —$CONR_6R_6$, and 21) cycloalkyl, which may be optionally substituted with one or more $R_{20}$'s;

C is:
  alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) —$S(O)_pR_6$, 15) —$SO_2NHR_6$, 16) —$COOR_6$, 17) —$NHC(CN)NHR_6$, and 18) cycloalkyl, which may be optionally substituted with one or more $R_{20}$'s;

$R_1$ is:
  heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) —$SO_2NHR_6$, 19) —$COOR_6$, 20) —NHC(CN)$NHR_6$, 21) —$CONR_6R_6$, 22) —$CONR_9NR_9R_{10}$, and 23) cycloalkyl, which may be optionally substituted with one or more $R_{20}$'s;

$R_6$, at each occurrence, is independently:
(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, 22) —NHC(CN)$NHR_{36}$, and 23) cycloalkyl, which may be optionally substituted with one or more $R_{20}$'s;
(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which maybe optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, 24) —NHC(CN)$NHR_{36}$, and 25) cycloalkyl, which may be optionally substituted with one or more $R_{20}$'s;
(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which maybe optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —NHC(CN)$NHR_{36}$, and 26) cycloalkyl, which may be optionally substituted with one or more $R_{20}$'s;
(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —NHC(CN)$NHR_{36}$, and 26) cycloalkyl, which may be optionally substituted with one or more $R_{20}$'s;
(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —NHC(CN)$NHR_{36}$, and 26) cycloalkyl, which may be optionally substituted with one or more $R_{20}$'s; or
(f) hydrogen;

or two $R_6$'s are taken together to form a 3- to 9-membered ring, which optionally may contain 1-4 heteroatoms selected from N, O, and S and be optionally substituted with one or more $R_{20}$'s;

$R_9$ and $R_{10}$ are independently: (a) hydrogen; (b) —[(C=O)$O_r]_s$aryl, wherein the aryl may be optionally substituted with one or more $R_{20}$'s; (c) —[(C=O)$O_r]_s$($C_2$-$C_8$)-alkenyl, wherein the alkenyl may be optionally substituted with one or more $R_{20}$'s; (d) —[(C=O)$O_r]_s$($C_1$-$C_8$) alkyl, wherein the alkyl may be optionally substituted with one or more $R_{20}$'s; (e) heterocyclyl optionally substituted with one or more $R_{20}$'s; (f), —$CONR_{26}R_{26}$; (g) —($C_2$-$C_6$)-alkynyl; (h) —$COR_{26}$; (i) —$S(O)_pR_{26}$; (j) —$SO_2NHR_{26}$; (k) —$COOR_{26}$; (l) —NHC(CN)$NHR_{26}$; or (m) —[(C=O)$O_r]_s$cycloalkyl, wherein the cycloalkyl may be optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and he optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) =O, q) —($C_2$-$C_6$)-alkynyl; (r) —$COR_{26}$; (s) —$S(O)_pR_{26}$; (t) —$SO_2NHR_{26}$; (u) —$COOR_{26}$; (v) —NHC(CN)$NHR_{26}$; (w) cycloalkyl, which may be optionally substituted with one or more $R_{21}$'s; (x) cycloalkylalkyl, which may be optionally substituted with one or more $R_{21}$'s; or (y) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) =O; (r) ($C_2$-$C_6$)-alkynyl; (s) cycloalkyl; (t) cycloalkylalkyl; (u) —$COR_{26}$; (v) —$S(O)_pR_{26}$; (w) —$SO_2NHR_{26}$; (x) —$COOR_{26}$; or (y) —NHC(CN)$NHR_{26}$;

$R_{26}$, at each occurrence, is independently:
(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, 22) —NHC(CN)$NHR_{36}$, and 23) cycloalkyl, which may be optionally substituted with one or more $R_{40}$'s;
(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, 24) —NHC(CN)$NHR_{36}$, and 25) cycloalkyl, which may be optionally substituted with one or more $R_{40}$'s;
(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which maybe optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —NHC(CN)$NHR_{36}$, and 26) cycloalkyl, which may be optionally substituted with one or more $R_{40}$'s;
(d) heteroaryl, which may be optionally substituted with one or more substituents selected from the group consisting 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —NHC(CN)$NHR_{36}$, and 26) cycloalkyl, which may be optionally substituted with one or more $R_{40}$'s;
(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —NHC(CN)$NHR_{36}$, and 26) cycloalkyl, which may be optionally substituted with one or more $R_{40}$'s; or
(f) hydrogen;
or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —[(C=O)$O_r$]$_s$ aryl, —[(C=O)$O_r$]$_s$alkenyl, —[(C=O)$O_r$]$_s$alkyl, heterocyclyl, —$CONR_{36}R_{36}$, alkynyl, —$COR_{36}$, —$S(O)_p$ $R_{36}$, —$SO_2NHR_{36}$, —$COOR_{36}$, —$C(CN)NHR_{36}$, or cycloalkyl, wherein the aryl, alkyl, alkenyl, cycloalkyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, =O, alkynyl, cycloalkyl, cycloalkylalkyl, —$COR_{49}$, —$S(O)_pR_{49}$, —$SO_2NHR_{49}$, —$COOR_{49}$, or —$NHC(CN)NHR_{49}$;

$R_{49}$ and $R_{50}$, at each occurrence, are independently hydrogen, alkyl, aryl, cycloalkyl, heteroaryl or heterocyclyl, other than heteroaryl;

r 0 to 5;

s is 0 to 4; and p is 1 or 2;

excluding compounds having the following formula:

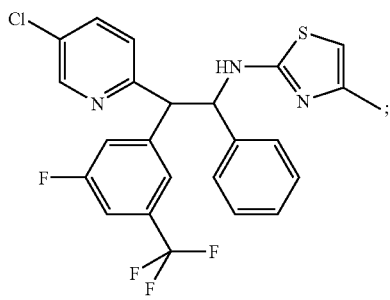

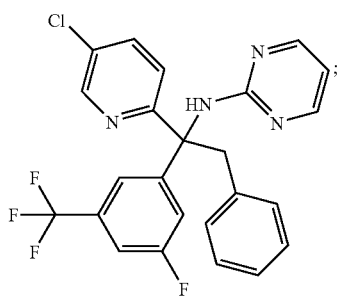

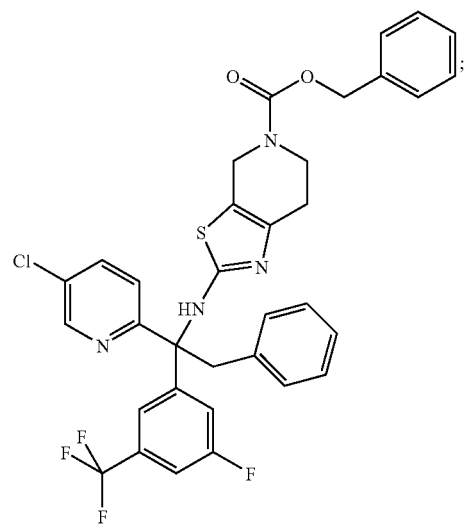

-continued

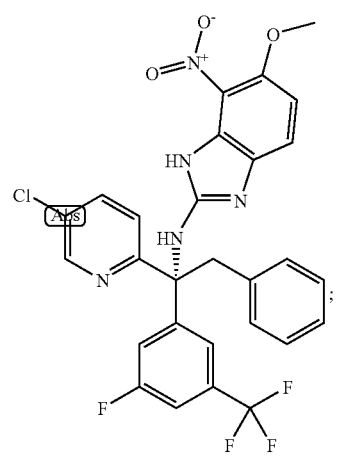

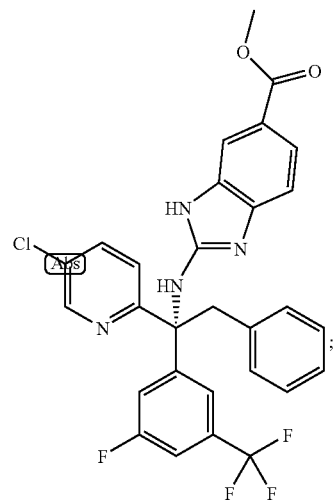

-continued

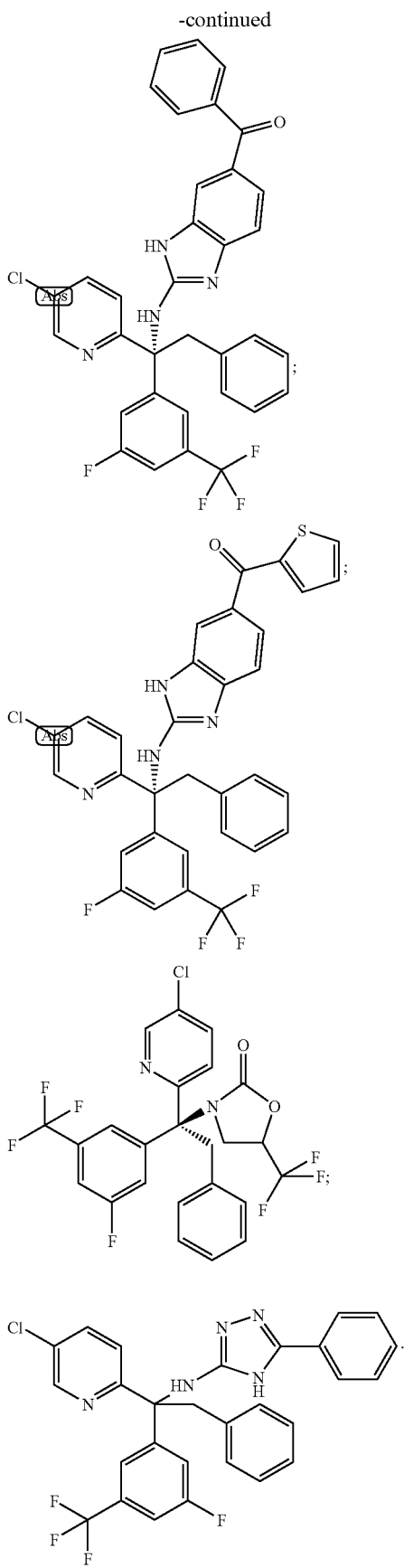

2. A compound of claim 1, wherein the compound is a compound of formula Ib

3. A compound of claim 1, wherein:

B is:
  phenyl, which is substituted with one or more substituents selected from the group consisting of: 1) halo, 2) $(C_1$-$C_6)$-alkyl, which may be optionally substituted with one or more $R_{20}$'s, 3) —$OR_6$, 4) $(C_1$-$C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) —$S(O)_pR_6$, 17) —$SO_2NHR_6$, 18) —$COOR_6$ and 19) —$NHC(CN)NHR_6$;

C is:
  alkyl, which may be optionally substituted with one or more substituents selected from the group consisting of: 1) halo, 2) $(C_1$-$C_6)$-alkyl, which may be optionally substituted with one or more $R_{20}$'s, 3) —$OR_6$, 4) $(C_1$-$C_6)$-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) —$S(O)_pR_6$, 15) —$SO_2NHR_6$, 16) —$COOR_6$, and 17) —$NHC(CN)NHR_6$;

$R_1$ is:
  heteroaryl, which may be optionally substituted with one or more substituents selected from the group consisting of: 1) halo, 2) $(C_1$-$C_6)$-alkyl, which may be optionally substituted with one or more $R_{20}$'s, 3) —$OR_6$, 4) $(C_1$-$C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which maybe optionally substituted with one or more $R_{20}$'s, 14) halo($C_1$-$C_6$)alkyl, 15) —$COR_6$, 16) =O, 17) —$S(O)_pR_6$, 18) —$SO_2NHR_6$, 19) —$COOR_6$s, 20) —$NHC(CN)NHR_6$, 21) —$CONR_6R_6$, and 22) —$CONR_9NR_9R_{10}$;

$R_6$, at each occurrence, is independently:
  (a) alkyl, which may be optionally substituted with one or more substituents selected from the group consisting of: 1) halo, 2) —OH, 3) $(C_1$-$C_6)$-alkyl, which may be optionally substituted with one or more $R_{20}$'s, 4) —$OR_{36}$, 5) $(C_1$-$C_6)$-alkylthio, 6) cyano, 7) nitro, 8)

—NR$_9$R$_{10}$, 9) aryl, which may be optionally substituted with one or more R$_{20}$'s, 10) heteroaryl, which may be optionally substituted with one or more R$_{20}$'s, 11) heterocyclyl, which may be optionally substituted with one or more R$_{20}$'s, 12) halo(C$_1$-C$_6$)alkyl, 13) (C$_2$-C$_6$)-alkenyl, 14) —COOH, 15) —CONR$_{36}$R$_{36}$, 16) =O, 17) (C$_2$-C$_6$)-alkynyl, 18) —COR$_{36}$, 19) —S(O)$_p$R$_{36}$, 20) —SO$_2$NHR$_{36}$, 21) —COOR$_{36}$, and 22) —NHC(CN)NHR$_{36}$;

(b) aryl, which may be optionally substituted with one or more substituents selected from the group consisting of: 1) halo, 2) —OH, 3) (C$_1$-C$_6$)-alkyl, which may be optionally substituted with one or more R$_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) arylalkyl, which may be optionally substituted with one or more R$_{20}$'s, 11) heteroaryl, which may be optionally substituted with one or more R$_{20}$'s, 12) heteroarylalkyl, which may be optionally substituted with one or more R$_{20}$'s, 13) heterocyclyl, which may be optionally substituted with one or more R$_{20}$'s, 14) heterocyclylalkyl, which may be optionally substituted with one or more R$_{20}$'s, 15) halo(C$_1$-C$_6$)alkyl, 16) —COOH, 17) —CONR$_{36}$R$_{36}$, 18) =O, 19) (C$_2$-C$_6$)-alkynyl, 20) —COR$_{36}$, 21) —S(O)$_p$R$_{36}$, 22) —SO$_2$NHR$_{36}$, 23) —COOR$_{36}$, and 24) —NHC(CN)NHR$_{36}$;

(c) cycloalkyl, which may be optionally substituted with one or more substituents selected from the group consisting of; 1) halo, 2) —OH, 3) (C$_1$-C$_6$)-alkyl, which may be optionally substituted with one or more R$_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) arylalkyl, which may be optionally substituted with one or more R$_{20}$'s, 11) heteroaryl, which may be optionally substituted with one or more R$_{20}$'s, 12) heteroarylalkyl, which may be optionally substituted with one or more R$_{20}$'s, 13) heterocyclyl, which may be optionally substituted with one or more R$_{20}$'s, 14) heterocyclylalkyl, which may be optionally substituted with one or more R$_{20}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(d) heteroaryl, which may be optionally substituted with one or more substituents selected from the group consisting of: 1) halo, 2) —OH, 3) (C$_1$-C$_6$)-alkyl, which may be optionally substituted with one or more R$_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) arylalkyl, which may be optionally substituted with one or more R$_{20}$'s, 11) heteroaryl, which may be optionally substituted with one or more R$_{20}$'s, 12) heteroarylalkyl, which may be optionally substituted with one or more R$_{20}$'s, 13) heterocyclyl, which may be optionally substituted with one or more R$_{20}$'s, 14) heterocyclylalkyl, which maybe optionally substituted with one or more R$_{20}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(e) heterocyclyl, other than heteroaryl, which may be optionally substituted with one or more substituents selected from the group consisting of 1) halo, 2) —OH, 3) (C$_1$-C$_6$)-alkyl, which may be optionally substituted with one or more R$_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) arylalkyl, which may be optionally substituted with one or more R$_{20}$'s, 11) heteroaryl, which may be optionally substituted with one or more R$_{20}$'s, 12) heteroarylalkyl, which may be optionally substituted with one or more R$_{20}$'s, 13) heterocyclyl, which may be optionally substituted with one or more R$_{20}$'s, 14) heterocyclylalkyl, which may be optionally substituted with one or more R$_{20}$'s, 15) halo(C$_1$-C$_6$) alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$; or (f) hydrogen;

or two R$_6$'s are taken together to form a 3- to 9-membered ring, which optionally may contain 1-4 heteroatoms selected from N, O, and S and be optionally substituted with one or more R$_{20}$'s;

R$_9$ and R$_{10}$ are independently: (a) hydrogen; (b) —[(C=O)O$_r$]$_s$aryl, wherein the aryl may be optionally substituted with one or more R$_{20}$'s; (c) —[(C=O)O$_r$]$_s$(C$_2$-C$_8$)-alkenyl, wherein the alkenyl may be optionally substituted with one or more R$_{20}$'s; (d) —[C=O)O$_r$]$_s$(C$_1$-C$_8$)alkyl, wherein the alkyl may be optionally substituted with one or more R$_{20}$'s; (e) heterocyclyl optionally substituted with one or more R$_{20}$'s; (f) —CONR$_{26}$R$_{26}$; (g) —(C$_2$-C$_6$)-alkynyl; (h) —COR$_{26}$; (i) —S(O)$_p$R$_{26}$; (j) —SO$_2$NHR$_{26}$; (k) —COOR$_{26}$; or (l) —NHC(CN)NHR$_{26}$;

or R$_9$ and R$_{10}$ are taken together with the nitrogen to which both are attached to form a 3- to 8-membered ring, which may optionally contain 1-4 heteroatoms selected from N, O, and S and may be optionally substituted with one or more R$_{20}$'s;

R$_{20}$ is: (a) halo; (b) (C$_1$-C$_6$)-alkyl, which may be optionally substituted with one or more R$_{21}$'s; (c) —OR$_{26}$; (d) (C$_1$-C$_6$)-alkylthio; (e) cyano; (f) nitro; (g) —NR$_{29}$R$_{30}$; (h) aryl, which may be optionally substituted with one or more R$_{21}$'s ; (i) arylalkyl, which may be optionally substituted with one or more R$_{21}$'s; (j) heteroaryl, which may be optionally substituted with one or more R$_{21}$'s; (k) heteroarylalkyl, which may be optionally substituted with one or more R$_{21}$s; (l) heterocyclyl, which may be optionally substituted with one or more R$_{21}$'s; (m) heterocyclylalkyl, which may be optionally substituted with one or more R$_{21}$'s; (n) halo(C$_1$-C$_6$)alkyl; (o) (C$_2$-C$_6$)-alkenyl; (p) =O; (q) —(C$_2$-C$_6$)-alkynyl; (r) —COR$_{26}$; (s) —S(O)$_p$R$_{26}$; (t) —SO$_2$NHR$_{26}$; (u) —COOR$_{26}$; (v) —NHC(CN)NHR$_{26}$; (w) cycloalkyl, which may be optionally substituted with one or more R$_{21}$'s; (x) cycloalkylalkyl, which may be optionally substituted with one or more R$_{21}$'s; or (y) —CONR$_{26}$R$_{26}$;

R$_{21}$ is: (a) halo; (b) (C$_1$-C$_6$)-alkyl; (c) —OR$_{26}$; (d) (C$_1$-C$_6$)-alkylthio; (e) cyano; (f) nitro; (g) —NR$_{29}$R$_{30}$; (h) aryl; (i) arylalkyl; j) heteroaryl; (k) heteroarylalkyl; (l) heterocyclyl; (m) heterocyclylalkyl; (n) halo(C$_1$-C$_6$)alkyl; (o) —CONR$_{26}$R$_{26}$; (p) (C$_2$-C$_6$)-alkenyl; (q) =O; (r) (C$_2$-C$_6$)-alkynyl; (s) cycloalkyl; (t) cycloalkylalkyl; (u) —COR$_{26}$; (v) —S(O)R$_{26}$; (w) —SO$_2$NHR$_{26}$; (x) —COOR$_{26}$; or (y) —NHC(CN)NHR$_{26}$;

R$_{26}$, at each occurrence, is independently:
(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$O_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heteroaryl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) $COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which maybe optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)R_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_3$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)R_{36}$, 23) —$SO_2NHR_{36}$, 24) —$COOR_{36}$, and 25) —NHC(CN)$NHR_{36}$; or (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —[(C=O)$O_r$]$_s$alkenyl, —[(C=)$O_r$]$_s$alkyl, heterocyclyl, —$CONR_{36}R_{36}$, alkenyl, $COR_{36}$, —$S(O)_pR_{36}$, —$SO_2NHR_{36}$, —$COOR_{36}$, or —C(CN)$NHR_{36}$, wherein the aryl, alkyl, alkenyl or heterocyclyl may be optionally substituted with one or more $R_{40}$'s;

or $R_{29}$ and $R_{30}$ are taken together wioth the nitrogen to which both are attached to form a 3- to 8-membered ring, which may optionally contain 1-4 heteroatoms selected from N, O, and S and may be optionally substituted with one or more $R_{40}$'s;

$R_{36}$ at occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{45}R_{50}$, aryl, arylalkyl, heteroaryl, heteroarylalkyl, heterocycylyl, heterocyclylalkyl, haloalkyl, haloalkyloxy, —$CONR_{49}R_{50}$, alkenyl, arylalkyloxy, =O, alkynyl, cycloalkyl, cycloalkylalkyl, —$COR_{49}$, —$S(O)_pR_{49}$, —$SO_2NHR_{49}$, —$COOR_{49}$, or —NHC(CN)$NHR_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

4. A compound of claim 1, wherein:

B is:
phenyl, which is substituted with one or more substituents selected from the group consisting of: 1) halo, 2) ($C_1$-$C_6$alkyl, which may be optionally substituted with one or more $R_{20}$s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) —$S(O)_pR_6$, 17) —$SO_2NHR_6$, 18) —$COOR_6$ and 19) —NHC(CN)$NHR_6$;

C is:
alkyl, which may be optionally substituted with one or more substituents selected from the group consisting of 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) —$S(O)_pR_6$, 15) —$SO_2NHR_6$, 16) —$COOR_6$, and 17) —NHC(CN)$NHR_6$;

$R_1$, is:
heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which maybe optionally substituted with one or more $R_{20}$'s, 10) heteroaryl, which maybe optionally substituted with one or more 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) —$SO_2NHR_6$, 19) —$COOR_6$, 20) —NHC(CN)$NHR_6$, 21) —$CONR_6R_6$, and 22) —$CONR_9NR_9R_{10}$;

$R_6$, at each occurrence, is independently:
(a) alkyl, which may be optionally substituted with one or more substituents selected from the group consisting of 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)R_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) $COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

or two $R_6$'s are taken together to form a 3- to 9-membered ring, which optionally may contain 1-4 heteroatoms selected from N, O, and S and may be optionally substituted with one or more $R_{20}$'s;

$R_9$ and $R_{10}$ are independently: (a) hydrogen; (b) —[(C=O)$O_r$]$_s$aryl, wherein the aryl may be optionally substituted with one or more $R_{20}$'s; (c) —[(C=O)$O_r$]$_s$($C_2$-$C_8$)-alkenyl, wherein the alkenyl may be optionally substituted with one or more $R_{20}$'s; (d) —[(C=O)$O_r$]$_s$($C_1$-C8) alkyl, wherein the alkyl may be optionally substituted with one or more $R_{20}$'s; (e) heterocyclyl optionally substituted with one or more $R_{20}$'s; (f) $CONR_{26}R_{26}$; (g) —($C_2$-$C_6$)-alkynyl; (h) —$COR_{26}$; (i) —$S(O)_pR_{26}$; (j) —$SO_2NHR_{26}$; (k) —$COOR_{26}$; or (l) —NHC(CN)NHR$_{26}$;

or $R_9$ and $R_{10}$ are taken together with the nitrogen to which both are attached to form a 3- to 8-membered ring, which may optionally contain 1-4 heteroatoms selected from N, O, and S and may be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) =O; (q) —($C_2$-$C_6$)-alkynyl; (r) —$COR_{26}$; (s) —$S(O)_pR_{26}$; (t) —$SO_2NHR_{26}$; (u) —$COOR_{26}$; (v) —NHC(CN)NHR$_{26}$; (w) cycloalkyl, which may be optionally substituted with one or more $R_{21}$'s; (x) cycloalkylalkyl, which may be optionally substituted with one or more $R_{21}$'s, or (y) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{36}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) =O; (r) ($C_2$-$C_6$)-alkynyl; (s) cycloalkyl; (t) cycloalkylalkyl; (u) —$COR_{26}$; (v) —$S(O)_pR_{26}$; (w) —$SO_2NHR_{26}$; (x) —$COOR_{26}$; or (y) —NHC(CN)NHR$_{26}$;

$R_{26}$, at each occurrence, is independently:
  (a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)OR_{36}$, 20) —$SO_2NHR_{36}$, 21) —$COOR_{36}$, and 22) —NHC(CN)NHR$_{36}$;
  (b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)R_{36}$, 22) —$SO_2NHR_{36}$, 23) —$COOR_{36}$, and 24) —NHC(CN)NHR$_{36}$;
  (c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)R_{36}$, 23) —$SO_2NHR_{36}$, 24) —$COOR_{36}$, and 25) —NHC(CN)NHR$_{36}$;
  (d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)NHR$_{36}$;
  (e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)NHR$_{36}$; or
  (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —[(C=O)O$_r$]$_s$aryl, —[(C=O)O$_r$]$_s$alkenyl, —[(C=O)O$_r$]$_s$alkyl, heterocyclyl, —CONR$_{36}$R$_{36}$, alkynyl, —COR$_{36}$, —S(O)$_p$R$_3$, —SO$_2$NHR$_{36}$, —COOR$_{36}$, or —C(CN)NHR$_{36}$, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and may be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —NR$_{49}$R$_{50}$, aryl, arylalkyl, heteroaryl, heteroarylalkyl, heterocyclyl, heterocyclylalkyl, haloalkyl, haloalkyloxy, —CONR$_{49}$R$_{50}$, alkenyl, arylalkyloxy, =O, alkynyl, cycloalkyl, cycloalkylalkyl, —COR$_{49}$, —S(O)$_p$R$_{49}$, —SO$_2$NHR$_{49}$, —COOR$_{49}$, or —NHC(CN)NHR$_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

5. A compound of claim 1, wherein:

B is:
phenyl, which is substituted with one or more substituents selected from the group consisting of: 1) halo, 2) (C$_1$-C$_6$)-alkyl, which may be optionally substituted with one or more $R_{20}$'s, 3) —OR$_6$, 4) (C$_1$-C$_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo(C$_1$-C$_6$)alkyl, 15) —COR$_6$, 16) —S(O)$_p$R$_6$, 17) —SO$_2$NHR$_6$, 18) —COOR$_6$, and 19) —NHC(CN)NHR$_6$;

C is alkyl, which may be optionally substituted with one or more substituents selected from the group consisting of: 1) halo, 2) (C$_1$-C$_6$)-alkyl, which may be optionally substituted with one or more $R_{20}$'s, 3) —OR$_6$, 4) (C$_1$-C$_6$)-alkylthio, 5) cyano, 6) nitro, 7) —NR$_9$R$_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo(C$_1$-C$_6$)alkyl, 12) —COR$_6$, 13) —CONR$_6$R$_6$, 14) —S(O)$_p$R$_6$, 15) —SO$_2$NHR$_6$, 16) —COOR$_6$ and 17) —NHC(CN)NHR$_6$;

$R_1$ is heteroaryl, which may be optionally substituted with one or more substituents selected from the group consisting of: 1) halo, 2) (C$_1$-$_6$)-alkyl, which may be optionally substituted with one or more $R_{20}$'s, 3) —OR$_6$, 4) (C$_1$-C$_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo(C$_1$-C$_6$)alkyl, 15) —COR$_6$, 16) =O, 17) —S(O)$_p$R$_6$, 18) —SO$_2$NHR$_6$, 19) —COOR$_6$, 20) —NHC(CN)NHR$_6$, 21) —CONR$_6$, and 22) —CONR$_9$NR$_9$R$_{10}$;

$R_6$, at each occurrence, is independently:
(a) alkyl, which may be optionally substituted with one or more substituents selected from the group consisting of: 1) halo, 2) —OH, 3) (C$_1$-C$_6$)-alkyl, which may be optionally substituted with one or more $R_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more $R_{20}$'s, 10) heteroaryl, which maybe optionally substituted with one or more $R_{20}$'s, 11) heterocyclyl, which may be optionally substituted with one or more $R_{20}$'s, 12) halo(C$_1$-C$_6$)alkyl, 13) (C$_2$-C$_6$)-alkenyl, 14) —COOH, 15) —CONR$_{36}$R$_{36}$, 16) =O, 17) (C$_2$-C$_6$)-alkynyl, 18) —COR$_{36}$, 19) —S(O)$_p$R$_{36}$, 20) —SO$_2$NHR$_{36}$, 21) —COOR$_{36}$, and 22) —NHC(CN)NHR$_{36}$;

(b) aryl, which may be optionally substituted with one or more substituents selected from the group consisting of: 1) halo, 2) —OH, 3) (C$_1$-C$_6$)-alkyl, which may be optionally substituted with one or more $R_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which maybe optionally substituted with one or more $R_{20}$'s, 15) halo(C$_1$-C$_6$)alkyl, 16) —COOH, 17) —CONR$_{36}$R$_{36}$, 18) =O, 19) (C$_2$-C$_6$)-alkynyl, 20) —COR$_{36}$, 21) —S(O)$_p$R$_{36}$, 22) —SO$_2$NHR$_{36}$, 23) —COOR$_{36}$, and 24) —NHC(CN)NHR$_{36}$;

(c) cycloalkyl, which may be optionally substituted with one or more substituents selected from the group consisting of: 1) halo, 2) —OH, 3) (C$_1$-C$_6$)-alkyl, which may be optionally substituted with one or more $R_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(d) heteroaryl, which may be optionally substituted with one or more substituents selected from the group consisting of: 1) halo, 2) —OH, 3) (C$_1$-C$_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOR, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$; or (f) hydrogen;

or two $R_6$'s are taken together to form a 3- to 9-membered ring, which optionally may contain 1-4 heteroatoms selected from N, O, and S and may be optionally substituted with one or more $R_{20}$'s;

$R_9$ and $R_{10}$ are independently: (a) hydrogen; (b) —[(C=O)$O_r]_s$aryl, wherein the aryl may be optionally substituted with one or more $R_{20}$'s; (c) —[(C=O)$O_r]_s$($C_2$-$C_8$)-alkenyl, wherein the alkenyl may be optionally substituted with one or more $R_{20}$'s; (d) —[(C=O)$O_r]_s$($C_1$-$C_8$) alkyl, wherein the alkyl may be optionally substituted with one or more $R_{20}$'s; (e) heterocyclyl optionally substituted with one or more $R_{20}$'s; (f) —$CONR_{26}R_{26}$; (g) —($C_2$-$C_6$)-alkynyl; (h) —$COR_{26}$; (i) —$S(O)_pR_{26}$; 6) —$SO_2NHR_{26}$; (k) —$COOR_{26}R_{26}$; or (l) —$NHC(CN)NHR_{26}$;

or $R_9$ and $R_{10}$ are taken together with the nitrogen to which both are attached to form a 3- to 8-membered ring, which may optionally contain 1-4 heteroatoms selected from N, O, and S and may be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) =O; (q) —($C_2$-$C_6$)-alkynyl; (r) —$COR_{26}$; (s) —$S(O)_pR_{26}$; (t) —$SO_2NHR_{26}$; (u) —$COOR_{26}$; (v) —$NHC(CN)NHR_{26}$; (w) cycloalkyl, which may be optionally substituted with one or more $R_{21}$'s; (x) cycloalkylalkyl, which may be optionally substituted with one or more $R_{21}$'s; or (y) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) =O; (r) ($C_2$-$C_6$)-alkynyl; (s) cycloalkyl; (t) cycloalkylalkyl; (u) —$COR_{26}$; (v) —$S(O)_pR_{26}$; (w) —$SO_2NHR_{26}$; (x) —$COOR_{26}$; or (y) —$NHC(CN)NHR_{26}$;

$R_{26}$, at each occurrence, is independently:

(a) alkyl, which may be optionally substituted with one or more substituents selected from the group consisting of: 1) halo, 2) —OH, 3) ($C_2$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —$NHC(CN)NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —$NHC(CN)NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylailcyl, which may be optionally substituted with one or more $R_{40}$'s, 11) heteroaryl, which may be optionally substituted with one or more $R_{40}$'s, 12) heteroarylalkyl, which may he optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of 1) halo, 2) —OH, 3) ($C_1$-$C_6$)-alkyl, which may be optionally substituted with one or more $R_{40}$'s, 4) —$O_{36}$, 5) ($C_1$-$C_6$)-alkylthio, 6) cyano, 7) nitro, 8) —$NR_{29}R_{30}$, 9) aryl, which maybe optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$) alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (1) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —[(C=O)$O_r$]$_s$ aryl, —[(C=O)$O_r$]$_s$alkenyl, —[(C=O)$O_r$]$_s$alkyl, heterocyclyl, —$CONR_{36}R_{36}$, alkyny, —$COR_{36}$, —$S(O)_p R_{36}$, —$SO_2NHR_{36}$, $COOR_{36}$, or C(CN)$NHR_{36}$, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and may be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocylylalkyl, haloalkyl, haloalkyloxy, —$CONR_{49}R_{50}$, alkenyl, arylalkyloxy, =O, alkynyl, cycloalkyl, cycloalkylalkyl, —$COR_{49}$, —$S(O)_pR_{49}$, —$SO_2NHR_{49}$, —$COOR_{49}$, or —NHC(CN)$NHR_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

6. A compound of claim 1, wherein:

B is:
  phenyl, which is substituted with one or more substituents selected from the group consisting of: 1) halo, 2) ($C_1$-$C_6$)-alkyl, which maybe optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$) alkyl;

C is alkyl, which may he optionally substituted with one or more substituents selected from the group consisting of: 1) halo, 2) —$OR_6$, 3) —$NR_9R_{10}$, 4) aryl, which may be optionally substituted with one or more $R_{20}$'s, 5) heteroaryl, which may be optionally substituted with one or more $R_{20}$'s, 6) heterocyclyl, which may be optionally substituted with one or more $R_{20}$'s, 7) —$CONR_6R_6$, and 8) —$COOR_6$;

$R_1$ is a nitrogen, sulfur or oxygen containing heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which maybe optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) —$SO_2R_6$, 19) —$COOR_6$, 20) —NHC(CN)$NHR_6$, 21) —$CONR_6R_6$, and 22) —$CONR_9NR_9R_{10}$;

$R_6$, at each occurrence, is independently:
  (a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —$NHC(CN)NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$) alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$; or (f) hydrogen;

$R_9$ and $R_{10}$ are independently: (a) hydrogen;, (b) —$[(C=O)O_r]_s$aryl, wherein the aryl may be optionally substituted with one or more $R_{20}$'s; (c) —$[(C=O)O_r]_s$($C_1$-$C_8$)alkyl, wherein the alkyl may be optionally substituted with one or more $R_{20}$'s; or (d) heterocyclyl optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$'s is: (a) halo; (b) ($C_1$-$C_6$)-alkyl, which maybe optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which maybe optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) =O; (q) —($C_2$-$C_6$)-alkynyl; (r) —$COR_{26}$; (s) —$S(O)_pR_{26}$; (t) —$SO_2NHR_{26}$; (u) —$COOR_{26}$; (v) —$NHC(CN)NHR_{26}$; (w) cycloalkyl, which may be optionally substituted with one or more $R_{21}$'s; (x) cycloalkylalkyl, which may be optionally substituted with one or more $R_{21}$'s; or (y) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) =O; (r) ($C_2$-$C_6$)-alkynyl; (s) cycloalkyl; (t) cycloalkylalkyl; (u) —$COR_{26}$; (v) —$S(O)_pR_{26}$; (w) —$SO_2NHR_{26}$; (x) —$COOR_{26}$; or (y) —$NHC(CN)NHR_{26}$;

$R_{26}$, at each occurrence, is independently:

(a) alkyl, which may be optionally substituted with one or more substituents selected from the group consisting of: 1) halo, 2) —OR, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which maybe optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —$NHC(CN)NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —CONR$_{36}$R$_{36}$, 18) =O, 19) ($C_2$-$C_6$)-alkynyl, 20) —COR$_{36}$, 21) —S(O)$_p$R$_{36}$, 22) —SO$_2$NHR$_{36}$, 23) —COOR$_{36}$, and 24) —NHC(CN)NHR$_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_3$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_3$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$R$_{36}$, 24) —COOR$_{36}$, and 25) —NHC(CN)NHR$_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$; or (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —[(C=O)O$_r$]$_s$aryl, —[(C=O)O$_r$]$_s$alkeny, —[(C=O)O$_r$]$_s$alkyl, heterocyclyl, —CONR$_{36}$R$_{36}$alkynyl, —COR$_{36}$, —S(O)$_p$R$_{36}$, —SO$_2$NHR$_{36}$, —COOR$_{36}$, or —C(CN)NHR$_{36}$, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and may be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —NR$_{49}$R$_{50}$, aryl, arylalkyl, heteroaryl, heteroarylalkyl, heterocyclyl, heterocyclylalkyl, haloalkyl, haloalkyloxy, —CONR$_{49}$R$_{50}$, alkenyl, arylalkyloxy, =O, alkynyl, cycloalkyl, cycloalkylalkyl, —COR$_{49}$, —S(O)$_p$R$_{49}$, —SO$_2$NHR$_{49}$, —COOR$_{49}$, or —NHC(CN)NHR$_{49}$;

$R_{49}$ and $R_{59}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

7. A compound of claim 1, wherein:

B is:
phenyl, which is substituted with one or more substituents selected from the group consisting of 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl;

C is alkyl, which may be optionally substituted with one or more substituents selected from the group consisting of: 1) halo, 2) —OR$_6$, 3) —NR$_9$R$_{10}$, 4) aryl, which may be optionally substituted with one or more $R_{20}$'s, 5) a nitrogen containing heteroaryl, which may be optionally substituted with one or more $R_{20}$'s, 6) —CONR$_6$R$_6$, and 7) —COOR$_6$;

$R_1$ is a 5- to 14-membered nitrogen, sulfur or oxygen containing heteroaryl, which may be optionally substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —S(O)$_p$R$_6$, 18) —SO$_2$NHR$_6$, 19) —COOR$_6$, 20) —NHC(CN)NHR$_6$, 21) —CONR$_6$R$_6$, and 22) —CONR$_9$NR$_9$R$_{10}$;

$R_6$, at each occurrence, is independently:
(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —CONR$_{36}$R$_{36}$, 16) =O, 17) ($C_2$-$C_6$)-alkynyl, 18) —COR$_{36}$, 19) —S(O)$_p$R$_{36}$, 20) —SO$_2$NHR$_{36}$, 21) —COOR$_{36}$, and 22) —NHC(CN)NHR$_{36}$;
(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —CONR$_{36}$R$_{36}$, 18) =O, 19) ($C_2$-$C_6$)-alkynyl, 20) —COR$_{36}$, 21) —S(O)$_p$R$_{36}$, 22) —SO$_2$NHR$_{36}$, 23) —COOR$_{36}$, and 24) —NHC(CN)NHR$_{36}$;
(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;
(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;
(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11.) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$; or
(f) hydrogen;

or two $R_6$'s are taken together to form a 3- to 9-membered ring, which optionally may contain 1-4 heteroatoms selected from N, O, and S and may be optionally substituted with one or more $R_{20}$'s;

$R_9$ and $R_{10}$ are independently: (a) hydrogen; (b) —[(C=O)O$_r$]$_s$aryl, wherein the aryl may be optionally substituted with one or more $R_{20}$'s; or (c) —[(C=O)O$_r$]$_s$($C_1$-$C_8$)alkyl, wherein the alkyl may be optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —OR$_{26}$; (d) ($C_1$-$C_6$)-alkylthio; (e) cyano; (f) nitro; (g) —NR$_{29}$R$_{36}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) =O; (q) —($C_2$-$C_6$)-alkynyl; (r) —COR$_{26}$; (s) —S(O)$_p$R$_{26}$; (t) —SO$_2$NHR$_{26}$; (u) —COOR$_{26}$; (v) —NHC(CN)NHR$_{26}$; (w) cycloalkyl, which may be optionally substituted with one or more $R_{21}$'s; (x) cycloalkylalkyl, which may be optionally substituted with one or more $R_{21}$'s; or (y) —CONR$_{26}$R$_{26}$;

$R_{21}$ is: (a) halo; (b) ($C_1$-$C_6$)-alkyl; (c) —OR$_{26}$; (d) ($C_1$-$C_6$)-alkylthio; (e) cyano; (f) nitro; (g) —NR$_{29}$R$_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl;

(o) —CONR$_{26}$R$_{26}$; (p) (C$_2$-C$_6$)-alkenyl; (q) =O; (r) (C$_2$-C$_6$)-alkynyl; (s) cycloalkyl; (t) cycloalkylalkyl; (u) —COR$_{26}$; (v) —S(O)$_p$R$_{26}$; (w) —SO$_2$NHR$_{26}$; (x) —COOR$_{26}$; or (y) —NHC(CN)NHR$_{26}$;

R$_{26}$, at each occurrence, is independently:
- (a) alkyl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) heteroaryl, which may be optionally substituted with one or more R$_{40}$'s, 11) heterocyclyl, which may be optionally substituted with one or more R$_{40}$'s, 12) halo(C$_1$-C$_6$)alkyl, 13) (C$_2$-C$_6$)-alkenyl, 14) —COOH, 15) —CONR$_{36}$R$_{36}$, 16) =O, 17) (C$_2$-C$_6$)-alkynyl, 18) —COR$_{36}$, 19) —S(O)$_p$R$_{36}$, 20) —SO$_2$NHR$_{36}$, 21) —COOR$_{36}$, and 22) —NHC(CN)NHR$_{36}$;
- (b) aryl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) arylalkyl, which may be optionally substituted with one or more R$_{40}$'s, 11) heteroaryl, which may be optionally substituted with one or more R$_{40}$'s, 12) heteroarylalkyl, which may be optionally substituted with one or more R$_{40}$'s, 13) heterocyclyl, which may be optionally substituted with one or more R$_{40}$'s, 14) heterocyclylalkyl, which may be optionally substituted with one or more R$_{40}$'s 15) halo(C3C6)alkyl, 16) —COOH, 17) —CONR$_{36}$R$_{36}$, 18) =O, 19) (C$_2$-C$_6$)-alkynyl, 20) —COR$_{36}$, 21) —S(O)$_p$R$_{36}$, 22) —SO$_2$NHR$_{36}$, 23) —COOR$_{36}$, and 24) —NHC(CN)NHR$_{36}$;
- (c) cycloalkyl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) arylalkyl, which may be optionally substituted with one or more R$_{40}$'s, 11) heteroaryl, which may be optionally substituted with one or more R$_{40}$'s, 12) heteroarylalkyl, which may be optionally substituted with one or more R$_{40}$'s, 13) heterocyclyl, which maybe optionally substituted with one or more R$_{40}$'s, 14) heterocyclylalkyl, which may be optionally substituted with one or more R$_{40}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;
- (d) heteroaryl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) arylalkyl, which may be optionally substituted with one or more R$_{40}$'s, 11) heteroaryl, which may be optionally substituted with one or more R$_{40}$'s, 12) heteroarylalkyl, which may be optionally substituted with one or more R$_{40}$'s, 13) heterocyclyl, which may be optionally substituted with one or more R$_{40}$'s, 14) heterocyclylalkyl, which may be optionally substituted with one or more R$_{40}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;
- (e) heterocyclyl, other than heteroaryl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) arylalkyl, which may be optionally substituted with one or more R$_{40}$'s, 11) heteroaryl, which may be optionally substituted with one or more R$_{40}$'s, 12) heteroarylalkyl, which may be optionally substituted with one or more R$_{40}$'s, 13) heterocyclyl, which may be optionally substituted with one or more R$_{40}$'s, 14) heterocyclylalkyl, which may be optionally substituted with one or more R$_{40}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$; or
- (f) hydrogen;

or two R$_{26}$'s are taken together to form a 3- to 9-membered ring, which optionally may contain 1-4 heteroatoms selected from N, O, and S and he optionally substituted with one or more R$_{40}$'s;

R$_{29}$ and R$_{30}$ are independently hydrogen, —[(C=O)O$_r$]$_s$aryl, —[(C=O)O$_r$]$_s$alkenyl, —[(C=O)O$_r$]$_s$alkyl, heterocyclyl, —CONR$_{36}$R$_{36}$, alkyny —COR$_{36}$, —S(O)$_p$R$_{36}$, —SO$_2$NHR$_{36}$, —COOR$_{36}$, or —C(CN)NHR$_{36}$, wherein the aryl, alkyl, alkenyl or heterocyclyl may be optionally substituted with one or more R$_{40}$'s;

or R$_{29}$ and R$_{30}$ are taken together with the nitrogen to which both are attached to form a 3- to 8-membered ring, which may optionally contain 1-4 heteroatoms selected from N, O, and S and may be optionally substituted with one or more R$_{40}$'s;

R$_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more R$_{40}$'s;

R$_{40}$ is halo, —OH, alkyl, alkyloxy, alkylthio, cyano, nitro, —NR$_{49}$R$_{50}$, aryl, arylalkyl, heteroaryl, heteroarylalkyl, heterocyclyl, heterocyclylalkyl, haloalkyl, haloalkyloxy, —CONR$_{49}$R$_{50}$, alkenyl, arylalkyloxy, =O, alkynyl, cycloalkyl, cycloalkylalkyl, —COR$_{49}$, —S(O)$_p$R$_{49}$, —SO$_2$NHR$_{49}$, —COOR$_{49}$, or —NHC(CN)NHR$_{49}$;

R$_{49}$ and R$_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

8. A compound of claim 1, wherein:

B is:
  phenyl, which is substituted with one or more substituents selected from the group consisting of 1) halo, 2) (C$_1$-C$_6$)-alkyl, which may be optionally substituted with one or more R$_{20}$'s, 3) —OR$_6$, 4) (C$_1$-C$_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl;

C is alkyl, which may be optionally substituted with one or more substituents selected from the group consisting of: 1) halo, 2) phenyl, which may be optionally substituted with one or more $R_{20}$'s, or 3) a 5- or 6-membered nitrogen containing heteroaryl, which may be optionally substituted with one or more $R_{20}$'s;

$R_1$ is a 5- to 14-membered nitrogen or sulfur containing heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) —$SO_2NHR_6$, 19) —$COOR_6$, 20) —NHC(CN)$NHR_6$, 21) —$CONR_6R_6$, and 22) —$CONR_9NR_9R_{10}$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which maybe optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_1$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R10$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_3$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

$R_9$ and $R_{10}$ are independently: (a) hydrogen; or (b) —[(C=O)$O_r$]$_s$($C_1$-$C_8$)alkyl, wherein the alkyl may be optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) =O; (q) —($C_2$-$C_6$)-alkynyl; (r) —$COR_{26}$; (s) —$S(O)_pR_{26}$; (t) —$SO_2NHR_{26}$; (u) —$COOR_{26}$; (v) —$NHC(CN)NHR_{26}$; (w) cycloalkyl, which may be optionally substituted with one or more $R_{21}$'s; (x) cycloalkylalkyl, which may be optionally substituted with one or more $R_{21}$'s; or (y) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) =O; (r) ($C_2$-$C_6$)-alkynyl; (s) cycloalkyl; (t) cycloalkylalkyl; (u) —$COR_{26}$; (v) —$S(O)_pR_{26}$; (w) —$SO_2NHR_{26}$; (x) —$COOR_{26}$; or (y) —$NHC(CN)NHR_{26}$;

$R_{26}$, at each occurrence, is independently:
(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —$NHC(CN)NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —$NHC(CN)NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$; or (f) hydrogen;

$R_{29}$ and $R_{30}$ are independently hydrogen, —$[(C=O)O_r]_s$aryl, —$[(C=O)O_r]_s$alkenyl, —$[(C=O)O_r]_s$alkyl, heterocyclyl, —$CONR_{36}R_{36}$, alkynyl, —$COR_{36}$, —$S(O)_pR_{36}$, —$SO_2NHR_{36}$, —$COOR_{36}$, or —$C(CN)NHR_{36}$, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and may be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, =O, alkynyl, cycloalkyl, cycloalkylalkyl, —$COR_{49}$, —$S(O)_pR_{49}$, —$SO_2NHR_9$, —$COOR_{49}$, or —$NHC(CN)NHR_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

9. A compound of claim 1, wherein:

A is a substituted pyridyl selected from the group defined for A:

B is phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl;

C is alkyl, which may be optionally substituted with one or more substituents selected from the group consisting of: 1) phenyl, which may be optionally substituted with one or more $R_{20}$'s, or 2) a 5- or 6-membered nitrogen containing heteroaryl, which may be optionally substituted with one or more $R_{20}$'s;

$R_1$ is a 5- to 14-membered nitrogen containing heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$COOR_6$, 18) —$CONR_6R_6$, and 19) —$CONR_9NR_9R_{10}$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —$NHC(CN)NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —$NHC(CN)NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which maybe optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(e) heterocyclyl, other than heteroaryl, which may be optionally substituted with one or more substituents selected from the group consisting of: 1) halo, 2) —OH, 3)($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$; or (f) hydrogen;

$R_9$ and $R_{10}$ are independently: (a) hydrogen; or (b) —[(C=O)O$_r$]$_s$($C_1$-$C_8$)alkyl, wherein the alkyl may be optionally substituted with one or more $R_{20}$'s;

$R_{20}$ is: (a) halo; (b) ($C_1$-$C_6$)-alkyl, which may be optionally substituted with one or more $R_{21}$'s; (c) —OR$_{26}$; (d) ($C_1$-$C_6$)-alkylthio; (e) cyano; (f) nitro; (g) —NR$_{29}$R$_{39}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) —($C_2$-$C_6$)-alkynyl; (q) —COR$_{26}$; (r) —COOR$_{26}$; (s) cycloalkyl, which may be optionally substituted with one or more $R_{21}$'s; (t) cycloalkylalkyl, which may be optionally substituted with one or more $R_{21}$'s; or (u) —CONR$_{26}$R$_{26}$;

$R_{21}$ is: (a) halo; (b) ($C_1$-$C_6$)-alkyl; (c) —OR$_{26}$; (d) ($C_1$-$C_6$)-alkylthio; (e) cyano; (f) nitro; (g) —NR$_{29}$R$_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —CONR$_{26}$R$_{26}$; (p) ($C_2$-$C_6$)-alkenyl; (q) ($C_2$-$C_6$)-alkynyl; (r) cycloalkyl; (s) cycloalkylalkyl; (t) —COR$_{26}$; or (u) —COOR$_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —CONR$_{36}$R$_{36}$, 16) =O, 17) ($C_2$-$C_6$)-alkynyl, 18) —COR$_{36}$, 19) —S(O)$_p$R$_{36}$, 20) —SO$_2$NHR$_{36}$, 21) —COOR$_{36}$, and 22) —NHC(CN)NHR$_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —CONR$_{36}$R$_{36}$, 18) =O, 19) ($C_2$-$C_6$)-alkynyl, 20) —COR$_{36}$, 21) —S(O)$_p$R$_{36}$, 22) —SO$_2$NHR$_{36}$, 23) —COOR$_{36}$, and 24) —NHC(CN)NHR$_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$; or (f) hydrogen;

$R_{29}$ and $R_{30}$ are independently hydrogen or —[(C=O)O$_r$]$_s$alkyl, wherein the alkyl may be optionally substituted with one or more $R_{40}$'s;

$R_{36}$, at each occurrence, is independently alkyl, aryl, heteroaryl or heterocyclyl, other than heteroaryl, wherein the alkyl, aryl, heteroaryl or heterocyclyl may be optionally substituted with one or more $R_{40}$'s;

$R_{40}$'s is halo, —OH, alkyl, alkyloxy, alkylthio, cyano, nitro, aryl, arylalkyl, heteroaryl, heteroarylalkyl, heterocyclyl, heterocyclylalkyl, haloalkyl, haloalkyloxy, alkenyl, arylalkyloxy, =O, alkynyl, cycloalkyl or cycloalkylalkyl;

r is 0 to 2;

s is 0 to 1; and p is 1 or 2.

10. A compound of claim 9, wherein:

C is methylphenyl, which may be optionally substituted with one or more $R_{20}$'s;

$R_1$ is a 5- to 14-membered nitrogen containing heteroaryl, which may be optionally substituted with one or more substituents selected from the group consisting of: 1) halo, 2) $(C_1-C_6)$-alkyl, which may be optionally substituted with one or more $R_{20}$'s, 3) —OR$_6$, 4) $(C_1-C_6)$-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1-C_6$)alkyl, 15) —COR$_6$, 16) =O, 17) —COOR$_6$, 18) —CONR$_6$R$_6$, and 19) —CONR$_9$NR$_9$R$_{10}$;

$R_6$, at each occurrence, is independently:
(a) alkyl, which may be optionally substituted with one or more substituents selected from the group consisting of: 1) halo, 2) —OH, 3) $(C_1-C_6)$-alkyl, 4) —OR$_{36}$, 5) $(C_1-C_6)$-alkylthio, 6) cyano, 7) nitro, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1-C_6$)alkyl, 12) $(C_2-C_6)$-alkenyl, 13) —COOH, 14) $(C_2-C_6)$-alkynyl, 15) —COR$_{36}$, and 16) —COOR$_{36}$; or
(b) hydrogen;

$R_9$ and $R_{10}$ are independently: (a) hydrogen; or (b) —[(C=O)O$_r$]$_s$(C$_1$-C$_8$)alkyl, wherein the alkyl may be optionally substituted with one or more $R_{20}$'s;

$R_{20}$ is: (a) halo; (b) $(C_1-C_6)$-alkyl; (c) —O$_{26}$; (d) $(C_1-C_6)$-alkylthio; (e) cyano; (f) nitro; (g) aryl, which may be optionally substituted with one or more $R_{21}$'s; (h) arylalkyl, which may be optionally substituted with one or more $R_{21}$'s; (i) heteroaryl, which may be optionally substituted with one or more $R_{21}$'s; (j) heteroarylalkyl, which may be optionally substituted with one or more $R_{21}$'s; (k) heterocyclyl, which may be optionally substituted with one or more $R_{21}$'s; (l) heterocyclylalkyl, which may be optionally substituted with one or more $R_{21}$'s; (m) halo($C_1-C_6$)alkyl; (n) $(C_2-C_6)$-alkenyl; (o) —$(C_2-C_6)$-alkynyl; (p) —COR$_{26}$; (q) —COOR$_{26}$; (r) cycloalkyl, which may be optionally substituted with one or more $R_{21}$'s; or (s) cycloalkylalkyl, which may be optionally substituted with one or more $R_{21}$'s;

$R_{21}$ is: (a) halo; (b) $(C_1-C_6)$-alkyl; (c) —OR$_{26}$; (d) $(C_1-C_6)$-alkylthio; (e) cyano; (f) nitro; (g) aryl; (h) arylalkyl; (i) heteroaryl; (j) heteroarylalkyl; (k) heterocyclyl; (l) heterocyclylalkyl; (m) halo($C_1-C_6$)alkyl; (n) $(C_2-C_6)$-alkenyl; (o) $(C_2-C_6)$-alkynyl; (p) cycloalkyl; (q) cycloalkylalkyl; (r) —COR$_{26}$; or (s) —COOR$_{26}$;

$R_{26}$, at each occurrence, is independently:
(a) alkyl, which may be optionally substituted with one or more substituents selected from the group consisting of: 1) halo, 2) —OH, 3) $(C_1-C_6)$-alkyl, 4) —OR$_{36}$, 5) $(C_1-C_6)$-alkylthio, 6) cyano, 7) nitro, 8) aryl, which may be optionally substituted with one or more $R_{40}$'s, 9) heteroaryl, which may be optionally substituted with one or more $R_{40}$'s, 10) heterocyclyl, which may be optionally substituted with one or more $R_{40}$'s, 11) halo($C_1-C_6$)alkyl, 12) $(C_2-C_6)$-alkenyl, 13) —COOH, 14) $(C_2-C_6)$-alkynyl, 15) —COR$_{36}$, or 16) —COOR$_{36}$; or
(b) hydrogen;

$R_{36}$, at each occurrence, is independently alkyl, aryl or heteroaryl, wherein the alkyl, aryl or heteroaryl may be optionally substituted with one or more $R_{40}$'s; and $R_{40}$ is halo, —OH, alkyl, alkyloxy, alkylthio, cyano, nitro, aryl, arylalkyl, heteroaryl, heteroarylalkyl, heterocyclyl, heterocyclylalkyl, haloalkyl, haloalkyloxy, alkenyl, arylalkyloxy, alkynyl, cycloalkyl or cycloalkylalkyl.

11. A compound of claim 1, wherein:

A is:

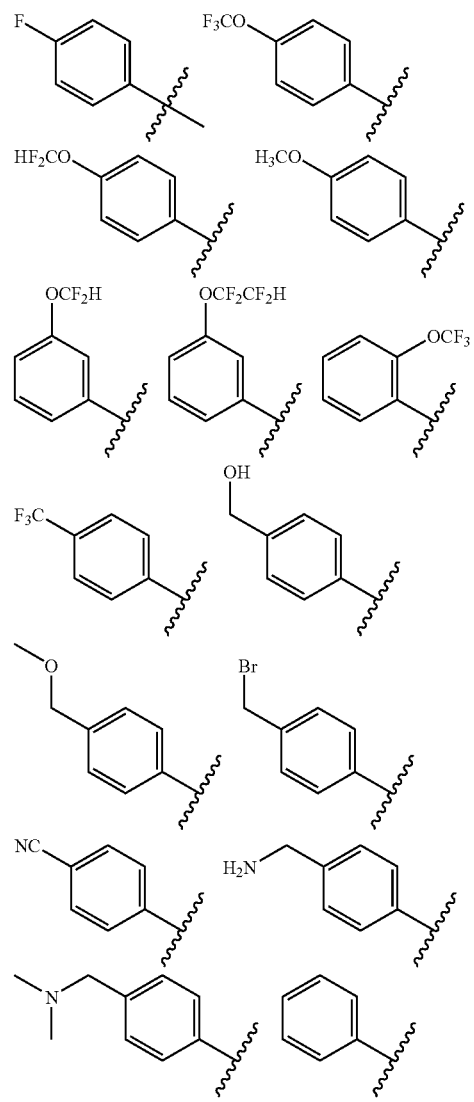

-continued
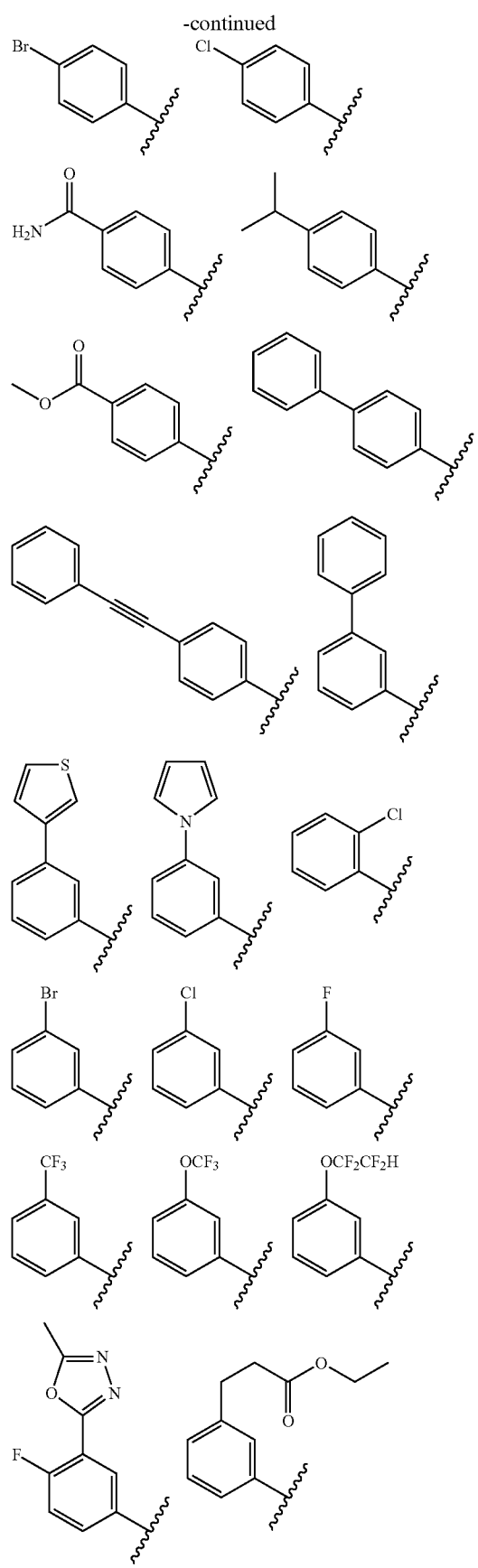
-continued
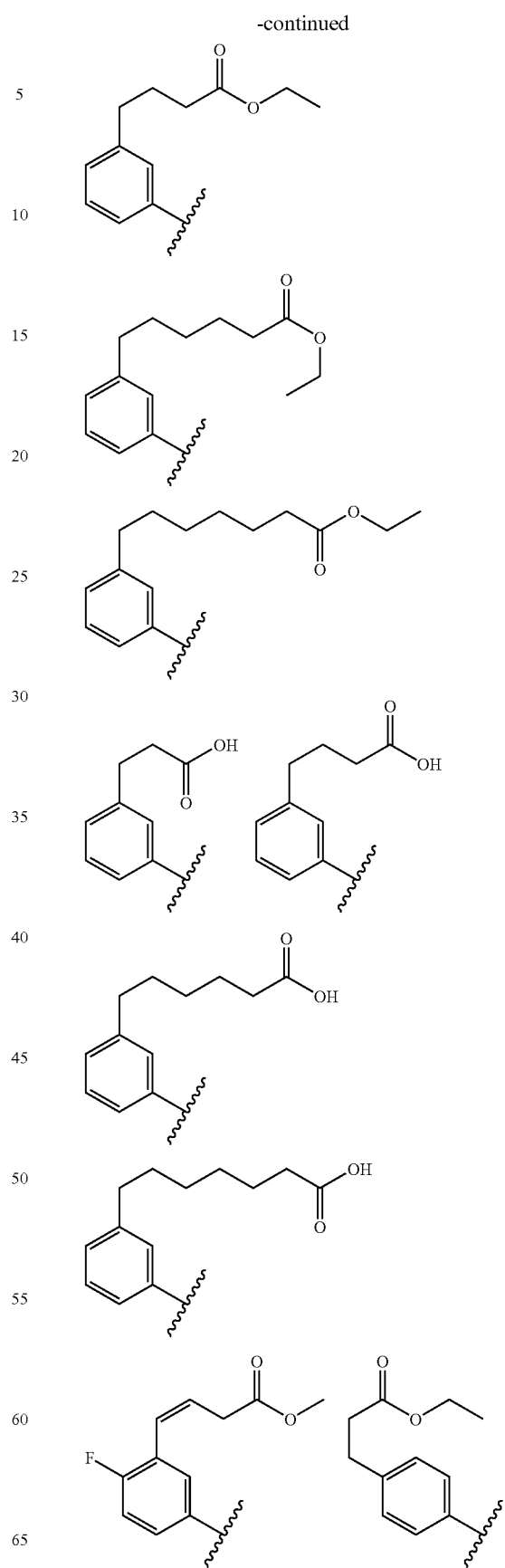

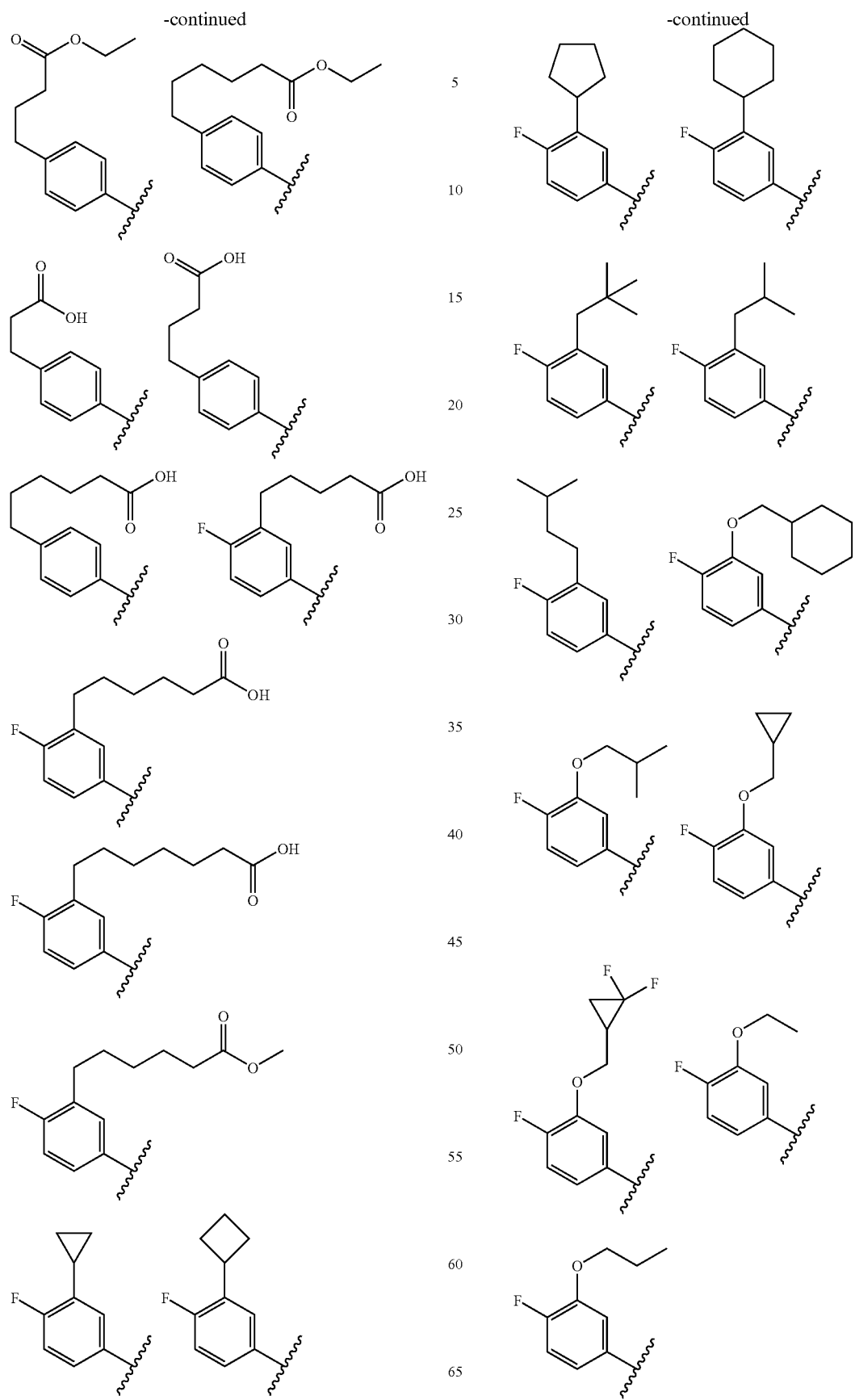

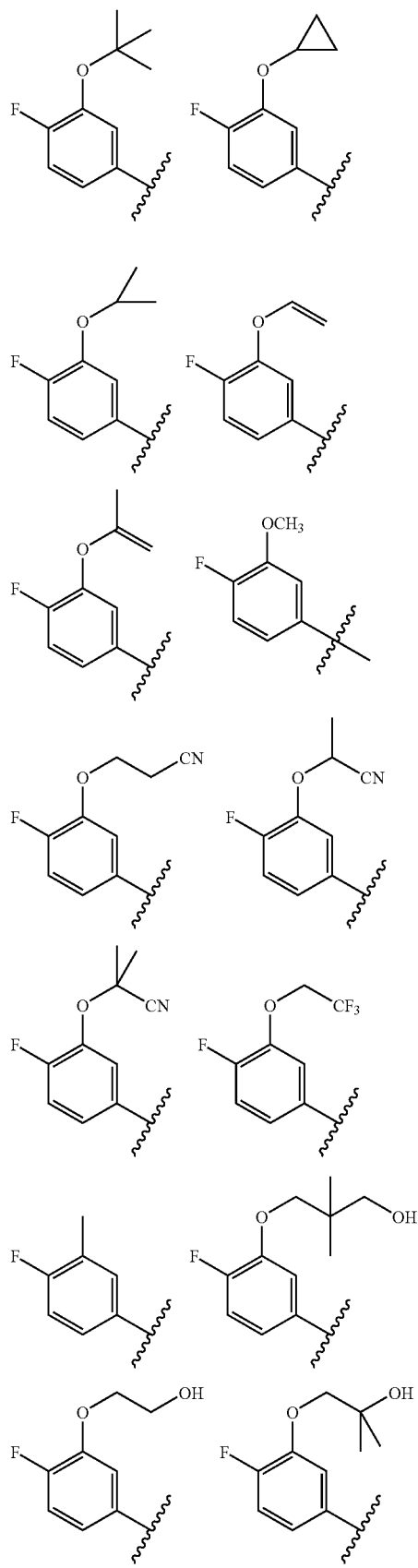
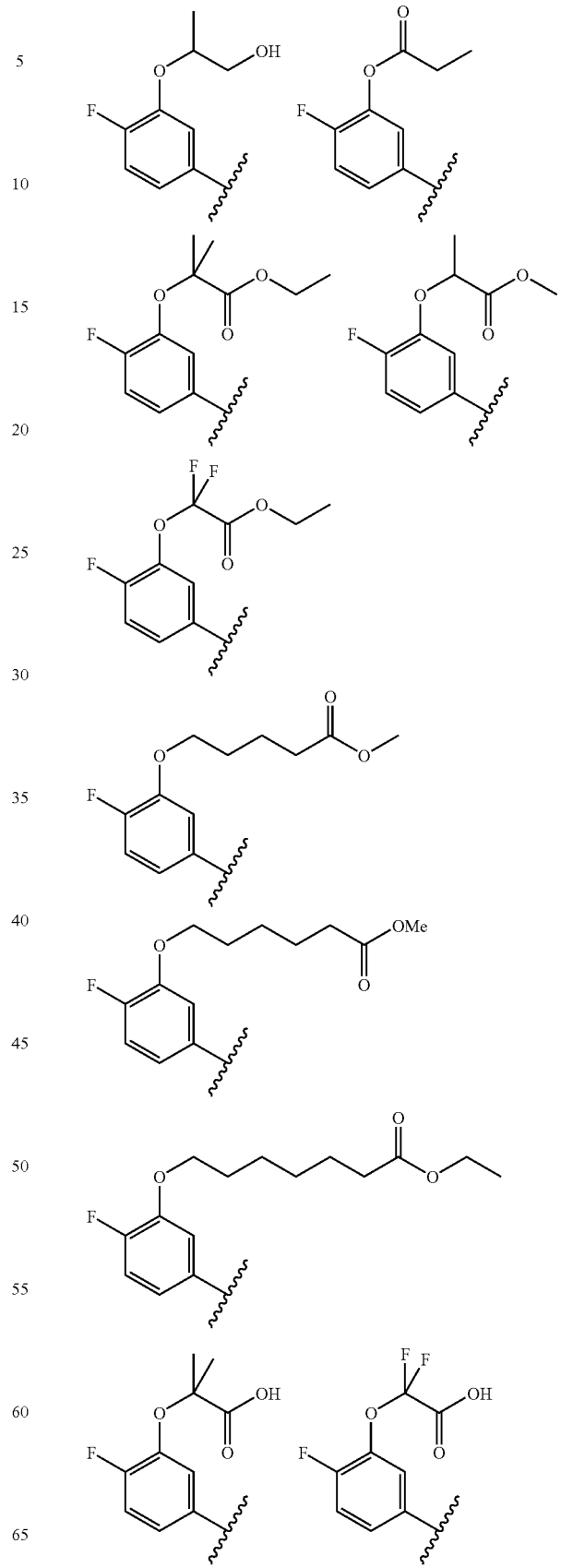

-continued
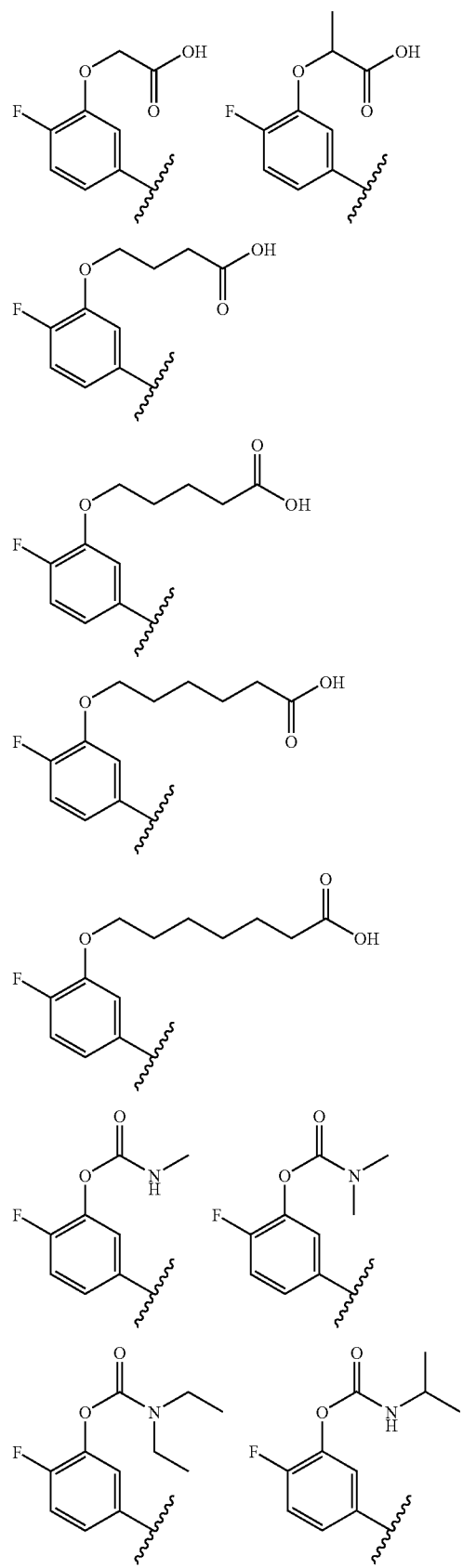
-continued
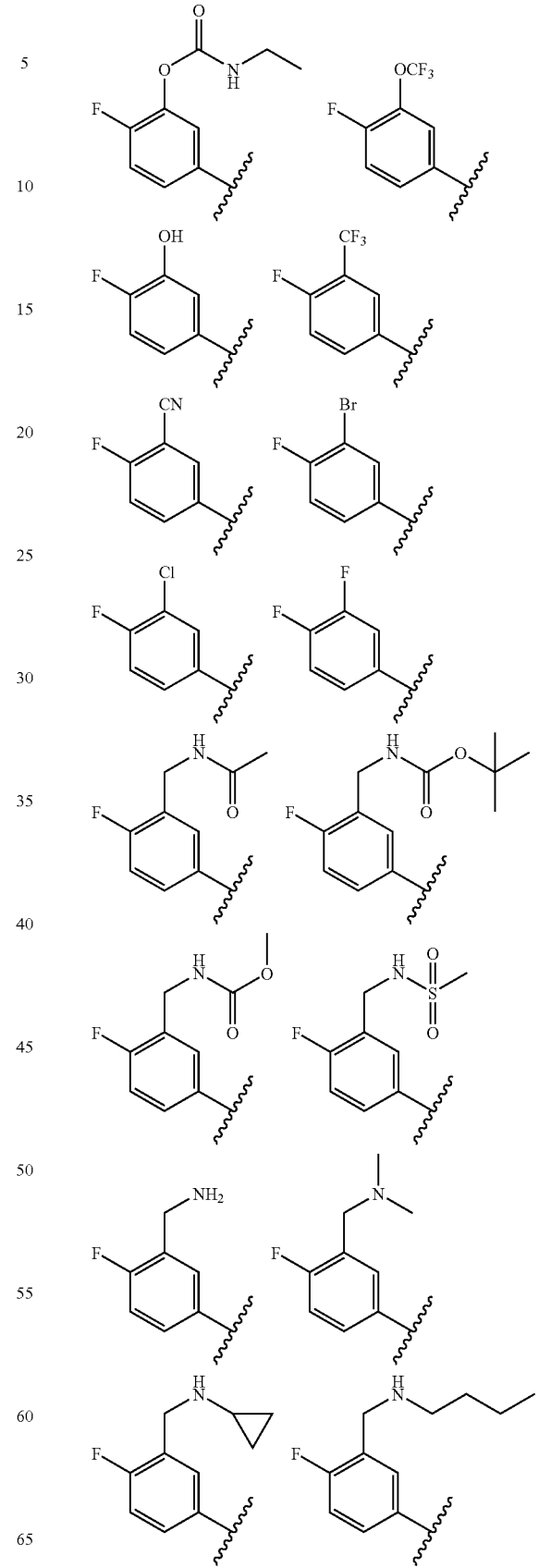

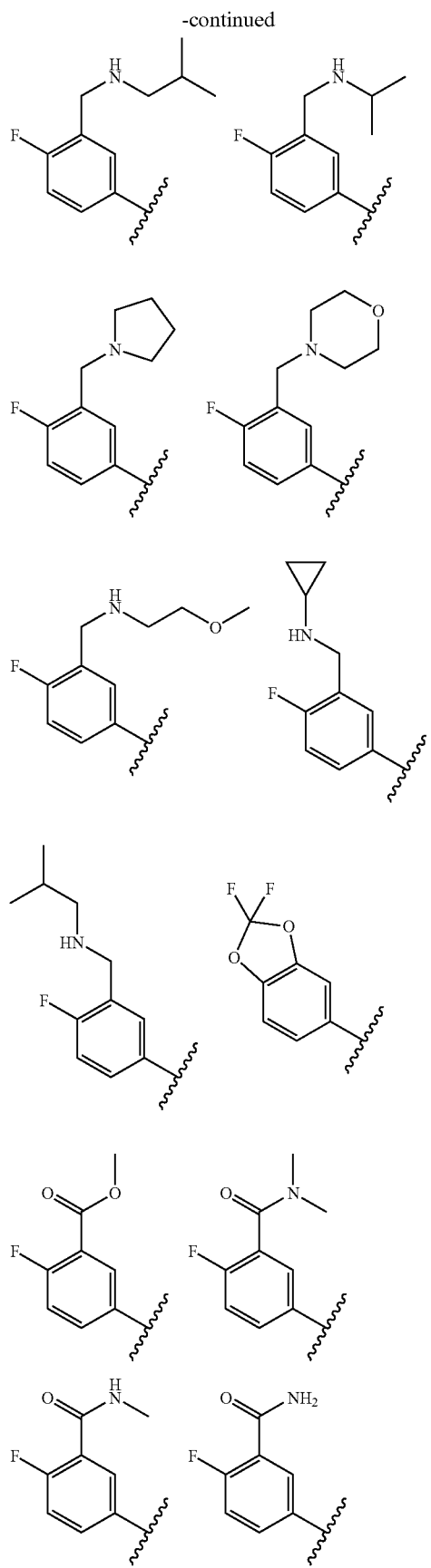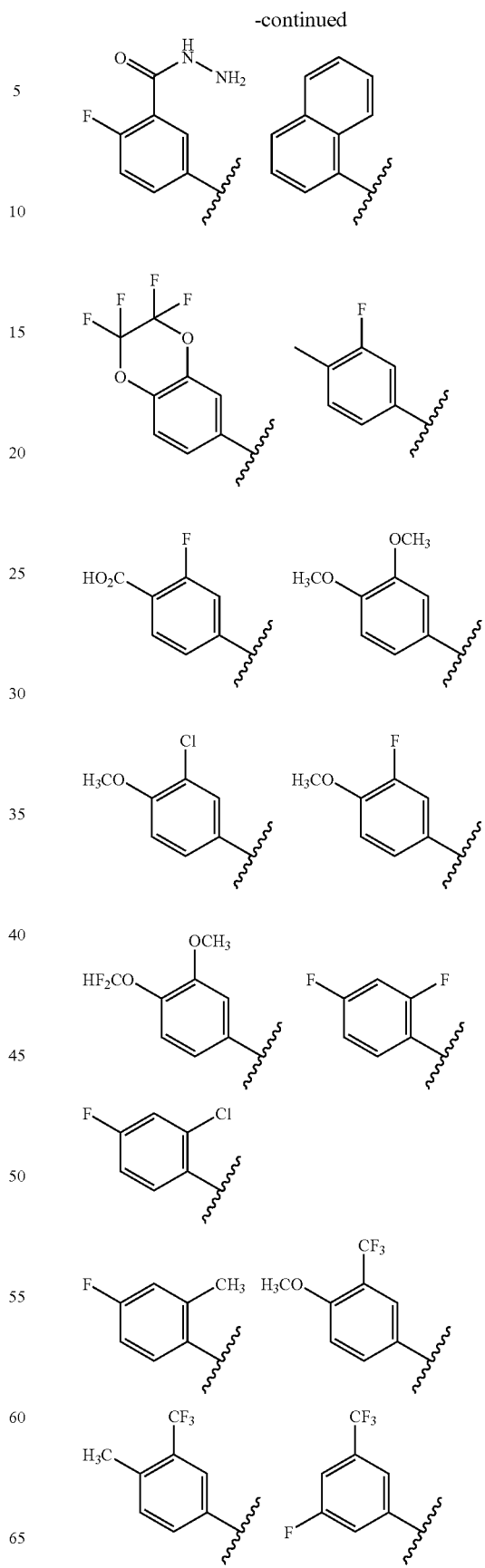

-continued
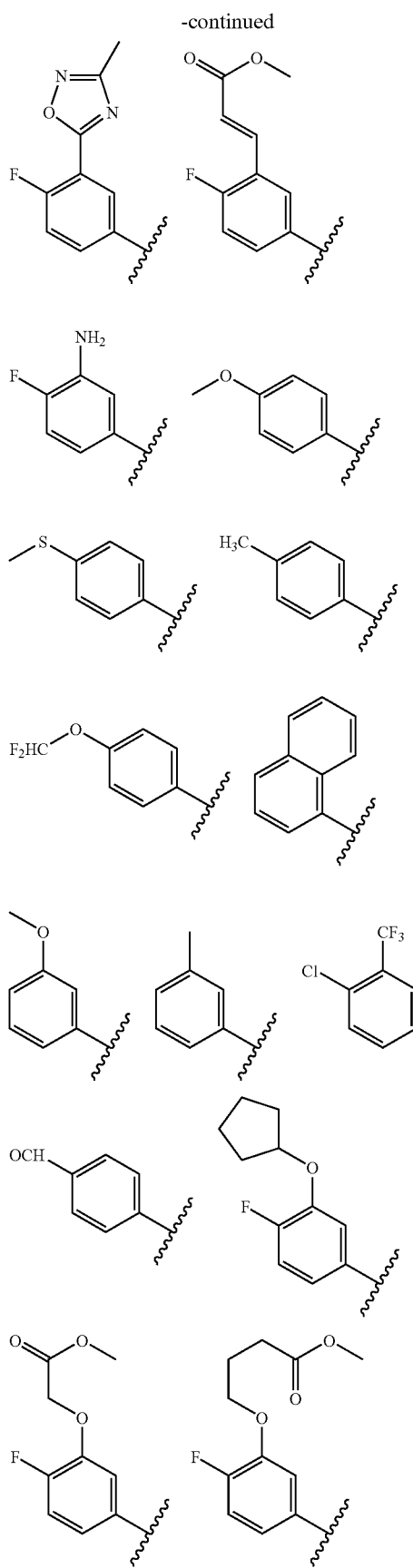
-continued
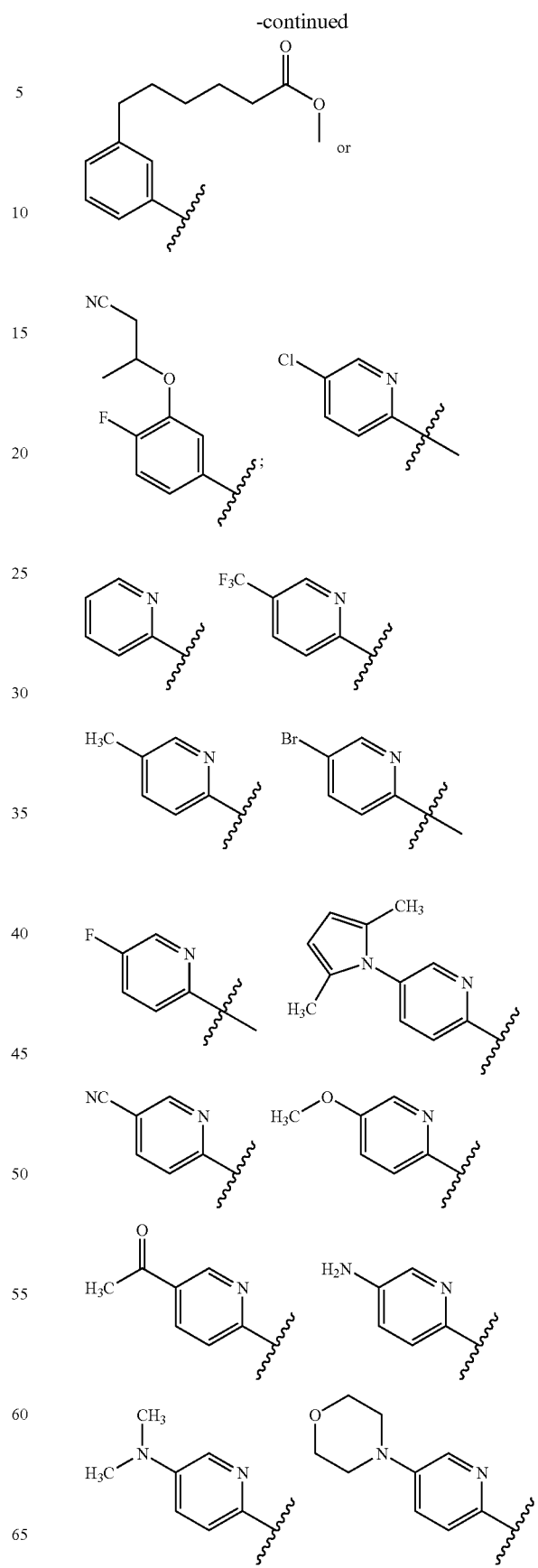

-continued
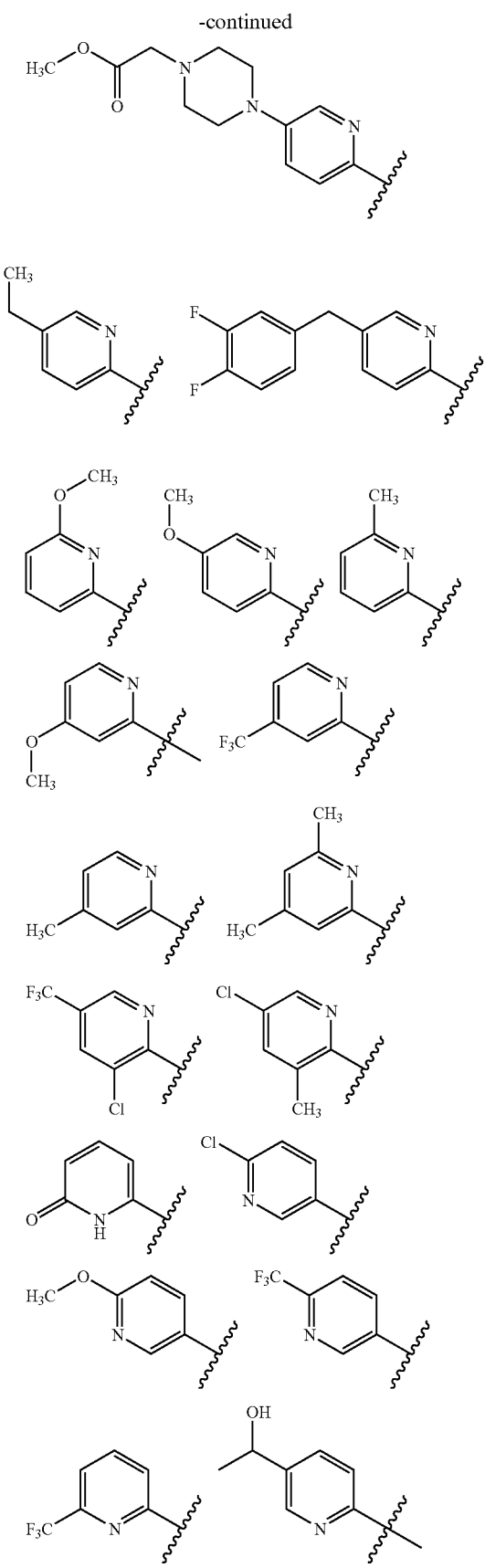
-continued
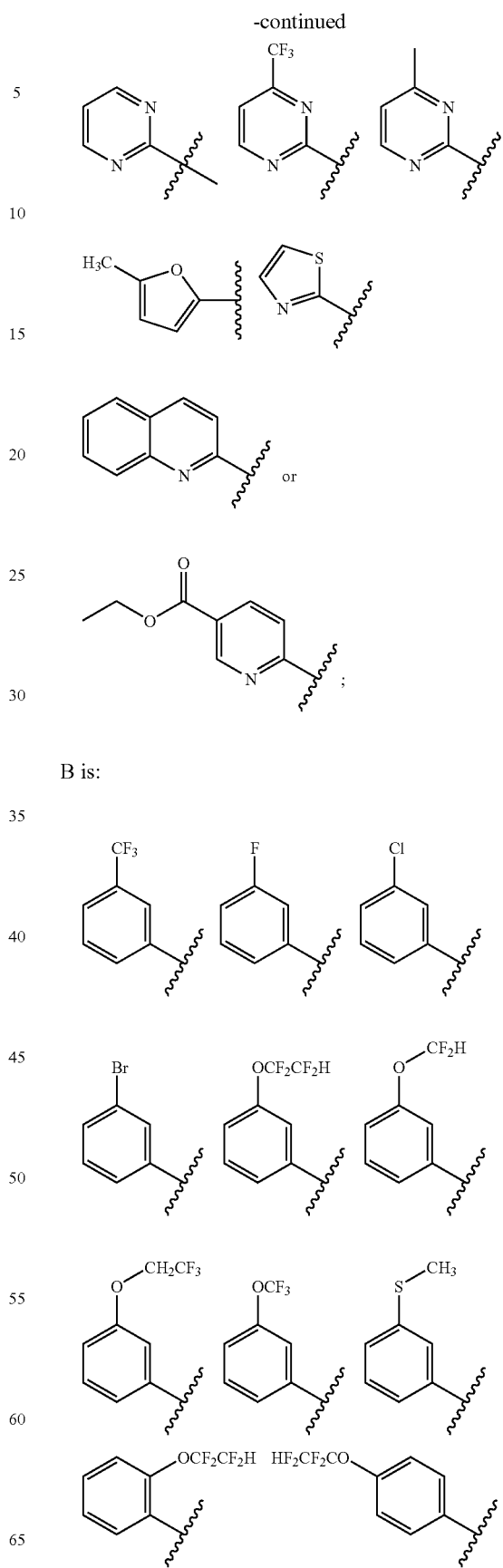
B is:

-continued
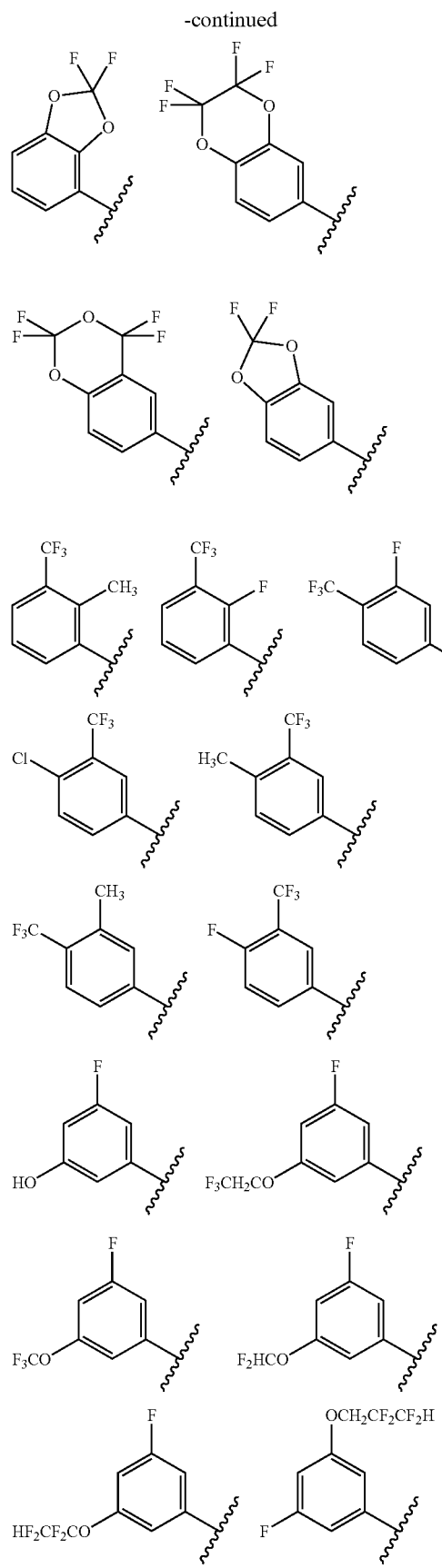
-continued
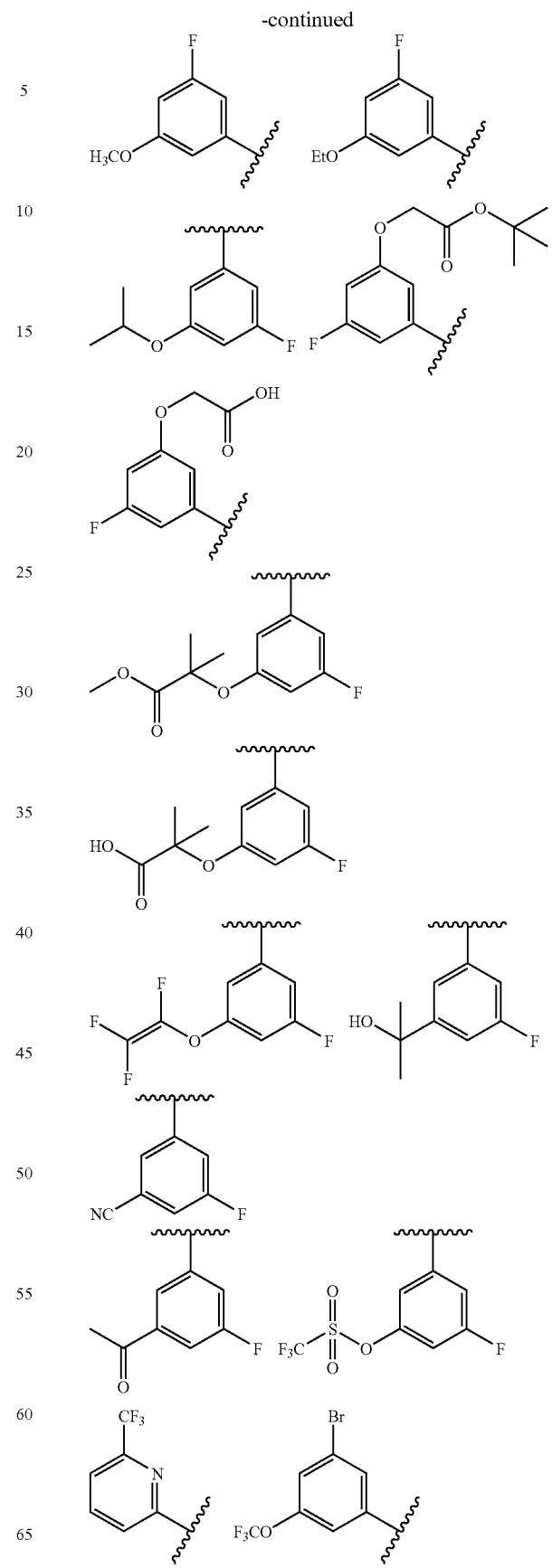

-continued
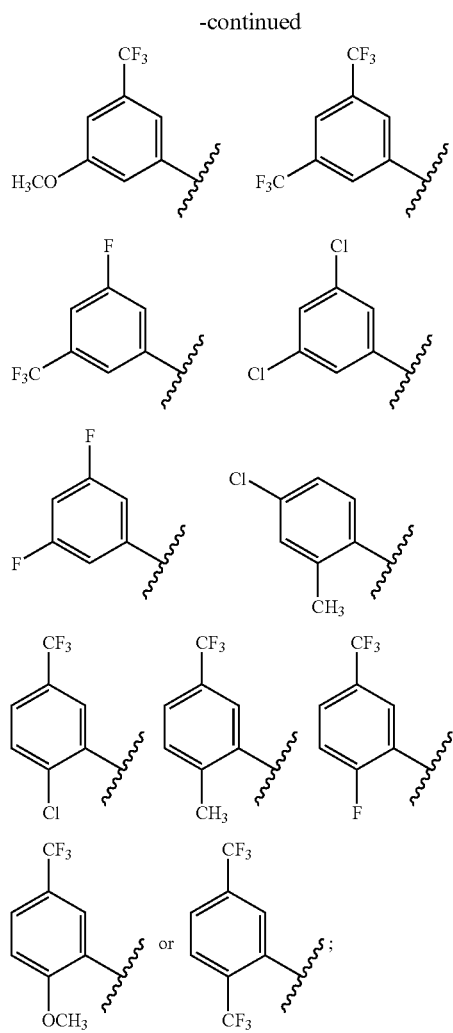
C is:
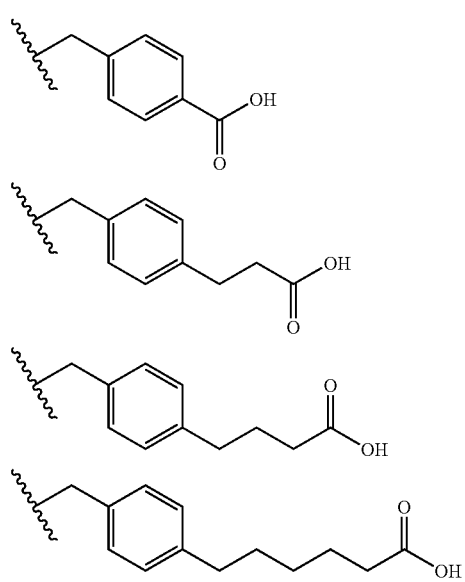
-continued
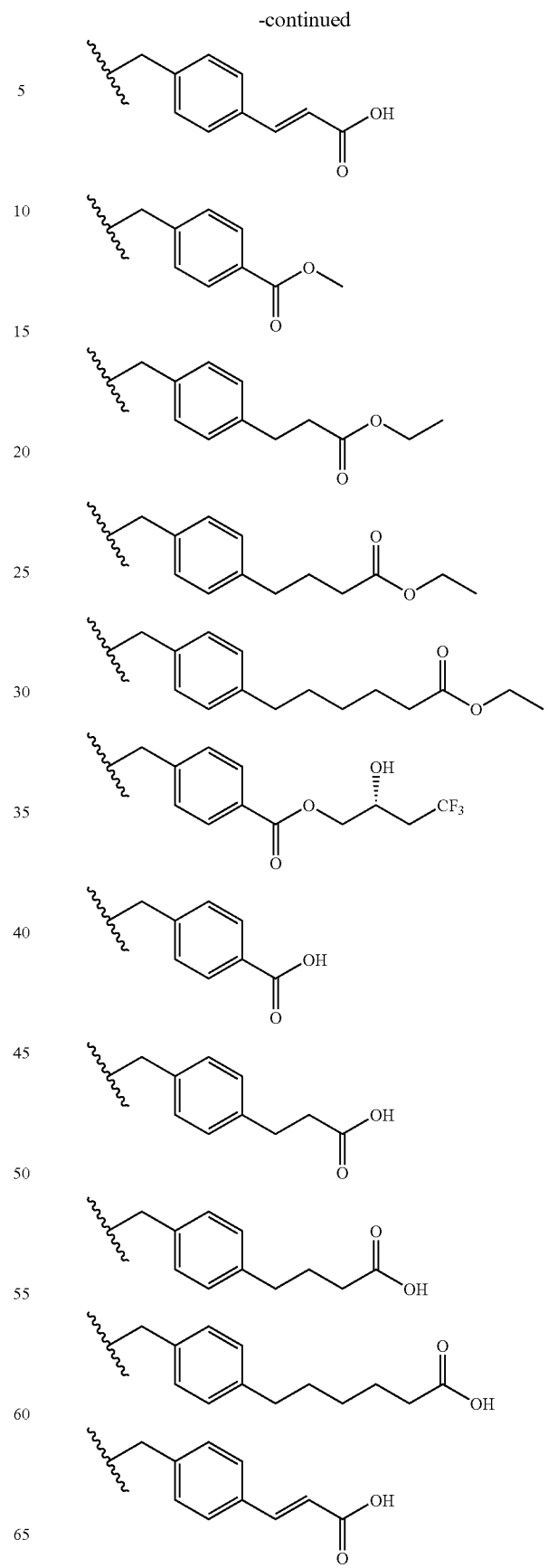

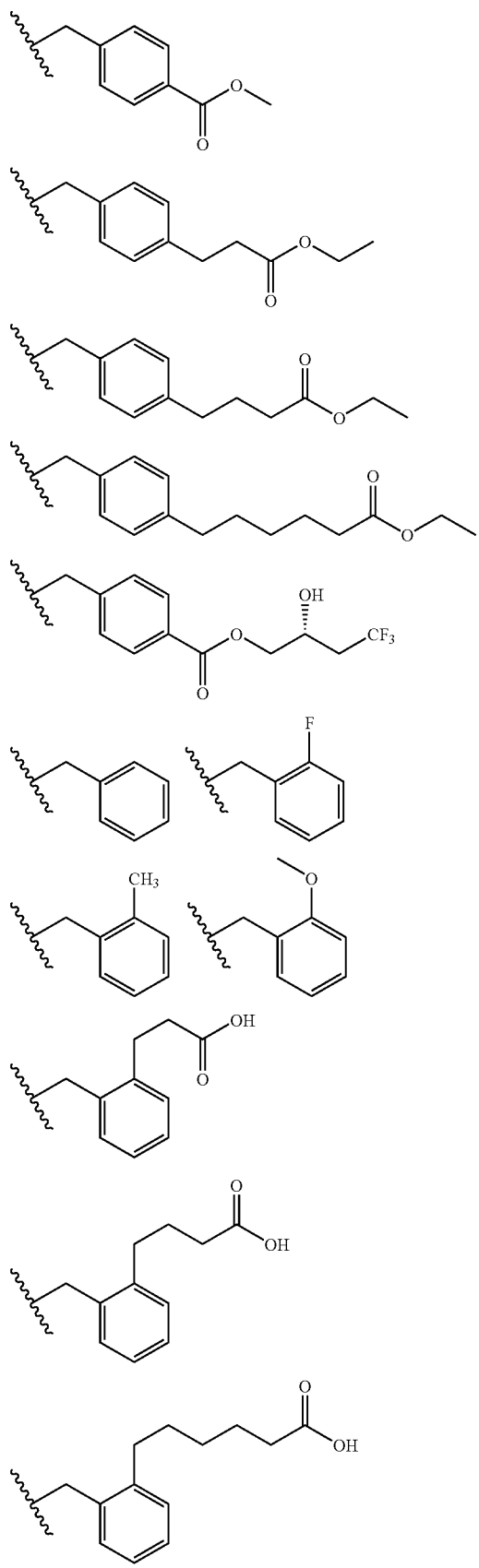
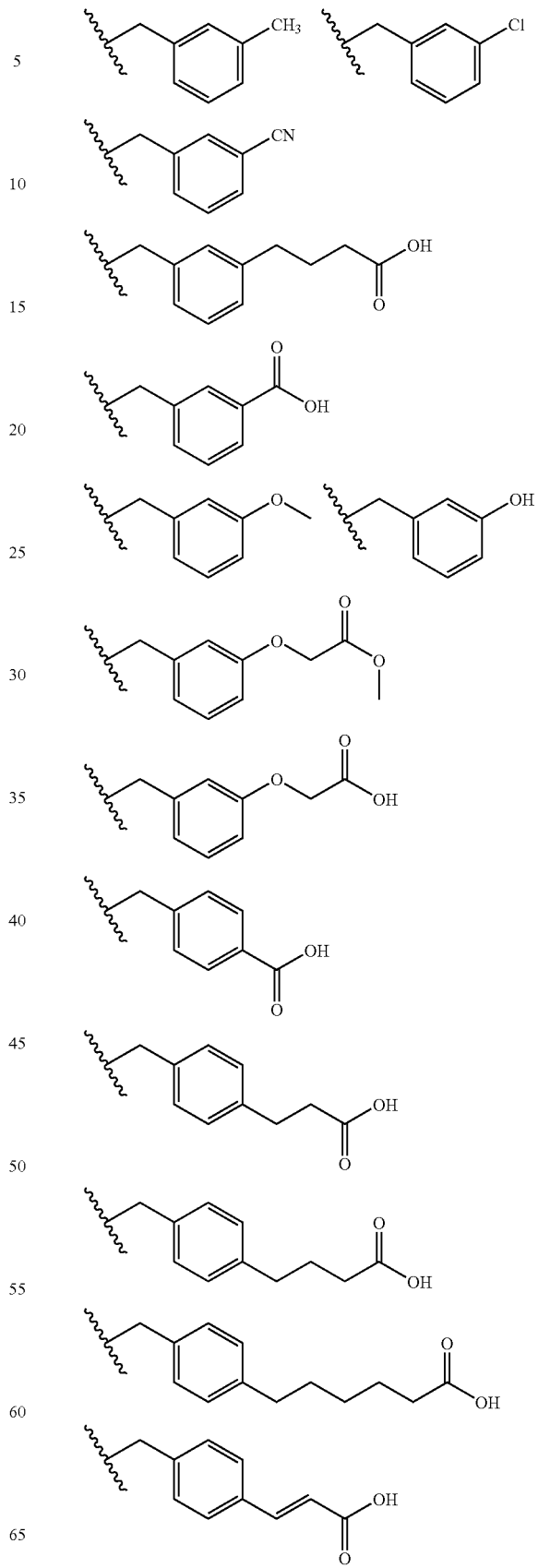

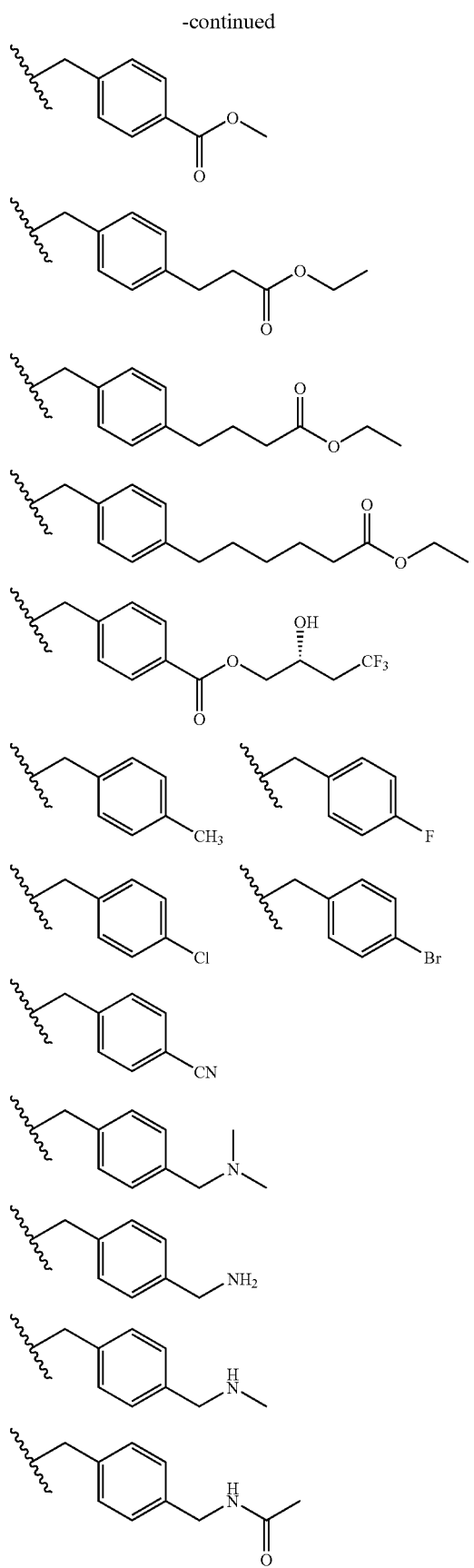
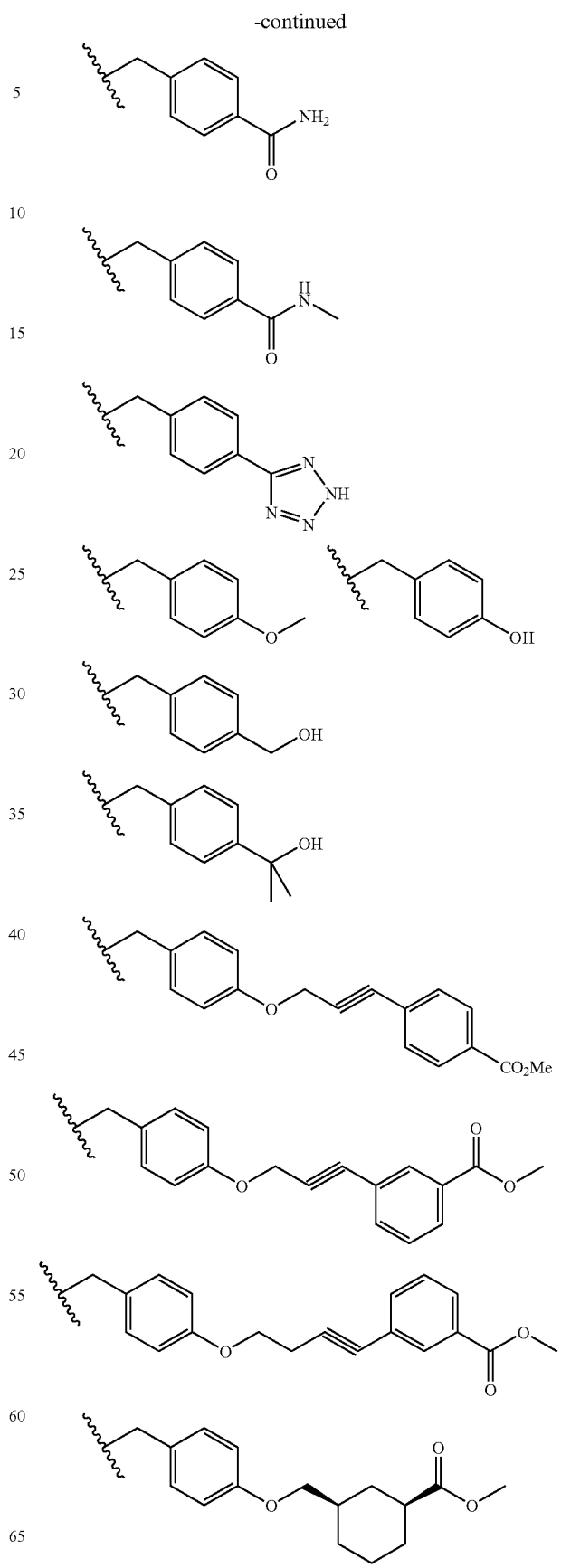

-continued
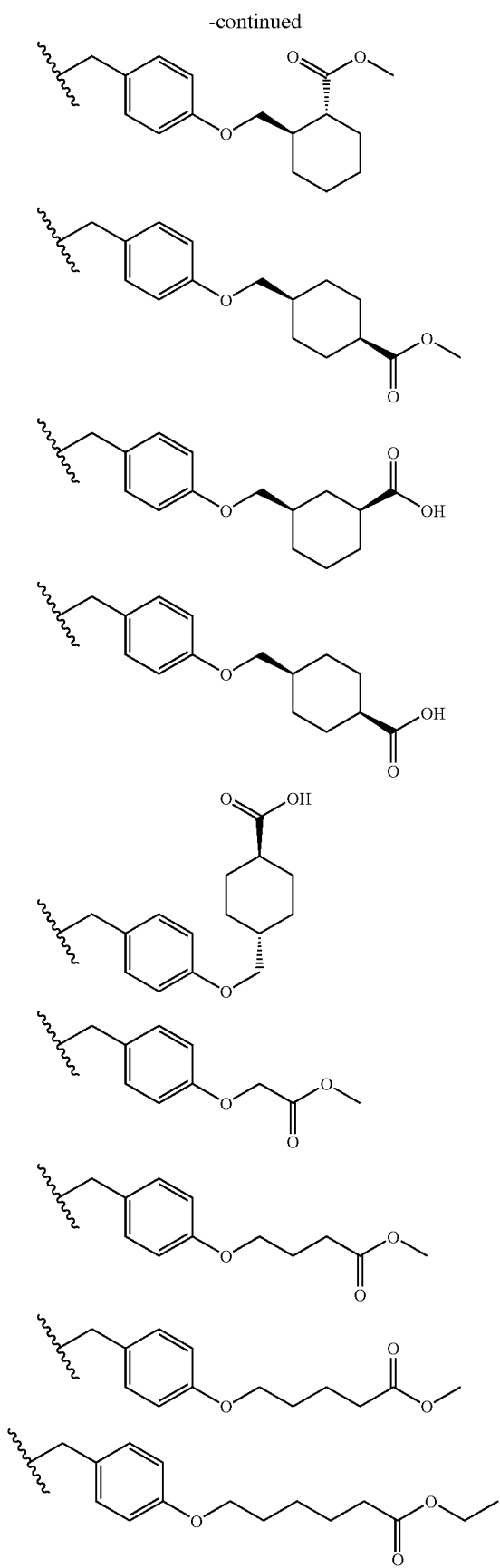
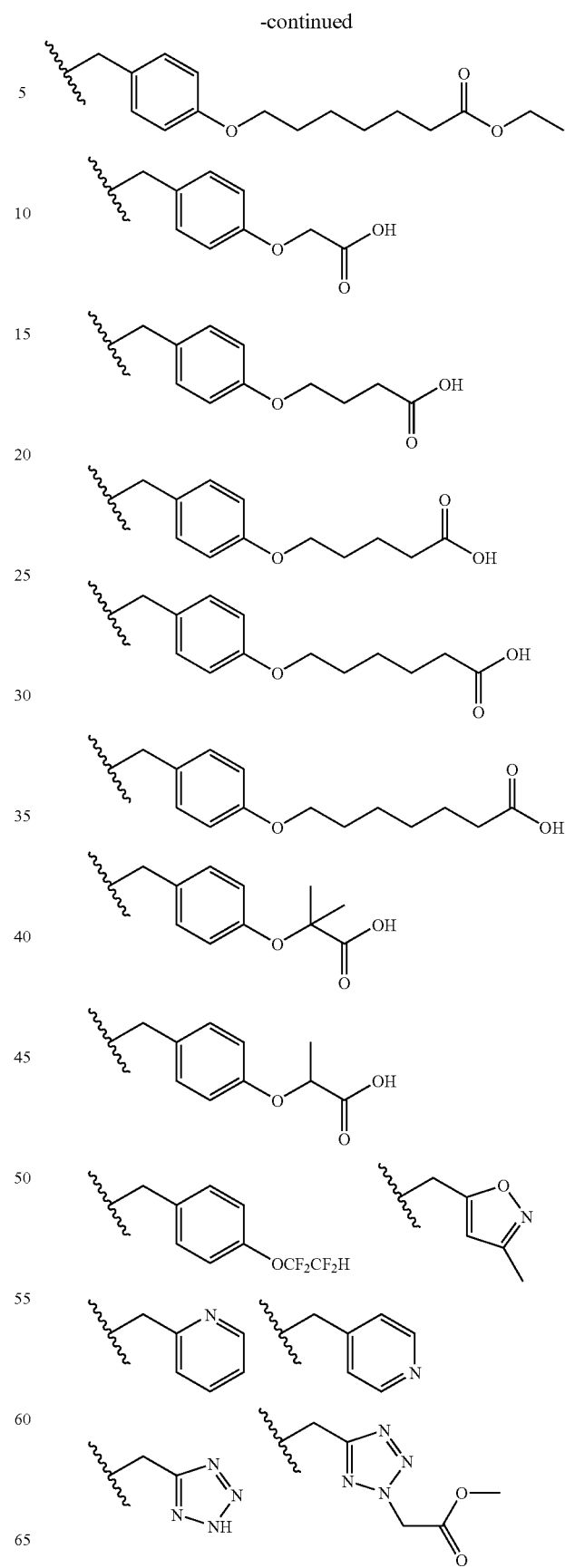

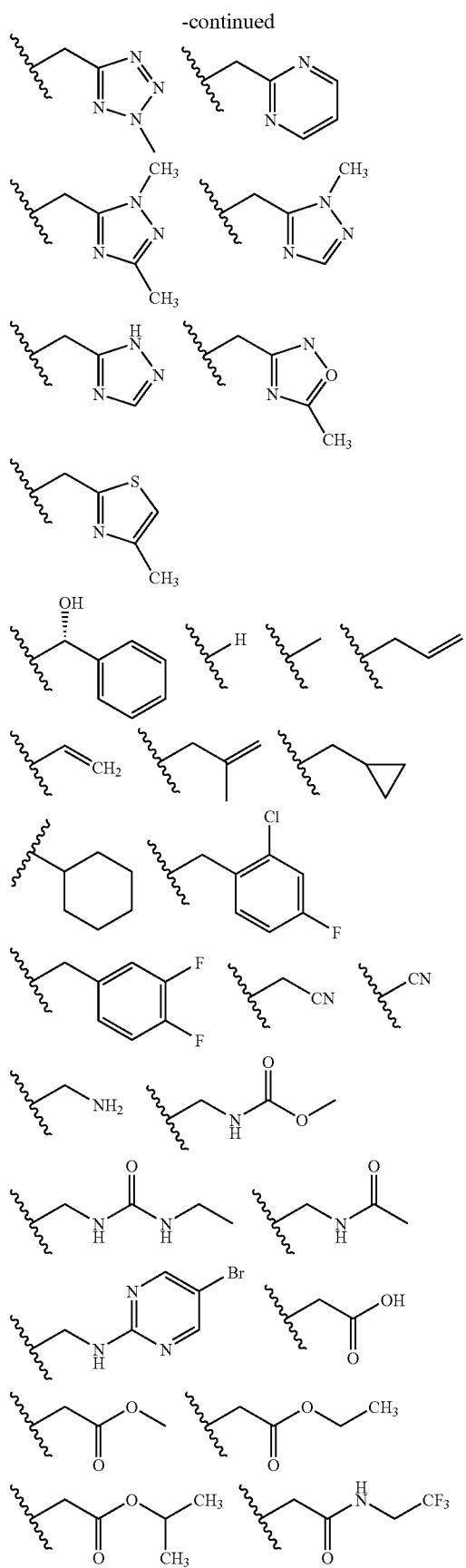
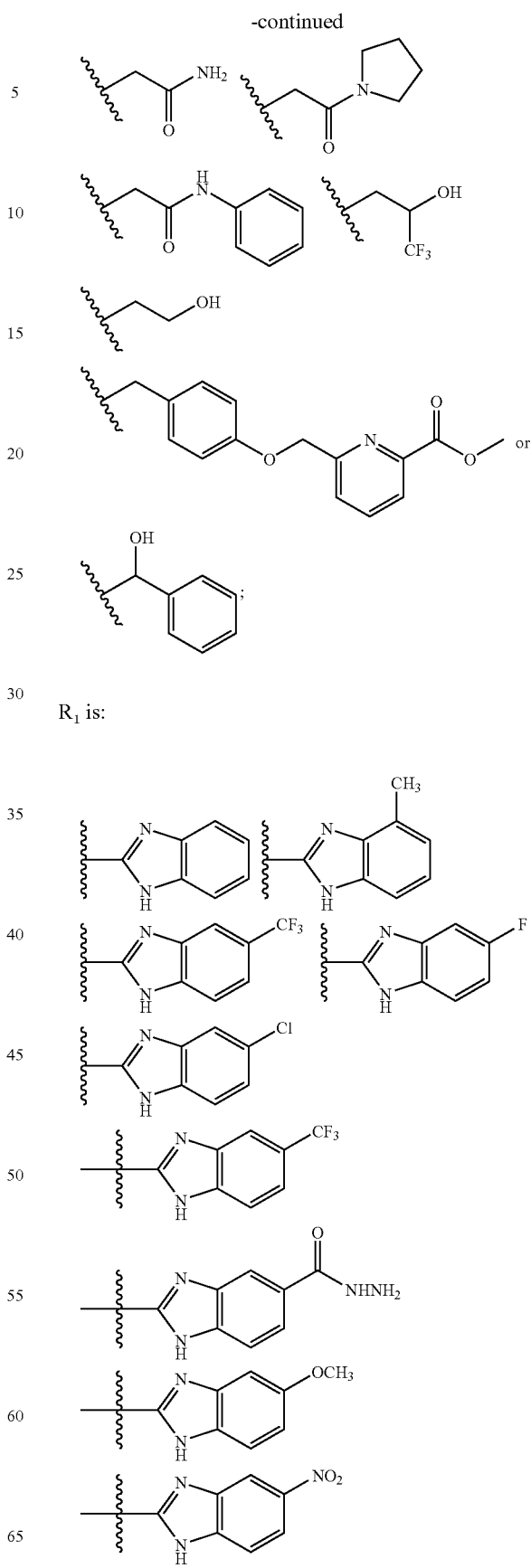
$R_1$ is:

-continued

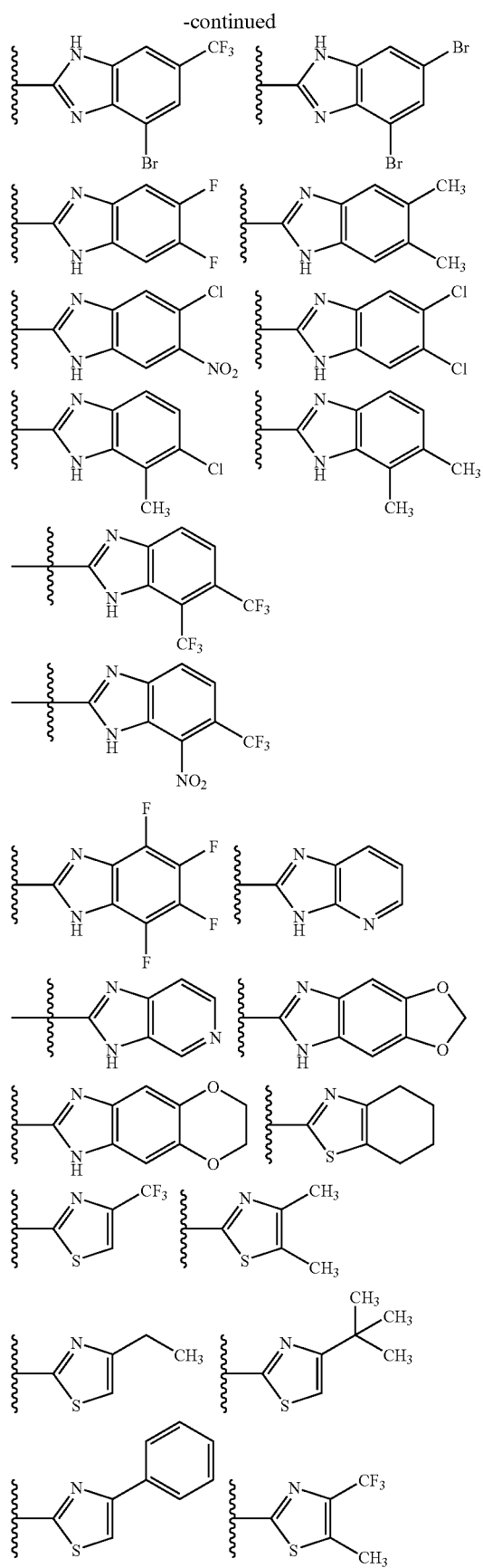
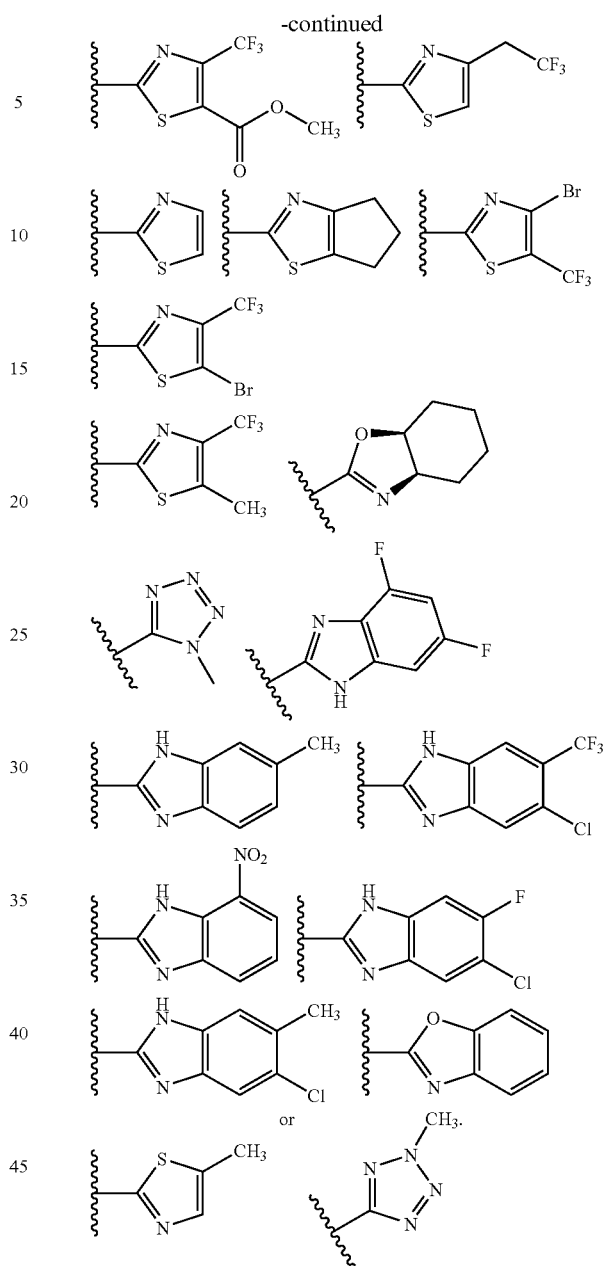

12. A pharmaceutical composition comprising a compound of claim 1.

13. The pharmaceutical composition of claim 12 further comprising a pharmaceutically acceptable carrier.

14. The pharmaceutical composition of claim 12 further comprising at least one additional therapeutic agent, wherin the at least one additional therapeutic agent is selected from a HMG-CoA reductase inhibitor, a cholesterol synthesis inhibitor, a cholesterol absorption inhibitor, another CETP inhibitor, a MTP/Apo B secretion inhibitor, a PPAR modulator, an ACAT inhibitor, a bile acid sequestrant, a bile acid reuptake inhibitor, an ileal bile acid transporter inhibitor, an ACC inhibitor, an antihypertensive, a selective estrogen receptor modulator, a selective androgen receptor modulator, an antidiabetic, aspirin and niacin.

15. A compound according to claim 1 selected from the group consisting of
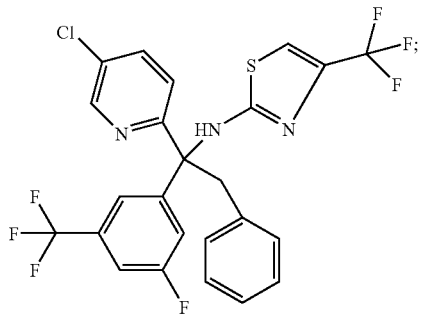
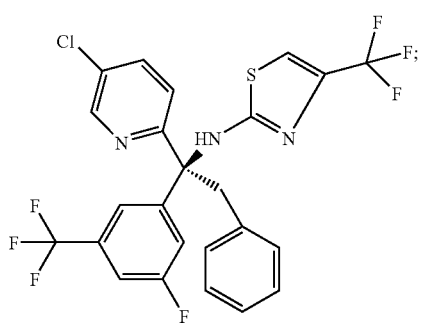
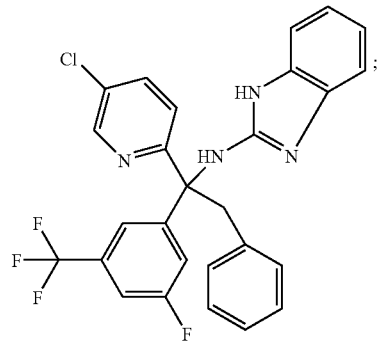
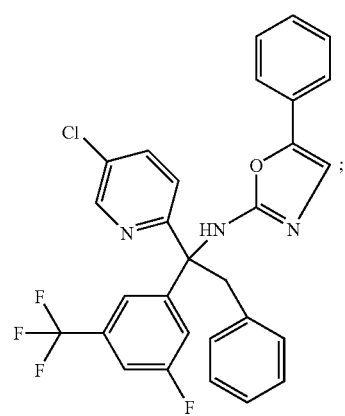
-continued
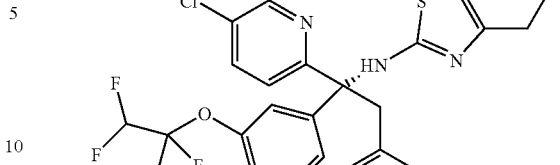
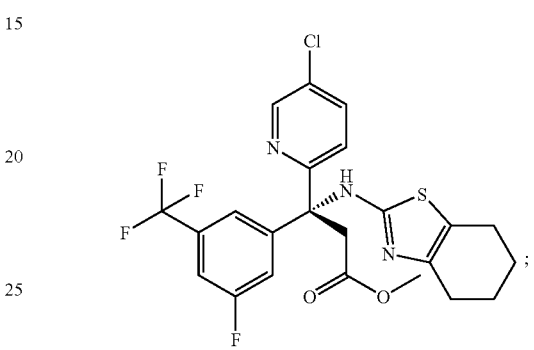
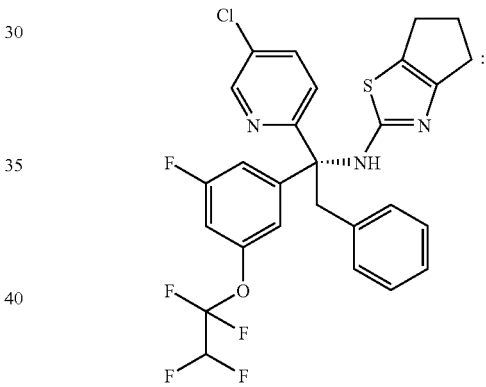
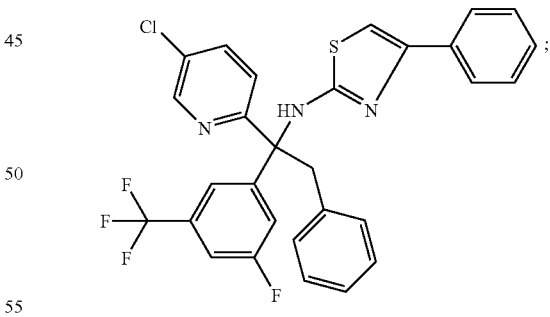
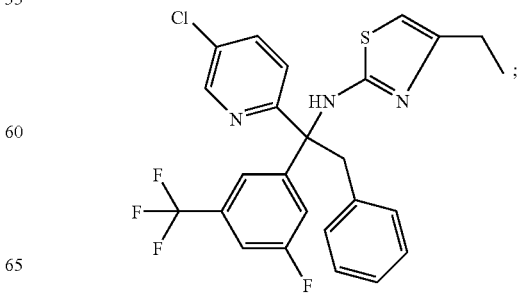

-continued
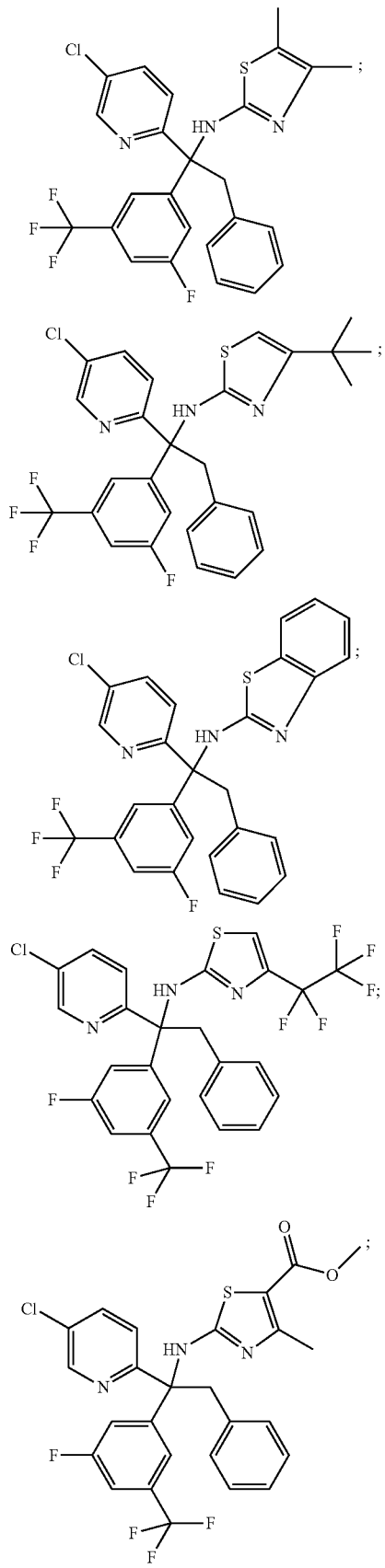
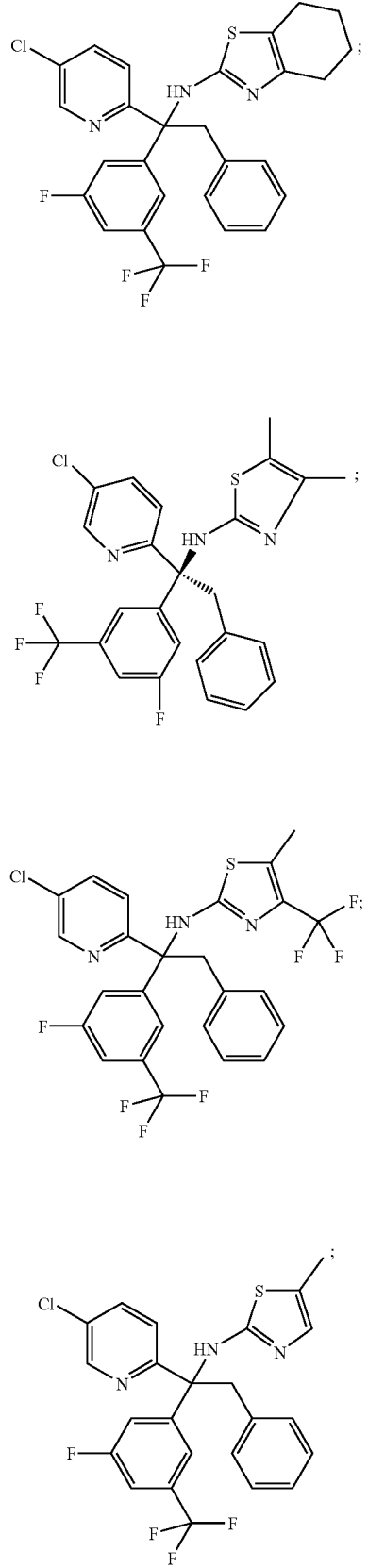

-continued
291
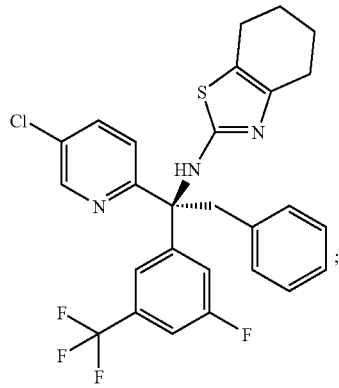
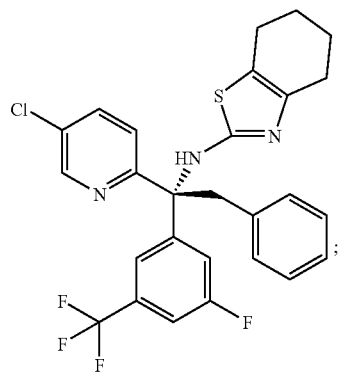
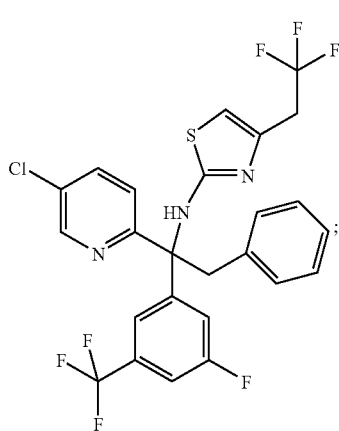
292
-continued
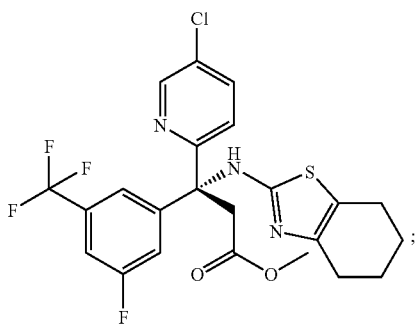
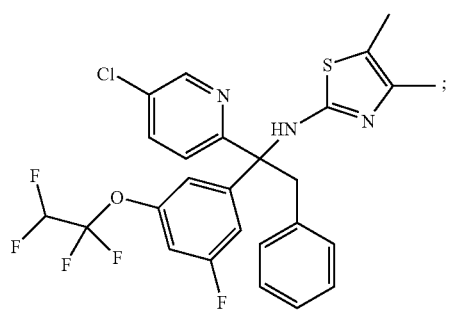
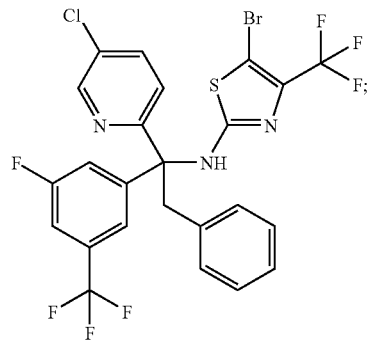
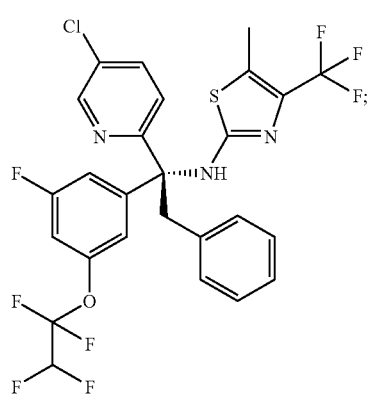

-continued
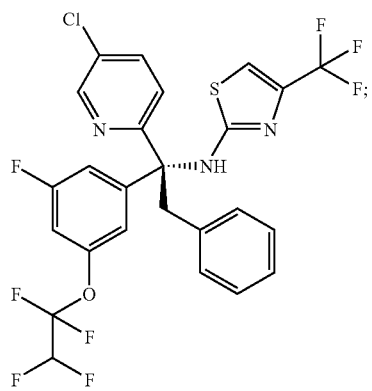
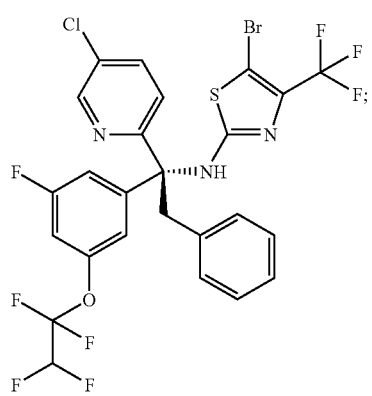
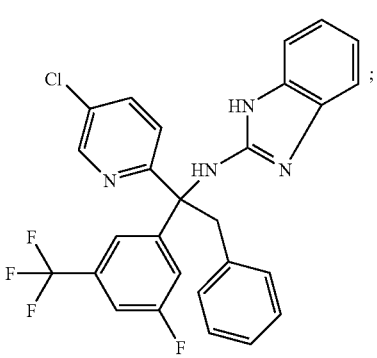
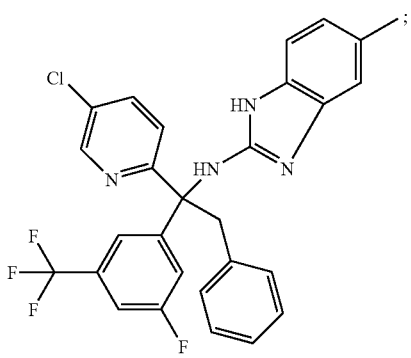
-continued
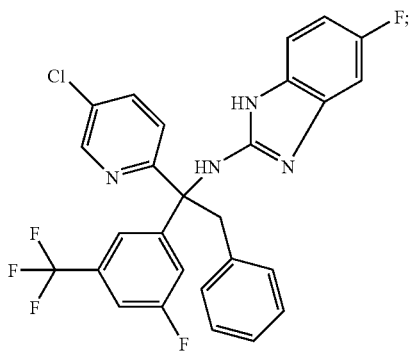
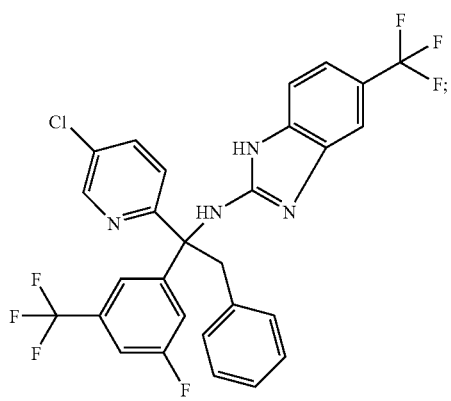
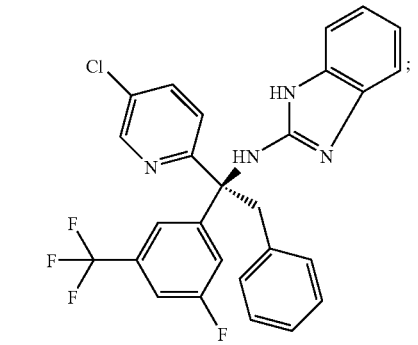
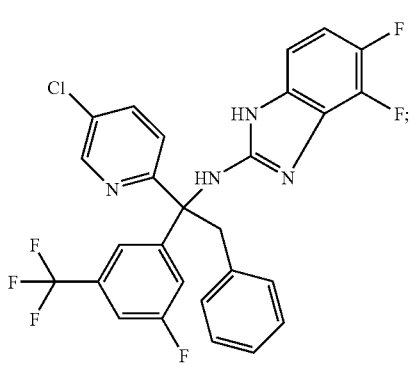

-continued
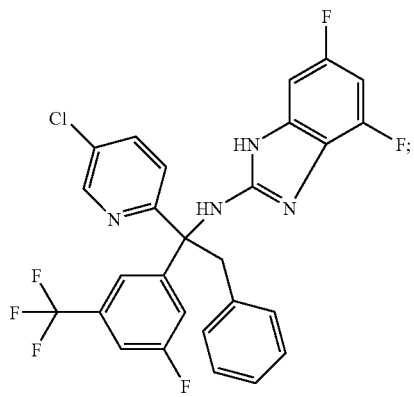
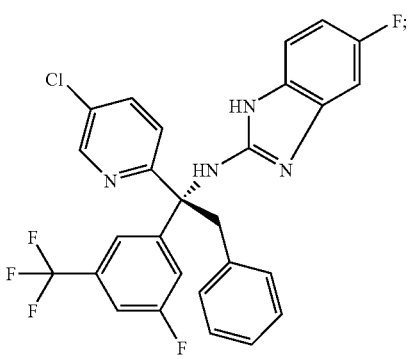
-continued
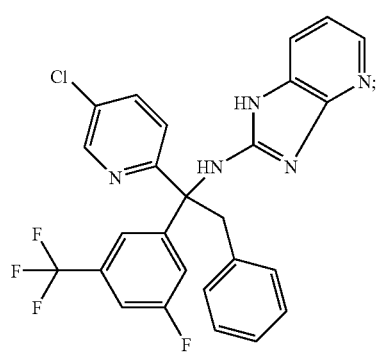
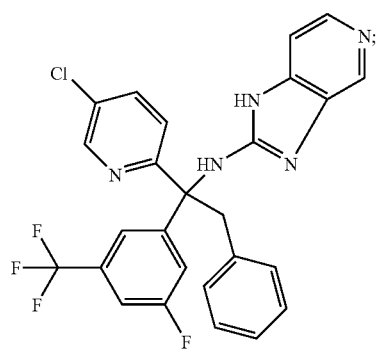
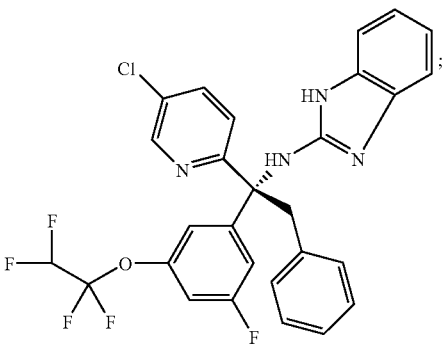

297
-continued
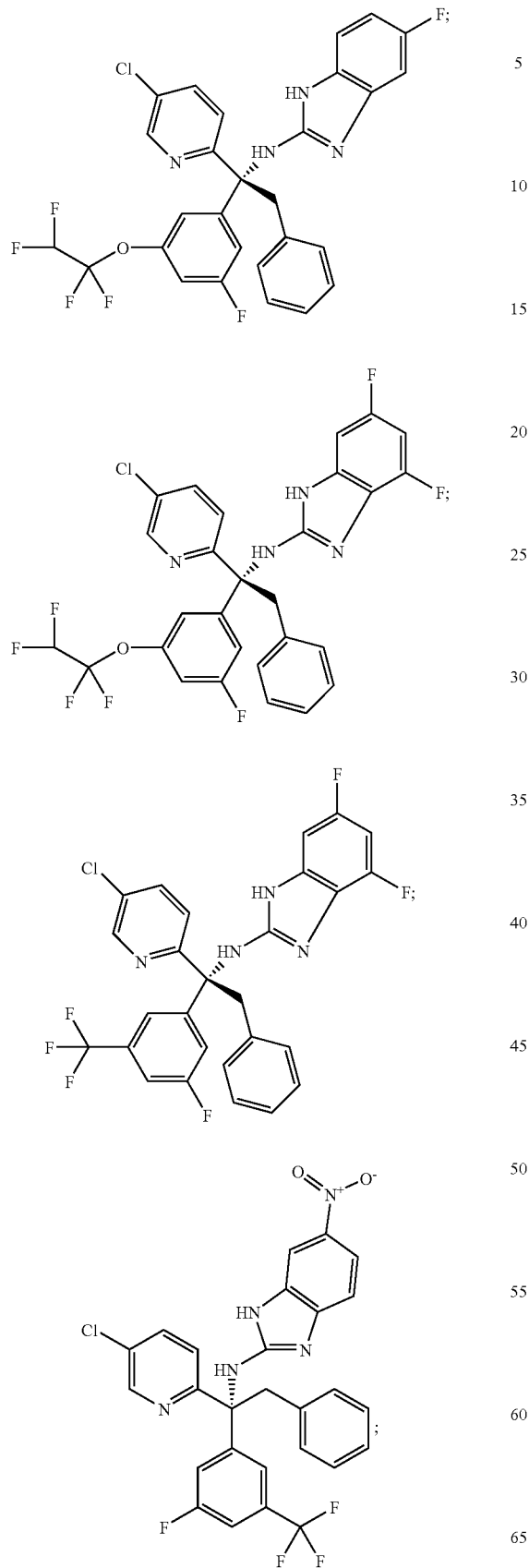
298
-continued
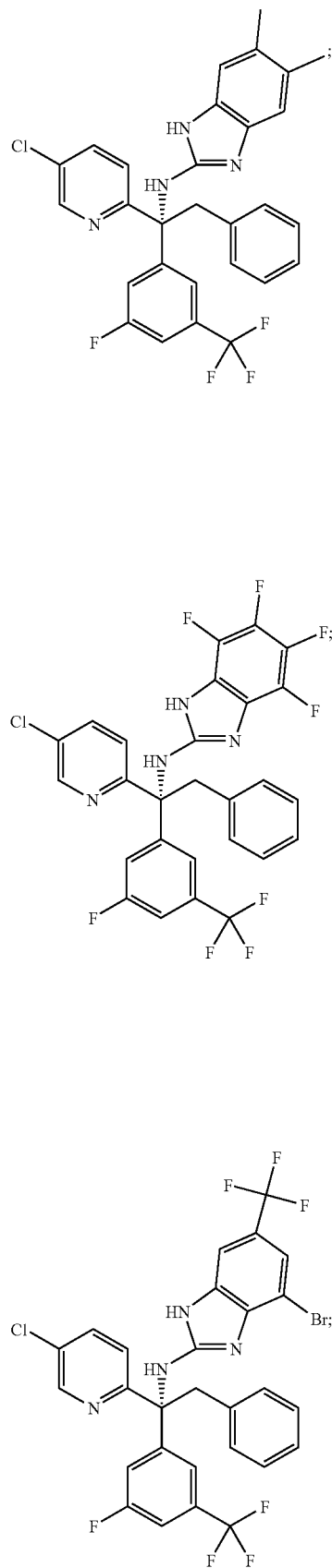

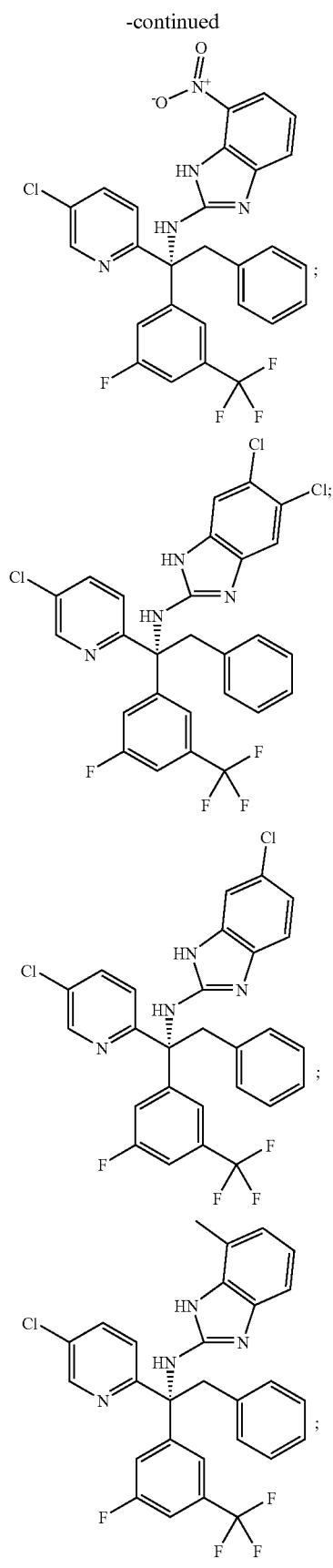
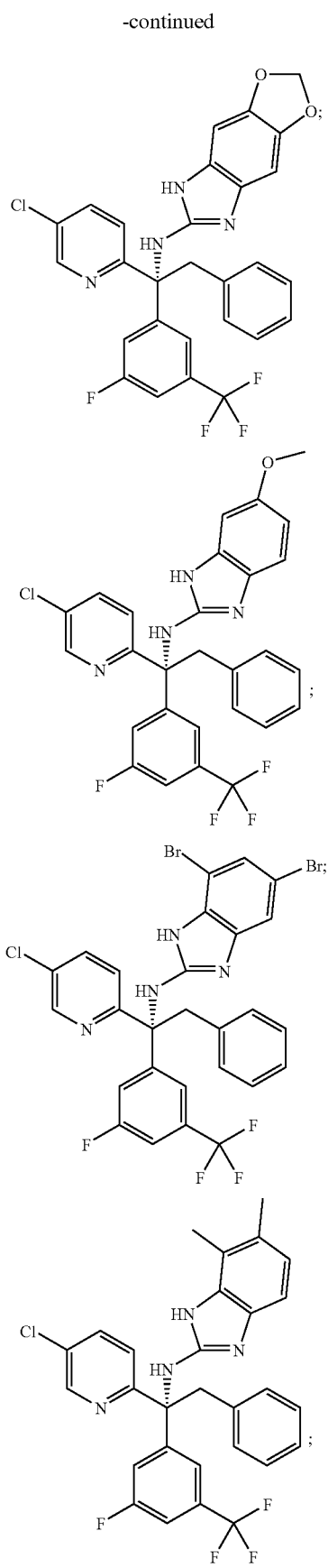

-continued
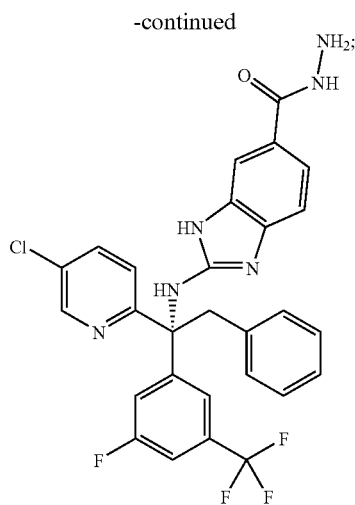
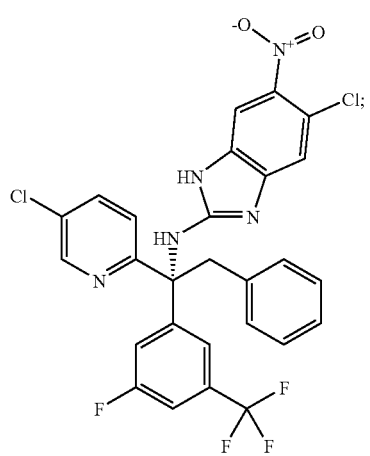
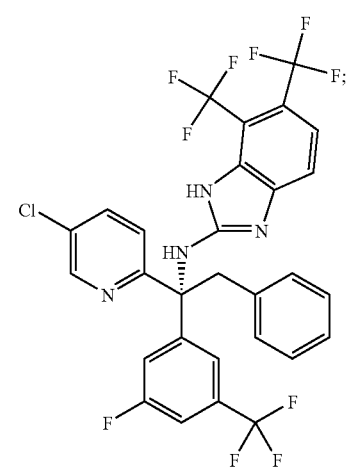
-continued
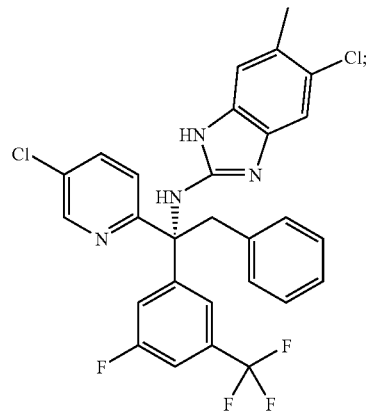
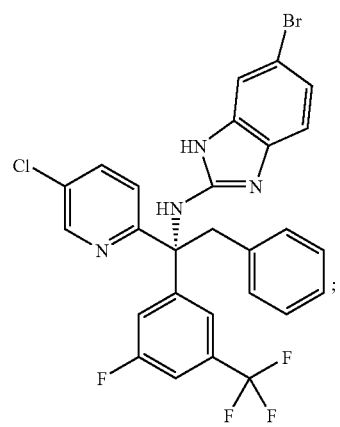
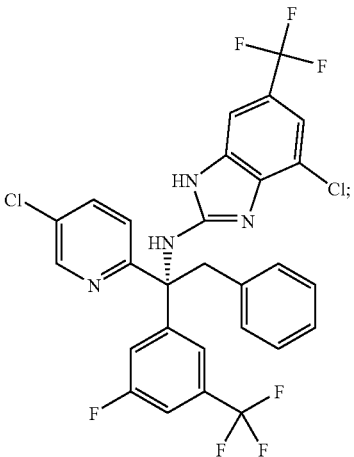

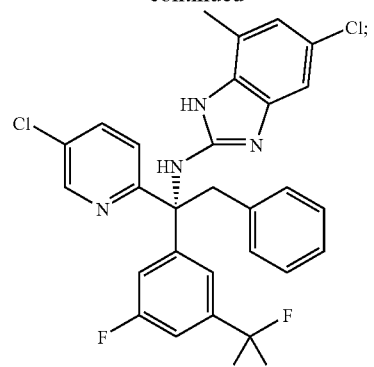
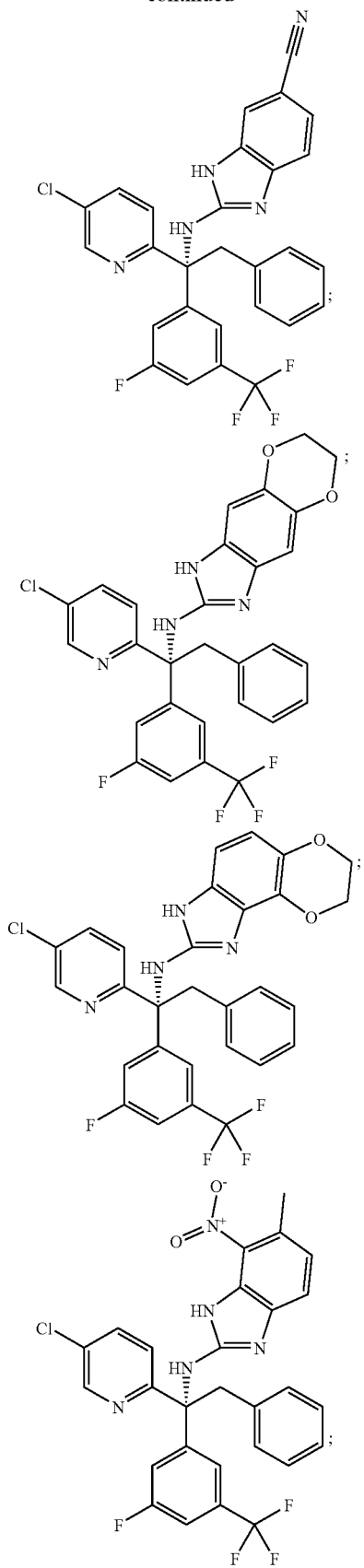

-continued
305
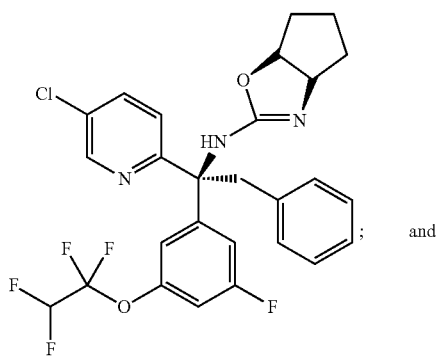
; and
306
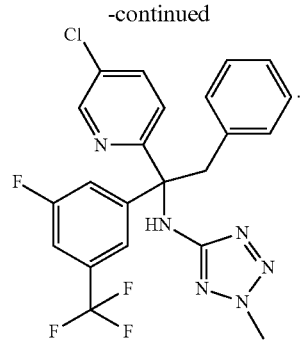
.
* * * * *

UNITED STATES PATENT AND TRADEMARK OFFICE
CERTIFICATE OF CORRECTION

PATENT NO. : 7,652,023 B2
APPLICATION NO. : 11/560388
DATED : January 26, 2010
INVENTOR(S) : Yufeng Wang et al.

It is certified that error appears in the above-identified patent and that said Letters Patent is hereby corrected as shown below:

In the Claims:

Claim 1:
Column 218, line 61, change "NHC(CN)NHR$_6$" to -- —NHC(CN)NHR6 --.
Column 219, line 21, change "he" to -- be --.
Column 219, line 41, change "maybe" to -- may be --.
Column 219, line 43, change "he" to -- be --.
Column 219, line 56, change "he" to -- be --.
Column 219, line 57, change "(C$_1$-C$_6$)-alkyithio" to -- (C$_1$-C$_6$)-alkylthio --.
Column 219, line 61, change "maybe" to -- may be --.
Column 220, line 61, after "(f)", delete ",".
Column 220, line 64, change "—[(C=O)O$_{r]s}$cycloalkyl" to -- —[(C=O)O$_r$]$_s$cycloalkyl --.
Column 221, line 2, change "he" to -- be --.
Column 221, line 28, change "—S(O))$_p$R$_{26}$" to -- —S(O)$_p$R$_{26}$ --.
Column 221, line 61, change "—O" to -- =O --.
Column 222, line 7, change "maybe" to -- may be --.
Column 222, lines 20 and 21, after "consisting", insert -- of: --.
Column 222, line 43, after "more", insert -- R$_{40}$'s, --.
Column 223, line 28, change "r 0" to -- r is 0 --.
Column 223, lines 38 to 48, change " 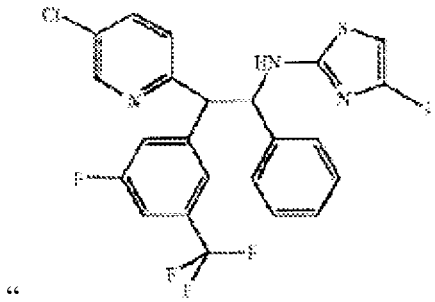 " to -- 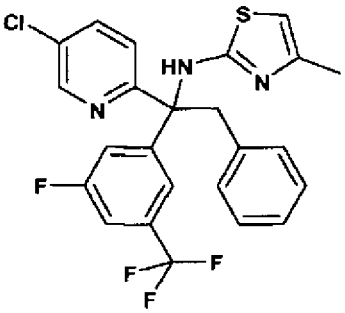 . --.

Signed and Sealed this
Twenty-eighth Day of February, 2012

David J. Kappos
*Director of the United States Patent and Trademark Office*

CERTIFICATE OF CORRECTION (continued)
U.S. Pat. No. 7,652,023 B2

Page 2 of 20

In the Claims:

Claim 1 (continued):

Column 224, lines 27 to 43, change

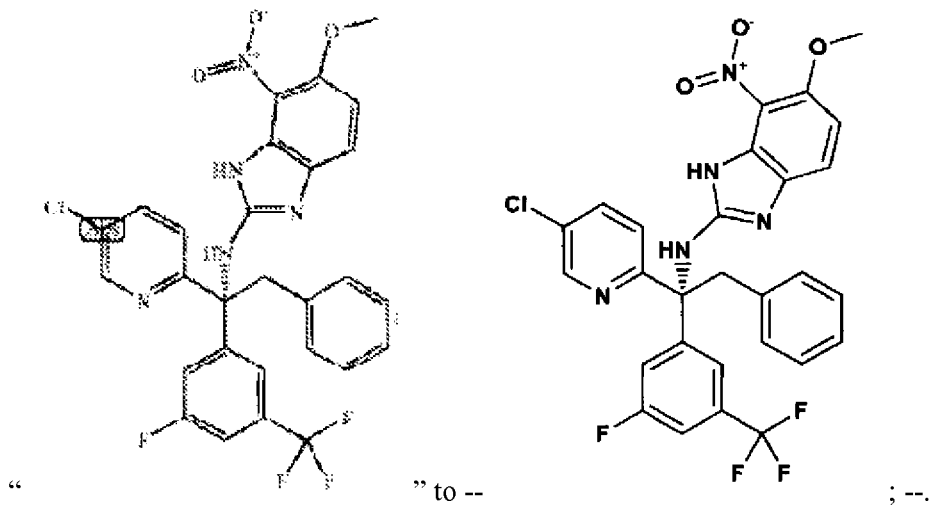

" to -- ; --.

Column 224, lines 48 to 66, change

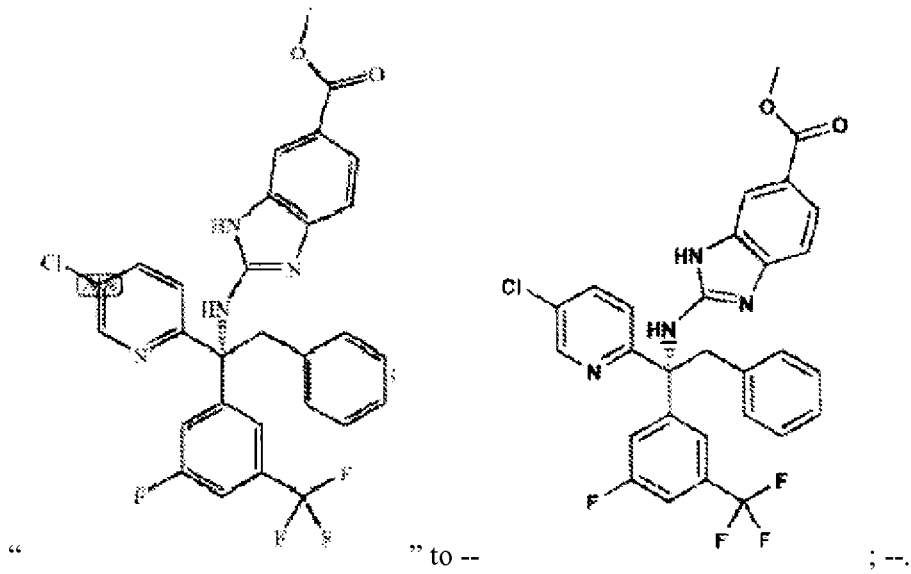

" to -- ; --.

CERTIFICATE OF CORRECTION (continued)

U.S. Pat. No. 7,652,023 B2

In the Claims:

Claim 1 (continued):

Column 225, lines 3 to 22, change

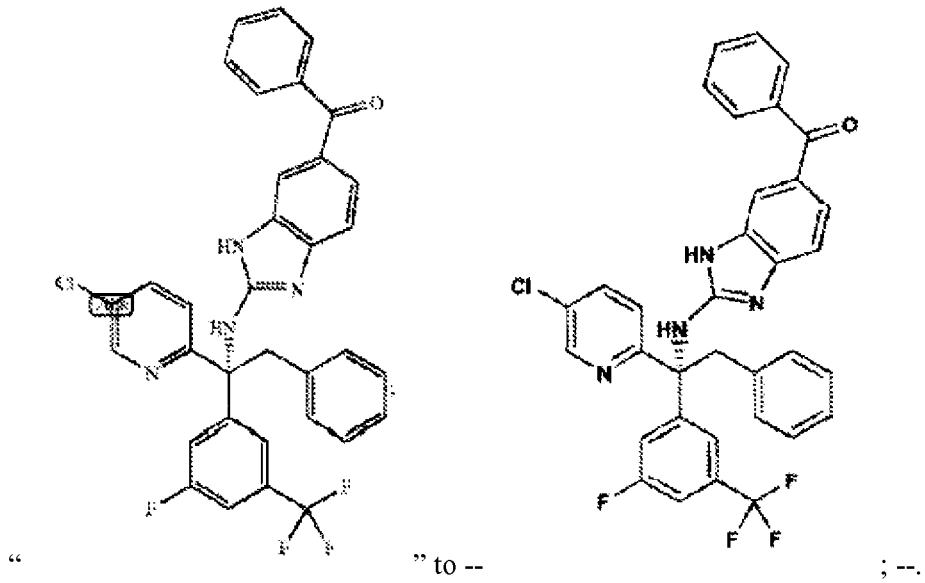

" to -- ; --.

Column 225, lines 23 to 40, change

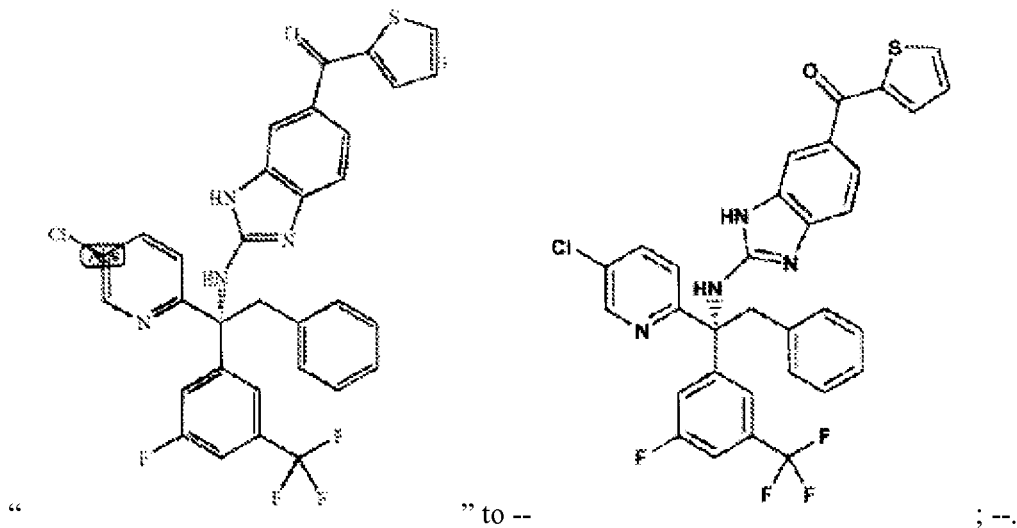

" to -- ; --.

Claim 3:
    Column 226, line 57, change "maybe" to -- may be --.
    Column 226, line 59, change "—COOR$_6$s" to -- —COOR$_6$ --.
    Column 227, line 30, change "of;" to -- of: --.
    Column 227, line 60, change "maybe" to -- may be --.
    Column 228, line 1, after "of", insert -- : --.

CERTIFICATE OF CORRECTION (continued)
U.S. Pat. No. 7,652,023 B2

Column 228, line 27, change "—[C=O)O_r]_s(C_1-C_8)alkyl" to -- —[(C=O)O_r]_s(C_1-C_8)alkyl --.
Column 228, line 47, change "R_21s" to -- R_21's --.
Column 228, line 61, change "—O" to -- =O --.
Column 228, line 63, change "—S(O)R_26" to -- —S(O)_pR_26 --.
Column 229, line 7, change "heteroaryl" to -- heterocyclyl --.
Column 229, line 12, change "COOR_36" to -- —COOR_36 --.
Column 229, line 24, change "maybe" to -- may be --.
Column 229, line 31, change "—S(O)R_36" to -- —S(O)_pR_36 --.
Column 229, line 49, change "—S(O)O_pR_36" to -- —S(O)_pR_36 --.
Column 229, line 57, change "—NR_29R_3" to -- —NR_29R_30 --.
Column 230, line 28, after "hydrogen,", insert -- —[(C=O)O_r]_saryl, --.
Column 230, line 29, change "—[(C=)O_r]_salkyl" to -- —[(C=O)O_r]_salkyl --.
Column 230, line 30, change "COR_36" to -- —COR_36 --.
Column 230, line 31, change "—C(CN)NHR_36" to -- —NHC(CN)NHR_36 --.
Column 230, line 34, change "wioth" to -- with --.
Column 230, line 39, change "R_36 at" to -- R_36, at each --.
Column 230, line 45, change "—NR_45R_50" to -- —NR_49R_50 --.
Column 230, line 46, change "heterocycylyl" to -- heterocyclyl --.

Claim 4:
Column 230, line 60, change "(C_1-C_6alkyl" to -- (C_1-C_6)-alkyl --.
Column 230, line 61, change "R_20S" to -- R_20's --.
Column 231, line 10, after "of", insert -- : --.
Column 231, line 20, after "R_1", delete ",".
Column 231, line 28, change "maybe" to -- may be --.
Column 231, line 29, change "maybe" to -- may be --.
Column 231, line 30, after "more", insert -- R_20's, --.
Column 231, line 42, after "of", insert -- : --.
Column 231, line 52, change "—S(O)R_36" to -- —S(O)_pR_36 --.
Column 231, line 56, after "of", insert -- : --.
Column 232, line 22, change "COOR_36" to -- —COOR_36 --.
Column 233, line 25, change "R_21's; R_21s;" to -- R_21's; --.
Column 233, line 56, change "—S(O)OR_36" to -- —S(O)_pR_36 --.
Column 234, line 7, change "—S(O)R_36" to -- —S(O)_pR_36 --.
Column 234, line 25, change "—S(O)R_36" to -- —S(O)_pR_36 --.
Column 234, lines 44 and 45, change "(C_2-C_6-alkynyl" to -- (C_2-C_6)-alkynyl --.
Column 235, lines 7 and 8, change "—S(O)_pR_3" to -- —S(O)_pR_36 --.
Column 235, line 8, change "—C(CN)NHR_36" to -- —NHC(CN)NHR_36 --.

Claim 5:
Column 235, line 65, change "(C_1-6)-alkyl" to -- (C_1-C_6)-alkyl --.
Column 236, line 11, change "—CONR_6" to -- —CONR_6R_6 --.
Column 236, line 21, change "maybe" to -- may be --.
Column 236, line 41, change "maybe" to -- may be --.

CERTIFICATE OF CORRECTION (continued)

U.S. Pat. No. 7,652,023 B2

Claim 5 (continued):
    Column 236, line 61, change "—O" to -- =O --.
    Column 237, line 13, change "—COOR" to -- —COOH --.
    Column 237, line 49, change "6)" to -- (j) --.
    Column 237, line 50, change "—COOR$_{26}$R$_{26}$" to -- —COOR$_{26}$ --.
    Column 238, line 19, change "(C$_2$-C$_6$)-alkyl" to -- (C$_1$-C$_6$)-alkyl --.
    Column 239, line 7, change "arylailcyl" to -- arylalkyl --.
    Column 239, line 11, change "he" to -- be --.
    Column 239, line 25, change "—O$_{36}$" to -- —OR$_{36}$ --.
    Column 239, line 27, change "maybe" to -- may be --.
    Column 239, line 40, change "(1)" to -- (f) --.
    Column 239, line 47, change "alkyny" to -- alkynyl --.
    Column 239, line 48, change "COOR$_{36}$, or C(CN)NHR$_{36}$" to -- —COOR$_{36}$, or —NHC(CN)NHR$_{36}$ --.
    Column 239, line 64, change "heterocylylalkyl" to -- heterocyclylalkyl --.

Claim 6:
    Column 240, line 11, change "maybe" to -- may be --.
    Column 240, line 24, change "he" to -- be --.
    Column 240, line 38, change "maybe" to -- may be --.
    Column 240, line 47, change "—SO$_2$R$_6$" to -- —SO$_2$NHR$_6$ --.
    Column 241, line 7, after "more", insert -- R$_{20}$'s, --.
    Column 241, line 64, change "he" to -- be --.
    Column 242, line 7, after "hydrogen;", delete ",".
    Column 242, line 18, change "maybe" to -- may be --.
    Column 242, line 22, change "maybe" to -- may be --.
    Column 242, line 47, change "—OR" to -- —OH --.
    Column 242, line 52, change "maybe" to -- may be --.
    Column 243, line 14, change "—OR$_3$" to -- —OR$_{36}$ --.
    Column 243, line 43, change "halo(C$_3$-C$_6$)alkyl" to -- halo(C$_1$-C$_6$)alkyl --.
    Column 243, line 46, change "—SO$_2$R$_{36}$" to -- —SO$_2$NHR$_{36}$ --.
    Column 244, line 6, change "—[(C=O)O$_r$]$_s$alkeny" to -- —[(C=O)O$_r$]$_s$alkenyl --.
    Column 244, line 8, change "—C(CN)NHR$_{36}$" to -- —NHC(CN)NHR$_{36}$ --.
    Column 244, line 27, change "R$_{59}$" to -- R$_{50}$ --.

Claim 7:
    Column 244, line 36, after "of", insert -- : --.
    Column 246, line 20, after "11", delete ".".
    Column 246, line 54, change "(1)" to -- (l) --.
    Column 247, line 17, change "—O" to -- =O --.
    Column 247, line 34, change "halo(C3C6)alkyl" to -- halo(C$_1$-C$_6$)alkyl --.
    Column 247, line 49, change "maybe" to -- may be --.
    Column 248, line 31, change "he" to -- be --.
    Column 248, line 35, change "alkyny" to -- alkynyl, --.
    Column 248, line 36, change "—C(CN)NHR$_{36}$" to -- —NHC(CN)NHR$_{36}$ --.

CERTIFICATE OF CORRECTION (continued)
U.S. Pat. No. 7,652,023 B2

In the Claims:

Claim 8:
    Column 249, line 32, change "—O" to -- =O --.
    Column 249, line 57, change "maybe" to -- may be --.
    Column 250, line 22, after "of", insert -- : --.
    Column 250, line 25, change "—NR$_9$R10" to -- —NR$_9$R$_{10}$ --.
    Column 250, line 44, change "—OR$_3$" to -- —OR$_{36}$ --.
    Column 251, line 25, change "—S(O) $_p$R$_{26}$" to -- —S(O)$_p$R$_{26}$ --.
    Column 253, line 6, change "—SO$_2$NHR$_9$" to -- —SO$_2$NHR$_{49}$ --.

Claim 9:
    Column 254, line 26, change "maybe" to -- may be --.
    Column 255, line 15, change "—NR$_{29}$R$_{39}$" to -- —NR$_{29}$R$_{30}$ --.
    Column 256, lines 61 and 62, change "—[(C—O)O$_r$]$_s$alkyl" to -- —[(C=O)O$_r$]$_s$alkyl --.

Claim 10:
    Column 257, line 34, change "(C$_1$-C$_6$)-alkyltbio" to -- (C$_1$-C$_6$)-alkylthio --.
    Column 257, line 47, change "—O$_{26}$" to -- —OR$_{26}$ --.

CERTIFICATE OF CORRECTION (continued)
U.S. Pat. No. 7,652,023 B2

In the Claims:

Claim 11:
    Column 258, lines 23 to 66, after "A is:", delete

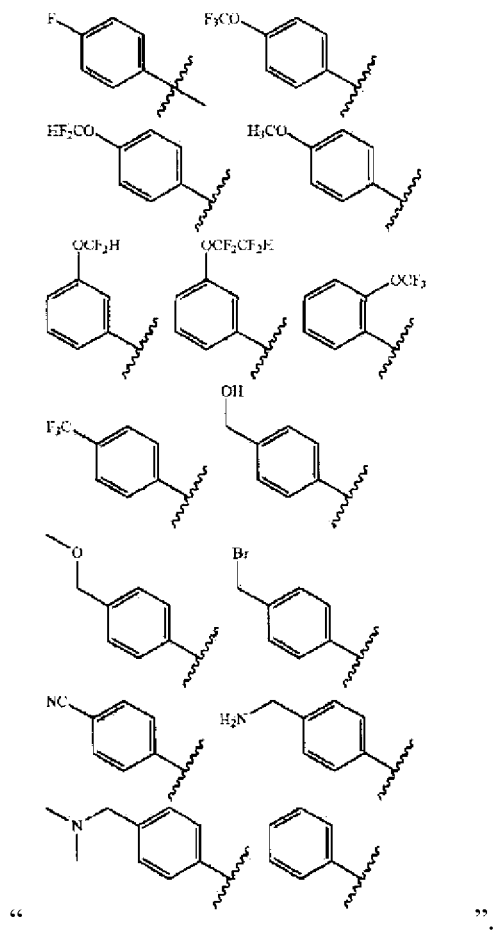

"                                        ".

In the Claims:

CERTIFICATE OF CORRECTION (continued)
U.S. Pat. No. 7,652,023 B2

Claim 11 (continued):
    Column 259, lines 1 to 66, after "-continued", delete

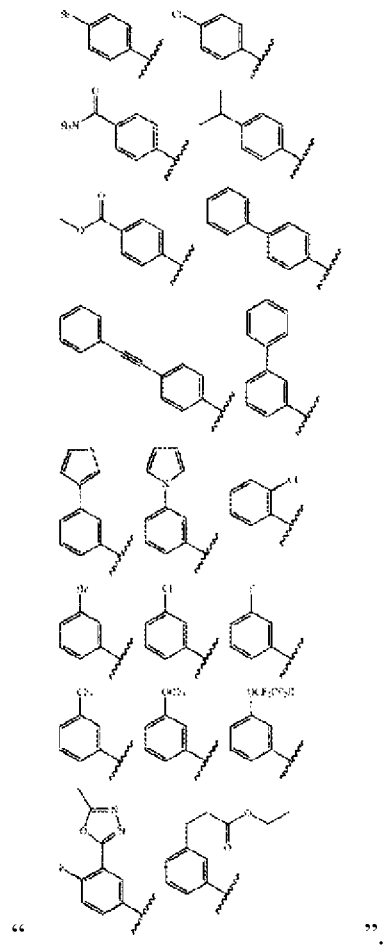

"            ".

In the Claims:

Claim 11 (continued):
Column 260, lines 1 to 66, after "-continued", delete
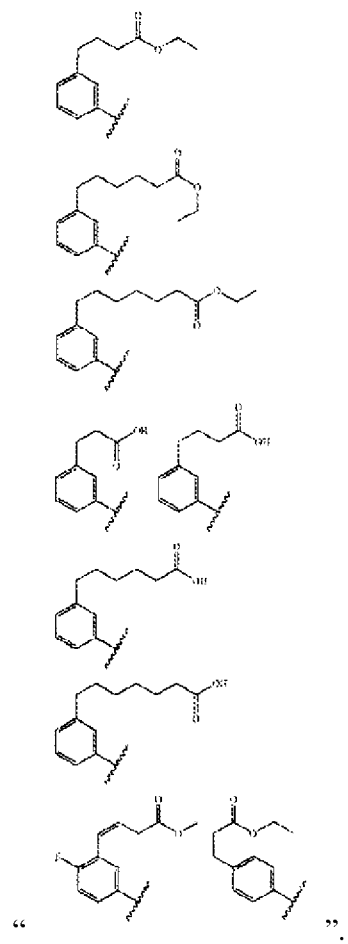
"                                                ".
In the Claims:

CERTIFICATE OF CORRECTION (continued)
U.S. Pat. No. 7,652,023 B2

Claim 11 (continued):
Column 261, lines 1 to 66, after "-continued", delete

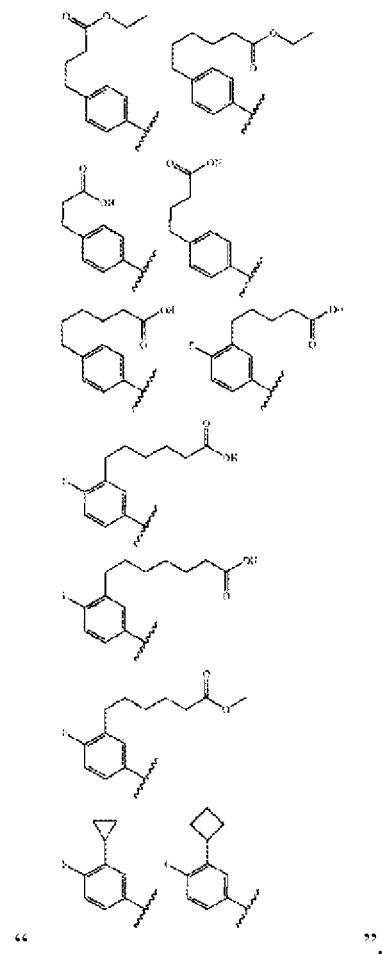

" "

In the Claims:

CERTIFICATE OF CORRECTION (continued)
U.S. Pat. No. 7,652,023 B2

Claim 11 (continued):
    Column 262, lines 1 to 66, after "-continued", delete

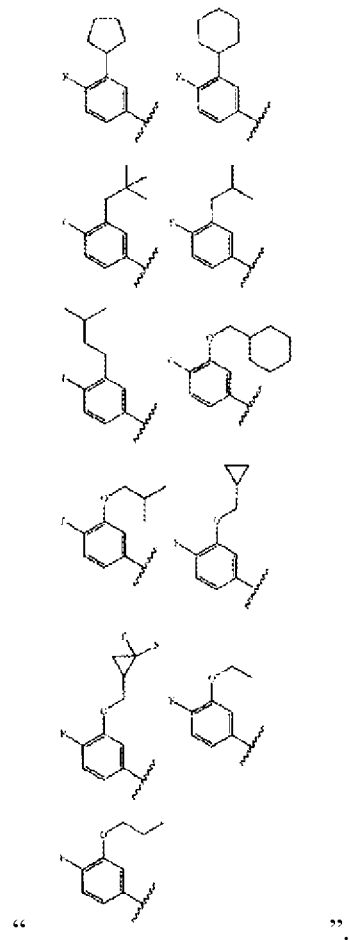

" ".

In the Claims:

CERTIFICATE OF CORRECTION (continued)
U.S. Pat. No. 7,652,023 B2

Claim 11 (continued):
Column 263, lines 1 to 66, after "-continued", delete

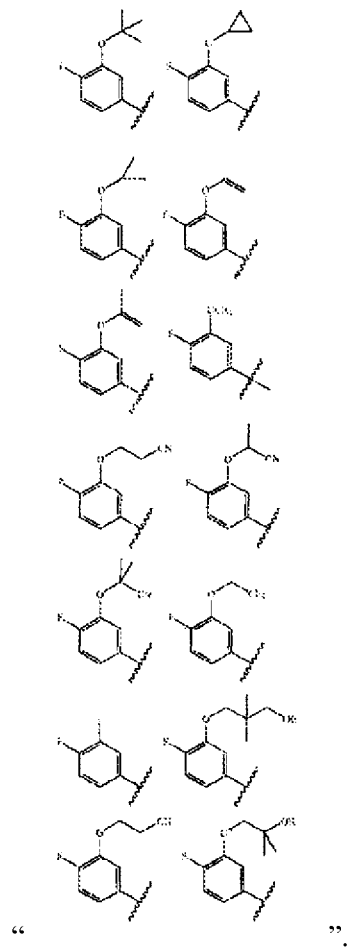

" ".

In the Claims:

CERTIFICATE OF CORRECTION (continued)
U.S. Pat. No. 7,652,023 B2

Claim 11 (continued):
　　Column 264, lines 1 to 66, after "-continued", delete

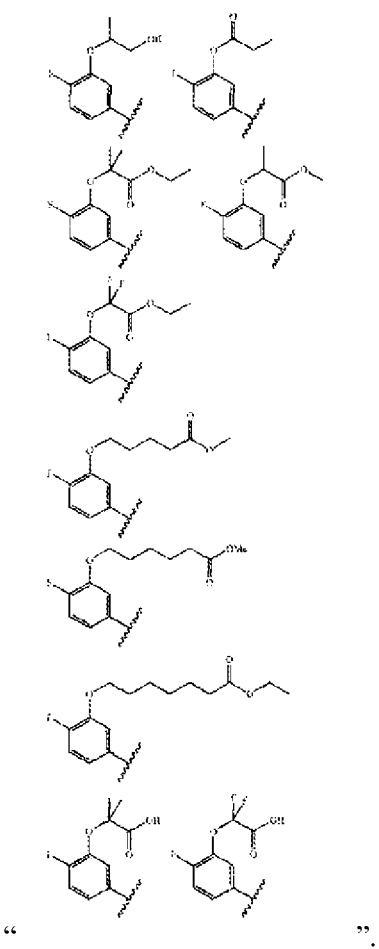

"　　" ".

In the Claims:

CERTIFICATE OF CORRECTION (continued)
U.S. Pat. No. 7,652,023 B2

Claim 11 (continued):
Column 265, lines 1 to 66, after "-continued", delete

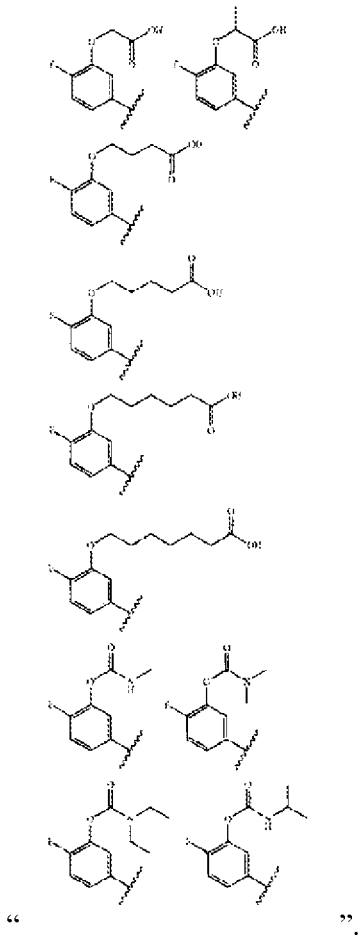

" ".

In the Claims:

CERTIFICATE OF CORRECTION (continued)
U.S. Pat. No. 7,652,023 B2

Claim 11 (continued):
    Column 266, lines 1 to 66, after "-continued", delete

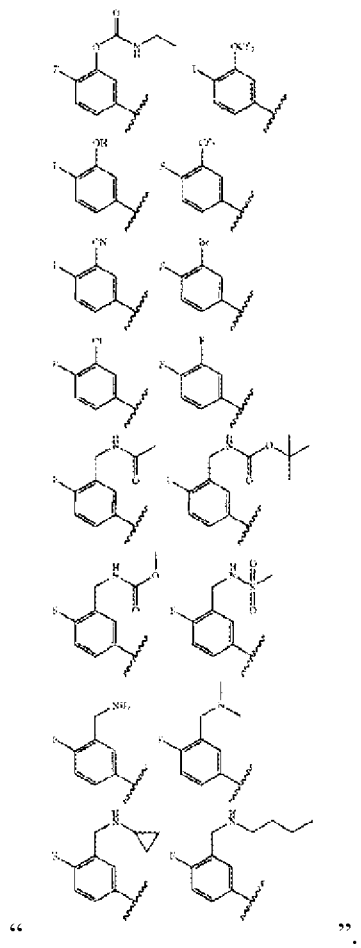

"       ".

In the Claims:

CERTIFICATE OF CORRECTION (continued)
U.S. Pat. No. 7,652,023 B2

Claim 11 (continued):
Column 267, lines 1 to 66, after "-continued", delete

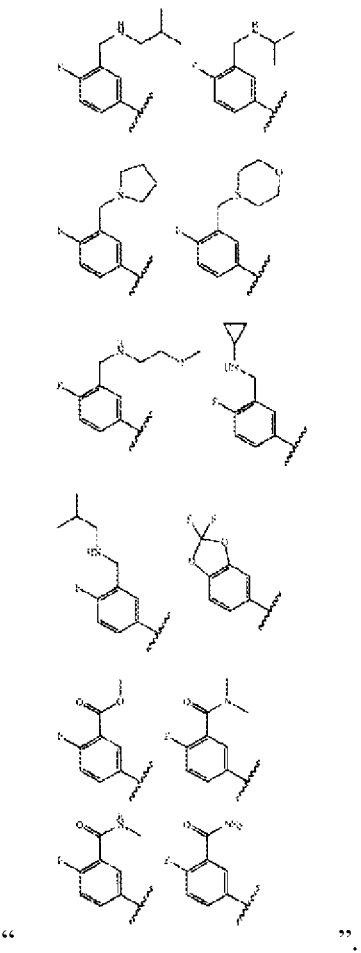

" ".

In the Claims:

CERTIFICATE OF CORRECTION (continued)
U.S. Pat. No. 7,652,023 B2

Claim 11 (continued):
 Column 268, lines 1 to 66, after "-continued", delete

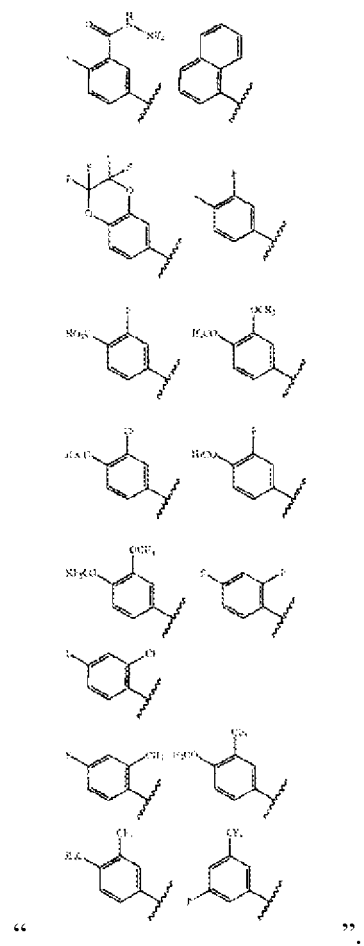

" ".

In the Claims:

CERTIFICATE OF CORRECTION (continued)
U.S. Pat. No. 7,652,023 B2

Claim 11 (continued):
Column 269, lines 1 to 66, after "-continued", delete

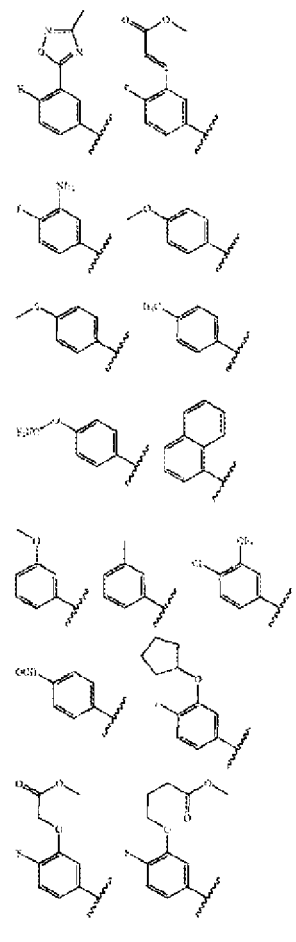

" ".

Column 270, lines 1 to 23, after "-continued", delete

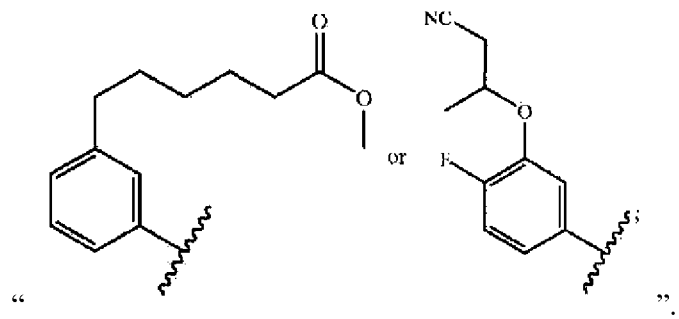

" ".

In the Claims:

Claim 11 (continued):
Column 272, lines 2 to 15, after " 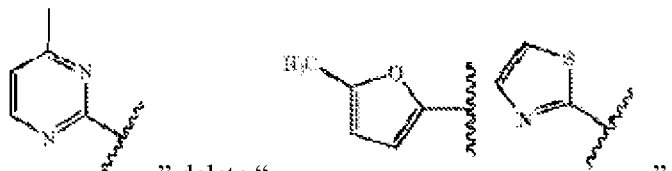 " delete "                    ".
Column 273, lines 1 to 21, after "-continued", delete
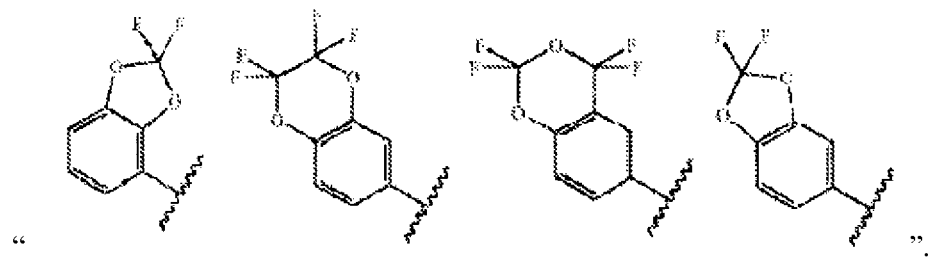
"                                                                                                                                             ".
Column 283, lines 26 to 30, after " 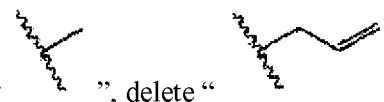 ", delete "        ".
Column 283, lines 27 to 34, after "        ", delete "        "
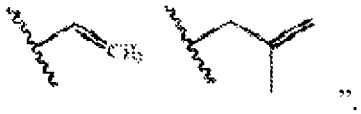
".
Column 283, lines 35 to 40, after "  ", delete "        ".
Column 283, lines 41 to 44, after " 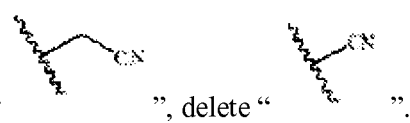 ", delete "        ".
In the Claims:

CERTIFICATE OF CORRECTION (continued)
U.S. Pat. No. 7,652,023 B2

Claim 11 (continued):

Column 285, lines 42 to 50, after "  ".

delete " 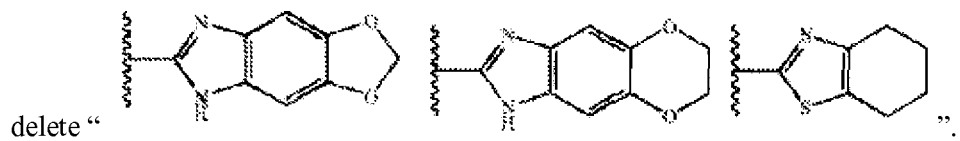 ".

Column 286, lines 9 to 12, after " 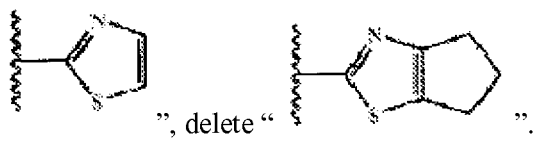 ".

Column 286, lines 17 to 21, after "  ".

Claim 14:
Column 286, line 57, change "wherin" to -- wherein --.